United States Patent [19]
Grote et al.

[11] Patent Number: 5,948,932
[45] Date of Patent: Sep. 7, 1999

[54] PHENYLACETIC ACID DERIVATIVES, PROCESSES AND INTERMEDIATES FOR USE IN PRODUCING THEM AND AGENTS CONTAINING THEM

[75] Inventors: Thomas Grote, Schifferstadt; Herbert Bayer, Mannheim; Ruth Müller, Friedelsheim; Hubert Sauter, Mannheim; Reinhard Kirstgen, Neustadt; Volker Harries, Frankenthal; Gisela Lorenz, Hambach; Eberhard Ammermann, Heppenheim; Siegfried Strathmann, Limburgerhof, all of Germany

[73] Assignee: BASF Aktiengesellschaft, Ludwigshafen, Germany

[21] Appl. No.: 09/051,591

[22] PCT Filed: Oct. 11, 1996

[86] PCT No.: PCT/EP96/04446

§ 371 Date: Apr. 15, 1998

§ 102(e) Date: Apr. 15, 1998

[87] PCT Pub. No.: WO97/15552

PCT Pub. Date: May 1, 1997

[30] Foreign Application Priority Data

Oct. 23, 1995 [DE] Germany .............. 195 39 324

[51] Int. Cl.⁶ .................................. C07C 255/04
[52] U.S. Cl. ............................................ 558/422
[58] Field of Search ............................. 558/422

[56] References Cited

FOREIGN PATENT DOCUMENTS 2005345  6/1990  Canada .
95/18789  7/1995  WIPO .

*Primary Examiner*—Johann Richter
*Assistant Examiner*—Ebenezer Sackey
*Attorney, Agent, or Firm*—Keil & Weinkauf

[57] ABSTRACT

Phenylacetic acid derivatives of the formula I

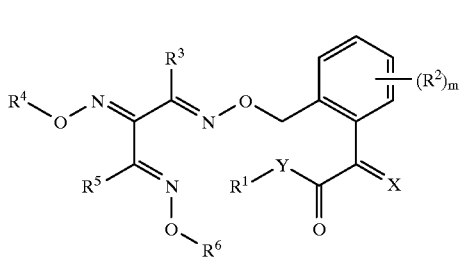

where the substituents and the index have the following meanings:

x is $NOCH_3$, $CHOCH_3$, $CHCH_3$;

Y is O, NR $R^1$,R independently of one another are hydrogen and $C_1$–$C_4$-alkyl;

$R^2$ is cyano, nitro, trifluoromethyl, halogen, alkyl and alkoxy;

m is 0, 1 or 2, it being possible for the radicals $R^2$ to be different when m is 2;

$R^3$ is hydrogen, cyano, $C_1$–$C_4$-alkyl, $C_1$–$C_4$-haloalkyl, $C_3$–$C_6$-cycloalkyl;

$R^4$, $R^5$ and $R^6$ have the meanings given in claim 1, and their salts, a process and intermediates for the preparation of these compounds, and compositions comprising them for controlling animal pests and harmful fungi.

14 Claims, No Drawings

PHENYLACETIC ACID DERIVATIVES, PROCESSES AND INTERMEDIATES FOR USE IN PRODUCING THEM AND AGENTS CONTAINING THEM

The present invention relates to phenylacetic acid derivatives of the formula I

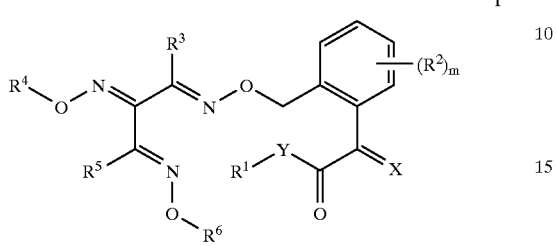

where the substituents and the index have the following meanings:

X is $NOCH_3$, $CHOCH_3$, $CHCH_3$;

Y is O, NR $R^1$, R independently of one another are hydrogen and $C_1$–$C_4$-alkyl;

$R^2$ is cyano, nitro, trifluoromethyl, halogen, $C_1$–$C_4$-alkyl and $C_1$–$C_4$-alkoxy;

m is 0, 1 or 2, it being possible for the radicals $R^2$ to be different when m is 2;

$R^3$ is hydrogen, cyano, $C_1$–$C_4$-alkyl, $C_1$–$C_4$-haloalkyl, $C_3$–$C_6$-cycloalkyl;

$R^4$, $R^6$ independently of one another are hydrogen, $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^7)$—$A_n$—$R^8$;

aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkyl-aminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy or $C(=NOR^7)$—$A_n$—$R^8$;

is hydrogen, $C_1$–$C_6$-alkyl, $C_2$–$C_6$-alkenyl, $C_2$–$C_6$-alkynyl, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^7)$—$A_n$—$R^8$;

$C_3$–$C_6$-cycloalkyl, $C_3$–$C_6$-cycloalkenyl, heterocyclyl, aryl, hetaryl, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothio-carbonyl, $C_2$–$C_6$-alkenyl, $C_2$–$C_6$-alkenyloxy, benzyl, benzyloxy, aryl, aryloxy, hetaryl and hetaryloxy;

where

A is oxygen, sulfur or nitrogen and where the nitrogen has attached to it hydrogen or $C_1-C_6$-alkyl;

n is 0 or 1;

$R^7$ is hydrogen or $C_1-C_6$-alkyl and $R^8$ is hydrogen or $C_1-C_6$-alkyl, and their salts.

Moreover, the invention relates to processes and intermediates for the preparation of these compounds and to compositions comprising them for controlling animal pests and harmful fungi.

Phenylacetic acid derivatives for use in pest control have already been disclosed in the literature (EP-A 422 597, EP-A 463 488, EP-A 370 629, EP-A 460 575, EP-A 472 300, WO-A 90/07,493, WO-A 92/13,830, WO-A 92/18,487, WO-A 95/18,789, WO-A 95/21,153, WO-A 95/21,154).

It was an object of the present invention to provide novel compounds having an improved action.

We have found that this object is achieved by the phenylacetic acid derivatives I defined at the outset. Moreover, we have found processes and intermediates for their preparation, as well as compositions comprising them for controlling animal pests and harmful fungi and their use for this purpose.

The compounds I can be obtained by various routes by processes known per se from the literature.

In principle, it is irrelevant when synthesizing the compounds I whether the group $—C(X)—COYR^1$ or the group

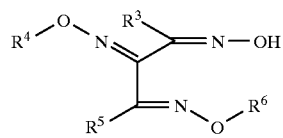

is constructed first.

The construction of the group $—C(X)—CO_2R^1$ is disclosed, for example, in the literature cited at the outset.

1. To synthesize the compounds of the formula I, a procedure is generally followed in which a benzyl derivative of the formula II is reacted with a hydroxyimine of the formula III.

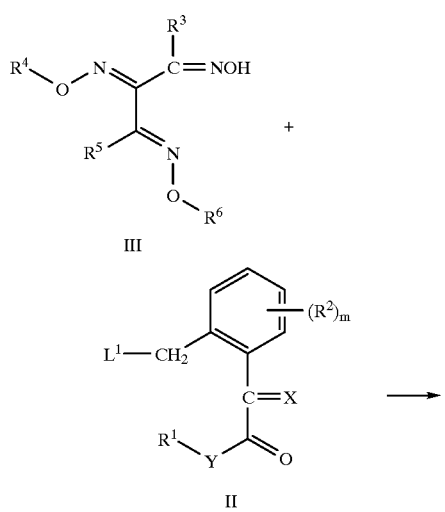

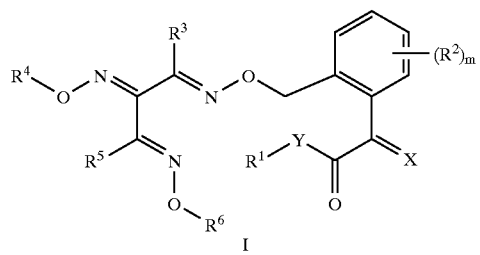

I $L^1$ in formula II is a nucleophilically exchangeable leaving group, eg. halogen or sulfonate groups, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate, and triethylamine, following the methods described in Houben-Weyl, Vol. E 14b, p. 370 et seq. and Houben-Weyl, Vol. 10/1, p. 1189 et seq.

The hydroxyimines III required are obtained, for example, as described in Equation 1 by a series of nitrosation, alkylation and oximation reactions from appropriate carbonyl compounds XIV.

Equation 1

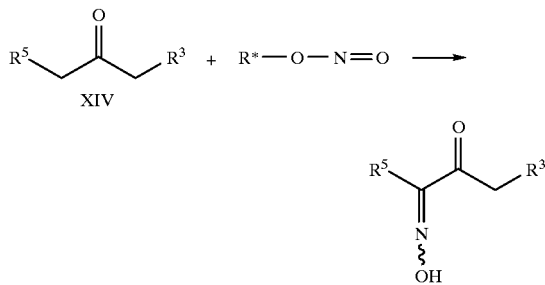

Basic or acidic catalysis allows the α-keto-oxime XV to be prepared from the ketone XIV and an organic nitrite following the methods described in Houben-Weyl Vol. 10/4, p. 17 et seq.

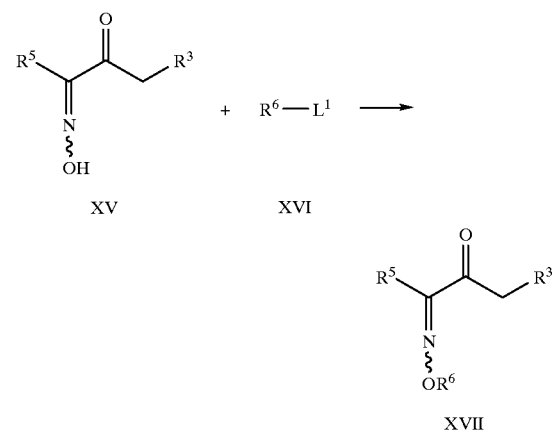

The keto-oxime ether XVII which is required is obtained, for example, by reacting XV with a nucleophilically substituted reagent XVI.

$L^1$ in formula XVI is a nucleophilically exchangeable leaving group, eg. halogen or sulfonate groups, preferably chlorine, bromine, iodine, mesylate, tosylate or triflate.

The reaction is carried out in a manner known per se in an inert organic solvent in the presence of a base, eg. potassium carbonate, potassium hydroxide, sodium hydride, triethylamine and pyridine, following the methods described in Houben-Weyl, Vol. 14b p. 307 et seq., p. 370 et seq. and p. 385 et seq.; Houben-Weyl Vol. 10/4 p. 55 et seq., p. 180 et seq. and p. 217 et seq.; Houben-Weyl Vol. E5, p. 780 et seq.

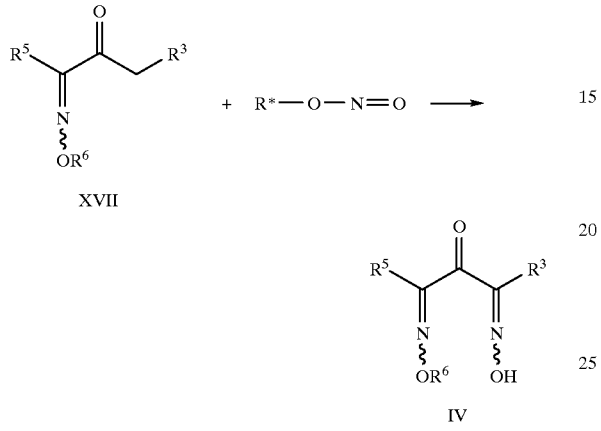

Basic or acidic catalysis allows the α-keto-oxime IV to be prepared from the ketone XVII and an organic nitrite following the methods described in Houben-Weyl Vol. 10/4 p. 17 et seq.

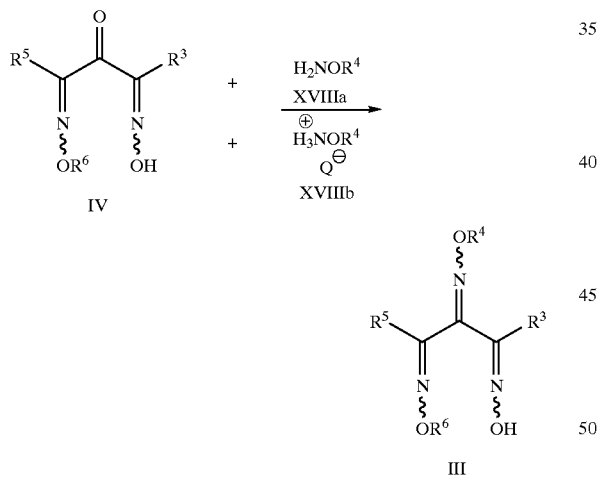

The hydroxyimine III which is required is obtained, for example, by reacting an appropriate α-keto-oxime IV with an oxyamine XVIIIa or a salt thereof XVIIIb. $Q^{\ominus}$ in formula XVIIIb is the anion of an acid, in particular of an inorganic acid, eg. halide, such as chloride.

The reaction is carried out in a manner known per se in an inert organic solvent following the methods described in EP-A 513 580; Houben-Weyl Vol. 10/4 p. 73 et seq.; Houben-Weyl Vol. E14b p. 369 et seq. and p. 385 et seq.

1.1 Alternatively, the compounds I can also be obtained by first reacting the benzyl derivative II with the carbonylhydroxyimino derivative IV to give a corresponding benzyloxyimine of the formula V, and this is subsequently reacted with the hydroxylamine VIa or a salt thereof VIb to give I.

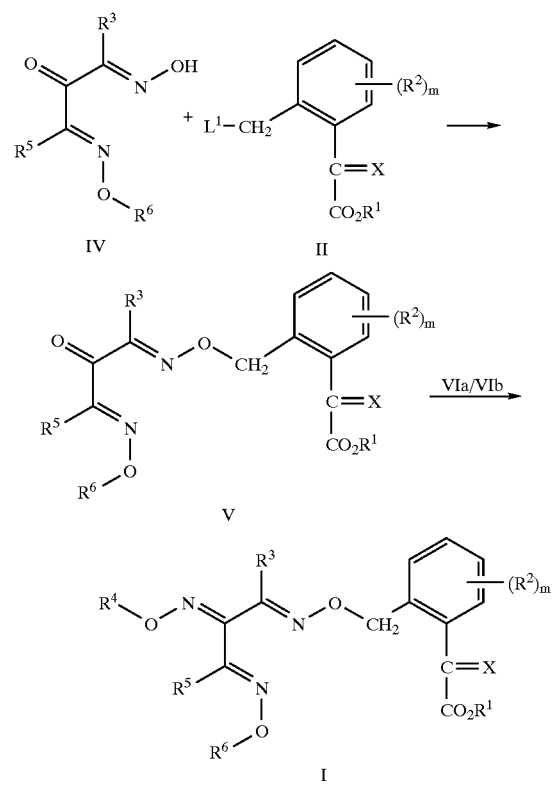

The reaction is carried out in a manner known per se in an inert organic solvent following the methods described in Houben-Weyl, Vol. E 14b, p. 369 et seq.; Houben-Weyl, Vol. 10/1, p. 1189 et seq. and Houben-Weyl, Vol. 10/4, p. 73 et seq. or EP-A 513 580.

1.2 A further possibility for preparing the compounds I is to react the benzyl derivative II with N-hydroxyphthalimide followed by hydrazinolysis to give the benzylhydroxylamine IIa and to further react IIa with a carbonyl compound VII.

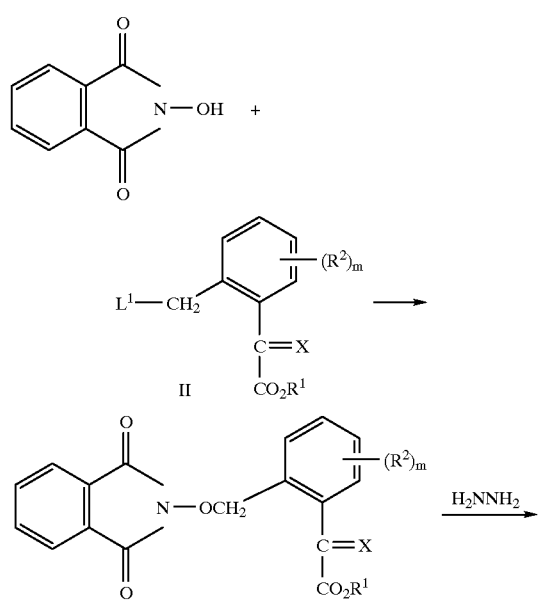

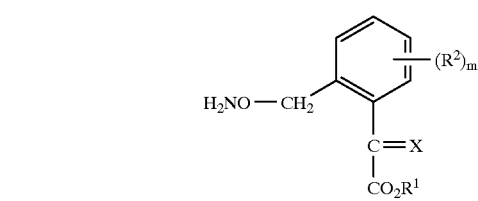

IIa

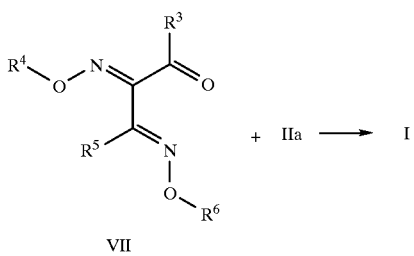

VII

2. Compounds I are preferably obtained by first converting a compound IV with a lactone IX to give the corresponding benzoic acid X, following the methods described in EP-A 493 711, and converting X into the cyanocarboxylic acids XI via the corresponding halides, and these cyanocarboxylic acids XI are converted into the α-keto-esters XII via a Pinner reaction (Angew. Chem. 94, 1 (1982)) and the product is further reacted to the α-keto-amides XIII (cf. EP 348 766, DE 37 05 389, EP 178 826, DE 36 23 92; Houben-Weyl Vol. E5 p. 941 et seq.).

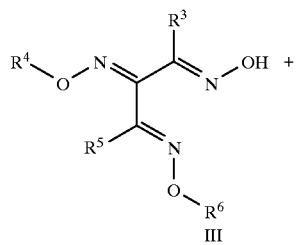

III

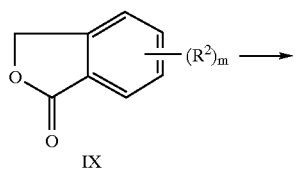

IX

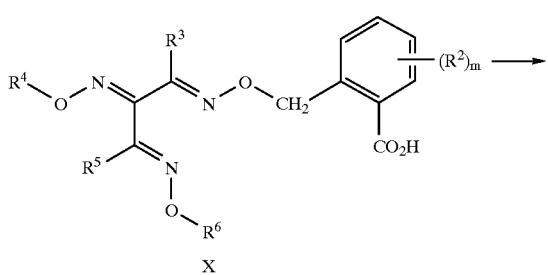

X

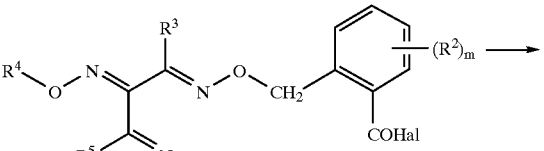

(Hal=Halogen)
Xa

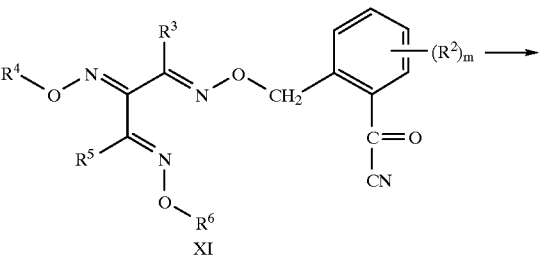

XI

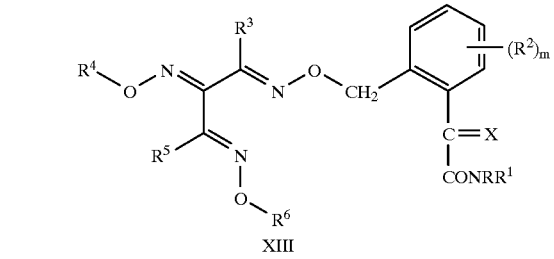

R ≠ H)
XII

XIII

The α-keto-esters XII and the α-keto-amides XIII can be converted into the compounds I by customary methods (cf. EP-A 178 926, EP-A 513 580, DE-A 36 23 921, EP-A 398 692).

Compounds I where $R^1$ is hydrogen are obtained by this process by hydrolyzing the esters XV and subsequently reacting the product to give I.

The compounds I where Y is NH can also be obtained from the corresponding esters (Y=O) by reacting them with amines of the formulae [sic] $R^1NH_2$.

Those compounds II which are not already known (EP-A 513 580, EP-A 477 631, EP-A 463 488, EP-A 251 082, EP 400 417, EP 585 751) can be prepared by the methods described in these publications.

Due to their C=C and C=N double bonds, the compounds I may be obtained from their preparation in the form of E/Z isomer mixtures which can be separated into the individual compounds in the customary manner, for example by crystallization or chromatography.

If isomer mixtures are obtained from the synthesis, it is, however, generally not absolutely necessary to separate them since the individual isomers can be converted into each other in some cases during formulation for use or upon use (for example under the action of light, acid or bases). Analogous conversions can also take place after use, for example in the treated plant when plants are treated, or in the harmful fungus or animal pest to be controlled.

In relation to the C=X double bond, the E-isomers of the compounds I are preferred with a view to their activity (configuration based on the —OCH$_3$ or the —CH$_3$ group relative to the —CO$_2$R$^1$ group).

In relation to the —C(R$^3$)=NOCH$_2$— double bond, the cis-isomers of the compounds I are preferred with a view to their activity (configuration based on the radical R$^3$ relative to the —OCH$_2$— group).

Collective terms which generally represent the groups below are used in the definitions of the compounds I given at the outset:

Halogen: fluorine, chlorine, bromine and iodine;

Alkyl: straight-chain or branched alkyl groups having 1 to 4, 6 or 10 carbon atoms, eg. C$_1$–C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethyl-butyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methyl-propyl and 1-ethyl-2-methylpropyl;

Haloalkyl: straight-chain or branched alkyl groups having 1 to 6 carbon atoms, it being possible for some or all of the hydrogen atoms in these groups to be replaced by halogen atoms as mentioned above, eg. C$_1$–C$_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Cycloalkyl: monocyclic alkyl groups having 3 to 6 carbon ring members, eg. cyclopropyl, cyclobutyl, cyclopentyl and cyclohexyl;

Alkenyl: straight-chain or branched alkenyl groups having 2 to 6 or 10 carbon atoms and one double bond in any position, eg. C$_2$–C$_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkynyl: straight-chain or branched alkynyl groups having 2 to 10 carbon atoms and one triple bond in any position, eg. C$_2$–C$_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-Hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

Heterocyclyl or heterocyclyloxy, heterocyclylthio and heterocyclylamino: three- to six-membered, saturated or partially unsaturated mono- or polycyclic heterocycles which contain one to three hetero atoms selected from a group consisting of oxygen, nitrogen and sulfur and which are bonded to the skeleton directly or (heterocyclyloxy) via an oxygen atom or (heterocyclylthio) via a sulfur atom or (heterocyclylamino) via a nitrogen atom, eg. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl [sic], 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydro-fur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5- dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl, Aryl or aryloxy, arylthio, arylcarbonyl and arylsulfonyl: aromatic mono- or polycyclic hydrocarbon radicals which are bonded to the skeleton directly or (aryloxy) via an oxygen atom (—O—) or (arylthio) via a sulfur atom (—S—) or (arylcarbonyl) via a carbonyl group (—CO—) or (arylsulfonyl) via a sulfonyl group (—SO$_2$—), eg. phenyl, naphthyl and phenanthrenyl, or phenyloxy, naphthyloxy and phenanthrenyloxy and the corresponding carbonyl and sulfonyl radicals;

Hetaryl or hetaryloxy, hetarylthio, hetarylcarbonyl and hetarylsulfonyl: aromatic mono- or polycyclic radicals which, besides carbon ring members, can additionally contain one to four nitrogen atoms or one to three nitrogen atoms and one oxygen or one sulfur atom or one oxygen or one sulphur atom and which are bonded to the skeleton directly or (hetaryloxy) via an oxygen atom (—O—) or (hetarylthio) via a sulfur atom (—S—) or (hetarylcarbonyl) via a carbonyl group (—CO—) or (hetarylsulfonyl) via a sulfonyl group (—SO$_2$—), eg.

5-membered hetaryl containing one to three nitrogen atoms: 5-membered hetaryl ring groups which, besides carbon atoms, can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and one sulfur or oxygen atom or one oxygen or one sulfur atom: 5-membered hetaryl ring groups which, besides carbon atoms, contain one to four nitrogen atoms or one to three nitrogen atoms and one sulfur or oxygen atom or one oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered hetaryl containing one to three nitrogen atoms or one nitrogen atom and/or one oxygen or sulfur atom: 5-membered hetaryl ring groups which, besides carbon atoms, can contain one to four nitrogen atoms or one to three nitrogen atoms and one sulfur or oxygen atom or one oxygen or one sulfur atom as ring members and in which two adjacent carbon ring members or one nitrogen and one adjacent carbon ring member can be bridged via a buta-1,3-diene-1,4-diyl group;

5-membered hetaryl bonded via nitrogen and containing one to four nitrogen atoms, or benzo-fused 5-membered hetaryl bonded via nitrogen and containing one to three nitrogen atoms: 5-membered hetaryl ring groups which, besides carbon atoms, can contain one to four nitrogen atoms, or one to three nitrogen atoms, as ring members, and in which two adjacent carbon ring members or one nitrogen and one adjacent carbon ring member can be bridged via a buta-1,3-diene-1,4-diyl group, these rings being bonded to the skeleton via one of the nitrogen ring members;

6-membered hetaryl containing one to three, or one to four. nitrogen atoms: 6-membered hetaryl ring groups which, besides carbon atoms, can contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl containing one to four nitrogen atoms: 6-membered hetaryl ring groups where two adjacent carbon ring members can be bridged via a buta-1,3-diene-1,4-diyl group, eg. quinoline, isoquinoline, quinazoline and quinoxaline, and the corresponding oxy, thio, carbonyl or sulfonyl groups.

Hetarylamino: aromatic mono- or polycyclic radicals which, besides carbon ring members, can additionally contain one to four nitrogen atoms or one to three nitrogen atoms and one oxygen or one sulfur atom and which are bonded to the skeleton via a nitrogen atom.

The term "partially or fully halogenated" is intended to express that some or all of the hydrogen atoms in groups which are thus characterized can be replaced by identical or different halogen atoms as mentioned above.

With a view to their biological action, preferred compounds of the formula I are those where m is 0.

Equally preferred are compounds of the formula I where $R^1$ is methyl.

Also preferred compounds I are those where $R^3$ is hydrogen, cyano, cyclopropyl, methyl, ethyl, 1-methylethyl or $CF_3$.

Moreover, preferred compounds I are those where $R^3$ is methyl.

Also preferred compounds I are those where $R^3$ is cyano.

Furthermore, preferred compounds I are those where $R^3$ is cyclopropyl.

Other preferred compounds I are those where $R^3$ is $CF_3$.

Other preferred compounds I are those where $R^5$ is hydrogen, cyclopropyl, methyl, ethyl, iso-propyl, unsubstituted or substituted aryl or hetaryl.

Moreover, preferred compounds I are those where $R^5$ is methyl.

Other preferred compounds I are those where $R^5$ is ethyl.

Moreover, preferred compounds I are those where $R^5$ is iso-propyl.

Moreover, preferred compounds I are those where $R^5$ is cyclopropyl.

Furthermore, preferred compounds I are those where $R^5$ is $CF_3$.

Other preferred compounds I are those where $R^5$ is unsubstituted or substituted aryl or hetaryl.

Other preferred compounds I are those where $R^5$ is unsubstituted or substituted pyridyl, pyrimidyl, pyrazinyl, pyridazinyl or triazinyl.

Other preferred compounds I are those where $R^5$ is unsubstituted or substituted furyl, thienyl or pyrrolyl.

Other preferred compounds I are those where $R^5$ is unsubstituted or substituted oxazolyl, thiazolyl, isoxazolyl, isothiazolyl, pyrazolyl or imidazolyl.

Other preferred compounds I are those where $R^5$ is unsubstituted or substituted oxdiazolyl [sic], thiadiazolyl or triazolyl.

Furthermore, preferred compounds I are those where $R^5$ is phenyl which is unsubstituted or has attached to it one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino, $C_1$–$C_4$-alkylsulfonyl, $C_1$–$C_4$-alkoxycarbonyl, $C_1$–$C_4$-alkyl-aminocarbonyl or di-$C_1$–$C_4$-alkylaminocarbonyl.

Furthermore, preferred compounds I are those where $R^4$ is hydrogen, $C_1$–$C_6$-alkyl, $C_2$–$C_6$-alkenyl, $C_2$–$C_6$-alkynyl, allyl, arylalkyl, hetarylalkyl, aryloxyalkyl, hetaryloxyalkyl, aryl or hetaryl.

Other preferred compounds I are those where $R^4$ is $C_1$–$C_6$-alkyl.

Moreover, preferred compounds I are those where $R^4$ is methyl, ethyl, 2-propenyl or 2-propynyl.

Other preferred compounds of the formula I are those where $R^6$ is $C_1$–$C_6$-alkyl, $C_2$–$C_6$-alkenyl, $C_2$–$C_6$-alkynyl, arylalkyl, hetarylalkyl, aryloxyalkyl or hetaryloxyalkyl.

Moreover, preferred compounds I are those where $R^6$ is methyl, ethyl or propargyl.

Other preferred compounds are those where $R^6$ is arylalkyl or hetarylalkyl.

Moreover, preferred compounds I are those where $R^6$ is aryloxyalkyl or hetaryloxyalkyl.

Also preferred compounds of the formula I are those where X is $NOCH_3$.

Also preferred compounds of the formula I are those where X is $CHOCH_3$.

Also preferred compounds of the formula I are those where X is $CHCH_3$.

Other preferred compounds of the formula I are those where Y is O.

Other preferred compounds of the formula I are those where Y is NH.

Furthermore, preferred compounds of the formula I are those where the substituents are selected from a combination of the above-described preferred substituents.

With a view to their use, especially preferred compounds I are those listed in the tables which follow.

With a view to their use, compounds I of the formulae I.1–I.4 which are listed in the tables below are especially preferred:

I.1

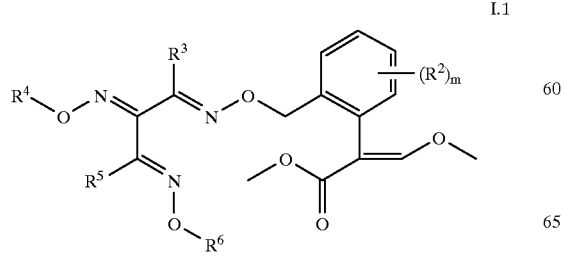

I.2

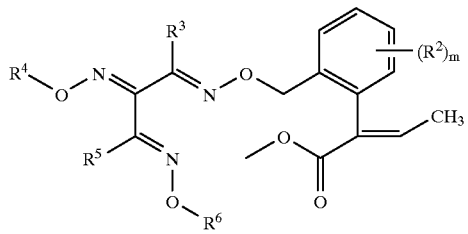

I.3

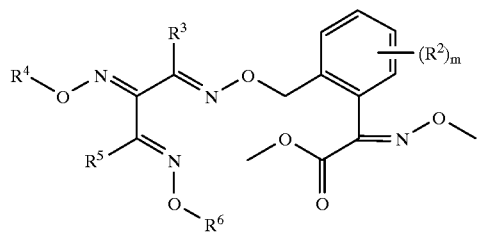

I.4

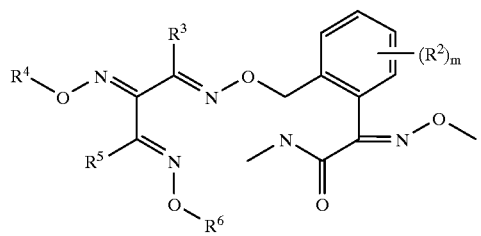

TABLE A

| No. | $R^6$ |
|---|---|
| 1 | H |
| 2 | $CH_3$ |
| 3 | $CH_2CH_3$ |
| 4 | $CH_2CH_2CH_3$ |
| 5 | $CH(CH_3)_2$ |
| 6 | cyclopropyl |
| 7 | $(CH_2)_3CH_3$ |
| 8 | $CH(CH_3)CH_2CH_3$ |
| 9 | $CH_2CH(CH_3)_2$ |
| 10 | $C(CH_3)_3$ |
| 11 | cyclobutyl |
| 12 | $(CH_2)_4CH_3$ |
| 13 | $CH(CH_3)(CH_2)_2CH_3$ |
| 14 | $CH_2CH(CH_3)CH_2CH_3$ |
| 15 | $(CH_2)_2CH(CH_3)_2$ |
| 16 | $CH_2C(CH_3)_3$ |
| 17 | $CH(CH_2CH_3)_2$ |
| 18 | $C(CH_3)_2CH_2CH_3$ |
| 19 | $CH(CH_3)CH(CH_3)_2$ |
| 20 | cyclopentyl |
| 21 | $(CH_2)_5CH_3$ |
| 22 | $CH(CH_3)(CH_2)_3CH_3$ |
| 23 | $CH(CH_2CH_3)(CH_2)_2CH_3$ |
| 24 | $CH_2CH(CH_3)(CH_2)_2CH_3$ |
| 25 | $(CH_2)_2CH(CH_3)CH_2CH_3$ |
| 26 | $(CH_2)_3CH(CH_3)_2$ |
| 27 | $(CH_2)_2C(CH_3)_3$ |
| 28 | $CH_2CH(CH_2CH_3)_2$ |
| 29 | $CH(CH_3)CH(CH_3)CH_2CH_3$ |
| 30 | $CH(CH_3)CH_2CH(CH_3)_2$ |
| 31 | $CH_2CH(CH_3)CH(CH_3)_2$ |
| 32 | $CH(CH_3)C(CH_3)_3$ |
| 33 | $CH(CH_2CH_3)CH(CH_3)_2$ |
| 34 | $C(CH_3)_2CH_2CH_2CH_3$ |
| 35 | $CH_2C(CH_3)_2CH_2CH_3$ |
| 36 | $C(CH_3)_2CH(CH_3)_2$ |

TABLE A-continued

| No. | R⁶ |
|---|---|
| 37 | cyclohexyl |
| 38 | $CH_2CN$ |
| 39 | $(CH_2)_2CN$ |
| 40 | $(CH_2)_3CN$ |
| 41 | $(CH_2)_4CN$ |
| 42 | $CH_2NO_2$ |
| 43 | $(CH_2)_2NO_2$ |
| 44 | $(CH_2)_3NO_2$ |
| 45 | $(CH_2)_4NO_2$ |
| 46 | $(CH_2)_2OH$ |
| 47 | $(CH_2)_3OH$ |
| 48 | $(CH_2)_4OH$ |
| 49 | $(CH_2)_2NH2$ |
| 50 | $(CH_2)_3NH2$ |
| 51 | $(CH_2)_4NH2$ |
| 52 | $(CH_2)_2NHCH_3$ |
| 53 | $(CH_2)_3NHCH_3$ |
| 54 | $(CH_2)_4NHCH_3$ |
| 55 | $(CH_2)_2N(CH_3)_2$ |
| 56 | $(CH_2)_3N(CH_3)_2$ |
| 57 | $(CH_2)_4N(CH_3)_2$ |
| 58 | $(CH_2)_2N(CH_2CH_3)_2$ |
| 59 | $(CH_2)_3N(CH_2CH_3)_2$ |
| 60 | $(CH_2)_4N(CH_2CH_3)_2$ |
| 61 | $(CH_2)_2OCH_3$ |
| 62 | $(CH_2)_3OCH_3$ |
| 63 | $(CH_2)_4OCH_3$ |
| 64 | $(CH_2)_2OCH_2CH_3$ |
| 65 | $(CH_2)_3OCH_2CH_3$ |
| 66 | $(CH_2)_4OCH_2CH_3$ |
| 67 | $(CH_2)_2O(CH_2)_2CH_3$ |
| 68 | $(CH_2)_3O(CH_2)_2CH_3$ |
| 69 | $(CH_2)_4O(CH_2)_2CH_3$ |
| 70 | $(CH_2)_2OCH(CH_3)_2$ |
| 71 | $(CH_2)_3OCH(CH_3)_2$ |
| 72 | $(CH_2)_4OCH(CH_3)_2$ |
| 73 | $(CH_2)_2OC(CH_3)_3$ |
| 74 | $(CH_2)_3OC(CH_3)_3$ |
| 75 | $(CH_2)_4OC(CH_3)_3$ |
| 76 | $(CH_2)_2OCF_3$ |
| 77 | $(CH_2)_3OCF_3$ |
| 78 | $(CH_2)_4OCF_3$ |
| 79 | $(CH_2)_2SCH_3$ |
| 80 | $CH_3(CH_2)_3SCH_3$ |
| 81 | $(CH_2)_4SCH_3$ |
| 82 | $(CH_2)_2SOCH_3$ |
| 83 | $(CH_2)_3SOCH_3$ |
| 84 | $(CH_2)_4SOCH_3$ |
| 85 | $(CH_2)_2SO_2CH_3$ |
| 86 | $(CH_2)_3SO_2CH_3$ |
| 87 | $(CH_2)_4SO_2CH_3$ |
| 88 | $CH_2$-cyclopropyl |
| 89 | $(CH_2)_2$-cyclopropyl |
| 90 | $(CH_2)_3$-cyclopropyl |
| 91 | $(CH_2)_4$-cyclopropyl |
| 92 | $CH_2$-cyclopentyl |
| 93 | $(CH_2)_2$-cyclopentyl |
| 94 | $(CH_2)_3$-cyclopentyl |
| 95 | $(CH_2)_4$-cyclopentyl |
| 96 | $CH_2$-cyclohexyl |
| 97 | $(CH_2)_2$-cyclohexyl |
| 98 | $(CH_2)_3$-cyclohexyl |
| 99 | $(CH_2)_4$-cyclohexyl |
| 100 | $CHF_2$ |
| 101 | $CF_3$ |
| 102 | $CH_2CHF_2$ |
| 103 | $CH_2CF_3$ |
| 104 | $CHFCHF_2$ |
| 105 | $CH_2CH_2F$ |
| 106 | $CHFCH_3$ |
| 107 | $CHFCF_3$ |
| 108 | $CF_2CHF_2$ |
| 109 | $CF_2CHFCF_3$ |
| 110 | $CH_2CCl_3$ |
| 111 | $CF_2CHCl_2$ |
| 112 | $CF_2CHFCl$ |
| 113 | $CF_2CHFBr$ |
| 114 | $CH(CF_3)_2$ |
| 115 | $CH(CF_3)CH_3$ |
| 116 | $CH_2CH_2CF_3$ |
| 117 | $CH_2CHFCH_3$ |
| 118 | $CH_2CF_2CF_3$ |
| 119 | $CH_2CH_2CH_2F$ |
| 120 | $CH_2CF_2CF_2CF_3$ |
| 121 | $CH_2CH_2CHFCH_3$ |
| 122 | $CH_2CH_2CH_2CH_2F$ |
| 123 | $CH_2CH_2Cl$ |
| 124 | $CH_2CHClCH_3$ |
| 125 | $CH_2CH_2CH_2Cl$ |
| 126 | $CH_2CH_2CHClCH_3$ |
| 127 | $CH_2CH_2CH_2CH_2Cl$ |
| 128 | $CH_2CH_2Br$ |
| 129 | $CH_2CHBrCH_3$ |
| 130 | $CH_2CH_2CH_2Br$ |
| 131 | $CH_2CH_2CHBrCH_3$ |
| 132 | $CH_2CH_2CH_2CH_2Br$ |
| 133 | $CH_2$—$C_6H_5$ |
| 134 | $CH(CH_3)CN$ |
| 135 | $CH(CH_3)CH_2CN$ |
| 136 | $CH_2CH(CH_3)CN$ |
| 137 | $CH(CH_3)CH(CH_3)CN$ |
| 138 | $CH(CH_3)(CH_2)_2CN$ |
| 139 | $CH_2CH(CH_3)CH_2CN$ |
| 140 | $(CH_2)_2CH(CH_3)CN$ |
| 141 | $CH(CH_3)CH(CH_3)CH_2CN$ |
| 142 | $CH(CH_3)CH_2CH(CH_3)CN$ |
| 143 | $CH_2CH(CH_3)CH(CH_3)CN$ |
| 144 | $CH(CH_3)CH(CH_3)CH(CH_3)CN$ |
| 145 | $CH(CH_3)(CH_2)_3CN$ |
| 146 | $CH(CH_3)NO_2$ |
| 147 | $CH(CH_3)CH_2NO_2$ |
| 148 | $CH_2CH(CH_3)NO_2$ |
| 149 | $CH(CH_3)CH(CH_3)NO_2$ |
| 150 | $CH(CH_3)(CH_2)_2NO_2$ |
| 151 | $CH_2CH(CH_3)CH_2NO_2$ |
| 152 | $(CH_2)_2CH(CH_3)NO_2$ |
| 153 | $CH(CH_3)CH(CH_3)CH_2NO_2$ |
| 154 | $CH(CH_3)CH_2CH(CH_3)NO_2$ |
| 155 | $CH_2CH(CH_3)CH(CH_3)NO_2$ |
| 156 | $CH(CH_3)CH(CH_3)CH(CH_3)NO_2$ |
| 157 | $CH(CH_3)(CH_2)_3NO_2$ |
| 158 | $CH(CH_3)CH_2OH$ |
| 159 | $CH_2CH(CH_3)OH$ |
| 160 | $CH(CH_3)CH(CH_3)OH$ |
| 161 | $CH(CH_3)(CH_2)_2OH$ |
| 162 | $CH_2CH(CH_3)CH_2OH$ |
| 163 | $(CH_2)_2CH(CH_3)OH$ |
| 164 | $CH(CH_3)CH(CH_3)CH_2OH$ |
| 165 | $CH(CH_3)CH_2CH(CH_3)OH$ |
| 166 | $CH_2CH(CH_3)CH(CH_3)OH$ |
| 167 | $CH(CH_3)CH(CH_3)CH(CH_3)OH$ |
| 168 | $CH(CH_3)(CH_2)_3OH$ |
| 169 | $CH(CH_3)CH_2OCH_3$ |
| 170 | $CH_2CH(CH_3)OCH_3$ |
| 171 | $CH(CH_3)CH(CH_3)OCH_3$ |
| 172 | $CH(CH_3)(CH_2)_2OCH_3$ |
| 173 | $CH_2CH(CH_3)CH_2OCH_3$ |
| 174 | $(CH_2)_2CH(CH_3)OCH_3$ |
| 175 | $CH(CH_3)CH(CH_3)CH_2OCH_3$ |
| 176 | $CH(CH_3)CH_2CH(CH_3)OCH_3$ |
| 177 | $CH_2CH(CH_3)CH(CH_3)OCH_3$ |
| 178 | $CH(CH_3)CH(CH_3)CH(CH_3)OCH_3$ |
| 179 | $CH(CH_3)(CH_2)_3OCH_3$ |
| 180 | $CH(CH_3)CH_2OCH_2CH_3$ |
| 181 | $CH_2CH(CH_3)OCH_2CH_3$ |
| 182 | $CH(CH_3)CH(CH_3)OCH_2CH_3$ |
| 183 | $CH(CH_3)(CH_2)_2OCH_2CH_3$ |
| 184 | $CH_2CH(CH_3)CH_2OCH_2CH_3$ |
| 185 | $(CH_2)_2CH(CH_3)OCH_2CH_3$ |
| 186 | $CH(CH_3)CH(CH_3)CH_2OCH_2CH_3$ |
| 187 | $CH(CH_3)CH_2CH(CH_3)OCH_2CH_3$ |
| 188 | $CH_2CH(CH_3)CH(CH_3)OCH_2CH_3$ |
| 189 | $CH(CH_3)CH(CH_3)CH(CH_3)OCH_2CH_3$ |
| 190 | $CH(CH_3)(CH_2)_3OCH_2CH_3$ |

TABLE A-continued

| No. | R⁶ |
|---|---|
| 191 | CH(CH₃)CH₂O(CH₂)₂CH₃ |
| 192 | CH₂CH(CH₃)O(CH₂)₂CH₃ |
| 193 | CH(CH₃)CH(CH₃)O(CH₂)₂CH₃ |
| 194 | CH(CH₃)(CH₂)₂O(CH₂)₂CH₃ |
| 195 | CH₂CH(CH₃)CH₂O(CH₂)₂CH₃ |
| 196 | (CH₂)₂CH(CH₃)O(CH₂)₂CH₃ |
| 197 | CH(CH₃)CH(CH₃)CH₂O(CH₂)₂CH₃ |
| 198 | CH(CH₃)CH₂CH(CH₃)O(CH₂)₂CH₃ |
| 199 | CH(CH₃)CH₂CH(CH₃)O(CH₂)₂CH₃ |
| 200 | CH(CH₃)CH(CH₃)CH(CH₃)O(CH₂)₂CH₃ |
| 201 | CH(CH₃)(CH₂)₃O(CH₂)₂CH₃ |
| 202 | CH(CH₃)CH₂OCH(CH₃)₂ |
| 203 | CH₂CH(CH₃)OCH(CH₃)₂ |
| 204 | CH(CH₃)CH(CH₃)OCH(CH₃)₂ |
| 205 | CH(CH₃)(CH₂)₂OCH(CH₃)₂ |
| 206 | CH₂CH(CH₃)CH₂OCH(CH₃)₂ |
| 207 | (CH₂)₂CH(CH₃)OCH(CH₃)₂ |
| 208 | CH(CH₃)CH(CH₃)CH₂OCH(CH₃)₂ |
| 209 | CH(CH₃)CH₂CH(CH₃)OCH(CH₃)₂ |
| 210 | CH₂CH(CH₃)CH(CH₃)OCH(CH₃)₂ |
| 211 | CH(CH₃)CH(CH₃)CH(CH₃)OCH(CH₃)₂ |
| 212 | CH(CH₃)(CH₂)₃OCH(CH₃)₂ |
| 213 | CH(CH₃)CH₂OC(CH₃)₃ |
| 214 | CH₂CH(CH₃)OC(CH₃)₃ |
| 215 | CH(CH₃)CH(CH₃)OC(CH₃)₃ |
| 216 | CH(CH₃)(CH₂)₂OC(CH₃)₃ |
| 217 | CH₂CH(CH₃)CH₂OC(CH₃)₃ |
| 218 | (CH₂)₂CH(CH₃)OC(CH₃)₃ |
| 219 | CH(CH₃)CH(CH₃)CH₂OC(CH₃)₃ |
| 220 | CH(CH₃)CH₂CH(CH₃)OC(CH₃)₃ |
| 221 | CH₂CH(CH₃)CH(CH₃)OC(CH₃)₃ |
| 222 | CH(CH₃)CH(CH₃)CH(CH₃)OC(CH₃)₃ |
| 223 | CH(CH₃)(CH₂)₃OC(CH₃)₃ |
| 224 | CH(CH₃)CH₂OCF₃ |
| 225 | CH₂CH(CH₃)OCF₃ |
| 226 | CH(CH₃)CH(CH₃)OCF₃ |
| 227 | CH(CH₃)(CH₂)₂OCF₃ |
| 228 | CH₂CH(CH₃)CH₂OCF₃ |
| 229 | (CH₂)₂CH(CH₃)OCF₃ |
| 230 | CH(CH₃)CH(CH₃)CH₂OCF₃ |
| 231 | CH(CH₃)CH₂CH(CH₃)OCF₃ |
| 232 | CH₂CH(CH₃)CH(CH₃)OCF₃ |
| 233 | CH(CH₃)CH(CH₃)CH(CH₃)OCF₃ |
| 234 | CH(CH₃)(CH₂)₃OCF₃ |
| 235 | CH(CH₃)CH₂SCH₃ |
| 236 | CH₂CH(CH₃)SCH₃ |
| 237 | CH(CH₃)CH(CH₃)SCH₃ |
| 238 | CH(CH₃)(CH₂)₂SCH₃ |
| 239 | CH₂CH(CH₃)CH₂SCH₃ |
| 240 | (CH₂)₂CH(CH₃)SCH₃ |
| 241 | CH(CH₃)CH(CH₃)CH₂SCH₃ |
| 242 | CH(CH₃)CH₂CH(CH₃)SCH₃ |
| 243 | CH₂CH(CH₃)CH(CH₃)SCH₃ |
| 244 | CH(CH₃)CH(CH₃)CH(CH₃)SCH₃ |
| 245 | CH(CH₃)(CH₂)₃SCH₃ |
| 246 | CH(CH₃)CH₂SOCH₃ |
| 247 | CH₂CH(CH₃)SOCH₃ |
| 248 | CH(CH₃)CH(CH₃)SOCH₃ |
| 249 | CH(CH₃)(CH₂)₂SOCH₃ |
| 250 | CH₂CH(CH₃)CH₂SOCH₃ |
| 251 | (CH₂)₂CH(CH₃)SOCH₃ |
| 252 | CH(CH₃)CH(CH₃)CH₂SOCH₃ |
| 253 | CH(CH₃)CH₂CH(CH₃)SOCH₃ |
| 254 | CH₂CH(CH₃)CH(CH₃)SOCH₃ |
| 255 | CH(CH₃)CH(CH₃)CH(CH₃)SOCH₃ |
| 256 | CH(CH₃)(CH₂)₃SOCH₃ |
| 257 | CH(CH₃)CH₂SO₂CH₃ |
| 258 | CH₂CH(CH₃)SO₂CH₃ |
| 259 | CH(CH₃)CH(CH₃)SO₂CH₃ |
| 260 | CH(CH₃)(CH₂)₂SO₂CH₃ |
| 261 | CH₂CH(CH₃)CH₂SO₂CH₃ |
| 262 | (CH₂)₂CH(CH₃)SO₂CH₃ |
| 263 | CH(CH₃)CH(CH₃)CH₂SO₂CH₃ |
| 264 | CH(CH₃)CH₂CH(CH₃)SO₂CH₃ |
| 265 | CH₂CH(CH₃)CH(CH₃)SO₂CH₃ |
| 266 | CH(CH₃)CH(CH₃)CH(CH₃)SO₂CH₃ |
| 267 | CH(CH₃)(CH₂)₃SO₂CH₃ |
| 268 | CH(CH₃)-cyclopropyl |
| 269 | CH(CH₃)CH₂-cyclopropyl |
| 270 | CH₂CH(CH₃)-cyclopropyl |
| 271 | CH(CH₃)CH(CH₃)-cyclopropyl |
| 272 | CH(CH₃)(CH₂)₂-cyclopropyl |
| 273 | CH₂CH(CH₃)CH₂-cyclopropyl |
| 274 | (CH₂)₂CH(CH₃)-cyclopropyl |
| 275 | CH(CH₃)CH(CH₃)CH₂-cyclopropyl |
| 276 | CH(CH₃)CH₂CH(CH₃)-cyclopropyl |
| 277 | CH₂CH(CH₃)CH(CH₃)-cyclopropyl |
| 278 | CH(CH₃)CH(CH₃)CH(CH₃)-cyclopropyl |
| 279 | CH(CH₃)(CH₂)₃-cyclopropyl |
| 280 | CH(CH₃)-cyclopentyl |
| 281 | CH(CH₃)CH₂-cyclopentyl |
| 282 | CH₂CH(CH₃)-cyclopentyl |
| 283 | CH(CH₃)CH(CH₃)-cyclopentyl |
| 284 | CH(CH₃)(CH₂)₂-cyclopentyl |
| 285 | CH₂CH(CH₃)CH₂-cyclopentyl |
| 286 | (CH₂)₂CH(CH₃)-cyclopentyl |
| 287 | CH(CH₃)CH(CH₃)CH₂-cyclopentyl |
| 288 | CH(CH₃)CH₂CH(CH₃)-cyclopentyl |
| 289 | CH₂CH(CH₃)CH(CH₃)-cyclopentyl |
| 290 | CH(CH₃)CH(CH₃)CH(CH₃)-cyclopentyl |
| 291 | CH(CH₃)(CH₂)₃-cyclopentyl |
| 292 | CH(CH₃)-cyclohexyl |
| 293 | CH(CH₃)CH₂-cyclohexyl |
| 294 | CH₂CH(CH₃)-cyclohexyl |
| 295 | CH(CH₃)CH(CH₃)-cyclohexyl |
| 296 | CH(CH₃)(CH₂)₂-cyclohexyl |
| 297 | CH₂CH(CH₃)CH₂-cyclohexyl |
| 298 | (CH₂)₂CH(CH₃)-cyclohexyl |
| 299 | CH(CH₃)CH(CH₃)CH₂-cyclohexyl |
| 300 | CH(CH₃)CH₂CH(CH₃)-cyclohexyl |
| 301 | CH₂CH(CH₃)CH(CH₃)-cyclohexyl |
| 302 | CH(CH₃)CH(CH₃)CH(CH₃)-cyclohexyl |
| 303 | CH(CH₃)(CH₂)₃-cyclohexyl |
| 304 | CH(CH₃)CHF₂ |
| 305 | CF(CH₃)CHF₂ |
| 306 | CH(CH₃)CH₂F |
| 307 | CF(CH₃)CH₃ |
| 308 | CF(CH₃)CF₃ |
| 309 | CH(CH₃)CCl₃ |
| 310 | CH(CH₃)CH₂CF₃ |
| 311 | CH₂CH(CH₃)CF₃ |
| 312 | CH(CH₃)CH(CH₃)CF₃ |
| 313 | CH(CH₃)CF₂CF₃ |
| 314 | CH(CH₃)-phenyl |
| 315 | CH(CH₃)CH₂-phenyl |
| 316 | CH₂CH(CH₃)-phenyl |
| 317 | CH(CH₃)CH(CH₃)-phenyl |
| 318 | CH(CH₃)(CH₂)₂-phenyl |
| 319 | CH₂CH(CH₃)CH₂-phenyl |
| 320 | (CH₂)₂CH(CH₃)-phenyl |
| 321 | CH(CH₃)CH(CH₃)CH₂-phenyl |
| 322 | CH(CH₃)CH₂CH(CH₃)-phenyl |
| 323 | CH₂CH(CH₃)CH(CH₃)-phenyl |
| 324 | CH(CH₃)CH(CH₃)CH(CH₃)-phenyl |
| 325 | CH(CH₃)(CH₂)₃-phenyl |
| 326 | 2-F—C₆H₄—CH₂ |
| 327 | 3-F—C₆H₄—CH₂ |
| 328 | 4-F—C₆H₄—CH₂ |
| 329 | 2,3-F₂—C₆H₃—CH₂ |
| 330 | 2,4-F₂—C₆H₃—CH₂ |
| 331 | 2,5-F₂—C₆H₃—CH₂ |
| 332 | 2,6-F₂—C₆H₃—CH₂ |
| 333 | 3,4-F₂—C₆H₃—CH₂ |
| 334 | 3,5-F₂—C₆H₃—CH₂ |
| 335 | 2-Cl—C₆H₄—CH₂ |
| 336 | 3-Cl—C₆H₄—CH₂ |
| 337 | 4-Cl—C₆H₄—CH₂ |
| 338 | 2,3-Cl₂—C₆H₃—CH₂ |
| 339 | 2,4-Cl₂—C₆H₃—CH₂ |
| 340 | 2,5-Cl₂—C₆H₃—CH₂ |
| 341 | 2,6-Cl₂—C₆H₃—CH₂ |
| 342 | 3,4-Cl₂—C₆H₃—CH₂ |
| 343 | 3,5-Cl₂—C₆H₃—CH₂ |
| 344 | 2,3,4-Cl₃—C₆H₂—CH₂ |

TABLE A-continued

| No. | R⁶ |
|-----|-----|
| 345 | 2,3,5-Cl₃—C₆H₂—CH₂ |
| 346 | 2,3,6-Cl₃—C₆H₂—CH₂ |
| 347 | 2,4,5-Cl₃—C₆H₂—CH₂ |
| 348 | 2,4,6-Cl₃—C₆H₂—CH₂ |
| 349 | 3,4,5-Cl₃—C₆H₂—CH₂ |
| 350 | 2-Br—C₆H₄—CH₂ |
| 351 | 3-Br—C₆H₄—CH₂ |
| 352 | 4-Br—C₆H₄—CH₂ |
| 353 | 2,3-Br₂—C₆H₃—CH₂ |
| 354 | 2,4-Br₂—C₆H₃—CH₂ |
| 355 | 2,5-Br₂—C₆H₃—CH₂ |
| 356 | 2,6-Br₂—C₆H₃—CH₂ |
| 357 | 3,4-Br₂—C₆H₃—CH₂ |
| 358 | 3,5-Br₂—C₆H₃—CH₂ |
| 359 | 2-F, 3-Cl—C₆H₃—CH₂ |
| 360 | 2-F, 4-Cl—C₆H₃—CH₂ |
| 361 | 2-F, 5-Cl—C₆H₃—CH₂ |
| 362 | 2-F, 3-Br—C₆H₃—CH₂ |
| 363 | 2-F, 4-Br—C₆H₃—CH₂ |
| 364 | 2-F, 5-Br—C₆H₃—CH₂ |
| 365 | 2-Cl, 3-F—C₆H₃—CH₂ |
| 366 | 2-Cl, 4-F—C₆H₃—CH₂ |
| 367 | 2-Cl, 5-F—C₆H₃—CH₂ |
| 368 | 2-Cl, 3-Br—C₆H₃—CH₂ |
| 369 | 2-Cl, 4-Br—C₆H₃—CH₂ |
| 370 | 2-Cl, 5-Br—C₆H₃—CH₂ |
| 371 | 2-Br, 3-F—C₆H₃—CH₂ |
| 372 | 2-Br, 4-F—C₆H₃—CH₂ |
| 373 | 2-Br, 5-F—C₆H₃—CH₂ |
| 374 | 2-Br, 3-Cl—C₆H₃—CH₂ |
| 375 | 2-Br, 4-Cl—C₆H₃—CH₂ |
| 376 | 2-Br, 5-Cl—C₆H₃—CH₂ |
| 377 | 4-Cl, 3,5-Br₂—C₆H₂—CH₂ |
| 378 | 2-CN—C₆H₄—CH₂ |
| 379 | 3-CN—C₆H₄—CH₂ |
| 380 | 4-CN—C₆H₄—CH₂ |
| 381 | 2-NO₂—C₆H₄—CH₂ |
| 382 | 3-NO₂—C₆H₄—CH₂ |
| 383 | 4-NO₂—C₆H₄—CH₂ |
| 384 | 2-CH₃—C₆H₄—CH₂ |
| 385 | 3-CH₃—C₆H₄—CH₂ |
| 386 | 4-CH₃—C₆H₄—CH₂ |
| 387 | 2,3-(CH₃)₂—C₆H₃—CH₂ |
| 388 | 2,4-(CH₃)₂—C₆H₃—CH₂ |
| 389 | 2,5-(CH₃)₂—C₆H₃—CH₂ |
| 390 | 2,6-(CH₃)₂—C₆H₃—CH₂ |
| 391 | 3,4-(CH₃)₂—C₆H₃—CH₂ |
| 392 | 3,5-(CH₃)₂—C₆H₃—CH₂ |
| 393 | 2-CH₂CH₃—C₆H₄—CH₂ |
| 394 | 3-CH₂CH₃—C₆H₄—CH₂ |
| 395 | 4-CH₂CH₃—C₆H₄—CH₂ |
| 396 | 2-CH(CH₃)₂—C₆H₄—CH₂ |
| 397 | 3-CH(CH₃)₂—C₆H₄—CH₂ |
| 398 | 4-CH(CH₃)₂—C₆H₄—CH₂ |
| 399 | 3-C(CH₃)₃—C₆H₄—CH₂ |
| 400 | 4-C(CH₃)₃—C₆H₄—CH₂ |
| 401 | 2-C₆H₅—C₆H₄—CH₂ |
| 402 | 3-C₆H₅—C₆H₄—CH₂ |
| 403 | 4-C₆H₅—C₆H₄—CH₂ |
| 404 | 2-OCH₃—C₆H₄—CH₂ |
| 405 | 3-OCH₃—C₆H₄—CH₂ |
| 406 | 4-OCH₃—C₆H₄—CH₂ |
| 407 | 2,3-(OCH₃)₂—C₆H₃—CH₂ |
| 408 | 2,4-(OCH₃)₂—C₆H₃—CH₂ |
| 409 | 2,5-(OCH₃)₂—C₆H₃—CH₂ |
| 410 | 2,6-(OCH₃)₂—C₆H₃—CH₂ |
| 411 | 3,4-(OCH₃)₂—C₆H₃—CH₂ |
| 412 | 3,5-(OCH₃)₂—C₆H₃—CH₂ |
| 413 | 3,4,5-(OCH₃)₃—C₆H₂—CH₂ |
| 414 | 2-OCH₂CH₃—C₆H₄—CH₂ |
| 415 | 3-OCH₂CH₃—C₆H₄—CH₂ |
| 416 | 4-OCH₂CH₃—C₆H₄—CH₂ |
| 417 | 2-O(CH₂)₂CH₃—C₆H₄—CH₂ |
| 418 | 3-O(CH₂)₂CH₃—C₆H₄—CH₂ |
| 419 | 4-O(CH₂)₂CH₃—C₆H₄—CH₂ |
| 420 | 2-OCH(CH₃)₂—C₆H₄—CH₂ |
| 421 | 3-OCH(CH₃)₂—C₆H₄—CH₂ |
| 422 | 4-OCH(CH₃)₂—C₆H₄—CH₂ |
| 423 | 3-OC(CH₃)₃—C₆H₄—CH₂ |
| 424 | 4-OC(CH₃)₃—C₆H₄—CH₂ |
| 425 | 2-OCH₂CH=CH₂—C₆H₄—CH₂ |
| 426 | 3-OCH₂CH=CH₂—C₆H₄—CH₂ |
| 427 | 4-OCH₂CH=CH₂—C₆H₄—CH₂ |
| 428 | 2-CF₃—C₆H₄—CH₂ |
| 429 | 3-CF₃—C₆H₄—CH₂ |
| 430 | 4-CF₃—C₆H₄—CH₂ |
| 431 | 2-CO₂CH₃—C₆H₄—CH₂ |
| 432 | 3-CO₂CH₃—C₆H₄—CH₂ |
| 433 | 4-CO₂CH₃—C₆H₄—CH₂ |
| 434 | 2-CO₂CH₂CH₃—C₆H₄—CH₂ |
| 435 | 3-CO₂CH₂CH₃—C₆H₄—CH₂ |
| 436 | 4-CO₂CH₂CH₃—C₆H₄—CH₂ |
| 437 | 2-CONH₂—C₆H₄—CH₂ |
| 438 | 3-CONH₂—C₆H₄—CH₂ |
| 439 | 4-CONH₂—C₆H₄—CH₂ |
| 440 | 2-CON(CH₃)₂—C₆H₄—CH₂ |
| 441 | 3-CON(CH₃)₂—C₆H₄—CH₂ |
| 442 | 4-CON(CH₃)₂—C₆H₄—CH₂ |
| 443 | 2-CONHCH₃—C₆H₄—CH₂ |
| 444 | 3-CONHCH₃—C₆H₄—CH₂ |
| 445 | 4-CONHCH₃—C₆H₄—CH₂ |
| 446 | 2-NH₂—C₆H₄—CH₂ |
| 447 | 3-NH₂—C₆H₄—CH₂ |
| 448 | 4-NH₂—C₆H₄—CH₂ |
| 449 | 2-N(CH₃)₂—C₆H₄—CH₂ |
| 450 | 3-N(CH₃)₂—C₆H₄—CH₂ |
| 451 | 4-N(CH₃)₂—C₆H₄—CH₂ |
| 452 | 2-NHCH₃—C₆H₄—CH₂ |
| 453 | 3-NHCH₃—C₆H₄—CH₂ |
| 454 | 4-NHCH₃—C₆H₄—CH₂ |
| 455 | 2-CSNH₂—C₆H₄—CH₂ |
| 456 | 3-CSNH₂—C₆H₄—CH₂ |
| 457 | 4-CSNH₂—C₆H₄—CH₂ |
| 458 | 2-SCH₃—C₆H₄—CH₂ |
| 459 | 3-SCH₃—C₆H₄—CH₂ |
| 460 | 4-SCH₃—C₆H₄—CH₂ |
| 461 | 2-SOCH₃—C₆H₄—CH₂ |
| 462 | 3-SOCH₃—C₆H₄—CH₂ |
| 463 | 4-SOCH₃—C₆H₄—CH₂ |
| 464 | 2-SO₂CH₃—C₆H₄—CH₂ |
| 465 | 3-SO₂CH₃—C₆H₄—CH₂ |
| 466 | 4-SO₂CH₃—C₆H₄—CH₂ |
| 467 | 2-OCF₃—C₆H₄—CH₂ |
| 468 | 3-OCF₃—C₆H₄—CH₂ |
| 469 | 4-OCF₃—C₆H₄—CH₂ |
| 470 | 2-OCHF₂—C₆H₄—CH₂ |
| 471 | 3-OCHF₂—C₆H₄—CH₂ |
| 472 | 4-OCHF₂—C₆H₄—CH₂ |
| 473 | 3-CF₃, 4-OCF₃—C₆H₃—CH₂ |
| 474 | 2-CH₂CH₂F—C₆H₄—CH₂ |
| 475 | 3-CH₂CH₂F—C₆H₄—CH₂ |
| 476 | 4-CH₂CH₂F—C₆H₄—CH₂ |
| 477 | 2-CH₂CF₃—C₆H₄—CH₂ |
| 478 | 3-CH₂CF₃—C₆H₄—CH₂ |
| 479 | 4-CH₂CF₃—C₆H₄—CH₂ |
| 480 | 2-CF₂CHF₂—C₆H₄—CH₂ |
| 481 | 3-CF₂CHF₂—C₆H₄—CH₂ |
| 482 | 4-CF₂CHF₂—C₆H₄—CH₂ |
| 483 | 2-CHF₂—C₆H₄—CH₂ |
| 484 | 3-CHF₂—C₆H₄—CH₂ |
| 485 | 4-CHF₂—C₆H₄—CH₂ |
| 486 | naphthalin-1-yl-CH₂ |
| 487 | naphthalin-2-yl-CH₂ |
| 488 | pyridin-2-yl-CH₂ |
| 489 | pyridin-3-yl-CH₂ |
| 490 | pyridin-4-yl-CH₂ |
| 491 | 5-CH₃-pyridin-2-yl-CH₂ |
| 492 | 6-CH₃-pyridin-2-yl-CH₂ |
| 493 | 5-CH₃-pyridin-3-yl-CH₂ |
| 494 | 6-CH₃-pyridin-3-yl-CH₂ |
| 495 | 5-OCH₃-pyridin-2-yl-CH₂ |
| 496 | 6-OCH₃-pyridin-2-yl-CH₂ |
| 497 | 5-OCH₃-pyridin-3-yl-CH₂ |
| 498 | 6-OCH₃-pyridin-3-yl-CH₂ |

TABLE A-continued

| No. | R⁶ |
|---|---|
| 499 | 4-Cl-pyridin-2-yl-CH$_2$ |
| 500 | 5-Cl-pyridin-2-yl-CH$_2$ |
| 501 | 6-Cl-pyridin-2-yl-CH$_2$ |
| 502 | 2-Cl-pyridin-3-yl-CH$_2$ |
| 503 | 5-Cl-pyridin-3-yl-CH$_2$ |
| 504 | 6-Cl-pyridin-3-yl-CH$_2$ |
| 505 | 2-Cl-pyridin-4-yl-CH$_2$ |
| 506 | 3,5-Cl-pyridin-2-yl-CH$_2$ |
| 507 | pyrimidin-2-yl-CH$_2$ |
| 508 | 4-Cl-pyrimidin-2-yl-CH$_2$ |
| 509 | 5-Cl-pyrimidin-2-yl-CH$_2$ |
| 510 | 4-CH$_3$-pyrimidin-2-yl-CH$_2$ |
| 511 | 5-CH$_3$-pyrimidin-2-yl-CH$_2$ |
| 512 | 4-OCH$_3$-pyrimidin-2-yl-CH$_2$ |
| 513 | 5-OCH$_3$-pyrimidin-2-yl-CH$_2$ |
| 514 | 4-OCH$_2$CH$_3$-pyrimidin-2-yl-CH$_2$ |
| 515 | 5-OCH$_2$CH$_3$-pyrimidin-2-yl-CH$_2$ |
| 516 | pyrimidin-4-yl-CH$_2$ |
| 517 | 2-Cl-pyrimidin-4-yl-CH$_2$ |
| 518 | 6-Cl-pyrimidin-4-yl-CH$_2$ |
| 519 | 2,6-Cl$_2$-pyrimidin-4-yl-CH$_2$ |
| 520 | 2-CH$_3$-pyrimidin-4-yl-CH$_2$ |
| 521 | 6-CH$_3$-pyrimidin-4-yl-CH$_2$ |
| 522 | 2-OCH$_3$-pyrimidin-4-yl-CH$_2$ |
| 523 | 6-OCH$_3$-pyrimidin-4-yl-CH$_2$ |
| 524 | 2-OCH$_2$CH$_3$-pyrimidin-4-yl-CH$_2$ |
| 525 | 6-OCH$_2$CH$_3$-pyrimidin-4-yl-CH$_2$ |
| 526 | pyrimidin-5-yl-CH$_2$ |
| 527 | 2-Cl-pyrimidin-5-yl-CH$_2$ |
| 528 | 2-CH$_3$-pyrimidin-5-yl-CH$_2$ |
| 529 | 2-OCH$_3$-pyrimidin-5-yl-CH$_2$ |
| 530 | 2-OCH$_2$CH$_3$-pyrimidin-5-yl-CH$_2$ |
| 531 | furan-2-yl-CH$_2$ |
| 532 | 4-Br-furan-2-yl-CH$_2$ |
| 533 | 4-Cl-furan-2-yl-CH$_2$ |
| 534 | 4-CN-furan-2-yl-CH$_2$ |
| 535 | 4-CH$_3$-furan-2-yl-CH$_2$ |
| 536 | 5-Br-furan-2-yl-CH$_2$ |
| 537 | 5-Cl-furan-2-yl-CH$_2$ |
| 538 | 5-CN-furan-2-yl-CH$_2$ |
| 539 | 5-CH$_3$-furan-2-yl-CH$_2$ |
| 540 | furan-3-yl-CH$_2$ |
| 541 | 5-Br-furan-3-yl-CH$_2$ |
| 542 | 5-Cl-furan-3-yl-CH$_2$ |
| 543 | 5-CN-furan-3-yl-CH$_2$ |
| 544 | 5-CH$_3$-furan-3-yl-CH$_2$ |
| 545 | thien-2-yl-CH$_2$ |
| 546 | 4-Br-thien-2-yl-CH$_2$ |
| 547 | 4-Cl-thien-2-yl-CH$_2$ |
| 548 | 4-CN-thien-2-yl-CH$_2$ |
| 549 | 4-CH$_3$-thien-2-yl-CH$_2$ |
| 550 | 5-Br-thien-2-yl-CH$_2$ |
| 551 | 5-Cl-thien-2-yl-CH$_2$ |
| 552 | 5-CN-thien-2-yl-CH$_2$ |
| 553 | 5-CH$_3$-thien-2-yl-CH$_2$ |
| 554 | thien-3-yl-CH$_2$ |
| 555 | 5-Br-thien-3-yl-CH$_2$ |
| 556 | 5-Cl-thien-3-yl-CH$_2$ |
| 557 | 5-CN-thien-3-yl-CH$_2$ |
| 558 | 5-CH$_3$-thien-3-yl-CH$_2$ |
| 559 | oxazol-2-yl-CH$_2$ |
| 560 | 4-Br-oxazol-2-yl-CH$_2$ |
| 561 | 4-Cl-oxazol-2-yl-CH$_2$ |
| 562 | 4-CN-oxazol-2-yl-CH$_2$ |
| 563 | 4-CH$_3$-oxazol-2-yl-CH$_2$ |
| 564 | 5-Br-oxazol-2-yl-CH$_2$ |
| 565 | 5-Cl-oxazol-2-yl-CH$_2$ |
| 566 | 5-CN-oxazol-2-yl-CH$_2$ |
| 567 | 5-CH$_3$-oxazol-2-yl-CH$_2$ |
| 568 | oxazol-4-yl-CH$_2$ |
| 569 | 2-Br-oxazol-4-yl-CH$_2$ |
| 570 | 2-Cl-oxazol-4-yl-CH$_2$ |
| 571 | 2-CN-oxazol-4-yl-CH$_2$ |
| 572 | 2-CH$_3$-oxazol-4-yl-CH$_2$ |
| 573 | 2-C$_6$H$_5$-oxazol-4-yl-CH$_2$ |
| 574 | 5-Br-oxazol-4-yl-CH$_2$ |
| 575 | 5-Cl-oxazol-4-yl-CH$_2$ |
| 576 | 5-CN-oxazol-4-yl-CH$_2$ |
| 577 | 5-CH$_3$-oxazol-4-yl-CH$_2$ |
| 578 | oxazol-5-yl-CH$_2$ |
| 579 | 4-Br-oxazol-5-yl-CH$_2$ |
| 580 | 4-Cl-oxazol-5-yl-CH$_2$ |
| 581 | 4-CN-oxazol-5-yl-CH$_2$ |
| 582 | 4-CH$_3$-oxazol-5-yl-CH$_2$ |
| 583 | 2-Br-oxazol-5-yl-CH$_2$ |
| 584 | 2-Cl-oxazol-5-yl-CH$_2$ |
| 585 | 2-CN-oxazol-5-yl-CH$_2$ |
| 586 | 2-CH$_3$-oxazol-5-yl-CH$_2$ |
| 587 | isoxazol-3-yl-CH$_2$ |
| 588 | 4-Br-isoxazol-3-yl-CH$_2$ |
| 589 | 4-Cl-isoxazol-3-yl-CH$_2$ |
| 590 | 4-CN-isoxazol-3-yl-CH$_2$ |
| 591 | 4-CH$_3$-isoxazol-3-yl-CH$_2$ |
| 592 | 5-Br-isoxazol-3-yl-CH$_2$ |
| 593 | 5-Cl-isoxazol-3-yl-CH$_2$ |
| 594 | 5-CN-isoxazol-3-yl-CH$_2$ |
| 595 | 5-CH$_3$-isoxazol-3-yl-CH$_2$ |
| 596 | isoxazol-4-yl-CH$_2$ |
| 597 | 3-Br-isoxazol-4-yl-CH$_2$ |
| 598 | 3-Cl-isoxazol-4-yl-CH$_2$ |
| 599 | 3-CN-isoxazol-4-yl-CH$_2$ |
| 600 | 3-CH$_3$-isoxazol-4-yl-CH$_2$ |
| 601 | 5-Br-isoxazol-4-yl-CH$_2$ |
| 602 | 5-Cl-isoxazol-4-yl-CH$_2$ |
| 603 | 5-CN-isoxazol-4-yl-CH$_2$ |
| 604 | 5-CH$_3$-isoxazol-4-yl-CH$_2$ |
| 605 | 3,5-(CH$_3$)$_2$-isoxazol-4-yl-CH$_2$ |
| 606 | isoxazol-5-yl-CH$_2$ |
| 607 | 3-Br-isoxazol-5-yl-CH$_2$ |
| 608 | 3-Cl-isoxazol-5-yl-CH$_2$ |
| 609 | 3-CN-isoxazol-5-yl-CH$_2$ |
| 610 | 3-CH$_3$-isoxazol-5-yl-CH$_2$ |
| 611 | 3-C$_6$H$_5$-isoxazol-5-yl-CH$_2$ |
| 612 | 4-Cl, 3-C$_6$H$_5$-isoxazol-5-yl-CH$_2$ |
| 613 | 4-Br, 3-C$_6$H$_5$-isoxazol-5-yl-CH$_2$ |
| 614 | 4-Br-isoxazol-5-yl-CH$_2$ |
| 615 | 4-Cl-isoxazol-5-yl-CH$_2$ |
| 616 | 4-CN-isoxazol-5-yl-CH$_2$ |
| 617 | 4-CH$_3$-isoxazol-5-yl-CH$_2$ |
| 618 | thiazol-2-yl-CH$_2$ |
| 619 | 4-Br-thiazol-2-yl-CH$_2$ |
| 620 | 4-Cl-thiazol-2-yl-CH$_2$ |
| 621 | 4-CN-thiazol-2-yl-CH$_2$ |
| 622 | 4-CH$_3$-thiazol-2-yl-CH$_2$ |
| 623 | 5-Br-thiazol-2-yl-CH$_2$ |
| 624 | 5-Cl-thiazol-2-yl-CH$_2$ |
| 625 | 5-CN-thiazol-2-yl-CH$_2$ |
| 626 | 5-CH$_3$-thiazol-2-yl-CH$_2$ |
| 627 | thiazol-4-yl-CH$_2$ |
| 628 | 2-Br-thiazol-4-yl-CH$_2$ |
| 629 | 2-Cl-thiazol-4-yl-CH$_2$ |
| 630 | 2-CN-thiazol-4-yl-CH$_2$ |
| 631 | 2-CH$_3$-thiazol-4-yl-CH$_2$ |
| 632 | 5-Br-thiazol-4-yl-CH$_2$ |
| 633 | 5-Cl-thiazol-4-yl-CH$_2$ |
| 634 | 5-CN-thiazol-4-yl-CH$_2$ |
| 635 | 5-CH$_3$-thiazol-4-yl-CH$_2$ |
| 636 | thiazol-5-yl-CH$_2$ |
| 637 | 4-Br-thiazol-5-yl-CH$_2$ |
| 638 | 4-Cl-thiazol-5-yl-CH$_2$ |
| 639 | 4-CN-thiazol-5-yl-CH$_2$ |
| 640 | 4-CH$_3$-thiazol-5-yl-CH$_2$ |
| 641 | 2-Br-thiazol-5-yl-CH$_2$ |
| 642 | 2-Cl-thiazol-5-yl-CH$_2$ |
| 643 | 2-CN-thiazol-5-yl-CH$_2$ |
| 644 | 2-CH$_3$-thiazol-5-yl-CH$_2$ |
| 645 | isothiazol-3-yl-CH$_2$ |
| 646 | 4-Br-isothiazol-3-yl-CH$_2$ |
| 647 | 4-Cl-isothiazol-3-yl-CH$_2$ |
| 648 | 4-CN-isothiazol-3-yl-CH$_2$ |
| 649 | 4-CH$_3$-isothiazol-3-yl-CH$_2$ |
| 650 | 5-Br-isothiazol-3-yl-CH$_2$ |
| 651 | 5-Cl-isothiazol-3-yl-CH$_2$ |
| 652 | 5-CN-isothiazol-3-yl-CH$_2$ |

TABLE A-continued

| No. | R⁶ |
|---|---|
| 653 | 5-CH$_3$-isothiazol-3-yl-CH$_2$ |
| 654 | isothiazol-4-yl-CH$_2$ |
| 655 | 3-Br-isothiazol-4-yl-CH$_2$ |
| 656 | 3-Cl-isothiazol-4-yl-CH$_2$ |
| 657 | 3-CN-isothiazol-4-yl-CH$_2$ |
| 658 | 3-CH$_3$-isothiazol-4-yl-CH$_2$ |
| 659 | 5-Br-isothiazol-4-yl-CH$_2$ |
| 660 | 5-Cl-isothiazol-4-yl-CH$_2$ |
| 661 | 5-CN-isothiazol-4-yl-CH$_2$ |
| 662 | 5-CH$_3$-isothiazol-4-yl-CH$_2$ |
| 663 | 3,5-(CH$_3$)$_2$-isothiazol-4-yl-CH$_2$ |
| 664 | isothiazol-5-yl-CH$_2$ |
| 665 | 3-Br-isothiazol-5-yl-CH$_2$ |
| 666 | 3-Cl-isothiazol-5-yl-CH$_2$ |
| 667 | 3-CN-isothiazol-5-yl-CH$_2$ |
| 668 | 3-CH$_3$-isothiazol-5-yl-CH$_2$ |
| 669 | 4-Br-isothiazol-5-yl-CH$_2$ |
| 670 | 4-Cl-isothiazol-5-yl-CH$_2$ |
| 671 | 4-CN-isothiazol-5-yl-CH$_2$ |
| 672 | 4-CH$_3$-isothiazol-5-yl-CH$_2$ |
| 673 | imidazol-2-yl-CH$_2$ |
| 674 | 1-Cl-imidazol-2-yl-CH$_2$ |
| 675 | 1-Br-imidazol-2-yl-CH$_2$ |
| 676 | 1-CN-imidazol-2-yl-CH$_2$ |
| 677 | 1-CH$_3$-imidazol-2-yl-CH$_2$ |
| 678 | 4-Cl-imidazol-2-yl-CH$_2$ |
| 679 | 4-Br-imidazol-2-yl-CH$_2$ |
| 680 | 4-CN-imidazol-2-yl-CH$_2$ |
| 681 | 4-CH$_3$-imidazol-2-yl-CH$_2$ |
| 682 | 1-CH$_3$, 5-Cl-imidazol-2-yl-CH$_2$ |
| 683 | 1,4-(CH$_3$)$_2$-imidazol-2-yl-CH$_2$ |
| 684 | 1,5-(CH$_3$)$_2$-imidazol-2-yl-CH$_2$ |
| 685 | imidazol-4-yl-CH$_2$ |
| 686 | 2-Cl-imidazol-4-yl-CH$_2$ |
| 687 | 2-Br-imidazol-4-yl-CH$_2$ |
| 688 | 2-CN-imidazol-4-yl-CH$_2$ |
| 689 | 1-CH$_3$-imidazol-4-yl-CH$_2$ |
| 690 | 2-CH$_3$-imidazol-4-yl-CH$_2$ |
| 691 | 5-Cl-imidazol-4-yl-CH$_2$ |
| 692 | 5-Br-imidazol-4-yl-CH$_2$ |
| 693 | 5-CN-imidazol-4-yl-CH$_2$ |
| 694 | 5-CH$_3$-imidazol-4-yl-CH$_2$ |
| 695 | 1-CH$_3$,5-Cl-imidazol-4-yl-CH$_2$ |
| 696 | 1,2-(CH$_3$)$_2$-imidazol-4-yl-CH$_2$ |
| 697 | 1,5-(CH$_3$)$_2$-imidazol-4-yl-CH$_2$ |
| 698 | pyrazol-3-yl-CH$_2$ |
| 699 | 5-Br-pyrazol-3-yl-CH$_2$ |
| 700 | 5-Cl-pyrazol-3-yl-CH$_2$ |
| 701 | 5-CN-pyrazol-3-yl-CH$_2$ |
| 702 | 5-CH$_3$-pyrazol-3-yl-CH$_2$ |
| 703 | 1-C$_6$H$_5$-pyrazol-3-yl-CH$_2$ |
| 704 | 4-Br-pyrazol-3-yl-CH$_2$ |
| 705 | 4-Cl-pyrazol-3-yl-CH$_2$ |
| 706 | 4-CN-pyrazol-3-yl-CH$_2$ |
| 707 | 4-CH$_3$-pyrazol-3-yl-CH$_2$ |
| 708 | 1-CH$_3$-pyrazol-3-yl-CH$_2$ |
| 709 | 1,4-(CH$_3$)$_2$-pyrazol-3-yl-CH$_2$ |
| 710 | 1,5-(CH$_3$)$_2$-pyrazol-3-yl-CH$_2$ |
| 711 | 1-CH$_3$, 4-Cl-pyrazol-3-yl-CH$_2$ |
| 712 | 1-CH$_3$, 5-Cl-pyrazol-3-yl-CH$_2$ |
| 713 | pyrazol-4-yl-CH$_2$ |
| 714 | 3-Br-pyrazol-4-yl-CH$_2$ |
| 715 | 3-Cl-pyrazol-4-yl-CH$_2$ |
| 716 | 3-CN-pyrazol-4-yl-CH$_2$ |
| 717 | 3-CH$_3$-pyrazol-4-yl-CH$_2$ |
| 718 | 1-CH$_3$-pyrazol-4-yl-CH$_2$ |
| 719 | 1,5-(CH$_3$)$_2$-pyrazol-4-yl-CH$_2$ |
| 720 | 1,3-(CH$_3$)$_2$-pyrazol-4-yl-CH$_2$ |
| 721 | 1-CH$_3$, 3-Cl-pyrazol-4-yl-CH$_2$ |
| 722 | 1-CH$_3$, 5-Cl-pyrazol-4-yl-CH$_2$ |
| 723 | pyrazol-5-yl-CH$_2$ |
| 724 | 3-Br-pyrazol-5-yl-CH$_2$ |
| 725 | 3-Cl-pyrazol-5-yl-CH$_2$ |
| 726 | 3-CN-pyrazol-5-yl-CH$_2$ |
| 727 | 3-CH$_3$-pyrazol-5-yl-CH$_2$ |
| 728 | 1-CH$_3$-pyrazol-5-yl-CH$_2$ |
| 729 | 4-Br-pyrazol-5-yl-CH$_2$ |
| 730 | 4-Cl-pyrazol-5-yl-CH$_2$ |
| 731 | 4-CN-pyrazol-5-yl-CH$_2$ |
| 732 | 4-CH$_3$-pyrazol-5-yl-CH$_2$ |
| 733 | 1,3-(CH$_3$)$_2$-pyrazol-5-yl-CH$_2$ |
| 734 | 1,4-(CH$_3$)$_2$-pyrazol-5-yl-CH$_2$ |
| 735 | 1-CH$_3$,3-Cl-pyrazol-5-yl-CH$_2$ |
| 736 | 1-CH$_3$,4-Cl-pyrazol-5-yl-CH$_2$ |
| 737 | 1,3,4-oxadiazol-5-yl-CH$_2$ |
| 738 | 2-CH$_3$-1,3,4-oxadiazol-5-yl-CH$_2$ |
| 739 | 2-CF$_3$-1,3,4-oxadiazol-5-yl-CH$_2$ |
| 740 | 2-OCH$_3$-1,3,4-oxadiazol-5-yl-CH$_2$ |
| 741 | 2-Cl-1,3,4-oxadiazol-5-yl-CH$_2$ |
| 742 | 2-CH(CH$_3$)$_2$-1,3,4-oxadiazol-5-yl-CH$_2$ |
| 743 | 1,3,4-oxadiazol-2-yl-CH$_2$ |
| 744 | 5-CH$_3$-1,3,4-oxadiazol-2-yl-CH$_2$ |
| 745 | 5-CF$_3$-1,3,4-oxadiazol-2-yl-CH$_2$ |
| 746 | 5-OCH$_3$-1,3,4-oxadiazol-2-yl-CH$_2$ |
| 747 | 5-Cl-1,3,4-oxadiazol-2-yl-CH$_2$ |
| 748 | 5-CH(CH$_3$)$_2$-1,3,4-oxadiazol-2-yl-CH$_2$ |
| 749 | 5-C$_6$H$_5$-1,3,4-oxadiazol-2-yl-CH$_2$ |
| 750 | 1,2,4-oxadiazol-3-yl-CH$_2$ |
| 751 | 5-CH$_3$-1,2,4-oxadiazol-3-yl-CH$_2$ |
| 752 | 5-CF$_3$-1,2,4-oxadiazol-3-yl-CH$_2$ |
| 753 | 5-OCH$_3$-1,2,4-oxadiazol-3-yl-CH$_2$ |
| 754 | 5-Cl-1,2,4-oxadiazol-3-yl-CH$_2$ |
| 755 | 5-CH(CH$_3$)$_2$-1,2,4-oxadiazol-3-yl-CH$_2$ |
| 756 | 1,2,4-triazol-3-yl-CH$_2$ |
| 757 | 1-CH$_3$-1,2,4-triazol-3-yl-CH$_2$ |
| 758 | 5-CH$_3$-1,2,4-triazol-3-yl-CH$_2$ |
| 759 | 5-CF$_3$-1,2,4-triazol-3-yl-CH$_2$ |
| 760 | 5-OCH$_3$-1,2,4-triazol-3-yl-CH$_2$ |
| 761 | 5-Cl-1,2,4-triazol-3-yl-CH$_2$ |
| 762 | 5-CH(CH$_3$)$_2$-1,2,4-triazol-3-yl-CH$_2$ |
| 763 | 1-C$_6$H$_5$-1,2,4-triazol-3-yl-CH$_2$ |
| 764 | 1,3,4-thiadiazol-5-yl-CH$_2$ |
| 765 | 2-CH$_3$-1,3,4-thiadiazol-5-yl-CH$_2$ |
| 766 | 2-CF$_3$-1,3,4-thiadiazol-5-yl-CH$_2$ |
| 767 | 2-OCH$_3$-1,3,4-thiadiazol-5-yl-CH$_2$ |
| 768 | 2-CH$_2$OCH$_3$-1,3,4-thiadiazol-5-yl-CH$_2$ |
| 769 | 2-Cl-1,3,4-thiadiazol-5-yl-CH$_2$ |
| 770 | 2-CH(CH$_3$)$_2$-1,3,4-thiadiazol-5-yl-CH$_2$ |
| 771 | 1,3,4-thiadiazol-2-yl-CH$_2$ |
| 772 | 5-CH$_3$-1,3,4-thiadiazol-2-yl-CH$_2$ |
| 773 | 5-CF$_3$-1,3,4-thiadiazol-2-yl-CH$_2$ |
| 774 | 5-OCH$_3$-1,3,4-thiadiazol-2-yl-CH$_2$ |
| 775 | 5-Cl-1,3,4-thiadiazol-2-yl-CH$_2$ |
| 776 | 5-CH(CH$_3$)$_2$-1,3,4-thiadiazol-2-yl-CH$_2$ |
| 777 | 5-C$_6$H$_5$-1,3,4-thiadiazol-2-yl-CH$_2$ |
| 778 | 1,2,4-thiadiazol-3-yl-CH$_2$ |
| 779 | 5-CH$_3$-1,2,4-thiadiazol-3-yl-CH$_2$ |
| 780 | 5-CF$_3$-1,2,4-thiadiazol-3-yl-CH$_2$ |
| 781 | 5-OCH$_3$-1,2,4-thiadiazol-3-yl-CH$_2$ |
| 782 | 5-Cl-1,2,4-thiadiazol-3-yl-CH$_2$ |
| 783 | 5-CH(CH$_3$)$_2$-1,2,4-thiadiazol-3-yl-CH$_2$ |
| 784 | pyrrol-2-yl-CH$_2$ |
| 785 | 4-Cl-pyrrol-2-yl-CH$_2$ |
| 786 | 4-Br-pyrrol-2-yl-CH$_2$ |
| 787 | 4-CH$_3$-pyrrol-2-yl-CH$_2$ |
| 788 | 4-C$_6$H$_5$-pyrrol-2-yl-CH$_2$ |
| 789 | benzimidazol-2-yl-CH$_2$ |
| 790 | quinolin-2-yl-CH$_2$ |
| 791 | oxiranyl-CH$_2$ |
| 792 | 2-CH$_3$-oxiran-2-yl-CH$_2$ |
| 793 | 2-CH$_3$-oxiran-3-yl-CH$_2$ |
| 794 | 2,2-(CH$_3$)$_2$-oxiran-3-yl-CH$_2$ |
| 795 | 2,3-(CH$_3$)$_2$-oxiran-3-yl-CH$_2$ |
| 796 | 2,3,3-(CH$_3$)$_3$-oxiran-2-yl-CH$_2$ |
| 797 | oxiranyl-CH(CH$_3$) |
| 798 | 2-CH$_3$-oxiran-2-yl-CH(CH$_3$) |
| 799 | 2-CH$_3$-oxiran-3-yl-CH(CH$_3$) |
| 800 | 2,2-(CH$_3$)$_2$-oxiran-3-yl-CH(CH$_3$) |
| 801 | 2,3-(CH$_3$)$_2$-oxiran-3-yl-CH(CH$_3$) |
| 802 | 2,3,3-(CH$_3$)$_3$-oxiran-2-yl-CH(CH$_3$) |
| 803 | 1,1-Cl$_2$-cyclopropan-2-yl-CH$_2$ |
| 804 | 2-CH$_3$,1,1-Cl$_2$-cyclopropan-2-yl-CH$_2$[sic] |
| 805 | 2-CH$_3$,1,1-Cl$_2$-cyclopropan-3-yl-CH$_2$[sic] |
| 806 | 2,2-(CH$_3$)$_2$,1,1-Cl$_2$-cyclopropan-3-yl-CH$_2$[sic] |

TABLE A-continued

| No. | R⁶ |
|---|---|
| 807 | 2,3-(CH$_3$)$_2$,1,1-Cl$_2$-cyclopropan-3-yl-CH$_2$[sic] |
| 808 | 2,3,3-(CH$_3$)$_3$,1,1-Cl$_2$-cyclopropan-2-yl-CH$_2$[sic] |
| 809 | 1,1-Cl$_2$-cyclopropan-2-yl-CH(CH$_3$) |
| 810 | 2-CH$_3$,1,1-Cl$_2$-cyclopropan-2-yl-CH(CH$_3$) [sic] |
| 811 | 2-CH$_3$,1,1-Cl$_2$-cyclopropan-3-yl-CH(CH$_3$) [sic] |
| 812 | 2,2-(CH$_3$)$_2$,1,1-Cl$_2$-cyclopropan-3-yl-CH(CH$_3$) [sic] |
| 813 | 2,3-(CH$_3$)$_2$,1,1-Cl$_2$-cyclopropan-3-yl-CH(CH$_3$) [sic] |
| 814 | 2,3,3-(CH$_3$)$_3$,1,1-Cl$_2$-cyclopropan-2-yl-CH(CH$_3$) [sic] |
| 815 | 1,1-Br$_2$-cyclopropan-2-yl-CH$_2$ |
| 816 | 2-CH$_3$,1,1-Br$_2$-cyclopropan-2-yl-CH$_2$ [sic] |
| 817 | 2-CH$_3$,1,1-Br$_2$-cyclopropan-3-yl-CH$_2$ [sic] |
| 818 | 2,2-(CH$_3$)$_2$,1,1-Br$_2$-cyclopropan-3-yl-CH$_2$ [sic] |
| 819 | 2,3-(CH$_3$)$_2$,1,1-Br$_2$-cyclopropan-3-yl-CH$_2$ [sic] |
| 820 | 2,3,3-(CH$_3$)$_3$,1,1-Br$_2$-cyclopropan-2-yl-CH$_2$ [sic] |
| 821 | 1,1-Br$_2$-cyclopropan-2-yl-CH(CH$_3$) |
| 822 | 2-CH$_3$,1,1-Br$_2$-cyclopropan-2-yl-CH(CH$_3$) [sic] |
| 823 | 2-CH$_3$,1,1-Br$_2$-cyclopropan-3-yl-CH(CH$_3$) [sic] |
| 824 | 2,2-(CH$_3$)$_2$,1,1-Br$_2$-cyclopropan-3-yl-CH(CH$_3$) [sic] |
| 825 | 2,3-(CH$_3$)$_2$,1,1-Br$_2$-cyclopropan-3-yl-CH(CH$_3$) [sic] |
| 826 | 2,3,3-(CH$_3$)$_3$,1,1-Br$_2$-cyclopropan-2-yl-CH(CH$_3$) [sic] |
| 827 | CH$_2$CH=CH$_2$ |
| 828 | CH$_2$CCl=CH$_2$ |
| 829 | CH$_2$CH=CHCl (E) |
| 830 | CH$_2$CH=CHCl (Z) |
| 831 | CH$_2$CCl=CHCl (E) |
| 832 | CH$_2$CCl=CHCl (Z) |
| 833 | CH$_2$CH=CCl$_2$ |
| 834 | CH$_2$CCl=CCl$_2$ |
| 835 | CH$_2$CBr=CH$_2$ |
| 836 | CH$_2$CH=CHBr (E) |
| 837 | CH$_2$CH=CHBr (Z) |
| 838 | CH$_2$CBr=CHBr (E) |
| 839 | CH$_2$CBr=CHBr (Z) |
| 840 | CH$_2$CH=CBr$_2$ |
| 841 | CH$_2$CBr=CBr$_2$ |
| 842 | CH$_2$C(CH$_3$)=CH$_2$ |
| 843 | CH$_2$CH=CHCH$_3$ (E) |
| 844 | CH$_2$CH=CHCH$_3$ (Z) |
| 845 | CH$_2$C(CH$_3$)=CHCH$_3$ (E) |
| 846 | CH$_2$C(CH$_3$)=CHCH$_3$ (Z) |
| 847 | CH$_2$CH=C(CH$_3$)$_2$ |
| 848 | CH$_2$CH$_2$CH=CH$_2$ |
| 849 | CH$_2$CCl=CHCH$_3$ (E) |
| 850 | CH$_2$CCl=CHCH$_3$ (Z) |
| 851 | CH$_2$CH=CClCH$_3$ (E) |
| 852 | CH$_2$CH=CClCH$_3$ (Z) |
| 853 | CH$_2$C(CH$_3$)=C(CH$_3$)$_2$ |
| 854 | CH$_2$CBr=CHCH$_3$ (E) |
| 855 | CH$_2$CBr=CHCH$_3$ (Z) |
| 856 | CH$_2$CH=CBrCH$_3$ (E) |
| 857 | CH$_2$CH=CBrCH$_3$ (Z) |
| 858 | CH$_2$CH=CHCH$_2$Cl (E) |
| 859 | CH$_2$CH=CHCH$_2$Cl (Z) |
| 860 | CH$_2$CH=CHCH$_2$CH$_3$ (E) |
| 861 | CH$_2$CH=CHCH$_2$CH$_3$ (Z) |
| 862 | CH$_2$CH=CHCH$_2$Br (E) |
| 863 | CH$_2$CH=CHCH$_2$Br (Z) |
| 864 | CH$_2$CCl=CClCH$_2$Cl (E) |
| 865 | CH$_2$CCl=CClCH$_2$Cl (Z) |
| 866 | CH$_2$CF=CH$_2$ |
| 867 | CH$_2$CH=CHF (E) |
| 868 | CH$_2$CH=CHF (Z) |
| 869 | CH$_2$CH=CF$_2$ |
| 870 | CH$_2$CF=CHF (E) |
| 871 | CH$_2$CF=CHF (Z) |
| 872 | CH(CH$_3$)CH=CH$_2$ |
| 873 | CH(CH$_3$)CCl=CH$_2$ |
| 874 | CH(CH$_3$)CH=CHCl (E) |
| 875 | CH(CH$_3$)CH=CHCl (Z) |
| 876 | CH(CH$_3$)CCl=CHCl (E) |
| 877 | CH(CH$_3$)CCl=CHCl (Z) |
| 878 | CH(CH$_3$)CH=CCl$_2$ |
| 879 | CH(CH$_3$)CCl=CCl$_2$ |
| 880 | CH(CH$_3$)CBr=CH$_2$ |
| 881 | CH(CH$_3$)CH=CHBr (E) |
| 882 | CH(CH$_3$)CH=CHBr (Z) |
| 883 | CH(CH$_3$)CBr=CHBr (E) |
| 884 | CH(CH$_3$)CBr=CHBr (Z) |
| 885 | CH(CH$_3$)CH=CBr$_2$ |
| 886 | CH(CH$_3$)CBr=CBr$_2$ |
| 887 | CH(CH$_3$)C(CH$_3$)=CH$_2$ |
| 888 | CH(CH$_3$)CH=CHCH$_3$ (E) |
| 889 | CH(CH$_3$)CH=CHCH$_3$ (Z) |
| 890 | CH(CH$_3$)C(CH$_3$)=CHCH$_3$ (E) |
| 891 | CH(CH$_3$)C(CH$_3$)=CHCH$_3$ (Z) |
| 892 | CH(CH$_3$)CH=C(CH$_3$)$_2$ |
| 893 | CH(CH$_3$)CCl=CHCH$_3$ (E) |
| 894 | CH(CH$_3$)CCl=CHCH$_3$ (Z) |
| 895 | CH(CH$_3$)CH=CClCH$_3$ (E) |
| 896 | CH(CH$_3$)CH=CClCH$_3$ (Z) |
| 897 | CH(CH$_3$)CBr=CHCH$_3$ (E) |
| 898 | CH(CH$_3$)CBr=CHCH$_3$ (Z) |
| 899 | CH(CH$_3$)CH=CBrCH$_3$ (E) |
| 900 | CH(CH$_3$)CH=CBrCH$_3$ (Z) |
| 901 | CH(CH$_3$)CH=CHCH$_2$Cl (E) |
| 902 | CH(CH$_3$)CH=CHCH$_2$Cl (Z) |
| 903 | CH(CH$_3$)CH=CHCH$_2$CH$_3$ (E) |
| 904 | CH(CH$_3$)CH=CHCH$_2$CH$_3$ (Z) |
| 905 | CH(CH$_3$)CH=CHCH$_2$Br (E) |
| 906 | CH(CH$_3$)CH=CHCH$_2$Br (Z) |
| 907 | CH(CH$_3$)CCl=CClCH$_2$Cl (E) |
| 908 | CH(CH$_3$)CCl=CClCH$_2$Cl (Z) |
| 909 | CH(CH$_3$)CF=CH$_2$ |
| 910 | CH(CH$_3$)CH=CHF (E) |
| 911 | CH(CH$_3$)CH=CHF (Z) |
| 912 | CH(CH$_3$)CH=CF$_2$ |
| 913 | CH(CH$_3$)CF=CHF (E) |
| 914 | CH(CH$_3$)CF=CHF (Z) |
| 915 | CH$_2$CHClCH=CH$_2$ |
| 916 | CH$_2$CH$_2$CH=C(CH$_3$)$_2$ |
| 917 | CH$_2$CH$_2$C(CH$_3$)=CHCH$_3$ (E) |
| 918 | CH$_2$CH$_2$C(CH$_3$)=CHCH$_3$ (Z) |
| 919 | CH$_2$C≡CH |
| 920 | CH$_2$C≡CCl |
| 921 | CH$_2$C≡CBr |
| 922 | CH$_2$C≡CI |
| 923 | CH$_2$C≡CCH$_3$ |
| 924 | CH$_2$C≡CCH$_2$CH$_3$ |
| 925 | CH$_2$C≡CCH$_2$OH |
| 926 | CH$_2$C≡CCH$_2$NH$_2$ |
| 927 | CH$_2$C≡CCH$_2$Cl |
| 928 | CH$_2$C≡CCH$_2$OCH$_3$ |
| 929 | CH$_2$C≡CCH$_2$OCH$_2$CH$_3$ |
| 930 | CH$_2$C≡CCH$_2$SCH$_3$ |
| 931 | CH$_2$C≡CCH$_2$N(CH$_3$)$_2$ |
| 932 | CH$_2$C≡CC$_6$H$_5$ |
| 933 | CH$_2$CH$_2$C≡CH |
| 934 | CH$_2$CH$_2$C≡CCl |
| 935 | CH$_2$CH$_2$C≡CBr |
| 936 | CH$_2$CH$_2$C≡CI |
| 937 | CH$_2$CH$_2$C≡CCH$_3$ |
| 938 | CH$_2$CH$_2$C≡CCH$_2$CH$_3$ |
| 939 | CH$_2$CH$_2$C≡CCH$_2$OH |
| 940 | CH$_2$CH$_2$C≡CCH$_2$NH$_2$ |
| 941 | CH$_2$CH$_2$C≡CCH$_2$Cl |
| 942 | CH$_2$CH$_2$C≡CCH$_2$OCH$_3$ |
| 943 | CH$_2$CH$_2$C≡CCH$_2$OCH$_2$CH$_3$ |
| 944 | CH$_2$CH$_2$C≡CCH$_2$SCH$_3$ |
| 945 | CH$_2$CH$_2$C≡CCH$_2$N(CH$_3$)$_2$ |
| 946 | CH$_2$CH$_2$C≡CC$_6$H$_5$ |
| 947 | CH$_2$CH$_2$CH$_2$C≡CH |
| 948 | CH$_2$CH$_2$CH$_2$C≡CCl |
| 949 | CH$_2$CH$_2$CH$_2$C≡CBr |
| 950 | CH$_2$CH$_2$CH$_2$C≡CI |
| 951 | CH$_2$CH$_2$CH$_2$C≡CCH$_3$ |
| 952 | CH$_2$CH$_2$CH$_2$C≡CCH$_2$CH$_3$ |
| 953 | CH$_2$CH$_2$CH$_2$C≡CCH$_2$OH |
| 954 | CH$_2$CH$_2$CH$_2$C≡CCH$_2$NH$_2$ |

TABLE A-continued

| No. | R$^6$ |
|---|---|
| 955 | CH$_2$CH$_2$CH$_2$C≡CCH$_2$Cl |
| 956 | CH$_2$CH$_2$CH$_2$C≡CCH$_2$OCH$_3$ |
| 957 | CH$_2$CH$_2$CH$_2$C≡CCH$_2$OCH$_2$CH$_3$ |
| 958 | CH$_2$CH$_2$CH$_2$C≡CCH$_2$SCH$_3$ |
| 959 | CH$_2$CH$_2$CH$_2$C≡CCH$_2$N(CH$_3$)$_2$ |
| 960 | CH$_2$CH$_2$CH$_2$C≡CC$_6$H$_5$ |
| 961 | CH(CH$_3$)C≡CH |
| 962 | CH(CH$_3$)C≡CCl |
| 963 | CH(CH$_3$)C≡CBr |
| 964 | CH(CH$_3$)C≡CI |
| 965 | CH(CH$_3$)C≡CCH$_3$ |
| 966 | CH(CH$_3$)C≡CCH$_2$CH$_3$ |
| 967 | CH(CH$_3$)C≡CCH$_2$OH |
| 968 | CH(CH$_3$)C≡CCH$_2$NH$_2$ |
| 969 | CH(CH$_3$)C≡CCH$_2$Cl |
| 970 | CH(CH$_3$)C≡CCH$_2$OCH$_3$ |
| 971 | CH(CH$_3$)C≡CCH$_2$OCH$_2$CH$_3$ |
| 972 | CH(CH$_3$)C≡CCH$_2$SCH$_3$ |
| 973 | CH(CH$_3$)C≡CCH$_2$N(CH$_3$)$_2$ |
| 974 | CH(CH$_3$)C≡CC$_6$H$_5$ |

Table 1 (compounds 1.1–1.974)
Compounds of the general formula I.1 where
R$^3$=methyl
R$^4$=CH$_3$
R$^5$=H
and the substituent R$^6$ for a compound corresponds to a line of Table A.

Table 2 (compounds 2.1–2.974)
Compounds of the general formula I.2 where
R$^3$=methyl
R$^4$=CH$_3$
R$^5$=H
and the substituent R$^6$ for a compound corresponds to a line of Table A.

Table 3 (compounds 3.1–3.974)
Compounds of the general formula I.3 where
R$^3$=methyl
R$^4$=CH$_3$
R$^5$=H
and the substituent R$^6$ for a compound corresponds to a line of Table A.

Table 4 (compounds 4.1–4.974)
Compounds of the general formula I.4 where
R$^3$=methyl
R$^4$=CH$_3$
R$^5$=H
and the substituent R$^6$ for a compound corresponds to a line of Table A.

Table 5 (compounds 5.1–5.974)
Compounds of the general formula I.1 where
R$^3$=methyl
R$^4$=CH$_3$
R$^5$=CH$_3$
and the substituent R$^6$ for a compound corresponds to a line of Table A.

Table 6 (compounds 6.1–6.974)
compounds of the general formula I.2 where
R$^3$=methyl
R$^4$=CH$_3$
R$^5$=CH$_3$
and the substituent R$^6$ for a compound corresponds to a line of Table A.

Table 7 (compounds 7.1–7.974)
Compounds of the general formula I.3 where
R$^3$=methyl
R$^4$=CH$_3$
R$^5$=CH$_3$
and the substituent R$^6$ for a compound corresponds to a line of Table A.

Table 8 (compounds 8.1–8.974)
Compounds of the general formula I.4 where
R$^3$=methyl
R$^4$=CH$_3$
R$^5$=CH$_3$
and the substituent R$^6$ for a compound corresponds to a line of Table A.

Table 9 (compounds 9.1–9.974)
Compounds of the general formula I.1 where
R$^3$=methyl
R$^4$=CH$_3$
R$^5$=C$_2$H$_5$
and the substituent R$^6$ for a compound corresponds to a line of Table A.

Table 10 (compounds 10.1–10.974)
Compounds of the general formula I.2 where
R$^3$=methyl
R$^4$=CH$_3$
R$^5$=C$_2$H$_5$
and the substituent R$^6$ for a compound corresponds to a line of Table A.

Table 11 (compounds 11.1–11.974)
Compounds of the general formula I.3 where
R$^3$=methyl
R$^4$=CH$_3$
R$^5$=C$_2$H$_5$
and the substituent R$^6$ for a compound corresponds to a line of Table A.

Table 12 (compounds 12.1–12.974)
Compounds of the general formula I.4 where
R$^3$=methyl
R$^4$=CH$_3$
R$^5$=C$_2$H$_5$
and the substituent R$^6$ for a compound corresponds to a line of Table A.

Table 13 (compounds 13.1–13.974)
Compounds of the general formula I.1 where
R$^3$=methyl
R$^4$=CH$_3$
R$^5$=n-C$_3$H$_7$
and the substituent R$^6$ for a compound corresponds to a line of Table A.

Table 14 (compounds 14.1–14.974)
Compounds of the general formula I.2 where
R$^3$=methyl
R$^4$=CH$_3$
R$^5$=n-C$_3$H$_7$
and the substituent R$^6$ for a compound corresponds to a line of Table A.

Table 15 (compounds 15.1–15.974)
Compounds of the general formula I.3 where
R$^3$=methyl
R$^4$=CH$_3$
R$^5$=n-C$_3$H$_7$
and the substituent R$^6$ for a compound corresponds to a line of Table A.

Table 16 (compounds 16.1–16.974)
Compounds of the general formula I.4 where
$R^3$=methyl
$R^4$=$CH_3$
$R^5$=n-$C_3H_7$
and the substituent $R^6$ for a compound corresponds to a line of Table A.

Table 17 (compounds 17.1–17.974)
Compounds of the general formula I.1 where
$R^3$=methyl
$R^4$=$CH_3$
$R^5$=i-$C_3H_7$
and the substituent $R^6$ for a compound corresponds to a line of Table A.

Table 18 (compounds 18.1–18.974)
Compounds of the general formula I.2 where
$R^3$=methyl
$R^4$=$CH_3$
$R^5$=i-$C_3H_7$
and the substituent $R^6$ for a compound corresponds to a line of Table A.

Table 19 (compounds 19.1–19.974)
Compounds of the general formula I.3 where
$R^3$=methyl
$R^4$=$CH_3$
$R^5$=i-$C_3H_7$
and the substituent $R^6$ for a compound corresponds to a line of Table A.

Table 20 (compounds 20.1–20.974)
Compounds of the general formula I.4 where
$R^3$=methyl
$R^4$=$CH_3$
$R^5$=i-$C_3H_7$
and the substituent $R^6$ for a compound corresponds to a line of Table A.

Table 21 (compounds 21.1–21.974)
Compounds of the general formula I.1 where
$R^3$=methyl
$R^4$=$CH_3$
$R^5$=cyclopropyl
and the substituent $R^6$ for a compound corresponds to a line of Table A.

Table 22 (compounds 22.1–22.974)
Compounds of the general formula I.2 where
$R^3$=methyl
$R^4$=$CH_3$
$R^5$=cyclopropyl
and the substituent $R^6$ for a compound corresponds to a line of Table A.

Table 23 (compounds 23.1–23.974)
Compounds of the general formula I.3 where
$R^3$=methyl
$R^4$=$CH_3$
$R^5$=cyclopropyl
and the substituent $R^6$ for a compound corresponds to a line of Table A.

Table 24 (compounds 24.1–24.974)
Compounds of the general formula I.4 where
$R^3$=methyl
$R^4$=$CH_3$
$R^5$=cyclopropyl
and the substituent $R^6$ for a compound corresponds to a line of Table A.

Table 25 (compounds 25.1–25.974)
Compounds of the general formula I.1 where
$R^3$=methyl
$R^4$=$CH_3$
$R^5$=CN
and the substituent $R^6$ for a compound corresponds to a line of Table A.

Table 26 (compounds 26.1–26.974)
Compounds of the general formula I.2 where
$R^3$=methyl
$R^4$=$CH_3$
$R^5$=CN
and the substituent $R^6$ for a compound corresponds to a line of Table A.

Table 27 (compounds 27.1–27.974)
Compounds of the general formula I.3 where
$R^3$=methyl
$R^4$=$CH_3$
$R^5$=CN
and the substituent $R^6$ for a compound corresponds to a line of Table A.

Table 28 (compounds 28.1–28.974)
Compounds of the general formula I.4 where
$R^3$=methyl
$R^4$=$CH_3$
$R^5$=CN
and the substituent $R^6$ for a compound corresponds to a line of Table A.

Table 29 (compounds 29.1–29.974)
Compounds of the general formula I.1 where
$R^3$=methyl
$R^4$=$CH_3$
$R^5$=$C_6H_5$
and the substituent $R^6$ for a compound corresponds to a line of Table A.

Table 30 (compounds 30.1–30.974)
Compounds of the general formula I.2 where
$R^3$=methyl
$R^4$=$CH_3$
$R^5$=$C_6H_5$
and the substituent $R^6$ for a compound corresponds to a line of Table A.

Table 31 (compounds 31.1–31.974)
Compounds of the general formula I.3 where
$R^3$=methyl
$R^4$=$CH_3$
$R^5$=$C_6H_5$
and the substituent $R^6$ for a compound corresponds to a line of Table A.

Table 32 (compounds 32.1–32.974)
Compounds of the general formula I.4 where
$R^3$=methyl
$R^4$=$CH_3$
$R^5$=$C_6H_5$
and the substituent $R^6$ for a compound corresponds to a line of Table A.

Table 33 (compounds 33.1–33.974)
Compounds of the general formula I.1 where
$R^3$=methyl
$R^4$=$CH_3$
$R^5$=2-F—$C_6H_4$
and the substituent $R^6$ for a compound corresponds to a line of Table A.

Table 34 (compounds 34.1–34.974)
Compounds of the general formula I.2 where
$R^3$=methyl
$R^4$=$CH_3$
$R^5$=2-F—$C_6H_4$
and the substituent $R^6$ for a compound corresponds to a line of Table A.

Table 35 (compounds 35.1–35.974)
Compounds of the general formula I.3 where
$R^3$=methyl
$R^4$=$CH_3$
$R^5$=2-F—$C_6H_4$
and the substituent $R^6$ for a compound corresponds to a line of Table A.

Table 36 (compounds 36.1–36.974)
Compounds of the general formula I.4 where
$R^3$=methyl
$R^4$=$CH_3$
$R^5$=2-F—$C_6H_4$
and the substituent $R^6$ for a compound corresponds to a line of Table A.

Table 37 (compounds 37.1–37.974)
Compounds of the general formula I.1 where
$R^3$=methyl
$R^4$=$CH_3$
$R^5$=3-F—$C_6H_4$
and the substituent $R^6$ for a compound corresponds to a line of Table A.

Table 38 (compounds 38.1–38.974)
Compounds of the general formula I.2 where
$R^3$=methyl
$R^4$=$CH_3$
$R^5$=3-F—$C_6H_4$
and the substituent $R^6$ for a compound corresponds to a line of Table A.

Table 39 (compounds 39.1–39.974)
Compounds of the general formula I.3 where
$R^3$=methyl
$R^4$=$CH_3$
$R^5$=3-F—$C_6H_4$
and the substituent $R^6$ for a compound corresponds to a line of Table A.

Table 40 (compounds 40.1–40.974)
Compounds of the general formula I.4 where
$R^3$=methyl
$R^4$=$CH_3$
$R^5$=3-F—$C_6H_4$
and the substituent $R^6$ for a compound corresponds to a line of Table A.

Table 41 (compounds 41.1–41.974)
Compounds of the general formula I.1 where
$R^3$=methyl
$R^4$=$CH_3$
$R^5$=4-F—$C_6H_4$
and the substituent $R^6$ for a compound corresponds to a line of Table A.

Table 42 (compounds 42.1–42.974)
Compounds of the general formula I.2 where
$R^3$=methyl
$R^4$=$CH_3$
$R^5$=4-F—$C_6H_4$
and the substituent $R^6$ for a compound corresponds to a line of Table A.

Table 43 (compounds 43.1–43.974)
Compounds of the general formula I.3 where
$R^3$=methyl
$R^4$=$CH_3$
$R^5$=4-F—$C_6H_4$
and the substituent $R^6$ for a compound corresponds to a line of Table A.

Table 44 (compounds 44.1–44.974)
Compounds of the general formula I.4 where
$R^3$=methyl
$R^4$=$CH_3$
$R^5$=4-F—$C_6H_4$
and the substituent $R^6$ for a compound corresponds to a line of Table A.

Table 45 (compounds 45.1–45.974)
Compounds of the general formula I.1 where
$R^3$=methyl
$R^4$=$CH_3$
$R^5$=2-Cl—$C_6H_4$
and the substituent $R^6$ for a compound corresponds to a line of Table A.

Table 46 (compounds 46.1–46.974)
Compounds of the general formula I.2 where
$R^3$=methyl
$R^4$=$CH_3$
$R^5$=2-Cl—$C_6H_4$
and the substituent $R^6$ for a compound corresponds to a line of Table A.

Table 47 (compounds 47.1–47.974)
Compounds of the general formula I.3 where
$R^3$=methyl
$R^4$=$CH_3$
$R^5$=2-Cl—$C_6H_4$
and the substituent $R^6$ for a compound corresponds to a line of Table A.

Table 48 (compounds 48.1–48.974)
Compounds of the general formula I.4 where
$R^3$=methyl
$R^4$=$CH_3$
$R^5$=2-Cl—$C_6H_4$
and the substituent $R^6$ for a compound corresponds to a line of Table A.

Table 49 (compounds 49.1–49.974)
Compounds of the general formula I.1 where
$R^3$=methyl
$R^4$=$CH_3$
$R^5$=3-Cl—$C_6H_4$
and the substituent $R^6$ for a compound corresponds to a line of Table A.

Table 50 (compounds 50.1–50.974)
Compounds of the general formula I.2 where
$R^3$=methyl
$R^4$=$CH_3$
$R^5$=3-Cl—$C_6H_4$
and the substituent $R^6$ for a compound corresponds to a line of Table A.

Table 51 (compounds 51.1–51.974)
Compounds of the general formula I.3 where
$R^3$=methyl
$R^4$=$CH_3$
$R^5$=3-Cl—$C_6H_4$
and the substituent $R^6$ for a compound corresponds to a line of Table A.

Table 52 (compounds 52.1–52.974)
Compounds of the general formula I.4 where
$R^3$=methyl
$R^4$=$CH_3$
$R^5$=3-Cl—$C_6H_4$
and the substituent $R^6$ for a compound corresponds to a line of Table A.

Table 53 (compounds 53.1–53.974)
Compounds of the general formula I.1 where
$R^3$=methyl
$R^4$=$CH_3$
$R^5$=4-Cl—$C_6H_4$
and the substituent $R^6$ for a compound corresponds to a line of Table A.

Table 54 (compounds 54.1–54.974)
Compounds of the general formula I.2 where
$R^3$=methyl
$R^4$=$CH_3$
$R^5$=4-Cl—$C_6H_4$
and the substituent $R^6$ for a compound corresponds to a line of Table A.

Table 55 (compounds 55.1–55.974)
Compounds of the general formula I.3 where
$R^3$=methyl
$R^4$=$CH_3$
$R^5$=4-Cl—$C_6H_4$
and the substituent $R^6$ for a compound corresponds to a line of Table A.

Table 56 (compounds 56.1–56.974)
Compounds of the general formula I.4 where
$R^3$=methyl
$R^4$=$CH_3$
$R^5$=4-Cl—$C_6H_4$
and the substituent $R^6$ for a compound corresponds to a line of Table A.

Table 57 (compounds 57.1–57.974)
Compounds of the general formula I.1 where
$R^3$=methyl
$R^4$=$CH_3$
$R^5$=2-Br—$C_6H_4$
and the substituent $R^6$ for a compound corresponds to a line of Table A.

Table 58 (compounds 58.1–58.974)
Compounds of the general formula I.2 where
$R^3$=methyl
$R^4$=$CH_3$
$R^5$=2-Br—$C_6H_4$
and the substituent $R^6$ for a compound corresponds to a line of Table A.

Table 59 (compounds 59.1–59.974)
Compounds of the general formula I.3 where
$R^3$=methyl
$R^4$=$CH_3$
$R^5$=2-Br—$C_6H_4$
and the substituent $R^6$ for a compound corresponds to a line of Table A.

Table 60 (compounds 60.1–60.974)
Compounds of the general formula I.4 where
$R^3$=methyl
$R^4$=$CH_3$
$R^5$=2-Br—$C_6H_4$
and the substituent $R^6$ for a compound corresponds to a line of Table A.

Table 61 (compounds 61.1–61.974)
Compounds of the general formula I.1 where
$R^3$=methyl
$R^4$=$CH_3$
$R^5$=3-Br—$C_6H_4$
and the substituent $R^6$ for a compound corresponds to a line of Table A.

Table 62 (compounds 62.1–62.974)
Compounds of the general formula I.2 where
$R^3$=methyl
$R^4$=$CH_3$
$R^5$=3-Br—$C_6H_4$
and the substituent $R^6$ for a compound corresponds to a line of Table A.

Table 63 (compounds 63.1–63.974)
Compounds of the general formula I.3 where
$R^3$=methyl
$R^4$=$CH_3$
$R^5$=3-Br—$C_6H_4$
and the substituent $R^6$ for a compound corresponds to a line of Table A.

Table 64 (compounds 64.1–64.974)
Compounds of the general formula I.4 where
$R^3$=methyl
$R^4$=$CH_3$
$R^5$=3-Br—$C_6H_4$
and the substituent $R^6$ for a compound corresponds to a line of Table A.

Table 65 (compounds 65.1–65.974)
Compounds of the general formula I.1 where
$R^3$=methyl
$R^4$=$CH_3$
$R^5$=4-Br—$C_6H_4$
and the substituent $R^6$ for a compound corresponds to a line of Table A.

Table 66 (compounds 66.1–66.974)
Compounds of the general formula I.2 where
$R^3$=methyl
$R^4$=$CH_3$
$R^5$=4-Br—$C_6H_4$
and the substituent $R^6$ for a compound corresponds to a line of Table A.

Table 67 (compounds 67.1–67.974)
Compounds of the general formula I.3 where
$R^3$=methyl
$R^4$=$CH_3$
$R^5$=4-Br—$C_6H_4$
and the substituent $R^6$ for a compound corresponds to a line of Table A.

Table 68 (compounds 68.1–68.974)
Compounds of the general formula I.4 where
$R^3$=methyl
$R^4$=$CH_3$
$R^5$=4-Br—$C_6H_4$
and the substituent $R^6$ for a compound corresponds to a line of Table A.

Table 69 (compounds 69.1–69.974)
Compounds of the general formula I.1 where
$R^3$=methyl
$R^4$=$CH_3$
$R^5$=2,3-$F_2$—$C_6H_3$
and the substituent $R^6$ for a compound corresponds to a line of Table A.

Table 70 (compounds 70.1–70.974)
Compounds of the general formula I.2 where
$R^3$=methyl
$R^4$=$CH_3$
$R^5$=2,3-$F_2$—$C_6H_3$
and the substituent $R^6$ for a compound corresponds to a line of Table A.

Table 71 (compounds 71.1–71.974)
Compounds of the general formula I.3 where
$R^3$=methyl
$R^4$=$CH_3$
$R^5$=2,3-$F_2$—$C_6H_3$
and the substituent $R^6$ for a compound corresponds to a line of Table A.

Table 72 (compounds 72.1–72.974)
Compounds of the general formula I.4 where
$R^3$=methyl
$R^4$=$CH_3$
$R^5$=2,3-$F_2$—$C_6H_3$
and the substituent $R^6$ for a compound corresponds to a line of Table A.

Table 73 (compounds 73.1–73.974)
Compounds of the general formula I.1 where
$R^3$=methyl
$R^4$=$CH_3$
$R^5$=2,4-$F_2$—$C_6H_3$
and the substituent $R^6$ for a compound corresponds to a line of Table A.

Table 74 (compounds 74.1–74.974)
Compounds of the general formula I.2 where
$R^3$=methyl
$R^4$=$CH_3$
$R^5$=2,4-$F_2$—$C_6H_3$
and the substituent $R^6$ for a compound corresponds to a line of Table A.

Table 75 (compounds 75.1–75.974)
Compounds of the general formula I.3 where
$R^3$=methyl
$R^4$=$CH_3$
$R^5$=2,4-$F_2$—$C_6H_3$
and the substituent $R^6$ for a compound corresponds to a line of Table A.

Table 76 (compounds 76.1–76.974)
Compounds of the general formula I.4 where
$R^3$=methyl
$R^4$=$CH_3$
$R^5$=2,4-$F_2$—$C_6H_3$
and the substituent $R^6$ for a compound corresponds to a line of Table A.

Table 77 (compounds 77.1–77.974)
Compounds of the general formula I.1 where
$R^3$=methyl
$R^4$=$CH_3$
$R^5$=2,5-$F_2$—$C_6H_3$
and the substituent $R^6$ for a compound corresponds to a line of Table A.

Table 78 (compounds 78.1–78.974)
Compounds of the general formula I.2 where
$R^3$=methyl
$R^4$=$CH_3$
$R^5$=2,5-$F_2$—$C_6H_3$
and the substituent $R^6$ for a compound corresponds to a line of Table A.

Table 79 (compounds 79.1–79.974)
Compounds of the general formula I.3 where
$R^3$=methyl
$R^4$=$CH_3$
$R^5$=2,5-$F_2$—$C_6H_3$
and the substituent $R^6$ for a compound corresponds to a line of Table A.

Table 80 (compounds 80.1–80.974)
Compounds of the general formula I.4 where
$R^3$=methyl
$R^4$=$CH_3$
$R^5$=2, 5-$F_2$—$C_6H_3$
and the substituent $R^6$ for a compound corresponds to a line of Table A.

Table 81 (compounds 81.1–81.974)
Compounds of the general formula I.1 where
$R^3$=methyl
$R^4$=$CH_3$
$R^5$=3,4-$F_2$—$C_6H_3$
and the substituent $R^6$ for a compound corresponds to a line of Table A.

Table 82 (compounds 82.1–82.974)
Compounds of the general formula I.2 where
$R^3$=methyl
$R^4$=$CH_3$
$R^5$=3,4-$F_2$—$C_6H_3$
and the substituent $R^6$ for a compound corresponds to a line of Table A.

Table 83 (compounds 83.1–83.974)
Compounds of the general formula I.3 where
$R^3$=methyl
$R^4$=$CH_3$
$R^5$=3,4-$F_2$—$C_6H_3$
and the substituent $R^6$ for a compound corresponds to a line of Table A.

Table 84 (compounds 84.1–84.974)
Compounds of the general formula I.4 where
$R^3$=methyl
$R^4$=$CH_3$
$R^5$=3,4-$F_2$—$C_6H_3$
and the substituent $R^6$ for a compound corresponds to a line of Table A.

Table 85 (compounds 85.1–85.974)
Compounds of the general formula I.1 where
$R^3$=methyl
$R^4$=$CH_3$
$R^5$=3,5-$F_2$—$C_6H_3$
and the substituent $R^6$ for a compound corresponds to a line of Table A.

Table 86 (compounds 86.1–86.974)
Compounds of the general formula I.2 where
$R^3$=methyl
$R^4$=$CH_3$
$R^5$=3,5-$F_2$—$C_6H_3$
and the substituent $R^6$ for a compound corresponds to a line of Table A.

Table 87 (compounds 87.1–87.974)
Compounds of the general formula I.3 where
$R^3$=methyl
$R^4$=$CH_3$
$R^5$=3,5-$F_2$—$C_6H_3$
and the substituent $R^6$ for a compound corresponds to a line of Table A.

Table 88 (compounds 88.1–88.974)
Compounds of the general formula I.4 where
$R^3$=methyl
$R^4$=$CH_3$
$R^5$=3,5-$F_2$—$C_6H_3$
and the substituent $R^6$ for a compound corresponds to a line of Table A.

Table 89 (compounds 89.1–89.974)
Compounds of the general formula I.1 where
$R^3$=methyl
$R^4$=$CH_3$
$R^5$=2,3-$Cl_2$—$C_6H_3$
and the substituent $R^6$ for a compound corresponds to a line of Table A.

Table 90 (compounds 90.1–90.974)
Compounds of the general formula I.2 where
$R^3$=methyl
$R^4$=$CH_3$
$R^5$=2,3-$Cl_2$—$C_6H_3$
and the substituent $R^6$ for a compound corresponds to a line of Table A.

Table 91 (compounds 91.1–91.974)
Compounds of the general formula I.3 where
$R^3$=methyl
$R^4$=$CH_3$
$R^5$=2,3-$Cl_2$—$C_6H_3$
and the substituent $R^6$ for a compound corresponds to a line of Table A.

Table 92 (compounds 92.1–92.974)
Compounds of the general formula I.4 where
$R^3$=methyl
$R^4$=$CH_3$
$R^5$=2,3-$Cl_2$—$C_6H_3$
and the substituent $R^6$ for a compound corresponds to a line of Table A.

Table 93 (compounds 93.1–93.974)
Compounds of the general formula I.1 where
$R^3$=methyl
$R^4$=$CH_3$
$R^5$=2,4-$Cl_2$—$C_6H_3$
and the substituent $R^6$ for a compound corresponds to a line of Table A.

Table 94 (compounds 94.1–94.974)
Compounds of the general formula I.2 where
$R^3$=methyl
$R^4$=$CH_3$
$R^5$=2,4-$Cl_2$—$C_6H_3$
and the substituent $R^6$ for a compound corresponds to a line of Table A.

Table 95 (compounds 95.1–95.974)
Compounds of the general formula I.3 where
$R^3$=methyl
$R^4$=$CH_3$
$R^5$=2,4-$Cl_2$—$C_6H_3$
and the substituent $R^6$ for a compound corresponds to a line of Table A.

Table 96 (compounds 96.1–96.974)
Compounds of the general formula I.4 where
$R^3$=methyl
$R^4$=$CH_3$
$R^5$=2,4-$Cl_2$—$C_6H_3$
and the substituent $R^6$ for a compound corresponds to a line of Table A.

Table 97 (compounds 97.1–97.974)
Compounds of the general formula I.1 where
$R^3$=methyl
$R^4$=$CH_3$
$R^5$=2,5-$Cl_2$—$C_6H_3$
and the substituent $R^6$ for a compound corresponds to a line of Table A.

Table 98 (compounds 98.1–98.974)
Compounds of the general formula I.2 where
$R^3$=methyl
$R^4$=$CH_3$
$R^5$=2,5-$Cl_2$—$C_6H_3$
and the substituent $R^6$ for a compound corresponds to a line of Table A.

Table 99 (compounds 99.1–99.974)
Compounds of the general formula I.3 where
$R^3$=methyl
$R^4$=$CH_3$
$R^5$=2,5-$Cl_2$—$C_6H_3$
and the substituent $R^6$ for a compound corresponds to a line of Table A.

Table 100 (compounds 100.1–100.974)
Compounds of the general formula I.4 where
$R^3$=methyl
$R^4$=$CH_3$
$R^5$=2,5-$Cl_2$—$C_6H_3$
and the substituent $R^6$ for a compound corresponds to a line of Table A.

Table 101 (compounds 101.1–101.974)
Compounds of the general formula I.1 where
$R^3$=methyl
$R^4$=$CH_3$
$R^5$=3,4-$Cl_2$—$C_6H_3$
and the substituent $R^6$ for a compound corresponds to a line of Table A.

Table 102 (compounds 102.1–102.974)
Compounds of the general formula I.2 where
$R^3$=methyl
$R^4$=$CH_3$
$R^5$=3,4-$Cl_2$—$C_6H_3$
and the substituent $R^6$ for a compound corresponds to a line of Table A.

Table 103 (compounds 103.1–103.974)
Compounds of the general formula I.3 where
$R^3$=methyl
$R^4$=$CH_3$
$R^5$=3,4-$Cl_2$—$C_6H_3$
and the substituent $R^6$ for a compound corresponds to a line of Table A.

Table 104 (compounds 104.1–104.974)
Compounds of the general formula I.4 where
$R^3$=methyl
$R^4$=$CH_3$
$R^5$=3,4-$Cl_2$—$C_6H_3$
and the substituent $R^6$ for a compound corresponds to a line of Table A.

Table 105 (compounds 105.1–105.974)
Compounds of the general formula I.1 where
$R^3$=methyl
$R^4$=$CH_3$
$R^5$=3,5-$Cl_2$—$C_6H_3$
and the substituent $R^6$ for a compound corresponds to a line of Table A.

Table 106 (compounds 106.1–106.974)
  Compounds of the general formula I.2 where
  $R^3$=methyl
  $R^4$=$CH_3$
  $R^5$=3,5-$Cl_2$—$C_6H_3$
  and the substituent $R^6$ for a compound corresponds to a line of Table A.
Table 107 (compounds 107.1–107.974)
  Compounds of the general formula I.3 where
  $R^3$=methyl
  $R^4$=$CH_3$
  $R^5$=3,5-$Cl_2$—$C_6H_3$
  and the substituent $R^6$ for a compound corresponds to a line of Table A.
Table 108 (compounds 108.1–108.974)
  Compounds of the general formula I.4 where
  $R^3$=methyl
  $R^4$=$CH_3$
  $R^5$=3,5-$Cl_2$—$C_6H_3$
  and the substituent $R^6$ for a compound corresponds to a line of Table A.
Table 109 (compounds 109.1–109.974)
  Compounds of the general formula I.1 where
  $R^3$=methyl
  $R^4$=$CH_3$
  $R^5$=2-F; 3-Cl—$C_6H_3$
  and the substituent $R^6$ for a compound corresponds to a line of Table A.
Table 110 (compounds 110.1–110.974)
  Compounds of the general formula I.2 where
  $R^3$=methyl
  $R^4$=$CH_3$
  $R^5$=2-F; 3-Cl—$C_6H_3$
  and the substituent $R^6$ for a compound corresponds to a line of Table A.
Table 111 (compounds 111.1–111.974)
  Compounds of the general formula I.3 where
  $R^3$=methyl
  $R^4$=$CH_3$
  $R^5$=2-F; 3-Cl—$C_6H_3$
  and the substituent $R^6$ for a compound corresponds to a line of Table A.
Table 112 (compounds 112.1–112.974)
  Compounds of the general formula I.4 where
  $R^3$=methyl
  $R^4$=$CH_3$
  $R^5$=2-F; 3-Cl—$C_6H_3$
  and the substituent $R^6$ for a compound corresponds to a line of Table A.
Table 113 (compounds 113.1–113.974)
  Compounds of the general formula I.1 where
  $R^3$=methyl
  $R^4$=$CH_3$
  $R^5$=2-F; 4-Cl—$C_6H_3$
  and the substituent $R^6$ for a compound corresponds to a line of Table A.
Table 114 (compounds 114.1–114.974)
  Compounds of the general formula I.2 where
  $R^3$=methyl
  $R^4$=$CH_3$
  $R^5$=2-F; 4-Cl—$C_6H_3$
  and the substituent $R^6$ for a compound corresponds to a line of Table A.
Table 115 (compounds 115.1–115.974)
  Compounds of the general formula I.3 where
  $R^3$=methyl
  $R^4$=$CH_3$
  $R^5$=2-F; 4-Cl—$C_6H_3$
  and the substituent $R^6$ for a compound corresponds to a line of Table A.
Table 116 (compounds 116.1–116.974)
  Compounds of the general formula I.4 where
  $R^3$=methyl
  $R^4$=$CH_3$
  $R^5$=2-F; 4-Cl—$C_6H_3$
  and the substituent $R^6$ for a compound corresponds to a line of Table A.
Table 117 (compounds 117.1–117.974)
  Compounds of the general formula I.1 where
  $R^3$=methyl
  $R^4$=$CH_3$
  $R^5$=3-F; 4-Cl—$C_6H_3$
  and the substituent $R^6$ for a compound corresponds to a line of Table A.
Table 118 (compounds 118.1–118.974)
  Compounds of the general formula I.2 where
  $R^3$=methyl
  $R^4$=$CH_3$
  $R^5$=3-F; 4-Cl—$C_6H_3$
  and the substituent $R^6$ for a compound corresponds to a line of Table A.
Table 119 (compounds 119.1–119.974)
  Compounds of the general formula I.3 where
  $R^3$=methyl
  $R^4$=$CH_3$
  $R^5$=3-F; 4-Cl—$C_6H_3$
  and the substituent $R^6$ for a compound corresponds to a line of Table A.
Table 120 (compounds 120.1–120.974)
  Compounds of the general formula I.4 where
  $R^3$=methyl
  $R^4$=$CH_3$
  $R^5$=3-F; 4-Cl—$C_6H_3$
  and the substituent $R^6$ for a compound corresponds to a line of Table A.
Table 121 (compounds 121.1–121.974)
  Compounds of the general formula I.1 where
  $R^3$=methyl
  $R^4$=$CH_3$
  $R^5$=4-F; 3,5-$Cl_2$—$C_6H_2$
  and the substituent $R^6$ for a compound corresponds to a line of Table A.
Table 122 (compounds 122.1–122.974)
  Compounds of the general formula I.2 where
  $R^3$=methyl
  $R^4$=$CH_3$
  $R^5$=4-F; 3,5-$Cl_2$—$C_6H_2$
  and the substituent $R^6$ for a compound corresponds to a line of Table A.
Table 123 (compounds 123.1–123.974)
  Compounds of the general formula I.3 where
  $R^3$=methyl
  $R^4$=$CH_3$
  $R^5$=4-F; 3,5-$Cl_2$—$C_6H_2$
  and the substituent $R^6$ for a compound corresponds to a line of Table A.

Table 124 (compounds 124.1–124.974)
Compounds of the general formula I.4 where
$R^3$=methyl
$R^4$=$CH_3$
$R^5$=4-F; 3,5-$Cl_2$—$C_6H_2$
and the substituent $R^6$ for a compound corresponds to a line of Table A.

Table 125 (compounds 125.1–125.974)
Compounds of the general formula I.1 where
$R^3$ methyl
$R^4$=$CH_3$
$R^5$=2,3,4-$Cl_3$—$C_6H_2$
and the substituent $R^6$ for a compound corresponds to a line of Table A.

Table 126 (compounds 126.1–126.974)
Compounds of the general formula I.2 where
$R^3$=methyl
$R^4$=$CH_3$
$R^5$=2,3,4-$Cl_3$—$C_6H_2$
and the substituent $R^6$ for a compound corresponds to a line of Table A.

Table 127 (compounds 127.1–127.974)
Compounds of the general formula I.3 where
$R^3$=methyl
$R^4$=$CH_3$
$R^5$=2,3,4-$Cl_3$—$C_6H_2$
and the substituent $R^6$ for a compound corresponds to a line of Table A.

Table 128 (compounds 128.1–128.974)
Compounds of the general formula I.4 where
$R^3$=methyl
$R^4$=$CH_3$
$R^5$=2,3,4-$Cl_3$—$C_6H_2$
and the substituent $R^6$ for a compound corresponds to a line of Table A.

Table 129 (compounds 129.1–129.974)
Compounds of the general formula I.1 where
$R^3$=methyl
$R^4$=$CH_3$
$R^5$=2,3,5-$Cl_3$—$C_6H_2$
and the substituent $R^6$ for a compound corresponds to a line of Table A.

Table 130 (compounds 130.1–130.974)
Compounds of the general formula I.2 where
$R^3$=methyl
$R^4$=$CH_3$
$R^5$=2,3,5-$Cl_3$—$C_6H_2$
and the substituent $R^6$ for a compound corresponds to a line of Table A.

Table 131 (compounds 131.1–131.974)
Compounds of the general formula I.3 where
$R^3$=methyl
$R^4$=$CH_3$
$R^5$=2,3,5-$Cl_3$—$C_6H_2$
and the substituent $R^6$ for a compound corresponds to a line of Table A.

Table 132 (compounds 132.1–132.974)
Compounds of the general formula I.4 where
$R^3$=methyl
$R^4$=$CH_3$
$R^5$=2,3,5-$Cl_3$—$C_6H_2$
and the substituent $R^6$ for a compound corresponds to a line of Table A.

Table 133 (compounds 133.1–133.974)
Compounds of the general formula I.1 where
$R^3$=methyl
$R^4$=$CH_3$
$R^5$=2,4,5-$Cl_3$—$C_6H_2$
and the substituent $R^6$ for a compound corresponds to a line of Table A.

Table 134 (compounds 134.1–134.974)
Compounds of the general formula I.2 where
$R^3$=methyl
$R^4$=$CH_3$
$R^5$=2,4,5-$Cl_3$—$C_6H_2$
and the substituent $R^6$ for a compound corresponds to a line of Table A.

Table 135 (compounds 135.1–135.974)
Compounds of the general formula I.3 where
$R^3$=methyl
$R^4$=$CH_3$
$R^5$=2,4,5-$Cl_3$—$C_6H_2$
and the substituent $R^6$ for a compound corresponds to a line of Table A.

Table 136 (compounds 136.1–136.974)
Compounds of the general formula I.4 where
$R^3$=methyl
$R^4$=$CH_3$
$R^5$=2,4,5-$Cl_3$—$C_6H_2$
and the substituent $R^6$ for a compound corresponds to a line of Table A.

Table 137 (compounds 137.1–137.974)
Compounds of the general formula I.1 where
$R^3$=methyl
$R^4$=$CH_3$
$R^5$=2-CN—$C_6H_4$
and the substituent $R^6$ for a compound corresponds to a line of Table A.

Table 138 (compounds 138.1–138.974)
Compounds of the general formula I.2 where
$R^3$=methyl
$R^4$=$CH_3$
$R^5$=2-CN—$C_6H_4$
and the substituent $R^6$ for a compound corresponds to a line of Table A.

Table 139 (compounds 139.1–139.974)
Compounds of the general formula I.3 where
$R^3$=methyl
$R^4$=$CH_3$
$R^5$=2-CN—$C_6H_4$
and the substituent $R^6$ for a compound corresponds to a line of Table A.

Table 140 (compounds 140.1–140.974)
Compounds of the general formula I.4 where
$R^3$=methyl
$R^4$=$CH_3$
$R^5$=2-CN—$C_6H_4$
and the substituent $R^6$ for a compound corresponds to a line of Table A.

Table 141 (compounds 141.1–141.974)
Compounds of the general formula I.1 where
$R^3$=methyl
$R^4$=$CH_3$
$R^5$=3-CN—$C_6H_4$
and the substituent $R^6$ for a compound corresponds to a line of Table A.

Table 142 (compounds 142.1–142.974)
  Compounds of the general formula I.2 where
  $R^3$=methyl
  $R^4$=$CH_3$
  $R^5$=3-CN—$C_6H_4$
  and the substituent $R^6$ for a compound corresponds to a line of Table A.
Table 143 (compounds 143.1–143.974)
  Compounds of the general formula I.3 where
  $R^3$=methyl
  $R^4$=$CH_3$
  $R^5$=3-CN—$C_6H_4$
  and the substituent $R^6$ for a compound corresponds to a line of Table A.
Table 144 (compounds 144.1–144.974)
  Compounds of the general formula I.4 where
  $R^3$=methyl
  $R^4$=$CH_3$
  $R^5$=3-CN—$C_6H_4$
  and the substituent $R^6$ for a compound corresponds to a line of Table A.
Table 145 (compounds 145.1–145.974)
  Compounds of the general formula I.1 where
  $R^3$=methyl
  $R^4$=$CH_3$
  $R^5$=4-CN—$C_6H_4$
  and the substituent $R^6$ for a compound corresponds to a line of Table A.
Table 146 (compounds 146.1–146.974)
  Compounds of the general formula I.2 where
  $R^3$=methyl
  $R^4$=$CH_3$
  $R^5$=4-CN—$C_6H_4$
  and the substituent $R^6$ for a compound corresponds to a line of Table A.
Table 147 (compounds 147.1–147.974)
  Compounds of the general formula I.3 where
  $R^3$=methyl
  $R^4$=$CH_3$
  $R^5$=4-CN—$C_6H_4$
  and the substituent $R^6$ for a compound corresponds to a line of Table A.
Table 148 (compounds 148.1–148.974)
  Compounds of the general formula I.4 where
  $R^3$=methyl
  $R^4$=$CH_3$
  $R^5$=4-CN—$C_6H_4$
  and the substituent $R^6$ for a compound corresponds to a line of Table A.
Table 149 (compounds 149.1–149.974)
  Compounds of the general formula I.1 where
  $R^3$=methyl
  $R^4$=$CH_3$
  $R^5$=2-$NO_2$—$C_6H_4$
  and the substituent $R^6$ for a compound corresponds to a line of Table A.
Table 150 (compounds 150.1–150.974)
  Compounds of the general formula I.2 where
  $R^3$=methyl
  $R^4$=$CH_3$
  $R^5$=2-$NO_2$—$C_6H_4$
  and the substituent $R^6$ for a compound corresponds to a line of Table A.
Table 151 (compounds 151.1–151.974)
  Compounds of the general formula I.3 where
  $R^3$=methyl
  $R^4$=$CH_3$
  $R^5$=2-$NO_2$—$C_6H_4$
  and the substituent $R^6$ for a compound corresponds to a line of Table A.
Table 152 (compounds 152.1–152.974)
  Compounds of the general formula I.4 where
  $R^3$=methyl
  $R^4$=$CH_3$
  $R^5$=2-$NO_2$—$C_6H_4$
  and the substituent $R^6$ for a compound corresponds to a line of Table A.
Table 153 (compounds 153.1–153.974)
  Compounds of the general formula I.1 where
  $R^3$=methyl
  $R^4$=$CH_3$
  $R^5$=3-$NO_2$—$C_6H_4$
  and the substituent $R^6$ for a compound corresponds to a line of Table A.
Table 154 (compounds 154.1–154.974)
  Compounds of the general formula I.2 where
  $R^3$=methyl
  $R^4$=$CH_3$
  $R^5$=3-$NO_2$—$C_6H_4$
  and the substituent $R^6$ for a compound corresponds to a line of Table A.
Table 155 (compounds 155.1–155.974)
  Compounds of the general formula I.3 where
  $R^3$=methyl
  $R^4$=$CH_3$
  $R^5$=3-$NO_2$—$C_6H_4$
  and the substituent $R^6$ for a compound corresponds to a line of Table A.
Table 156 (compounds 156.1–156.974)
  Compounds of the general formula I.4 where
  $R^3$=methyl
  $R^4$=$CH_3$
  $R^5$=3-$NO_2$—$C_6H_4$
  and the substituent $R^6$ for a compound corresponds to a line of Table A.
Table 157 (compounds 157.1–157.974)
  Compounds of the general formula I.1 where
  $R^3$=methyl
  $R^4$=$CH_3$
  $R^5$=4-$NO_2$—$C_6H_4$
  and the substituent $R^6$ for a compound corresponds to a line of Table A.
Table 158 (compounds 158.1–158.974)
  Compounds of the general formula I.2 where
  $R^3$=methyl
  $R^4$=$CH_3$
  $R^5$=4-$NO_2$—$C_6H_4$
  and the substituent $R^6$ for a compound corresponds to a line of Table A.
Table 159 (compounds 159.1–159.974)
  Compounds of the general formula I.3 where
  $R^3$=methyl
  $R^4$=$CH_3$
  $R^5$=4-$NO_2$—$C_6H_4$
  and the substituent $R^6$ for a compound corresponds to a line of Table A.

Table 160 (compounds 160.1–160.974)
Compounds of the general formula I.4 where
$R^3$=methyl
$R^4$=$CH_3$
$R^5$=4-$NO_2$—$C_6H_4$
and the substituent $R^6$ for a compound corresponds to a line of Table A.

Table 161 (compounds 161.1–161.974)
Compounds of the general formula I.1 where
$R^3$=methyl
$R^4$=$CH_3$
$R^5$=2-$CH_3$—$C_6H_4$
and the substituent $R^6$ for a compound corresponds to a line of Table A.

Table 162 (compounds 162.1–162.974)
Compounds of the general formula I.2 where
$R^3$=methyl
$R^4$=$CH_3$
$R^5$=2-$CH_3$—$C_6H_4$
and the substituent $R^6$ for a compound corresponds to a line of Table A.

Table 163 (compounds 163.1–163.974)
Compounds of the general formula I.3 where
$R^3$=methyl
$R^4$=$CH_3$
$R^5$=2-$CH_3$—$C_6H_4$
and the substituent $R^6$ for a compound corresponds to a line of Table A.

Table 164 (compounds 164.1–164.974)
Compounds of the general formula I.4 where
$R^3$=methyl
$R^4$=$CH_3$
$R^5$=2-$CH_3$—$C_6H_4$
and the substituent $R^6$ for a compound corresponds to a line of Table A.

Table 165 (compounds 165.1–165.974)
Compounds of the general formula I.1 where
$R^3$=methyl
$R^4$=$CH_3$
$R^5$=3-$CH_3$—$C_6H_4$
and the substituent $R^6$ for a compound corresponds to a line of Table A.

Table 166 (compounds 166.1–166.974)
Compounds of the general formula I.2 where
$R^3$=methyl
$R^4$=$CH_3$
$R^5$=3-$CH_3$—$C_6H_4$
and the substituent $R^6$ for a compound corresponds to a line of Table A.

Table 167 (compounds 167.1–167.974)
Compounds of the general formula I.3 where
$R^3$=methyl
$R^4$=$CH_3$
$R^5$=3-$CH_3$—$C_6H_4$
and the substituent $R^6$ for a compound corresponds to a line of Table A.

Table 168 (compounds 168.1–168.974)
Compounds of the general formula I.4 where
$R^3$=methyl
$R^4$=$CH_3$
$R^5$=3-$CH_3$—$C_6H_4$
and the substituent $R^6$ for a compound corresponds to a line of Table A.

Table 169 (compounds 169.1–169.974)
Compounds of the general formula I.1 where
$R^3$=methyl
$R^4$=$CH_3$
$R^5$=4-$CH_3$—$C_6H_4$
and the substituent $R^6$ for a compound corresponds to a line of Table A.

Table 170 (compounds 170.1–170.974)
Compounds of the general formula I.2 where
$R^3$=methyl
$R^4$=$CH_3$
$R^5$=4-$CH_3$—$C_6H_4$
and the substituent $R^6$ for a compound corresponds to a line of Table A.

Table 171 (compounds 171.1–171.974)
Compounds of the general formula I.3 where
$R^3$=methyl
$R^4$=$CH_3$
$R^5$=4-$CH_3$—$C_6H_4$
and the substituent $R^6$ for a compound corresponds to a line of Table A.

Table 172 (compounds 172.1–172.974)
Compounds of the general formula I.4 where
$R^3$=methyl
$R^4$=$CH_3$
$R^5$=4-$CH_3$—$C_6H_4$
and the substituent $R^6$ for a compound corresponds to a line of Table A.

Table 173 (compounds 173.1–173.974)
Compounds of the general formula I.1 where
$R^3$=methyl
$R^4$=$CH_3$
$R^5$=2,4-$(CH_3)_2$—$C_6H_3$
and the substituent $R^6$ for a compound corresponds to a line of Table A.

Table 174 (compounds 174.1–174.974)
Compounds of the general formula I.2 where
$R^3$=methyl
$R^4$=$CH_3$
$R^5$=2,4-$(CH_3)_2$—$C_6H_3$
and the substituent $R^6$ for a compound corresponds to a line of Table A.

Table 175 (compounds 175.1–175.974)
Compounds of the general formula I.3 where
$R^3$=methyl
$R^4$=$CH_3$
$R^5$=2,4-$(CH_3)_2$—$C_6H_3$
and the substituent $R^6$ for a compound corresponds to a line of Table A.

Table 176 (compounds 176.1–176.974)
Compounds of the general formula I.4 where
$R^3$=methyl
$R^4$=$CH_3$
$R^5$=2,4-$(CH_3)_2$—$C_6H_3$
and the substituent $R^6$ for a compound corresponds to a line of Table A.

Table 177 (compounds 177.1–177.974)
Compounds of the general formula I.1 where
$R^3$=methyl
$R^4$=$CH_3$
$R^5$=2,5-$(CH_3)_2$—$C_6H_3$
and the substituent $R^6$ for a compound corresponds to a line of Table A.

Table 178 (compounds 178.1–178.974)
Compounds of the general formula I.2 where
$R^3$=methyl
$R^4$=$CH_3$
$R^5$=2,5-$(CH_3)_2$—$C_6H_3$
and the substituent $R^6$ for a compound corresponds to a line of Table A.

Table 179 (compounds 179.1–179.974)
Compounds of the general formula I.3 where
$R^3$=methyl
$R^4$=$CH_3$
$R^5$=2,5-$(CH_3)_2$—$C_6H_3$
and the substituent $R^6$ for a compound corresponds to a line of Table A.

Table 180 (compounds 180.1–180.974)
Compounds of the general formula I.4 where
$R^3$=methyl
$R^4$=$CH_3$
$R^5$=2,5-$(CH_3)_2$—$C_6H_3$
and the substituent $R^6$ for a compound corresponds to a line of Table A.

Table 181 (compounds 181.1–181.974)
Compounds of the general formula I.1 where
$R^3$=methyl
$R^4$=$CH_3$
$R^5$=3,4-$(CH_3)_2$—$C_6H_3$
and the substituent $R^6$ for a compound corresponds to a line of Table A.

Table 182 (compounds 182.1–182.974)
Compounds of the general formula I.2 where
$R^3$=methyl
$R^4$=$CH_3$
$R^5$=3,4-$(CH_3)_2$—$C_6H_3$
and the substituent $R^6$ for a compound corresponds to a line of Table A.

Table 183 (compounds 183.1–183.974)
Compounds of the general formula I.3 where
$R^3$=methyl
$R^4$=$CH_3$
$R^5$=3,4-$(CH_3)_2$—$C_6H_3$
and the substituent $R^6$ for a compound corresponds to a line of Table A.

Table 184 (compounds 184.1–184.974)
Compounds of the general formula I.4 where
$R^3$=methyl
$R^4$=$CH_3$
$R^5$=3,4-$(CH_3)_2$—$C_6H_3$
and the substituent $R^6$ for a compound corresponds to a line of Table A.

Table 185 (compounds 185.1–185.974)
Compounds of the general formula I.1 where
$R^3$=methyl
$R^4$=$CH_3$
$R^5$=3,5-$(CH_3)_2$—$C_6H_3$
and the substituent $R^6$ for a compound corresponds to a line of Table A.

Table 186 (compounds 186.1–186.974)
Compounds of the general formula I.2 where
$R^3$=methyl
$R^4$=$CH_3$
$R^5$=3,5-$(CH_3)_2$—$C_6H_3$
and the substituent $R^6$ for a compound corresponds to a line of Table A.

Table 187 (compounds 187.1–187.974)
Compounds of the general formula I.3 where
$R^3$=methyl
$R^4$=$CH_3$
$R^5$=3,5-$(CH_3)_2$—$C_6H_3$
and the substituent $R^6$ for a compound corresponds to a line of Table A.

Table 188 (compounds 188.1–188.974)
Compounds of the general formula I.4 where
$R^3$=methyl
$R^4$ $CH_3$
$R^5$=3,5-$(CH_3)_2$—$C_6H_3$
and the substituent $R^6$ for a compound corresponds to a line of Table A.

Table 189 (compounds 189.1–189.974)
Compounds of the general formula I.1 where
$R^3$=methyl
$R^4$=$CH_3$
$R^5$=3,4,5-$(CH_3)_3$—$C_6H_2$
and the substituent $R^6$ for a compound corresponds to a line of Table A.

Table 190 (compounds 190.1–190.974)
Compounds of the general formula I.2 where
$R^3$=methyl
$R^4$=$CH_3$
$R^5$=3,4,5-$(CH_3)_3$—$C_6H_2$
and the substituent $R^6$ for a compound corresponds to a line of Table A.

Table 191 (compounds 191.1–191.974)
Compounds of the general formula I.3 where
$R^3$=methyl
$R^4$=$CH_3$
$R^5$=3,4,5-$(CH_3)_3$—$C_6H_2$
and the substituent $R^6$ for a compound corresponds to a line of Table A.

Table 192 (compounds 192.1–192.974)
Compounds of the general formula I.4 where
$R^3$=methyl
$R^4$=$CH_3$
$R^5$=3,4,5-$(CH_3)_3$—$C_6H_2$
and the substituent $R^6$ for a compound corresponds to a line of Table A.

Table 193 (compounds 193.1–193.974)
Compounds of the general formula I.1 where
$R^3$=methyl
$R^4$=$CH_3$
$R^5$=4-$C_6H_5$—$C_6H_4$
and the substituent $R^6$ for a compound corresponds to a line of Table A.

Table 194 (compounds 194.1–194.974)
Compounds of the general formula I.2 where
$R^3$=methyl
$R^4$=$CH_3$
$R^5$=4-$C_6H_5$—$C_6H_4$
and the substituent $R^6$ for a compound corresponds to a line of Table A.

Table 195 (compounds 195.1–195.974)
Compounds of the general formula I.3 where
$R^3$=methyl
$R^4$=$CH_3$
$R^5$=4-$C_6H_5$—$C_6H_4$
and the substituent $R^6$ for a compound corresponds to a line of Table A.

Table 196 (compounds 196.1–196.974)
Compounds of the general formula I.4 where
$R^3$=methyl
$R^4$=$CH_3$
$R^5$=4-$C_6H_5$—$C_6H_4$
and the substituent $R^6$ for a compound corresponds to a line of Table A.

Table 197 (compounds 197.1–197.974)
Compounds of the general formula I.1 where
$R^3$=methyl
$R^4$=$CH_3$
$R^5$=3-Cl-4-$CH_3$—$C_6H_3$
and the substituent $R^6$ for a compound corresponds to a line of Table A.

Table 198 (compounds 198.1–198.974)
Compounds of the general formula I.2 where
$R^3$=methyl
$R^4$=$CH_3$
$R^5$=3-Cl-4-$CH_3$—$C_6H_3$
and the substituent $R^6$ for a compound corresponds to a line of Table A.

Table 199 (compounds 199.1–199.974)
Compounds of the general formula I.3 where
$R^3$=methyl
$R^4$=$CH_3$
$R^5$=3-Cl-4-$CH_3$—$C_6H_3$
and the substituent $R^6$ for a compound corresponds to a line of Table A.

Table 200 (compounds 200.1–200.974)
Compounds of the general formula I.4 where
$R^3$=methyl
$R^4$=$CH_3$
$R^5$=3-Cl-4-$CH_3$—$C_6H_3$
and the substituent $R^6$ for a compound corresponds to a line of Table A.

Table 201 (compounds 201.1–201.974)
Compounds of the general formula I.1 where
$R^3$=methyl
$R^4$=$CH_3$
$R^5$=2-$OCH_3$—$C_6H_4$
and the substituent $R^6$ for a compound corresponds to a line of Table A.

Table 202 (compounds 202.1–202.974)
Compounds of the general formula I.2 where
$R^3$=methyl
$R^4$=$CH_3$
$R^5$=2-$OCH_3$—$C_6H_4$
and the substituent $R^6$ for a compound corresponds to a line of Table A.

Table 203 (compounds 203.1–203.974)
Compounds of the general formula I.3 where
$R^3$=methyl
$R^4$=$CH_3$
$R^5$=2-$OCH_3$—$C_6H_4$
and the substituent $R^6$ for a compound corresponds to a line of Table A.

Table 204 (compounds 204.1–204.974)
Compounds of the general formula I.4 where
$R^3$=methyl
$R^4$=$CH_3$
$R^5$=2-$OCH_3$—$C_6H_4$
and the substituent $R^6$ for a compound corresponds to a line of Table A.

Table 205 (compounds 205.1–205.974)
Compounds of the general formula I.1 where
$R^3$=methyl
$R^4$=$CH_3$
$R^5$=3-$OCH_3$—$C_6H_4$
and the substituent $R^6$ for a compound corresponds to a line of Table A.

Table 206 (compounds 206.1–206.974)
Compounds of the general formula I.2 where
$R^3$=methyl
$R^4$=$CH_3$
$R^5$=2-$OCH_3$—$C_6H_4$
and the substituent $R^6$ for a compound corresponds to a line of Table A.

Table 207 (compounds 207.1–207.974)
Compounds of the general formula I.3 where
$R^3$=methyl
$R^4$=$CH_3$
$R^5$=3-$OCH_3$—$C_6H_4$
and the substituent $R^6$ for a compound corresponds to a line of Table A.

Table 208 (compounds 208.1–208.974)
Compounds of the general formula I.4 where
$R^3$=methyl
$R^4$=$CH_3$
$R^5$=3-$OCH_3$—$C_6H_4$
and the substituent $R^6$ for a compound corresponds to a line of Table A.

Table 209 (compounds 209.1–209.974)
Compounds of the general formula I.1 where
$R^3$=methyl
$R^4$=$CH_3$
$R^5$=4-$OCH_3$—$C_6H_4$
and the substituent $R^6$ for a compound corresponds to a line of Table A.

Table 210 (compounds 210.1–210.974)
Compounds of the general formula I.2 where
$R^3$=methyl
$R^4$=$CH_3$
$R^5$=4-$OCH_3$—$C_6H_4$
and the substituent $R^6$ for a compound corresponds to a line of Table A.

Table 211 (compounds 211.1–211.974)
Compounds of the general formula I.3 where
$R^3$=methyl
$R^4$=$CH_3$
$R^5$=4-$OCH_3$—$C_6H_4$
and the substituent $R^6$ for a compound corresponds to a line of Table A.

Table 212 (compounds 212.1–212.974)
Compounds of the general formula I.4 where
$R^3$=methyl
$R^4$=$CH_3$
$R^5$=4-$OCH_3$—$C_6H_4$
and the substituent $R^6$ for a compound corresponds to a line of Table A.

Table 213 (compounds 213.1–213.974)
Compounds of the general formula I.1 where
$R^3$=methyl
$R^4$=$CH_3$
$R^5$=2-$OCF_3$—$C_6H_4$
and the substituent $R^6$ for a compound corresponds to a line of Table A.

Table 214 (compounds 214.1–214.974)
  Compounds of the general formula I.2 where
  $R^3$=methyl
  $R^4$=$CH_3$
  $R^5$=2-$OCF_3$—$C_6H_4$
  and the substituent $R^6$ for a compound corresponds to a line of Table A.

Table 215 (compounds 215.1–215.974)
  Compounds of the general formula I.3 where
  $R^3$=methyl
  $R^4$=$CH_3$
  $R^5$=2-$OCF_3$—$C_6H_4$
  and the substituent $R^6$ for a compound corresponds to a line of Table A.

Table 216 (compounds 216.1–216.974)
  Compounds of the general formula I.4 where
  $R^3$=methyl
  $R^4$=$CH_3$
  $R^5$=2-$OCF_3$—$C_6H_4$
  and the substituent $R^6$ for a compound corresponds to a line of Table A.

Table 217 (compounds 217.1–217.974)
  Compounds of the general formula I.1 where
  $R^3$=methyl
  $R^4$=$CH_3$
  $R^5$=3-$OCF_3$—$C_6H_4$
  and the substituent $R^6$ for a compound corresponds to a line of Table A.

Table 218 (compounds 218.1–218.974)
  Compounds of the general formula I.2 where
  $R^3$=methyl
  $R^4$=$CH_3$
  $R^5$=2-$OCF_3$—$C_6H_4$
  and the substituent $R^6$ for a compound corresponds to a line of Table A.

Table 219 (compounds 219.1–219.974)
  Compounds of the general formula I.3 where
  $R^3$=methyl
  $R^4$=$CH_3$
  $R^5$=3-$OCF_3$—$C_6H_4$
  and the substituent $R^6$ for a compound corresponds to a line of Table A.

Table 220 (compounds 220.1–220.974)
  Compounds of the general formula I.4 where
  $R^3$=methyl
  $R^4$=$CH_3$
  $R^5$=3-$OCF_3$—$C_6H_4$
  and the substituent $R^6$ for a compound corresponds to a line of Table A.

Table 221 (compounds 221.1–221.974)
  Compounds of the general formula I.1 where
  $R^3$=methyl
  $R^4$=$CH_3$
  $R^5$=4-$OCF_3$—$C_6H_4$
  and the substituent $R^6$ for a compound corresponds to a line of Table A.

Table 222 (compounds 222.1–222.974)
  Compounds of the general formula I.2 where
  $R^3$=methyl
  $R^4$=$CH_3$
  $R^5$=4-$OCF_3$—$C_6H_4$
  and the substituent $R^6$ for a compound corresponds to a line of Table A.

Table 223 (compounds 223.1–223.974)
  Compounds of the general formula I.3 where
  $R^3$=methyl
  $R^4$=$CH_3$
  $R^5$=4-$OCF_3$—$C_6H_4$
  and the substituent $R^6$ for a compound corresponds to a line of Table A.

Table 224 (compounds 224.1–224.974)
  Compounds of the general formula I.4 where
  $R^3$=methyl
  $R^4$=$CH_3$
  $R^5$=4-$OCF_3$—$C_6H_4$
  and the substituent $R^6$ for a compound corresponds to a line of Table A.

Table 225 (compounds 226.1 [sic]-225.974)
  Compounds of the general formula I.1 where
  $R^3$=methyl
  $R^4$=$CH_3$
  $R^5$=3-Cl; 4-$OCH_3$—$C_6H_3$
  and the substituent $R^6$ for a compound corresponds to a line of Table A.

Table 226 (compounds 226.1–226.974)
  Compounds of the general formula I.2 where
  $R^3$=methyl
  $R^4$=$CH_3$
  $R^5$=3-Cl; 4-$OCH_3$—$C_6H_3$
  and the substituent $R^6$ for a compound corresponds to a line of Table A.

Table 227 (compounds 227.1–227.974)
  Compounds of the general formula I.3 where
  $R^3$=methyl
  $R^4$=$CH_3$
  $R^5$=3-Cl; 4-$OCH_3$—$C_6H_3$
  and the substituent $R^6$ for a compound corresponds to a line of Table A.

Table 228 (compounds 228.1–228.974)
  Compounds of the general formula I.4 where
  $R^3$=methyl
  $R^4$=$CH_3$
  $R^5$=3-Cl; 4-$OCH_3$—$C_6H_3$
  and the substituent $R^6$ for a compound corresponds to a line of Table A.

Table 229 (compounds 229.1–229.974)
  Compounds of the general formula I.1 where
  $R^3$=methyl
  $R^4$=$CH_3$

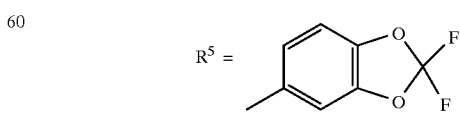

and the substituent $R^6$ for a compound corresponds to a line of Table A.

Table 230 (compounds 230.1–230.974)
  Compounds of the general formula I.2 where
  $R^3$=methyl
  $R^4$=$CH_3$ $R^5 =$ 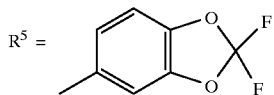

and the substituent $R^6$ for a compound corresponds to a line of Table A.
Table 231 (compounds 231.1–231.974)
  Compounds of the general formula I.3 where
  $R^3$=methyl
  $R^4$=$CH_3$ $R^5 =$ 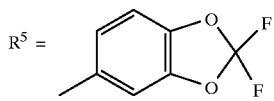

and the substituent $R^6$ for a compound corresponds to a line of Table A.
Table 232 (compounds 232.1–232.974)
  Compounds of the general formula I.4 where
  $R^3$=methyl
  $R^4$=$CH_3$ $R^5 =$ 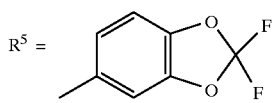

and the substituent $R^6$ for a compound corresponds to a line of Table A.
Table 233 (compounds 233.1–233.974)
  Compounds of the general formula I.1 where
  $R^3$=methyl
  $R^4$=$CH_3$
  $R^5$=pyridin-2-yl
and the substituent $R^6$ for a compound corresponds to a line of Table A.
Table 234 (compounds 234.1–234.974)
  Compounds of the general formula I.2 where
  $R^3$=methyl
  $R^4$=$CH_3$
  $R^5$=pyridin-2-yl
and the substituent $R^6$ for a compound corresponds to a line of Table A.
Table 235 (compounds 235.1–235.974)
  Compounds of the general formula I.3 where
  $R^3$=methyl
  $R^4$=$CH_3$
  $R^5$=pyridin-2-yl
and the substituent $R^6$ for a compound corresponds to a line of Table A.
Table 236 (compounds 236.1–236.974)
  Compounds of the general formula I.4 where
  $R^3$=methyl
  $R^4$=$CH_3$
  $R^5$=pyridin-2-yl
and the substituent $R^6$ for a compound corresponds to a line of Table A.
Table 237 (compounds 237.1–237.974)
  Compounds of the general formula I.1 where
  $R^3$=methyl
  $R^4$=$CH_3$
  $R^5$=pyridin-3-yl
and the substituent $R^6$ for a compound corresponds to a line of Table A.
Table 238 (compounds 238.1–238.974)
  Compounds of the general formula I.2 where
  $R^3$=methyl
  $R^4$=$CH_3$
  $R^5$=pyridin-3-yl
and the substituent $R^6$ for a compound corresponds to a line of Table A.
Table 239 (compounds 239.1–239.974)
  Compounds of the general formula I.3 where
  $R^3$=methyl
  $R^4$=$CH_3$
  $R^5$=pyridin-3-yl
and the substituent $R^6$ for a compound corresponds to a line of Table A.
Table 240 (compounds 240.1–240.974)
  Compounds of the general formula I.4 where
  $R^3$=methyl
  $R^4$=$CH_3$
  $R^5$=pyridin-3-yl
and the substituent $R^6$ for a compound corresponds to a line of Table A.
Table 241 (compounds 241.1–241.974)
  Compounds of the general formula I.1 where
  $R^3$=methyl
  $R^4$=$CH_3$
  $R^5$=pyridin-4-yl
and the substituent $R^6$ for a compound corresponds to a line of Table A.
Table 242 (compounds 242.1–242.974)
  Compounds of the general formula I.2 where
  $R^3$=methyl
  $R^4$=$CH_3$
  $R^5$=pyridin-4-yl
and the substituent $R^6$ for a compound corresponds to a line of Table A.
Table 243 (compounds 243.1–243.974)
  Compounds of the general formula I.3 where
  $R^3$=methyl
  $R^4$=$CH_3$
  $R^5$=pyridin-4-yl
and the substituent $R^6$ for a compound corresponds to a line of Table A.
Table 244 (compounds 244.1–244.974)
  Compounds of the general formula I.4 where
  $R^3$=methyl
  $R^4$=$CH_3$
  $R^5$=pyridin-4-yl
and the substituent $R^6$ for a compound corresponds to a line of Table A.
Table 245 (compounds 245.1–245.974)
  Compounds of the general formula I.1 where
  $R^3$=methyl
  $R^4$=$CH_3$
  $R^5$=3-$CH_3$-pyridin-2-yl
and the substituent $R^6$ for a compound corresponds to a line of Table A.

Table 246 (compounds 246.1–246.974)
Compounds of the general formula I.2 where
R$^3$=methyl
R$^4$=CH$_3$
R$^5$=3-CH$_3$-pyridin-2-yl
and the substituent R$^6$ for a compound corresponds to a line of Table A.

Table 247 (compounds 247.1–247.974)
Compounds of the general formula I.3 where
R$^3$=methyl
R$^4$=CH$_3$
R$^5$=3-CH$_3$-pyridin-2-yl
and the substituent R$^6$ for a compound corresponds to a line of Table A.

Table 248 (compounds 248.1–248.974)
Compounds of the general formula I.4 where
R$^3$=methyl
R$^4$=CH$_3$
R$^5$=3-CH$_3$-pyridin-2-yl
and the substituent R$^6$ for a compound corresponds to a line of Table A.

Table 249 (compounds 249.1–249.974)
Compounds of the general formula I.1 where
R$^3$=methyl
R$^4$=CH$_3$
R$^5$=4-CH$_3$-pyridin-2-yl
and the substituent R$^6$ for a compound corresponds to a line of Table A.

Table 250 (compounds 250.1–250.974)
Compounds of the general formula I.2 where
R$^3$=methyl
R$^4$=CH$_3$
R$^5$=4-CH$_3$-pyridin-2-yl
and the substituent R$^6$ for a compound corresponds to a line of Table A.

Table 251 (compounds 251.1–251.974)
Compounds of the general formula I.3 where
R$^3$=methyl
R$^4$=CH$_3$
R$^5$=4-CH$_3$-pyridin-2-yl
and the substituent R$^6$ for a compound corresponds to a line of Table A.

Table 252 (compounds 252.1–252.974)
Compounds of the general formula I.4 where
R$^3$=methyl
R$^4$=CH$_3$
R$^5$=4-CH$_3$-pyridin-2-yl
and the substituent R$^6$ for a compound corresponds to a line of Table A.

Table 253 (compounds 253.1–253.974)
Compounds of the general formula I.1 where
R$^3$=methyl
R$^4$=CH$_3$
R$^5$=3-OCH$_3$-pyridin-2-yl
and the substituent R$^6$ for a compound corresponds to a line of Table A.

Table 254 (compounds 254.1–254.974)
Compounds of the general formula I.2 where
R$^3$=methyl
R$^4$=CH$_3$
R$^5$=3-OCH$_3$-pyridin-2-yl
and the substituent R$^6$ for a compound corresponds to a line of Table A.

Table 255 (compounds 255.1–255.974)
Compounds of the general formula I.3 where
R$^3$=methyl
R$^4$=CH$_3$
R$^5$=3-OCH$_3$-pyridin-2-yl
and the substituent R$^6$ for a compound corresponds to a line of Table A.

Table 256 (compounds 256.1–256.974)
Compounds of the general formula I.4 where
R$^3$=methyl
R$^4$=CH$_3$
R$^5$=3-OCH$_3$-pyridin-2-yl
and the substituent R$^6$ for a compound corresponds to a line of Table A.

Table 257 (compounds 257.1–257.974)
Compounds of the general formula I.1 where
R$^3$=methyl
R$^4$=CH$_3$
R$^5$=4-Cl-pyridin-2-yl
and the substituent R$^6$ for a compound corresponds to a line of Table A.

Table 258 (compounds 258.1–258.974)
Compounds of the general formula I.2 where
R$^3$=methyl
R$^4$=CH$_3$
R$^5$=4-Cl-pyridin-2-yl
and the substituent R$^6$ for a compound corresponds to a line of Table A.

Table 259 (compounds 259.1–259.974)
Compounds of the general formula I.3 where
R$^3$=methyl
R$^4$=CH$_3$
R$^5$=4-Cl-pyridin-2-yl
and the substituent R$^6$ for a compound corresponds to a line of Table A.

Table 260 (compounds 260.1–260.974)
Compounds of the general formula I.4 where
R$^3$=methyl
R$^4$=CH$_3$
R$^5$=4-Cl-pyridin-2-yl
and the substituent R$^6$ for a compound corresponds to a line of Table A.

Table 261 (compounds 261.1–261.974)
Compounds of the general formula I.1 where
R$^3$=methyl
R$^4$=CH$_3$
R$^5$=5-Cl-pyridin-2-yl
and the substituent R$^6$ for a compound corresponds to a line of Table A.

Table 262 (compounds 262.1–262.974)
Compounds of the general formula I.2 where
R$^3$=methyl
R$^4$=CH$_3$
R$^5$=5-Cl-pyridin-2-yl
and the substituent R$^6$ for a compound corresponds to a line of Table A.

Table 263 (compounds 263.1–263.974)
Compounds of the general formula I.3 where
R$^3$=methyl
R$^4$=CH$_3$
R$^5$=5-Cl-pyridin-2-yl
and the substituent R$^6$ for a compound corresponds to a line of Table A.

Table 264 (compounds 264.1–264.974)
 Compounds of the general formula I.4 where
  $R^3$=methyl
  $R^4$=$CH_3$
  $R^5$=5-Cl-pyridin-2-yl
 and the substituent $R^6$ for a compound corresponds to a line of Table A.

Table 265 (compounds 265.1–265.974)
 Compounds of the general formula I.1 where
  $R^3$=methyl
  $R^4$=$CH_3$
  $R^5$=pyrimidin-2-yl
 and the substituent $R^6$ for a compound corresponds to a line of Table A.

Table 266 (compounds 266.1–266.974)
 Compounds of the general formula I.2 where
  $R^3$=methyl
  $R^4$=$CH_3$
  $R^5$=pyrimidin-2-yl
 and the substituent $R^6$ for a compound corresponds to a line of Table A.

Table 267 (compounds 267.1–267.974)
 Compounds of the general formula I.3 where
  $R^3$=methyl
  $R^4$=$CH_3$
  $R^5$=pyrimidin-2-yl
 and the substituent $R^6$ for a compound corresponds to a line of Table A.

Table 268 (compounds 268.1–268.974)
 Compounds of the general formula I.4 where
  $R^3$=methyl
  $R^4$=$CH_3$
  $R^5$=pyrimidin-2-yl
 and the substituent $R^6$ for a compound corresponds to a line of Table A.

Table 269 (compounds 269.1–269.974)
 Compounds of the general formula I.1 where
  $R^3$=methyl
  $R^4$=$CH_3$
  $R^5$=5-Cl-pyrimidin-2-yl
 and the substituent $R^6$ for a compound corresponds to a line of Table A.

Table 270 (compounds 270.1–270.974)
 Compounds of the general formula I.2 where
  $R^3$=methyl
  $R^4$=$CH_3$
  $R^5$=5-Cl-pyrimidin-2-yl
 and the substituent $R^6$ for a compound corresponds to a line of Table A.

Table 271 (compounds 271.1–271.974)
 Compounds of the general formula I.3 where
  $R^3$=methyl
  $R^4$=$CH_3$
  $R^5$=5-Cl-pyrimidin-2-yl
 and the substituent $R^6$ for a compound corresponds to a line of Table A.

Table 272 (compounds 272.1–272.974)
 Compounds of the general formula I.4 where
  $R^3$=methyl
  $R^4$=$CH_3$
  $R^5$=5-Cl-pyrimidin-2-yl
 and the substituent $R^6$ for a compound corresponds to a line of Table A.

Table 273 (compounds 273.1–273.974)
 Compounds of the general formula I.1 where
  $R^3$=methyl
  $R^4$=$CH_3$
  $R^5$=4-$CH_3$-pyrimidin-2-yl
 and the substituent $R^6$ for a compound corresponds to a line of Table A.

Table 274 (compounds 274.1–274.974)
 Compounds of the general formula I.2 where
  $R^3$=methyl
  $R^4$=$CH_3$
  $R^5$=4-$CH_3$-pyrimidin-2-yl
 and the substituent $R^6$ for a compound corresponds to a line of Table A.

Table 275 (compounds 275.1–275.974)
 Compounds of the general formula I.3 where
  $R^3$=methyl
  $R^4$=$CH_3$
  $R^5$=4-$CH_3$-pyrimidin-2-yl
 and the substituent $R^6$ for a compound corresponds to a line of Table A.

Table 276 (compounds 276.1–276.974)
 Compounds of the general formula I.4 where
  $R^3$=methyl
  $R^4$=$CH_3$
  $R^5$=4-$CH_3$-pyrimidin-2-yl
 and the substituent $R^6$ for a compound corresponds to a line of Table A.

Table 277 (compounds 277.1–277.974)
 Compounds of the general formula I.1 where
  $R^3$=methyl
  $R^4$=$CH_3$
  $R^5$=4-Cl-furan-2-yl
 and the substituent $R^6$ for a compound corresponds to a line of Table A.

Table 278 (compounds 278.1–278.974)
 Compounds of the general formula I.2 where
  $R^3$=methyl
  $R^4$=$CH_3$
  $R^5$=4-Cl-furan-2-yl
 and the substituent $R^6$ for a compound corresponds to a line of Table A.

Table 279 (compounds 279.1–279.974)
 Compounds of the general formula I.3 where
  $R^3$=methyl
  $R^4$=$CH_3$
  $R^5$=4-Cl-furan-2-yl
 and the substituent $R^6$ for a compound corresponds to a line of Table A.

Table 280 (compounds 280.1–280.974)
 Compounds of the general formula I.4 where
  $R^3$=methyl
  $R^4$=$CH_3$
  $R^5$=4-Cl-furan-2-yl
 and the substituent $R^6$ for a compound corresponds to a line of Table A.

Table 281 (compounds 281.1–281.974)
 Compounds of the general formula I.1 where
  $R^3$=methyl
  $R^4$=$CH_3$
  $R^5$=4-$CH_3$-furan-2-yl
 and the substituent $R^6$ for a compound corresponds to a line of Table A.

Table 282 (compounds 282.1–282.974)
Compounds of the general formula I.2 where
$R^3$=methyl
$R^4$=$CH_3$
$R^5$=4-$CH_3$-furan-2-yl
and the substituent $R^6$ for a compound corresponds to a line of Table A.

Table 283 (compounds 283.1–283.974)
Compounds of the general formula I.3 where
$R^3$=methyl
$R^4$=$CH_3$
$R^5$=4-$CH_3$-furan-2-yl
and the substituent $R^6$ for a compound corresponds to a line of Table A.

Table 284 (compounds 284.1–284.974)
Compounds of the general formula I.4 where
$R^3$=methyl
$R^4$=$CH_3$
$R^5$=4-$CH_3$-furan-2-yl
and the substituent $R^6$ for a compound corresponds to a line of Table A.

Table 285 (compounds 285.1–285.974)
Compounds of the general formula I.1 where
$R^3$=methyl
$R^4$=$CH_3$
$R^5$=thien-2-yl
and the substituent $R^6$ for a compound corresponds to a line of Table A.

Table 286 (compounds 286.1–286.974)
Compounds of the general formula I.2 where
$R^3$=methyl
$R^4$=$CH_3$
$R^5$=thien-2-yl
and the substituent $R^6$ for a compound corresponds to a line of Table A.

Table 287 (compounds 287.1–287.974)
Compounds of the general formula I.3 where
$R^3$=methyl
$R^4$=$CH_3$
$R^5$=thien-2-yl
and the substituent $R^6$ for a compound corresponds to a line of Table A.

Table 288 (compounds 288.1–288.974)
Compounds of the general formula I.4 where
$R^3$=methyl
$R^4$=$CH_3$
$R^5$=thien-2-yl
and the substituent $R^6$ for a compound corresponds to a line of Table A.

Table 289 (compounds 289.1–289.974)
Compounds of the general formula I.1 where
$R^3$=methyl
$R^4$=$CH_3$
$R^5$=thien-3-yl
and the substituent $R^6$ for a compound corresponds to a line of Table A.

Table 290 (compounds 290.1–290.974)
Compounds of the general formula I.2 where
$R^3$=methyl
$R^4$=$CH_3$
$R^5$=thien-3-yl
and the substituent $R^6$ for a compound corresponds to a line of Table A.

Table 291 (compounds 291.1–291.974)
Compounds of the general formula I.3 where
$R^3$=methyl
$R^4$=$CH_3$
$R^5$=thien-3-yl
and the substituent $R^6$ for a compound corresponds to a line of Table A.

Table 292 (compounds 292.1–292.974)
Compounds of the general formula I.4 where
$R^3$=methyl
$R^4$=$CH_3$
$R^5$=thien-3-yl
and the substituent $R^6$ for a compound corresponds to a line of Table A.

Table 293 (compounds 293.1–293.974)
Compounds of the general formula I.1 where
$R^3$=methyl
$R^4$=$CH_3$
$R^5$=oxazol-2-yl
and the substituent $R^6$ for a compound corresponds to a line of Table A.

Table 294 (compounds 294.1–294.974)
Compounds of the general formula I.2 where
$R^3$=methyl
$R^4$=$CH_3$
$R^5$=oxazol-2-yl
and the substituent $R^6$ for a compound corresponds to a line of Table A.

Table 295 (compounds 295.1–295.974)
Compounds of the general formula I.3 where
$R^3$=methyl
$R^4$=$CH_3$
$R^5$=oxazol-2-yl
and the substituent $R^6$ for a compound corresponds to a line of Table A.

Table 296 (compounds 296.1–296.974)
Compounds of the general formula I.4 where
$R^3$=methyl
$R^4$=$CH_3$
$R^5$=oxazol-2-yl
and the substituent $R^6$ for a compound corresponds to a line of Table A.

Table 297 (compounds 297.1–297.974)
Compounds of the general formula I.1 where
$R^3$=methyl
$R^4$=$CH_3$
$R^5$=isoxazol-3-yl
and the substituent $R^6$ for a compound corresponds to a line of Table A.

Table 298 (compounds 298.1–298.974)
Compounds of the general formula I.2 where
$R^3$=methyl
$R^4$=$CH_3$
$R^5$=isoxazol-3-yl
and the substituent $R^6$ for a compound corresponds to a line of Table A.

Table 299 (compounds 299.1–299.974)
Compounds of the general formula I.3 where
$R^3$=methyl
$R^4$=$CH_3$
$R^5$=isoxazol-3-yl
and the substituent $R^6$ for a compound corresponds to a line of Table A.

Table 300 (compounds 300.1–300.974)
Compounds of the general formula I.4 where
$R^3$=methyl
$R^4$=$CH_3$
$R^5$=isoxazol-3-yl
and the substituent $R^6$ for a compound corresponds to a line of Table A.

Table 301 (compounds 301.1–301.974)
Compounds of the general formula I.1 where
$R^3$=methyl
$R^4$=$CH_3$
$R^5$isoxazol-4-yl
and the substituent $R^6$ for a compound corresponds to a line of Table A.

Table 302 (compounds 302.1–302.974)
Compounds of the general formula I.2 where
$R^3$=methyl
$R^4$=$CH_3$
$R^5$=isoxazol-4-yl
and the substituent $R^6$ for a compound corresponds to a line of Table A.

Table 303 (compounds 303.1–303.974)
Compounds of the general formula I.3 where
$R^3$=methyl
$R^4$=$CH_3$
$R^5$=isoxazol-4-yl
and the substituent $R^6$ for a compound corresponds to a line of Table A.

Table 304 (compounds 304.1–304.974)
Compounds of the general formula I.4 where
$R^3$=methyl
$R^4$=$CH_3$
$R^5$=isoxazol-4-yl
and the substituent $R^6$ for a compound corresponds to a line of Table A.

Table 305 (compounds 305.1–305.974)
Compounds of the general formula I.1 where
$R^3$=methyl
$R^4$=$CH_3$
$R^5$=pyrazol-3-yl
and the substituent $R^6$ for a compound corresponds to a line of Table A.

Table 306 (compounds 306.1–306.974)
Compounds of the general formula I.2 where
$R^3$=methyl
$R^4$=$CH_3$
$R^5$=pyrazol-3-yl
and the substituent $R^6$ for a compound corresponds to a line of Table A.

Table 307 (compounds 307.1–307.974)
Compounds of the general formula I.3 where
$R^3$=methyl
$R^4$=$CH_3$
$R^5$=pyrazol-3-yl
and the substituent $R^6$ for a compound corresponds to a line of Table A.

Table 308 (compounds 308.1–308.974)
Compounds of the general formula I.4 where
$R^3$=methyl
$R^4$=$CH_3$
$R^5$=pyrazol-3-yl
and the substituent $R^6$ for a compound corresponds to a line of Table A.

Table 309 (compounds 309.1–309.974)
Compounds of the general formula I.1 where
$R^3$=methyl
$R^4$=$CH_3$
$R^5$=1,3,4-oxadiazol-5-yl
and the substituent $R^6$ for a compound corresponds to a line of Table A.

Table 310 (compounds 310.1–310.974)
Compounds of the general formula I.2 where
$R^3$=methyl
$R^4$=$CH_3$
$R^5$=1,3,4-oxadiazol-5-yl
and the substituent $R^6$ for a compound corresponds to a line of Table A.

Table 311 (compounds 311.1–311.974)
Compounds of the general formula I.3 where
$R^3$=methyl
$R^4$=$CH_3$
$R^5$=1,3,4-oxadiazol-5-yl
and the substituent $R^6$ for a compound corresponds to a line of Table A.

Table 312 (compounds 312.1–312.974)
Compounds of the general formula I.4 where
$R^3$=methyl
$R^4$=$CH_3$
$R^5$=1,3,4-oxadiazol-5-yl
and the substituent $R^6$ for a compound corresponds to a line of Table A.

Table 313 (compounds 313.1–313.974)
Compounds of the general formula I.1 where
$R^3$=methyl
$R^4$=$CH_3$
$R^5$=1,2,4-triazol-3-yl
and the substituent $R^6$ for a compound corresponds to a line of Table A.

Table 314 (compounds 314.1–314.974)
Compounds of the general formula I.2 where
$R^3$=methyl
$R^4$=$CH_3$
$R^5$=1,2,4-triazol-3-yl
and the substituent $R^6$ for a compound corresponds to a line of Table A.

Table 315 (compounds 315.1–315.974)
Compounds of the general formula I.3 where
$R^3$=methyl
$R^4$=$CH_3$
$R^5$=1,2,4-triazol-3-yl
and the substituent $R^6$ for a compound corresponds to a line of Table A.

Table 316 (compounds 316.1–316.974)
Compounds of the general formula I.4 where
$R^3$=methyl
$R^4$=$CH_3$
$R^5$=1,2,4-triazol-3-yl
and the substituent $R^6$ for a compound corresponds to a line of Table A.

Table 317 (compounds 317.1–317.974)
Compounds of the general formula I.1 where
$R^3$=methyl
$R^4$=$CH_3$
$R^5$=pyrrol-2-yl
and the substituent $R^6$ for a compound corresponds to a line of Table A.

Table 318 (compounds 318.1–318.974)
Compounds of the general formula I.2 where
$R^3$=methyl
$R^4$=$CH_3$
$R^5$=pyrrol-2-yl
and the substituent $R^6$ for a compound corresponds to a line of Table A.

Table 319 (compounds 319.1–319.974)
Compounds of the general formula I.3 where
$R^3$=methyl
$R^4$=$CH_3$
$R^5$=pyrrol-2-yl
and the substituent $R^6$ for a compound corresponds to a line of Table A.

Table 320 (compounds 320.1–320.974)
Compounds of the general formula I.4 where
$R^3$=methyl
$R^4$=$CH_3$
$R^5$=pyrrol-2-yl
and the substituent $R^6$ for a compound corresponds to a line of Table A.

Table 321 (compounds 321.1–321.974)
Compounds of the general formula I.1 where
$R^3$=methyl
$R^4$=$C_2H_5$
$R^5$=H
and the substituent $R^6$ for a compound corresponds to a line of Table A.

Table 322 (compounds 322.1–322.974)
Compounds of the general formula I.2 where
$R^3$=methyl
$R^4$=$C_2H_5$
$R^5$=H
and the substituent $R^6$ for a compound corresponds to a line of Table A.

Table 323 (compounds 323.1–323.974)
Compounds of the general formula I.3 where
$R^3$=methyl
$R^4$=$C_2H_5$
$R^5$=H
and the substituent $R^6$ for a compound corresponds to a line of Table A.

Table 324 (compounds 324.1–324.974)
Compounds of the general formula I.4 where
$R^3$=methyl
$R^4$=$C_2H_5$
$R^5$=H
and the substituent $R^6$ for a compound corresponds to a line of Table A.

Table 325 (compounds 325.1–325.974)
Compounds of the general formula I.1 where
$R^3$=methyl
$R^4$=$C_2H_5$
$R^5$=$CH_3$
and the substituent $R^6$ for a compound corresponds to a line of Table A.

Table 326 (compounds 326.1–326.974)
Compounds of the general formula I.2 where
$R^3$=methyl
$R^4$=$C_2H_5$
$R^5$=$CH_3$
and the substituent $R^6$ for a compound corresponds to a line of Table A.

Table 327 (compounds 327.1–327.974)
Compounds of the general formula I.3 where
$R^3$=methyl
$R^4$=$C_2H_5$
$R^5$=$CH_3$
and the substituent $R^6$ for a compound corresponds to a line of Table A.

Table 328 (compounds 328.1–328.974)
Compounds of the general formula I.4 where
$R^3$=methyl
$R^4$=$C_2H_5$
$R^5$=$CH_3$
and the substituent R for a compound corresponds to a line of Table A.

Table 329 (compounds 329.1–329.974)
Compounds of the general formula I.1 where
$R^3$=methyl
$R^4$=$C_2H_5$
$R^5$=$C_2H_5$
and the substituent $R^6$ for a compound corresponds to a line of Table A.

Table 330 (compounds 330.1–330.974)
Compounds of the general formula I.2 where
$R^3$=methyl
$R^4$=$C_2H_5$
$R^5$=$C_2H_5$
and the substituent $R^6$ for a compound corresponds to a line of Table A.

Table 331 (compounds 331.1–331.974)
Compounds of the general formula I.3 where
$R^3$=methyl
$R^4$=$C_2H_5$
$R^5$=$C_2H_5$
and the substituent $R^6$ for a compound corresponds to a line of Table A.

Table 332 (compounds 332.1–332.974)
Compounds of the general formula I.4 where
$R^3$=methyl
$R^4$=$C_2H_5$
$R^5$=$C_2H_5$
and the substituent $R^6$ for a compound corresponds to a line of Table A.

Table 333 (compounds 333.1–333.974)
Compounds of the general formula I.1 where
$R^3$=methyl
$R^4$=$C_2H_5$
$R^5$=n-$C_3H_7$
and the substituent $R^6$ for a compound corresponds to a line of Table A.

Table 334 (compounds 334.1–334.974)
Compounds of the general formula I.2 where
$R^3$=methyl
$R^4$=$C_2H_5$
$R^5$=n-$C_3H_7$
and the substituent $R^6$ for a compound corresponds to a line of Table A.

Table 335 (compounds 335.1–335.974)
Compounds of the general formula I.3 where
$R^3$=methyl
$R^4$=$C_2H_5$
$R^5$=n-$C_3H_7$
and the substituent $R^6$ for a compound corresponds to a line of Table A.

Table 336 (compounds 336.1–336.974)
Compounds of the general formula I.4 where
$R^3$=methyl
$R^4$=$C_2H_5$
$R^5$=n-$C_3H_7$
and the substituent $R^6$ for a compound corresponds to a line of Table A.

Table 337 (compounds 337.1–337.974)
Compounds of the general formula I.1 where
$R^3$=methyl
$R^4$=$C_2H_5$
$R^5$=i-$C_3H_7$
and the substituent $R^6$ for a compound corresponds to a line of Table A.

Table 338 (compounds 338.1–338.974)
Compounds of the general formula I.2 where
$R^3$=methyl
$R^4$=$C_2H_5$
$R^5$=i-$C_3H_7$
and the substituent $R^6$ for a compound corresponds to a line of Table A.

Table 339 (compounds 339.1–339.974)
Compounds of the general formula I.3 where
$R^3$=methyl
$R^4$=$C_2H_5$
$R^5$=i-$C_3H_7$
and the substituent $R^6$ for a compound corresponds to a line of Table A.

Table 340 (compounds 340.1–340.974)
Compounds of the general formula I.4 where
$R^3$=methyl
$R^4$=$C_2H_5$
$R^5$=i-$C_3H_7$
and the substituent $R^6$ for a compound corresponds to a line of Table A.

Table 341 (compounds 341.1–341.974)
Compounds of the general formula I.1 where
$R^3$=methyl
$R^4$=$C_2H_5$
$R^5$=cyclopropyl
and the substituent $R^6$ for a compound corresponds to a line of Table A.

Table 342 (compounds 342.1–342.974)
Compounds of the general formula I.2 where
$R^3$=methyl
$R^4$=$C_2H_5$
$R^5$=cyclopropyl
and the substituent $R^6$ for a compound corresponds to a line of Table A.

Table 343 (compounds 343.1–343.974)
Compounds of the general formula I.3 where
$R^3$=methyl
$R^4$=$C_2H_5$
$R^5$=cyclopropyl
and the substituent $R^6$ for a compound corresponds to a line of Table A.

Table 344 (compounds 344.1–344.974)
Compounds of the general formula I.4 where
$R^3$=methyl
$R^4$=$C_2H_5$
$R^5$=cyclopropyl
and the substituent $R^6$ for a compound corresponds to a line of Table A.

Table 345 (compounds 345.1–345.974)
Compounds of the general formula I.1 where
$R^3$=methyl
$R^4$=$C_2H_5$
$R^5$=CN
and the substituent $R^6$ for a compound corresponds to a line of Table A.

Table 346 (compounds 346.1–346.974)
Compounds of the general formula I.2 where
$R^3$=methyl
$R^4$=$C_2H_5$
$R^5$=CN
and the substituent $R^6$ for a compound corresponds to a line of Table A.

Table 347 (compounds 347.1–347.974)
Compounds of the general formula I.3 where
$R^3$=methyl
$R^4$=$C_2H_5$
$R^5$=CN
and the substituent $R^6$ for a compound corresponds to a line of Table A.

Table 348 (compounds 348.1–348.974)
Compounds of the general formula I.4 where
$R^3$=methyl
$R^4$=$C_2H_5$
$R^5$=CN
and the substituent $R^6$ for a compound corresponds to a line of Table A.

Table 349 (compounds 349.1–349.974)
Compounds of the general formula I.1 where
$R^3$=methyl
$R^4$=$C_2H_5$
$R^5$=$C_6H_5$
and the substituent $R^6$ for a compound corresponds to a line of Table A.

Table 350 (compounds 350.1–350.974)
Compounds of the general formula I.2 where
$R^3$=methyl
$R^4$=$C_2H_5$
$R^5$=$C_6H_5$
and the substituent $R^6$ for a compound corresponds to a line of Table A.

Table 351 (compounds 351.1–351.974)
Compounds of the general formula I.3 where
$R^3$=methyl
$R^4$=$C_2H_5$
$R^5$=$C_6H_5$
and the substituent $R^6$ for a compound corresponds to a line of Table A.

Table 352 (compounds 352.1–352.974)
Compounds of the general formula I.4 where
$R^3$=methyl
$R^4$=$C_2H_5$
$R^5$=$C_6H_5$
and the substituent $R^6$ for a compound corresponds to a line of Table A.

Table 353 (compounds 353.1–353.974)
Compounds of the general formula I.1 where
$R^3$=methyl
$R^4$=$C_2H_5$
$R^5$=2-F—$C_6H_4$
and the substituent $R^6$ for a compound corresponds to a line of Table A.

Table 354 (compounds 354.1–354.974)
Compounds of the general formula I.2 where
$R^3$=methyl
$R^4$=$C_2H_5$
$R^5$=2-F—$C_6H_4$
and the substituent $R^6$ for a compound corresponds to a line of Table A.

Table 355 (compounds 355.1–355.974)
Compounds of the general formula I.3 where
$R^3$=methyl
$R^4$=$C_2H_5$
$R^5$=2-F—$C_6H_4$
and the substituent $R^6$ for a compound corresponds to a line of Table A.

Table 356 (compounds 356.1–356.974)
Compounds of the general formula I.4 where
$R^3$=methyl
$R^4$=$C_2H_5$
$R^5$=2-F—$C_6H_4$
and the substituent $R^6$ for a compound corresponds to a line of Table A.

Table 357 (compounds 357.1–357.974)
Compounds of the general formula I.1 where
$R^3$=methyl
$R^4$=$C_2H_5$
$R^5$=3-F—$C_6H_4$
and the substituent $R^6$ for a compound corresponds to a line of Table A.

Table 358 (compounds 358.1–358.974)
Compounds of the general formula I.2 where
$R^3$=methyl
$R^4$=$C_2H_5$
$R^5$=3-F—$C_6H_4$
and the substituent $R^6$ for a compound corresponds to a line of Table A.

Table 359 (compounds 359.1–359.974)
Compounds of the general formula I.3 where
$R^3$=methyl
$R^4$=$C_2H_5$
$R^5$=3-F—$C_6H_4$
and the substituent $R^6$ for a compound corresponds to a line of Table A.

Table 360 (compounds 360.1–360.974)
Compounds of the general formula I.4 where
$R^3$=methyl
$R^4$=$C_2H_5$
$R^5$=3-F—$C_6H_4$
and the substituent $R^6$ for a compound corresponds to a line of Table A.

Table 361 (compounds 361.1–361.974)
Compounds of the general formula I.1 where
$R^3$=methyl
$R^4$=$C_2H_5$
$R^5$=4-F—$C_6H_4$
and the substituent $R^6$ for a compound corresponds to a line of Table A.

Table 362 (compounds 362.1–362.974)
Compounds of the general formula I.2 where
$R^3$=methyl
$R^4$=$C_2H_5$
$R^5$=4-F—$C_6H_4$
and the substituent $R^6$ for a compound corresponds to a line of Table A.

Table 363 (compounds 363.1–363.974)
Compounds of the general formula I.3 where
$R^3$=methyl
$R^4$=$C_2H_5$
$R^5$=4-F—$C_6H_4$
and the substituent $R^6$ for a compound corresponds to a line of Table A.

Table 364 (compounds 364.1–364.974)
Compounds of the general formula I.4 where
$R^3$=methyl
$R^4$=$C_2H_5$
$R^5$=4-F—$C_6H_4$
and the substituent $R^6$ for a compound corresponds to a line of Table A.

Table 365 (compounds 365.1–365.974)
Compounds of the general formula I.1 where
$R^3$=methyl
$R^4$=$C_2H_5$
$R^5$=2-Cl—$C_6H_4$
and the substituent $R^6$ for a compound corresponds to a line of Table A.

Table 366 (compounds 366.1–366.974)
Compounds of the general formula I.2 where
$R^3$=methyl
$R^4$=$C_2H_5$
$R^5$=2-Cl—$C_6H_4$
and the substituent $R^6$ for a compound corresponds to a line of Table A.

Table 367 (compounds 367.1–367.974)
Compounds of the general formula I.3 where
$R^3$=methyl
$R^4$=$C_2H_5$
$R^5$=2-Cl—$C_6H_4$
and the substituent $R^6$ for a compound corresponds to a line of Table A.

Table 368 (compounds 368.1–368.974)
Compounds of the general formula I.4 where
$R^3$=methyl
$R^4$=$C_2H_5$
$R^5$=2-Cl—$C_6H_4$
and the substituent $R^6$ for a compound corresponds to a line of Table A.

Table 369 (compounds 369.1–369.974)
Compounds of the general formula I.1 where
$R^3$=methyl
$R^4$=$C_2H_5$
$R^5$=3-Cl—$C_6H_4$
and the substituent $R^6$ for a compound corresponds to a line of Table A.

Table 370 (compounds 370.1–370.974)
Compounds of the general formula I.2 where
$R^3$=methyl
$R^4$=$C_2H_5$
$R^5$=3-Cl—$C_6H_4$
and the substituent $R^6$ for a compound corresponds to a line of Table A.

Table 371 (compounds 371.1–371.974)
Compounds of the general formula I.3 where
$R^3$=methyl
$R^4$=$C_2H_5$
$R^5$=3-Cl—$C_6H_4$
and the substituent $R^6$ for a compound corresponds to a line of Table A.

Table 372 (compounds 372.1–372.974)
    Compounds of the general formula I.4 where
    $R^3$=methyl
    $R^4$=$C_2H_5$
    $R^5$=3-Cl—$C_6H_4$
and the substituent $R^6$ for a compound corresponds to a line of Table A.

Table 373 (compounds 373.1–373.974)
    Compounds of the general formula I.1 where
    $R^3$=methyl
    $R^4$=$C_2H_5$
    $R^5$=4-Cl—$C_6H_4$
and the substituent $R^6$ for a compound corresponds to a line of Table A.

Table 374 (compounds 374.1–374.974)
    Compounds of the general formula I.2 where
    $R^3$=methyl
    $R^4$=$C_2H_5$
    $R^5$=4-Cl—$C_6H_4$
and the substituent $R^6$ for a compound corresponds to a line of Table A.

Table 375 (compounds 375.1–375.974)
    Compounds of the general formula I.3 where
    $R^3$=methyl
    $R^4$=$C_2H_5$
    $R^5$=4-Cl—$C_6H_4$
and the substituent $R^6$ for a compound corresponds to a line of Table A.

Table 376 (compounds 376.1–376.974)
    Compounds of the general formula I.4 where
    $R^3$=methyl
    $R^4$=$C_2H_5$
    $R^5$=4-Cl—$C_6H_4$
and the substituent $R^6$ for a compound corresponds to a line of Table A.

Table 377 (compounds 377.1–377.974)
    Compounds of the general formula I.1 where
    $R^3$=methyl
    $R^4$=$C_2H_5$
    $R^5$=2-Br—$C_6H_4$
and the substituent $R^6$ for a compound corresponds to a line of Table A.

Table 378 (compounds 378.1–378.974)
    Compounds of the general formula I.2 where
    $R^3$=methyl
    $R^4$=$C_2H_5$
    $R^5$=2-Br—$C_6H_4$
and the substituent $R^6$ for a compound corresponds to a line of Table A.

Table 379 (compounds 379.1–379.974)
    Compounds of the general formula I.3 where
    $R^3$=methyl
    $R^4$=$C_2H_5$
    $R^5$=2-Br—$C_6H_4$
and the substituent $R^6$ for a compound corresponds to a line of Table A.

Table 380 (compounds 380.1–380.974)
    Compounds of the general formula I.4 where
    $R^3$=methyl
    $R^4$=$C_2H_5$
    $R^5$=2-Br—$C_6H_4$
and the substituent $R^6$ for a compound corresponds to a line of Table A.

Table 381 (compounds 381.1–381.974)
    Compounds of the general formula I.1 where
    $R^3$=methyl
    $R^4$=$C_2H_5$
    $R^5$=3-Br—$C_6H_4$
and the substituent $R^6$ for a compound corresponds to a line of Table A.

Table 382 (compounds 382.1–382.974)
    Compounds of the general formula I.2 where
    $R^3$=methyl
    $R^4$=$C_2H_5$
    $R^5$=3-Br—$C_6H_4$
and the substituent $R^6$ for a compound corresponds to a line of Table A.

Table 383 (compounds 383.1–383.974)
    Compounds of the general formula I.3 where
    $R^3$=methyl
    $R^4$=$C_2H_5$
    $R^5$=3-Br—$C_6H_4$
and the substituent $R^6$ for a compound corresponds to a line of Table A.

Table 384 (compounds 384.1–384.974)
    Compounds of the general formula I.4 where
    $R^3$=methyl
    $R^4$=$C_2H_5$
    $R^5$=3-Br—$C_6H_4$
and the substituent $R^6$ for a compound corresponds to a line of Table A.

Table 385 (compounds 385.1–385.974)
    Compounds of the general formula I.1 where
    $R^3$=methyl
    $R^4$=$C_2H_5$
    $R^5$=4-Br—$C_6H_4$
and the substituent $R^6$ for a compound corresponds to a line of Table A.

Table 386 (compounds 386.1–386.974)
    Compounds of the general formula I.2 where
    $R^3$=methyl
    $R^4$=$C_2H_5$
    $R^5$=4-Br—$C_6H_4$
and the substituent $R^6$ for a compound corresponds to a line of Table A.

Table 387 (compounds 387.1–387.974)
    Compounds of the general formula I.3 where
    $R^3$=methyl
    $R^4$=$C_2H_5$
    $R^5$=4-Br—$C_6H_4$
and the substituent $R^6$ for a compound corresponds to a line of Table A.

Table 388 (compounds 388.1–388.974)
    Compounds of the general formula I.4 where
    $R^3$=methyl
    $R^4$=$C_2H_5$
    $R^5$=4-Br—$C_6H_4$
and the substituent $R^6$ for a compound corresponds to a line of Table A.

Table 389 (compounds 389.1–389.974)
    Compounds of the general formula I.1 where
    $R^3$=methyl
    $R^4$=$C_2H_5$
    $R^5$=2,3-$F_2$—$C_6H_3$
and the substituent $R^6$ for a compound corresponds to a line of Table A.

Table 390 (compounds 390.1–390.974)
Compounds of the general formula I.2 where
$R^3$=methyl
$R^4$=$C_2H_5$
$R^5$=2,3-$F_2$—$C_6H_3$
and the substituent $R^6$ for a compound corresponds to a line of Table A.

Table 391 (compounds 391.1–391.974)
Compounds of the general formula I.3 where
$R^3$=methyl
$R^4$=$C_2H_5$
$R^5$=2,3-$F_2$—$C_6H_3$
and the substituent $R^6$ for a compound corresponds to a line of Table A.

Table 392 (compounds 392.1–393.974 [sic])
Compounds of the general formula I.4 where
$R^3$=methyl
$R^4$=$C_2H_5$
$R^5$=2,3-$F_2$—$C_6H_3$
and the substituent $R^6$ for a compound corresponds to a line of Table A.

Table 393 (compounds 393.1–393.974)
Compounds of the general formula I.1 where
$R^3$=methyl
$R^4$=$C_2H_5$
$R^5$=2,4-$F_2$—$C_6H_3$
and the substituent $R^6$ for a compound corresponds to a line of Table A.

Table 394 (compounds 394.1–394.974)
Compounds of the general formula I.2 where
$R^3$=methyl
$R^4$=$C_2H_5$
$R^5$=2,4-$F_2$—$C_6H_3$
and the substituent $R^6$ for a compound corresponds to a line of Table A.

Table 395 (compounds 395.1–395.974)
Compounds of the general formula I.3 where
$R^3$=methyl
$R^4$=$C_2H_5$
$R^5$=2,4-$F_2$—$C_6H_3$
and the substituent $R^6$ for a compound corresponds to a line of Table A.

Table 396 (compounds 396.1–396.974)
Compounds of the general formula I.4 where
$R^3$=methyl
$R^4$=$C_2H_5$
$R^5$=2,4-$F_2$—$C_6H_3$
and the substituent $R^6$ for a compound corresponds to a line of Table A.

Table 397 (compounds 397.1–397.974)
Compounds of the general formula I.1 where
$R^3$=methyl
$R^4$=$C_2H_5$
$R^5$=2,5-$F_2$—$C_6H_3$
and the substituent $R^6$ for a compound corresponds to a line of Table A.

Table 398 (compounds 398.1–398.974)
Compounds of the general formula I.2 where
$R^3$=methyl
$R^4$=$C_2H_5$
$R^5$=2,5-$F_2$—$C_6H_3$
and the substituent $R^6$ for a compound corresponds to a line of Table A.

Table 399 (compounds 399.1–399.974)
Compounds of the general formula I.3 where
$R^3$=methyl
$R^4$=$C_2H_5$
$R^5$=2,5-$F_2$—$C_6H_3$
and the substituent $R^6$ for a compound corresponds to a line of Table A.

Table 400 (compounds 400.1–400.974)
Compounds of the general formula I.4 where
$R^3$=methyl
$R^4$=$C_2H_5$
$R^5$=2,5-$F_2$—$C_6H_3$
and the substituent $R^6$ for a compound corresponds to a line of Table A.

Table 401 (compounds 401.1–401.974)
Compounds of the general formula I.1 where
$R^3$=methyl
$R^4$=$C_2H_5$
$R^5$=3,4-$F_2$—$C_6H_3$
and the substituent $R^6$ for a compound corresponds to a line of Table A.

Table 402 (compounds 402.1–402.974)
Compounds of the general formula I.2 where
$R^3$=methyl
$R^4$=$C_2H_5$
$R^5$=3,4-$F_2$—$C_6H_3$
and the substituent $R^6$ for a compound corresponds to a line of Table A.

Table 403 (compounds 403.1–403.974)
Compounds of the general formula I.3 where
$R^3$=methyl
$R^4$=$C_2H_5$
$R^5$=3,4-$F_2$—$C_6H_3$
and the substituent $R^6$ for a compound corresponds to a line of Table A.

Table 404 (compounds 404.1–404.974)
Compounds of the general formula I.4 where
$R^3$=methyl
$R^4$=$C_2H_5$
$R^5$=3,4-$F_2$—$C_6H_3$
and the substituent $R^6$ for a compound corresponds to a line of Table A.

Table 405 (compounds 405.1–405.974)
Compounds of the general formula I.1 where
$R^3$=methyl
$R^4$=$C_2H_5$
$R^5$=3,5-$F_2$—$C_6H_3$
and the substituent $R^6$ for a compound corresponds to a line of Table A.

Table 406 (compounds 406.1–406.974)
Compounds of the general formula I.2 where
$R^3$=methyl
$R^4$=$C_2H_5$
$R^5$=3,5-$F_2$—$C_6H_3$
and the substituent $R^6$ for a compound corresponds to a line of Table A.

Table 407 (compounds 407.1–407.974)
Compounds of the general formula I.3 where
$R^3$=methyl
$R^4$=$C_2H_5$
$R^5$=3,5-$F_2$—$C_6H_3$
and the substituent $R^6$ for a compound corresponds to a line of Table A.

Table 408 (compounds 408.1–408.974)
Compounds of the general formula I.4 where
$R^3$=methyl
$R^4$=$C_2H_5$
$R^5$=3,5-$F_2$—$C_6H_3$
and the substituent $R^6$ for a compound corresponds to a line of Table A.

Table 409 (compounds 409.1–409.974)
Compounds of the general formula I.1 where
$R^3$=methyl
$R^4$=$C_2H_5$
$R^5$=2,3-$Cl_2$—$C_6H_3$
and the substituent $R^6$ for a compound corresponds to a line of Table A.

Table 410 (compounds 410.1–410.974)
Compounds of the general formula I.2 where
$R^3$=methyl
$R^4$=$C_2H_5$
$R^5$=2,3-$Cl_2$—$C_6H_3$
and the substituent $R^6$ for a compound corresponds to a line of Table A.

Table 411 (compounds 411.1–411.974)
Compounds of the general formula I.3 where
$R^3$=methyl
$R^4$=$C_2H_5$
$R^5$=2,3-$Cl_2$—$C_6H_3$
and the substituent $R^6$ for a compound corresponds to a line of Table A.

Table 412 (compounds 412.1–412.974)
Compounds of the general formula I.4 where
$R^3$=methyl
$R^4$=$C_2H_5$
$R^5$=2,3-$Cl_2$—$C_6H_3$
and the substituent $R^6$ for a compound corresponds to a line of Table A.

Table 413 (compounds 413.1–413.974)
Compounds of the general formula I.1 where
$R^3$=methyl
$R^4$=$C_2H_5$
$R^5$=2,4-$Cl_2$—$C_6H_3$
and the substituent $R^6$ for a compound corresponds to a line of Table A.

Table 414 (compounds 414.1–414.974)
Compounds of the general formula I.2 where
$R^3$=methyl
$R^4$=$C_2H_5$
$R^5$=2,4-$Cl_2$—$C_6H_3$
and the substituent $R^6$ for a compound corresponds to a line of Table A.

Table 415 (compounds 415.1–415.974)
Compounds of the general formula I.3 where
$R^3$=methyl
$R^4$=$C_2H_5$
$R^5$=2,4-$Cl_2$—$C_6H_3$
and the substituent $R^6$ for a compound corresponds to a line of Table A.

Table 416 (compounds 416.1–416.974)
Compounds of the general formula I.4 where
$R^3$=methyl
$R^4$=$C_2H_5$
$R^5$=2,4-$Cl_2$—$C_6H_3$
and the substituent $R^6$ for a compound corresponds to a line of Table A.

Table 417 (compounds 417.1–417.974)
Compounds of the general formula I.1 where
$R^3$=methyl
$R^4$=$C_2H_5$
$R^5$=2,5-$Cl_2$—$C_6H_3$
and the substituent $R^6$ for a compound corresponds to a line of Table A.

Table 418 (compounds 418.1–418.974)
Compounds of the general formula I.2 where
$R^3$=methyl
$R^4$=$C_2H_5$
$R^5$=2,5-$Cl_2$—$C_6H_3$
and the substituent $R^6$ for a compound corresponds to a line of Table A.

Table 419 (compounds 419.1–419.974)
Compounds of the general formula I.3 where
$R^3$=methyl
$R^4$=$C_2H_5$
$R^5$=2,5-$Cl_2$—$C_6H_3$
and the substituent $R^6$ for a compound corresponds to a line of Table A.

Table 420 (compounds 420.1–420.974)
Compounds of the general formula I.4 where
$R^3$=methyl
$R^4$=$C_2H_5$
$R^5$=2,5-$Cl_2$—$C_6H_3$
and the substituent $R^6$ for a compound corresponds to a line of Table A.

Table 421 (compounds 421.1–421.974)
Compounds of the general formula I.1 where
$R^3$=methyl
$R^4$=$C_2H_5$
$R^5$=3,4-$Cl_2$—$C_6H_3$
and the substituent $R^6$ for a compound corresponds to a line of Table A.

Table 422 (compounds 422.1–422.974)
Compounds of the general formula I.2 where
$R^3$=methyl
$R^4$=$C_2H_5$
$R^5$=3,4-$Cl_2$—$C_6H_3$
and the substituent $R^6$ for a compound corresponds to a line of Table A.

Table 423 (compounds 423.1–423.974)
Compounds of the general formula I.3 where
$R^3$=methyl
$R^4$=$C_2H_5$
$R^5$=3,4-$Cl_2$—$C_6H_3$
and the substituent $R^6$ for a compound corresponds to a line of Table A.

Table 424 (compounds 424.1–424.974)
Compounds of the general formula I.4 where
$R^3$=methyl
$R^4$=$C_2H_5$
$R^5$=3,4-$Cl_2$—$C_6H_3$
and the substituent $R^6$ for a compound corresponds to a line of Table A.

Table 425 (compounds 425.1–425.974)
Compounds of the general formula I.1 where
$R^3$=methyl
$R^4$=$C_2H_5$
$R^5$=3,5-$Cl_2$—$C_6H_3$
and the substituent $R^6$ for a compound corresponds to a line of Table A.

Table 426 (compounds 426.1–426.974)
Compounds of the general formula I.2 where
$R^3$=methyl
$R^4$=$C_2H_5$
$R^5$=3,5-$Cl_2$—$C_6H_3$
and the substituent $R^6$ for a compound corresponds to a line of Table A.

Table 427 (compounds 427.1–427.974)
Compounds of the general formula I.3 where
$R^3$=methyl
$R^4$=$C_2H_5$
$R^5$=3,5-$Cl_2$—$C_6H_3$
and the substituent $R^6$ for a compound corresponds to a line of Table A.

Table 428 (compounds 428.1–428.974)
Compounds of the general formula I.4 where
$R^3$=methyl
$R^4$=$C_2H_5$
$R^5$=3,5-$Cl_2$—$C_6H_3$
and the substituent $R^6$ for a compound corresponds to a line of Table A.

Table 429 (compounds 429.1–429.974)
Compounds of the general formula I.1 where
$R^3$=methyl
$R^4$=$C_2H_5$
$R^5$=2-F; 3-Cl—$C_6H_3$
and the substituent $R^6$ for a compound corresponds to a line of Table A.

Table 430 (compounds 430.1–430.974)
Compounds of the general formula I.2 where
$R^3$=methyl
$R^4$=$C_2H_5$
$R^5$=2-F; 3-Cl—$C_6H_3$
and the substituent $R^6$ for a compound corresponds to a line of Table A.

Table 431 (compounds 431.1–431.974)
Compounds of the general formula I.3 where
$R^3$=methyl
$R^4$=$C_2H_5$
$R^5$=2-F; 3-Cl—$C_6H_3$
and the substituent $R^6$ for a compound corresponds to a line of Table A.

Table 432 (compounds 432.1–432.974)
Compounds of the general formula I.4 where
$R^3$=methyl
$R^4$=$C_2H_5$
$R^5$=2-F; 3-Cl—$C_6H_3$
and the substituent $R^6$ for a compound corresponds to a line of Table A.

Table 433 (compounds 433.1–433.974)
Compounds of the general formula I.1 where
$R^3$=methyl
$R^4$=$C_2H_5$
$R^5$=2-F; 4-Cl—$C_6H_3$
and the substituent $R^6$ for a compound corresponds to a line of Table A.

Table 434 (compounds 434.1–434.974)
Compounds of the general formula I.2 where
$R^3$=methyl
$R^4$=$C_2H_5$
$R^5$=2-F; 4-Cl—$C_6H_3$
and the substituent $R^6$ for a compound corresponds to a line of Table A.

Table 435 (compounds 435.1–435.974)
Compounds of the general formula I.3 where
$R^3$=methyl
$R^4$=$C_2H_5$
$R^5$=2-F; 4-Cl—$C_6H_3$
and the substituent $R^6$ for a compound corresponds to a line of Table A.

Table 436 (compounds 436.1–436.974)
Compounds of the general formula I.4 where
$R^3$=methyl
$R^4$=$C_2H_5$
$R^5$=2-F; 4-Cl—$C_6H_3$
and the substituent $R^6$ for a compound corresponds to a line of Table A.

Table 437 (compounds 437.1–437.974)
Compounds of the general formula I.1 where
$R^3$=methyl
$R^4$=$C_2H_5$
$R^5$=3-F; 4-Cl—$C_6H_3$
and the substituent $R^6$ for a compound corresponds to a line of Table A.

Table 438 (compounds 438.1–438.974)
Compounds of the general formula I.2 where
$R^3$=methyl
$R^4$=$C_2H_5$
$R^5$=3-F; 4-Cl—$C_6H_3$
and the substituent $R^6$ for a compound corresponds to a line of Table A.

Table 439 (compounds 439.1–439.974)
Compounds of the general formula I.3 where
$R^3$=methyl
$R^4$=$C_2H_5$
$R^5$=3-F; 4-Cl—$C_6H_3$
and the substituent $R^6$ for a compound corresponds to a line of Table A.

Table 440 (compounds 440.1–440.974)
Compounds of the general formula I.4 where
$R^3$=methyl
$R^4$=$C_2H_5$
$R^5$=3-F; 4-Cl—$C_6H_3$
and the substituent $R^6$ for a compound corresponds to a line of Table A.

Table 441 (compounds 441.1–441.974)
Compounds of the general formula I.1 where
$R^3$=methyl
$R^4$=$C_2H_5$
$R^5$=4-F; 3,5-$Cl_2$—$C_6H_2$
and the substituent $R^6$ for a compound corresponds to a line of Table A.

Table 442 (compounds 442.1–442.974)
Compounds of the general formula I.2 where
$R^3$=methyl
$R^4$=$C_2H_5$
$R^5$=4-F; 3,5-$Cl_2$—$C_6H_2$
and the substituent $R^6$ for a compound corresponds to a line of Table A.

Table 443 (compounds 443.1–443.974)
Compounds of the general formula I.3 where
$R^3$=methyl
$R^4$=$C_2H_5$
$R^5$=4-F; 3,5-$Cl_2$—$C_6H_2$
and the substituent $R^6$ for a compound corresponds to a line of Table A.

Table 444 (compounds 444.1–444.974)
Compounds of the general formula I.4 where
$R^3$=methyl
$R^4$=$C_2H_5$
$R^5$=4-F; 3,5-$Cl_2$—$C_6H_2$
and the substituent $R^6$ for a compound corresponds to a line of Table A.

Table 445 (compounds 445.1–445.974)
Compounds of the general formula I.1 where
$R^3$=methyl
$R^4$=$C_2H_5$
$R^5$=2,3,4-$Cl_3$—$C_6H_2$
and the substituent $R^6$ for a compound corresponds to a line of Table A.

Table 446 (compounds 446.1–446.974)
Compounds of the general formula I.2 where
$R^3$=methyl
$R^4$=$C_2H_5$
$R^5$=2,3,4-$Cl_3$—$C_6H_2$
and the substituent $R^6$ for a compound corresponds to a line of Table A.

Table 447 (compounds 447.1–447.974)
Compounds of the general formula I.3 where
$R^3$=methyl
$R^4$=$C_2H_5$
$R^5$=2,3,4-$Cl_3$—$C_6H_2$
and the substituent $R^6$ for a compound corresponds to a line of Table A.

Table 448 (compounds 448.1–448.974)
Compounds of the general formula I.4 where
$R^3$=methyl
$R^4$=$C_2H_5$
$R^5$=2,3,4-$Cl_3$—$C_6H_2$
and the substituent $R^6$ for a compound corresponds to a line of Table A.

Table 449 (compounds 449.1–449.974)
Compounds of the general formula I.1 where
$R^3$=methyl
$R^4$=$C_2H_5$
$R^5$=2,3,5-$Cl_3$—$C_6H_2$
and the substituent $R^6$ for a compound corresponds to a line of Table A.

Table 450 (compounds 450.1–450.974)
Compounds of the general formula I.2 where
$R^3$=methyl
$R^4$=$C_2H_5$
$R^5$=2,3,5-$Cl_3$—$C_6H_2$
and the substituent $R^6$ for a compound corresponds to a line of Table A.

Table 451 (compounds 451.1–451.974)
Compounds of the general formula I.3 where
$R^3$=methyl
$R^4$=$C_2H_5$
$R^5$=2,3,5-$Cl_3$—$C_6H_2$
and the substituent $R^6$ for a compound corresponds to a line of Table A.

Table 452 (compounds 452.1–452.974)
Compounds of the general formula I.4 where
$R^3$=methyl
$R^4$=$C_2H_5$
$R^5$=2,3,5-$Cl_3$—$C_6H_2$
and the substituent $R^6$ for a compound corresponds to a line of Table A.

Table 453 (compounds 453.1–453.974)
Compounds of the general formula I.1 where
$R^3$=methyl
$R^4$=$C_2H_5$
$R^5$=2,4,5-$Cl_3$—$C_6H_2$
and the substituent $R^6$ for a compound corresponds to a line of Table A.

Table 454 (compounds 454.1–454.974)
Compounds of the general formula I.2 where
$R^3$=methyl
$R^4$=$C_2H_5$
$R^5$=2,4,5-$Cl_3$—$C_6H_2$
and the substituent $R^6$ for a compound corresponds to a line of Table A.

Table 455 (compounds 455.1–455.974)
Compounds of the general formula I.3 where
$R^3$=methyl
$R^4$=$C_2H_5$
$R^5$=2,4,5-$Cl_3$—$C_6H_2$
and the substituent $R^6$ for a compound corresponds to a line of Table A.

Table 456 (compounds 456.1–456.974)
Compounds of the general formula I.4 where
$R^3$=methyl
$R^4$=$C_2H_5$
$R^5$=2,4,5-$Cl_3$—$C_6H_2$
and the substituent $R^6$ for a compound corresponds to a line of Table A.

Table 457 (compounds 457.1–457.974)
Compounds of the general formula I.1 where
$R^3$=methyl
$R^4$=$C_2H_5$
$R^5$=2-CN—$C_6H_4$
and the substituent $R^6$ for a compound corresponds to a line of Table A.

Table 458 (compounds 458.1–458.974)
Compounds of the general formula I.2 where
$R^3$=methyl
$R^4$=$C_2H_5$
$R^5$=2-CN—$C_6H_4$
and the substituent $R^6$ for a compound corresponds to a line of Table A.

Table 459 (compounds 459.1–459.974)
Compounds of the general formula I.3 where
$R^3$=methyl
$R^4$=$C_2H_5$
$R^5$=2-CN—$C_6H_4$
and the substituent $R^6$ for a compound corresponds to a line of Table A.

Table 460 (compounds 460.1–460.974)
Compounds of the general formula I.4 where
$R^3$=methyl
$R^4$=$C_2H_5$
$R^5$=2-CN—$C_6H_4$
and the substituent $R^6$ for a compound corresponds to a line of Table A.

Table 461 (compounds 461.1–461.974)
Compounds of the general formula I.1 where
$R^3$=methyl
$R^4$=$C_2H_5$
$R^5$=3-CN—$C_6H_4$
and the substituent $R^6$ for a compound corresponds to a line of Table A.

Table 462 (compounds 462.1–462.974)
Compounds of the general formula I.2 where
$R^3$=methyl
$R^4=C_2H_5$
$R^5$=3-CN—$C_6H_4$
and the substituent $R^6$ for a compound corresponds to a line of Table A.

Table 463 (compounds 463.1–463.974)
Compounds of the general formula I.3 where
$R^3$=methyl
$R^4=C_2H_5$
$R^5$=3-CN—$C_6H_4$
and the substituent $R^6$ for a compound corresponds to a line of Table A.

Table 464 (compounds 464.1–464.974)
Compounds of the general formula I.4 where
$R^3$=methyl
$R^4=C_2H_5$
$R^5$=3-CN—$C_6H_4$
and the substituent $R^6$ for a compound corresponds to a line of Table A.

Table 465 (compounds 465.1–465.974)
Compounds of the general formula I.1 where
$R^3$=methyl
$R^4=C_2H_5$
$R^5$=4-CN—$C_6H_4$
and the substituent $R^6$ for a compound corresponds to a line of Table A.

Table 466 (compounds 466.1–466.974)
Compounds of the general formula I.2 where
$R^3$=methyl
$R^4=C_2H_5$
$R^5$=4-CN—$C_6H_4$
and the substituent $R^6$ for a compound corresponds to a line of Table A.

Table 467 (compounds 467.1–467.974)
Compounds of the general formula I.3 where
$R^3$=methyl
$R^4=C_2H_5$
$R^5$=4-CN—$C_6H_4$
and the substituent $R^6$ for a compound corresponds to a line of Table A.

Table 468 (compounds 468.1–468.974)
Compounds of the general formula I.4 where
$R^3$=methyl
$R^4=C_2H_5$
$R^5$=4-CN—$C_6H_4$
and the substituent $R^6$ for a compound corresponds to a line of Table A.

Table 469 (compounds 469.1–469.974)
Compounds of the general formula I.1 where
$R^3$=methyl
$R^4=C_2H_5$
$R^5$=2-$NO_2$—$C_6H_4$
and the substituent $R^6$ for a compound corresponds to a line of Table A.

Table 470 (compounds 470.1–470.974)
Compounds of the general formula I.2 where
$R^3$=methyl
$R^4=C_2H_5$
$R^5$=2-$NO_2$—$C_6H_4$
and the substituent $R^6$ for a compound corresponds to a line of Table A.

Table 471 (compounds 471.1–471.974)
Compounds of the general formula I.3 where
$R^3$=methyl
$R^4=C_2H_5$
$R^5$=2-$NO_2$—$C_6H_4$
and the substituent $R^6$ for a compound corresponds to a line of Table A.

Table 472 (compounds 472.1–472.974)
Compounds of the general formula I.4 where
$R^3$=methyl
$R^4=C_2H_5$
$R^5$=2-$NO_2$—$C_6H_4$
and the substituent $R^6$ for a compound corresponds to a line of Table A.

Table 473 (compounds 473.1–473.974)
Compounds of the general formula I.1 where
$R^3$=methyl
$R^4=C_2H_5$
$R^5$=3-$NO_2$—$C_6H_4$
and the substituent $R^6$ for a compound corresponds to a line of Table A.

Table 474 (compounds 474.1–474.974)
Compounds of the general formula I.2 where
$R^3$=methyl
$R^4=C_2H_5$
$R^5$=3-$NO_2$—$C_6H_4$
and the substituent $R^6$ for a compound corresponds to a line of Table A.

Table 475 (compounds 475.1–475.974)
Compounds of the general formula I.3 where
$R^3$=methyl
$R^4=C_2HS$
$R^5$=3-$NO_2$—$C_6H_4$
and the substituent $R^6$ for a compound corresponds to a line of Table A.

Table 476 (compounds 476.1–476.974)
Compounds of the general formula I.4 where
$R^3$=methyl
$R^4=C_2H_5$
$R^5$=3-$NO_2$—$C_6H_4$
and the substituent $R^6$ for a compound corresponds to a line of Table A.

Table 477 (compounds 477.1–477.974)
Compounds of the general formula I.1 where
$R^3$=methyl
$R^4=C_2H_5$
$R^5$=4-$NO_2$—$C_6H_4$
and the substituent $R^6$ for a compound corresponds to a line of Table A.

Table 478 (compounds 478.1–478.974)
Compounds of the general formula I.2 where
$R^3$=methyl
$R^4=C_2H_5$
$R^5$=4-$NO_2$—$C_6H_4$
and the substituent $R^6$ for a compound corresponds to a line of Table A.

Table 479 (compounds 479.1–479.974)
Compounds of the general formula I.3 where
$R^3$=methyl
$R^4=C_2H_5$
$R^5$=4-$NO_2$—$C_6H_4$
and the substituent $R^6$ for a compound corresponds to a line of Table A.

Table 480 (compounds 480.1–480.974)
Compounds of the general formula I.4 where
$R^3$=methyl
$R^4$=$C_2H_5$
$R^5$=4-$NO_2$—$C_6H_4$
and the substituent $R^6$ for a compound corresponds to a line of Table A.

Table 481 (compounds 481.1–481.974)
Compounds of the general formula I.1 where
$R^3$=methyl
$R^4$=$C_2H_5$
$R^5$=2-$CH_3$—$C_6H_4$
and the substituent $R^6$ for a compound corresponds to a line of Table A.

Table 482 (compounds 482.1–482.974)
Compounds of the general formula I.2 where
$R^3$=methyl
$R^4$=$C_2H_5$
$R^5$=2-$CH_3$—$C_6H_4$
and the substituent $R^6$ for a compound corresponds to a line of Table A.

Table 483 (compounds 483.1–483.974)
Compounds of the general formula I.3 where
$R^3$=methyl
$R^4$=$C_2H_5$
$R^5$=2-$CH_3$—$C_6H_4$
and the substituent $R^6$ for a compound corresponds to a line of Table A.

Table 484 (compounds 484.1–484.974)
Compounds of the general formula I.4 where
$R^3$=methyl
$R^4$=$C_2H_5$
$R^5$=2-$CH_3$—$C_6H_4$
and the substituent $R^6$ for a compound corresponds to a line of Table A.

Table 485 (compounds 485.1–485.974)
Compounds of the general formula I.1 where
$R^3$=methyl
$R^4$=$C_2H_5$
$R^5$=3-$CH_3$—$C_6H_4$
and the substituent $R^6$ for a compound corresponds to a line of Table A.

Table 486 (compounds 486.1–486.974)
Compounds of the general formula I.2 where
$R^3$=methyl
$R^4$=$C_2H_5$
$R^5$=3-$CH_3$—$C_6H_4$
and the substituent $R^6$ for a compound corresponds to a line of Table A.

Table 487 (compounds 487.1–487.974)
Compounds of the general formula I.3 where
$R^3$=methyl
$R^4$=$C_2H_5$
$R^5$=3-$CH_3$—$C_6H_4$
and the substituent $R^6$ for a compound corresponds to a line of Table A.

Table 488 (compounds 488.1–488.974)
Compounds of the general formula I.4 where
$R^3$=methyl
$R^4$=$C_2H_5$
$R^5$=3-$CH_3$—$C_6H_4$
and the substituent $R^6$ for a compound corresponds to a line of Table A.

Table 489 (compounds 489.1–489.974)
Compounds of the general formula I.1 where
$R^3$=methyl
$R^4$=$C_2H_5$
$R^5$=4-$CH_3$—$C_6H_4$
and the substituent $R^6$ for a compound corresponds to a line of Table A.

Table 490 (compounds 490.1–490.974)
Compounds of the general formula I.2 where
$R^3$=methyl
$R^4$=$C_2H_5$
$R^5$=4-$CH_3$—$C_6H_4$
and the substituent $R^6$ for a compound corresponds to a line of Table A.

Table 491 (compounds 491.1–491.974)
Compounds of the general formula I.3 where
$R^3$=methyl
$R^4$=$C_2H_5$
$R^5$=4-$CH_3$—$C_6H_4$
and the substituent $R^6$ for a compound corresponds to a line of Table A.

Table 492 (compounds 492.1–492.974)
Compounds of the general formula I.4 where
$R^3$=methyl
$R^4$=$C_2H_5$
$R^5$=4-$CH_3$—$C_6H_4$
and the substituent $R^6$ for a compound corresponds to a line of Table A.

Table 493 (compounds 493.1–493.974)
Compounds of the general formula I.1 where
$R^3$=methyl
$R^4$=$C_2H_5$
$R^5$=2,4-$(CH_3)_2$—$C_6H_3$
and the substituent $R^6$ for a compound corresponds to a line of Table A.

Table 494 (compounds 494.1–494.974)
Compounds of the general formula I.2 where
$R^3$=methyl
$R^4$=$C_2H_5$
$R^5$=2,4-$(CH_3)_2$—$C_6H_3$
and the substituent $R^6$ for a compound corresponds to a line of Table A.

Table 495 (compounds 495.1–495.974)
Compounds of the general formula I.3 where
$R^3$=methyl
$R^4$=$C_2H_5$
$R^5$=2,4-$(CH_3)_2$—$C_6H_3$
and the substituent $R^6$ for a compound corresponds to a line of Table A.

Table 496 (compounds 496.1–496.974)
Compounds of the general formula I.4 where
$R^3$=methyl
$R^4$=$C_2H_5$
$R^5$=2,4-$(CH_3)_2$—$C_6H_3$
and the substituent $R^6$ for a compound corresponds to a line of Table A.

Table 497 (compounds 497.1–497.974)
Compounds of the general formula I.1 where
$R^3$=methyl
$R^4$=$C_2H_5$
$R^5$=2,5-$(CH_3)_2$—$C_6H_3$
and the substituent $R^6$ for a compound corresponds to a line of Table A.

Table 498 (compounds 498.1–498.974)
Compounds of the general formula I.2 where
$R^3$=methyl
$R^4$=$C_2H_5$
$R^5$=2,5-$(CH_3)_2$—$C_6H_3$
and the substituent $R^6$ for a compound corresponds to a line of Table A.

Table 499 (compounds 499.1–179.974)
Compounds of the general formula I.3 where
$R^3$=methyl
$R^4$=$C_2H_5$
$R^5$=2,5-$(CH_3)_2$—$C_6H_3$
and the substituent $R^6$ for a compound corresponds to a line of Table A.

Table 500 (compounds 500.1–500.974)
Compounds of the general formula I.4 where
$R^3$=methyl
$R^4$=$C_2H_5$
$R^5$=2,5-$(CH_3)_2$—$C_6H_3$
and the substituent $R^6$ for a compound corresponds to a line of Table A.

Table 501 (compounds 501.1–501.974)
Compounds of the general formula I.1 where
$R^3$=methyl
$R^4$=$C_2H_5$
$R^5$=3,4-$(CH_3)_2$—$C_6H_3$
and the substituent $R^6$ for a compound corresponds to a line of Table A.

Table 502 (compounds 502.1–502.974)
Compounds of the general formula I.2 where
$R^3$=methyl
$R^4$=$C_2H_5$
$R^5$=3,4-$(CH_3)_2$—$C_6H_3$
and the substituent $R^6$ for a compound corresponds to a line of Table A.

Table 503 (compounds 503.1–503.974)
Compounds of the general formula I.3 where
$R^3$=methyl
$R^4$=$C_2H_5$
$R^5$=3,4-$(CH_3)_2$—$C_6H_3$
and the substituent $R^6$ for a compound corresponds to a line of Table A.

Table 504 (compounds 504.1–504.974)
Compounds of the general formula I.4 where
$R^3$=methyl
$R^4$=$C_2H_5$
$R^5$=3,4-$(CH_3)_2$—$C_6H_3$
and the substituent $R^6$ for a compound corresponds to a line of Table A.

Table 505 (compounds 505.1–505.974)
Compounds of the general formula I.1 where
$R^3$=methyl
$R^4$=$C_2H_5$
$R^5$=3,5-$(CH_3)_2$—$C_6H_3$
and the substituent $R^6$ for a compound corresponds to a line of Table A.

Table 506 (compounds 506.1–506.974)
Compounds of the general formula I.2 where
$R^3$=methyl
$R^4$=$C_2H_5$
$R^5$=3,5-$(CH_3)_2$—$C_6H_3$
and the substituent $R^6$ for a compound corresponds to a line of Table A.

Table 507 (compounds 507.1–507.974)
Compounds of the general formula I.3 where
$R^3$=methyl
$R^4$=$C_2H_5$
$R^5$=3,5-$(CH_3)_2$—$C_6H_3$
and the substituent $R^6$ for a compound corresponds to a line of Table A.

Table 508 (compounds 508.1–508.974)
Compounds of the general formula I.4 where
$R^3$=methyl
$R^4$=$C_2H_5$
$R^5$=3,5-$(CH_3)_2$—$C_6H_3$
and the substituent $R^6$ for a compound corresponds to a line of Table A.

Table 509 (compounds 509.1–509.974)
Compounds of the general formula I.1 where
$R^3$=methyl
$R^4$=$C_2H_5$
$R^5$=3,4,5-$(CH_3)_3$—$C_6H_2$
and the substituent $R^6$ for a compound corresponds to a line of Table A.

Table 510 (compounds 510.1–510.974)
Compounds of the general formula I.2 where
$R^3$=methyl
$R^4$=$C_2H_5$
$R^5$=3,4,5-$(CH_3)_3$—$C_6H_2$
and the substituent $R^6$ for a compound corresponds to a line of Table A.

Table 511 (compounds 511.1–511.974)
Compounds of the general formula I.3 where
$R^3$=methyl
$R^4$=$C_2H_5$
$R^5$=3,4,5-$(CH_3)_3$—$C_6H_2$
and the substituent $R^6$ for a compound corresponds to a line of Table A.

Table 512 (compounds 512.1–512.974)
Compounds of the general formula I.4 where
$R^3$=methyl
$R^4$=$C_2H_5$
$R^5$=3,4,5-$(CH_3)_3$—$C_6H_2$
and the substituent $R^6$ for a compound corresponds to a line of Table A.

Table 513 (compounds 513.1–513.974)
Compounds of the general formula I.1 where
$R^3$=methyl
$R^4$=$C_2H_5$
$R^5$=4-$C_6H_5$—$C_6H_4$
and the substituent $R^6$ for a compound corresponds to a line of Table A.

Table 514 (compounds 514.1–514.974)
Compounds of the general formula I.2 where
$R^3$=methyl
$R^4$=$C_2H_5$
$R^5$=4-$C_6H_5$—$C_6H_4$
and the substituent $R^6$ for a compound corresponds to a line of Table A.

Table 515 (compounds 515.1–515.974)
Compounds of the general formula I.3 where
$R^3$=methyl
$R^4$=$C_2H_5$
$R^5$=4-$C_6H_5$—$C_6H_4$
and the substituent $R^6$ for a compound corresponds to a line of Table A.

Table 516 (compounds 516.1–516.974)
  Compounds of the general formula I.4 where
    $R^3$=methyl
    $R^4$=$C_2H_5$
    $R^5$=4-$C_6H_5$—$C_6H_4$
  and the substituent $R^6$ for a compound corresponds to a line of Table A.
Table 517 (compounds 517.1–517.974)
  Compounds of the general formula I.1 where
    $R^3$=methyl
    $R^4$=$C_2H_5$
    $R^5$=3-Cl-4-$CH_3$—$C_6H_3$
  and the substituent $R^6$ for a compound corresponds to a line of Table A.
Table 518 (compounds 518.1–518.974)
  Compounds of the general formula I.2 where
    $R^3$=methyl
    $R^4$=$C_2H_5$
    $R^5$=3-Cl-4-$CH_3$—$C_6H_3$
  and the substituent $R^6$ for a compound corresponds to a line of Table A.
Table 519 (compounds 519.1–519.974)
  Compounds of the general formula I.3 where
    $R^3$=methyl
    $R^4$=$C_2H5$
    $R^5$=3-Cl-4-$CH_3$—$C_6H_3$
  and the substituent $R^6$ for a compound corresponds to a line of Table A.
Table 520 (compounds 520.1–520.974)
  Compounds of the general formula I.4 where
    $R^3$=methyl
    $R^4$=$C_2H_5$
    $R^5$=3-Cl-4-$CH_3$—$C_6H_3$
  and the substituent $R^6$ for a compound corresponds to a line of Table A.
Table 521 (compounds 521.1–521.974)
  Compounds of the general formula I.1 where
    $R^3$=methyl
    $R^4$=$C_2H_5$
    $R^5$=2-$OCH_3$—$C_6H_4$
  and the substituent $R^6$ for a compound corresponds to a line of Table A.
Table 522 (compounds 522.1–522.974)
  Compounds of the general formula I.2 where
    $R^3$=methyl
    $R^4$=$C_2H_5$
    $R^5$=2-$OCH_3$—$C_6H_4$
  and the substituent $R^6$ for a compound corresponds to a line of Table A.
Table 523 (compounds 523.1–523.974)
  Compounds of the general formula I.3 where
    $R^3$=methyl
    $R^4$=$C_2H_5$
    $R^5$=2-$OCH_3$—$C_6H_4$
  and the substituent $R^6$ for a compound corresponds to a line of Table A.
Table 524 (compounds 524.1–524.974)
  Compounds of the general formula I.4 where
    $R^3$=methyl
    $R^4$=$C_2H_5$
    $R^5$=2-$OCH_3$—$C_6H_4$
  and the substituent $R^6$ for a compound corresponds to a line of Table A.
Table 525 (compounds 525.1–525.974)
  Compounds of the general formula I.1 where
    $R^3$=methyl
    $R^4$=$C_2H_5$
    $R^5$=3-$OCH_3$—$C_6H_4$
  and the substituent $R^6$ for a compound corresponds to a line of Table A.
Table 526 (compounds 526.1–520.974)
  Compounds of the general formula I.2 where
    $R^3$=methyl
    $R^4$=$C_2H_5$
    $R^5$=3-$OCH_3$—$C_6H_4$
  and the substituent $R^6$ for a compound corresponds to a line of Table A.
Table 527 (compounds 527.1–527.974)
  Compounds of the general formula I.3 where
    $R^3$=methyl
    $R^4$=$C_2H_5$
    $R^5$=3-$OCH_3$—$C_6H_4$
  and the substituent $R^6$ for a compound corresponds to a line of Table A.
Table 528 (compounds 528.1–528.974)
  Compounds of the general formula 528 [sic] I.4 where
    $R^3$=methyl
    $R^4$=$C_2H_5$
    $R^5$=3-$OCH_3$—$C_6H_4$
  and the substituent $R^6$ for a compound corresponds to a line of Table A.
Table 529 (compounds 529.1–529.974)
  Compounds of the general formula I.1 where
    $R^3$=methyl
    $R^4$=$C_2H_5$
    $R^5$=4-$OCH_3$—$C_6H_4$
  and the substituent $R^6$ for a compound corresponds to a line of Table A.
Table 530 (compounds 530.1–530.974)
  Compounds of the general formula I.2 where
    $R^3$=methyl
    $R^4$=$C_2H_5$
    $R^5$=4-$OCH_3$—$C_6H_4$
  and the substituent $R^6$ for a compound corresponds to a line of Table A.
Table 531 (compounds 531.1–531.974)
  Compounds of the general formula I.3 where
    $R^3$=methyl
    $R^4$=$C_2H_5$
    $R^5$=4-$OCH_3$—$C_6H_4$
  and the substituent $R^6$ for a compound corresponds to a line of Table A.
Table 532 (compounds 532.1–532.974)
  Compounds of the general formula I.4 where
    $R^3$=methyl
    $R^4$=$C_2H_5$
    $R^5$=4-$OCH_3$—$C_6H_4$
  and the substituent $R^6$ for a compound corresponds to a line of Table A.
Table 533 (compounds 533.1–533.974)
  Compounds of the general formula I.1 where
    $R^3$=methyl
    $R^4$=$C_2H_5$
    $R^5$=2-$OCF3$—$C6H4$ [sic]
  and the substituent $R^6$ for a compound corresponds to a line of Table A.

Table 534 (compounds 534.1–534.974)
   Compounds of the general formula I.2 where
   $R^3$=methyl
   $R^4$=$C_2H_5$
   $R^5$=2-OCF3—C6H4 [sic]
   and the substituent $R^6$ for a compound corresponds to a line of Table A.
Table 535 (compounds 535.1–535.974)
   Compounds of the general formula I.3 where
   $R^3$=methyl
   $R^4$=$C_2H_5$
   $R^5$=2-OCF3—C6H4 [sic]
   and the substituent $R^6$ for a compound corresponds to a line of Table A.
Table 536 (compounds 536.1–536.974)
   Compounds of the general formula I.4 where
   $R^3$=methyl
   $R^4$=$C_2H_5$
   $R^5$=2-OCF3—C6H4 [sic]
   and the substituent $R^6$ for a compound corresponds to a line of Table A.
Table 537 (compounds 537.1–537.974)
   Compounds of the general formula I.1 where
   $R^3$=methyl
   $R^4$=$C_2H_5$
   $R^5$=3-OCF$_3$—C$_6$H$_4$
   and the substituent $R^6$ for a compound corresponds to a line of Table A.
Table 538 (compounds 538.1–538.974)
   Compounds of the general formula I.2 where
   $R^3$=methyl
   $R^4$=$C_2H_5$
   $R^5$=2-OCF$_3$—C$_6$H$_4$
   and the substituent $R^6$ for a compound corresponds to a line of Table A.
Table 539 (compounds 539.1–539.974)
   Compounds of the general formula I.3 where
   $R^3$=methyl
   $R^4$=$C_2H_5$
   $R^5$=3-OCF$_3$—C$_6$H$_4$
   and the substituent $R^6$ for a compound corresponds to a line of Table A.
Table 540 (compounds 540.1–540.974)
   Compounds of the general formula I.4 where
   $R^3$=methyl
   $R^4$=$C_2H_5$
   $R^5$=3-OCF$_3$—C$_6$H$_4$
   and the substituent $R^6$ for a compound corresponds to a line of Table A.
Table 541 (compounds 541.1–541.974)
   Compounds of the general formula I.1 where
   $R^3$=methyl
   $R^4$=$C_2H_5$
   $R^5$=4-OCF$_3$—C$_6$H$_4$
   and the substituent $R^6$ for a compound corresponds to a line of Table A.
Table 542 (compounds 542.1–542.974)
   Compounds of the general formula I.2 where
   $R^3$=methyl
   $R^4$=$C_2H_5$
   $R^5$=4-OCF$_3$—C$_6$H$_4$
   and the substituent $R^6$ for a compound corresponds to a line of Table A.
Table 543 (compounds 543.1–543.974)
   Compounds of the general formula I.3 where
   $R^3$=methyl
   $R^4$=$C_2H_5$
   $R^5$=4-OCF$_3$—C$_6$H$_4$
   and the substituent $R^6$ for a compound corresponds to a line of Table A.
Table 544 (compounds 544.1–544.974)
   Compounds of the general formula I.4 where
   $R^3$=methyl
   $R^4$=$C_2H_5$
   $R^5$=4-OCF$_3$—C$_6$H$_4$
   and the substituent $R^6$ for a compound corresponds to a line of Table A.
Table 545 (compounds 545.1–545.974)
   Compounds of the general formula I.1 where
   $R^3$=methyl
   $R^4$=$C_2H_5$
   $R^5$=3-Cl; 4-OCH$_3$—C$_6$H$_3$
   and the substituent $R^6$ for a compound corresponds to a line of Table A.
Table 546 (compounds 546.1–546.974)
   Compounds of the general formula I.2 where
   $R^3$=methyl
   $R^4$=$C_2H_5$
   $R^5$=3-Cl; 4-OCH$_3$—C$_6$H$_3$
   and the substituent $R^6$ for a compound corresponds to a line of Table A.
Table 547 (compounds 547.1–547.974)
   Compounds of the general formula I.3 where
   $R^3$=methyl
   $R^4$=$C_2H_5$
   $R^5$=3-Cl; 4-OCH$_3$—C$_6$H$_3$
   and the substituent $R^6$ for a compound corresponds to a line of Table A.
Table 548 (compounds 548.1–548.974)
   Compounds of the general formula I.4 where
   $R^3$=methyl
   $R^4$=$C_2H_5$
   $R^5$=3-Cl; 4-OCH$_3$—C$_6$H$_3$
   and the substituent $R^6$ for a compound corresponds to a line of Table A.
Table 549 (compounds 549.1–549.974)
   Compounds of the general formula I.1 where
   $R^3$=methyl
   $R^4$=$C_2H_5$

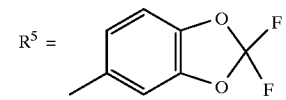

and the substituent $R^6$ for a compound corresponds to a line of Table A.

Table 550 (compounds 550.1–550.974)
  Compounds of the general formula I.2 where
  $R^3$=methyl
  $R^4$=$C_2H_5$

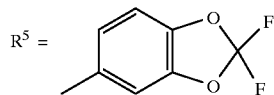
$R^5$ = and the substituent $R^6$ for a compound corresponds to a line of Table A.
Table 551 (compounds 551.1–551.974)
  Compounds of the general formula I.3 where
  $R^3$=methyl
  $R^4$=$C_2H_5$

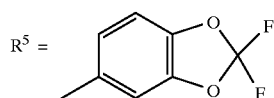
$R^5$ = and the substituent $R^6$ for a compound corresponds to a line of Table A.
Table 552 (compounds 552.1–552.974)
  Compounds of the general formula I.4 where
  $R^3$=methyl
  $R^4$=$C_2H_5$

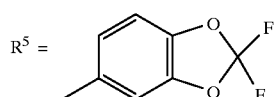
$R^5$ = and the substituent $R^6$ for a compound corresponds to a line of Table A.
Table 553 (compounds 553.1–553.974)
  Compounds of the general formula I.1 where
  $R^3$=methyl
  $R^4$=$C_2H_5$
  $R^5$=pyridin-2-yl
  and the substituent $R^6$ for a compound corresponds to a line of Table A.
Table 554 (compounds 554.1–554.974)
  Compounds of the general formula I.2 where
  $R^3$=methyl
  $R^4$=$C_2H_5$
  $R^5$=pyridin-2-yl
  and the substituent $R^6$ for a compound corresponds to a line of Table A.
Table 555 (compounds 555.1–555.974)
  Compounds of the general formula I.3 where
  $R^3$=methyl
  $R^4$=$C_2H_5$
  $R^5$=pyridin-2-yl
  and the substituent $R^6$ for a compound corresponds to a line of Table A.
Table 556 (compounds 556.1–556.974)
  Compounds of the general formula I.4 where
  $R^3$=methyl
  $R^4$=$C_2H_5$
  $R^5$=pyridin-2-yl
  and the substituent $R^6$ for a compound corresponds to a line of Table A.
Table 557 (compounds 557.1–557.974)
  Compounds of the general formula I.1 where
  $R^3$=methyl
  $R^4$=$C_2H_5$
  $R^5$=pyridin-3-yl
  and the substituent $R^6$ for a compound corresponds to a line of Table A.
Table 558 (compounds 558.1–558.974)
  Compounds of the general formula I.2 where
  $R^3$=methyl
  $R^4$=$C_2H_5$
  $R^5$=pyridin-3-yl
  and the substituent $R^6$ for a compound corresponds to a line of Table A.
Table 559 (compounds 559.1–559.974)
  Compounds of the general formula I.3 where
  $R^3$=methyl
  $R^4$=$C_2H_5$
  $R^5$=pyridin-3-yl
  and the substituent $R^6$ for a compound corresponds to a line of Table A.
Table 560 (compounds 560.1–560.974)
  Compounds of the general formula I.4 where
  $R^3$=methyl
  $R^4$=$C_2H_5$
  $R^5$=pyridin-3-yl
  and the substituent $R^6$ for a compound corresponds to a line of Table A.
Table 561 (compounds 561.1–561.974)
  Compounds of the general formula I.1 where
  $R^3$=methyl
  $R^4$=$C_2H_5$
  $R^5$=pyridin-4-yl
  and the substituent $R^6$ for a compound corresponds to a line of Table A.
Table 562 (compounds 562.1–562.974)
  Compounds of the general formula I.2 where
  $R^3$=methyl
  $R^4$=$C_2H_5$
  $R^5$=pyridin-4-yl
  and the substituent $R^6$ for a compound corresponds to a line of Table A.
Table 563 (compounds 563.1–563.974)
  Compounds of the general formula I.3 where
  $R^3$=methyl
  $R^4$=$C_2H_5$
  $R^5$=pyridin-4-yl
  and the substituent $R^6$ for a compound corresponds to a line of Table A.
Table 564 (compounds 564.1–564.974)
  Compounds of the general formula I.4 where
  $R^3$=methyl
  $R^4$=$C_2H_5$
  $R^5$=pyridin-4-yl
  and the substituent $R^6$ for a compound corresponds to a line of Table A.
Table 565 (compounds 565.1–565.974)
  Compounds of the general formula I.1 where
  $R^3$=methyl
  $R^4$=$C_2H_5$
  $R^5$=3-$CH_3$-pyridin-2-yl
  and the substituent $R^6$ for a compound corresponds to a line of Table A.

Table 566 (compounds 566.1–566.974)
  Compounds of the general formula I.2 where
  $R^3$=methyl
  $R^4$=$C_2H_5$
  $R^5$=3-$CH_3$-pyridin-2-yl
  and the substituent $R^6$ for a compound corresponds to a line of Table A.
Table 567 (compounds 567.1–567.974)
  Compounds of the general formula I.3 where
  $R^3$=methyl
  $R^4$=$C_2H_5$
  $R^5$=3-$CH_3$-pyridin-2-yl
  and the substituent $R^6$ for a compound corresponds to a line of Table A.
Table 568 (compounds 568.1–568.974)
  Compounds of the general formula I.4 where
  $R^3$=methyl
  $R^4$=$C_2H_5$
  $R^5$=3-$CH_3$-pyridin-2-yl
  and the substituent $R^6$ for a compound corresponds to a line of Table A.
Table 569 (compounds 569.1–569.974)
  Compounds of the general formula I.1 where
  $R^3$=methyl
  $R^4$=$C_2H_5$
  $R^5$=4-$CH_3$-pyridin-2-yl
  and the substituent $R^6$ for a compound corresponds to a line of Table A.
Table 570 (compounds 570.1–570.974)
  Compounds of the general formula I.2 where
  $R^3$=methyl
  $R^4$=$C_2H_5$
  $R^5$=4-$CH_3$-pyridin-2-yl
  and the substituent $R^6$ for a compound corresponds to a line of Table A.
Table 571 (compounds 571.1–571.974)
  Compounds of the general formula I.3 where
  $R^3$=methyl
  $R^4$=$C_2H_5$
  $R^5$=4-$CH_3$-pyridin-2-yl
  and the substituent $R^6$ for a compound corresponds to a line of Table A.
Table 572 (compounds 572.1–572.974)
  Compounds of the general formula I.4 where
  $R^3$=methyl
  $R^4$=$C_2H_5$
  $R^5$=4-$CH_3$-pyridin-2-yl
  and the substituent $R^6$ for a compound corresponds to a line of Table A.
Table 573 (compounds 573.1–573.974)
  Compounds of the general formula I.1 where
  $R^3$=methyl
  $R^4$=$C_2H_5$
  $R^5$=3-$OCH_3$-pyridin-2-yl
  and the substituent $R^6$ for a compound corresponds to a line of Table A.
Table 574 (compounds 574.1–574.974)
  Compounds of the general formula I.2 where
  $R^3$=methyl
  $R^4$=$C_2H_5$
  $R^5$=3-$OCH_3$-pyridin-2-yl
  and the substituent $R^6$ for a compound corresponds to a line of Table A.
Table 575 (compounds 575.1–575.974)
  Compounds of the general formula I.3 where
  $R^3$=methyl
  $R^4$=$C_2HS$
  $R^5$=3-$OCH_3$-pyridin-2-yl
  and the substituent $R^6$ for a compound corresponds to a line of Table A.
Table 576 (compounds 576.1–576.974)
  Compounds of the general formula I.4 where
  $R^3$=methyl
  $R^4$=$C_2H_5$
  $R^5$=3-$OCH_3$-pyridin-2-yl
  and the substituent $R^6$ for a compound corresponds to a line of Table A.
Table 577 (compounds 577.1–577.974)
  Compounds of the general formula I.1 where
  $R^3$=methyl
  $R^4$=$C_2H_5$
  $R^5$=4-Cl-pyridin-2-yl
  and the substituent $R^6$ for a compound corresponds to a line of Table A.
Table 578 (compounds 578.1–578.974)
  Compounds of the general formula I.2 where
  $R^3$=methyl
  $R^4$=$C_2H_5$
  $R^5$=4-Cl-pyridin-2-yl
  and the substituent $R^6$ for a compound corresponds to a line of Table A.
Table 579 (compounds 579.1–579.974)
  Compounds of the general formula I.3 where
  $R^3$=methyl
  $R^4$=$C_2H_5$
  $R^5$=4-Cl-pyridin-2-yl
  and the substituent $R^6$ for a compound corresponds to a line of Table A.
Table 580 (compounds 580.1–580.974)
  Compounds of the general formula I.4 where
  $R^3$=methyl
  $R^4$=$C_2H_5$
  $R^5$=4-Cl-pyridin-2-yl
  and the substituent $R^6$ for a compound corresponds to a line of Table A.
Table 581 (compounds 581.1–581.974)
  Compounds of the general formula I.1 where
  $R^3$=methyl
  $R^4$=$C_2H_5$
  $R^5$=5-Cl-pyridin-2-yl
  and the substituent $R^6$ for a compound corresponds to a line of Table A.
Table 582 (compounds 582.1–582.974)
  Compounds of the general formula I.2 where
  $R^3$=methyl
  $R^4$=$C_2H_5$
  $R^5$=5-Cl-pyridin-2-yl
  and the substituent $R^6$ for a compound corresponds to a line of Table A.
Table 583 (compounds 583.1–583.974)
  Compounds of the general formula I.3 where
  $R^3$=methyl
  $R^4$=$C_2H_5$
  $R^5$=5-Cl-pyridin-2-yl
  and the substituent $R^6$ for a compound corresponds to a line of Table A.

Table 584 (compounds 584.1–584.974)
Compounds of the general formula I.4 where
$R^3$=methyl
$R^4$=$C_2H_5$
$R^5$=5-Cl-pyridin-2-yl
and the substituent $R^6$ for a compound corresponds to a line of Table A.

Table 585 (compounds 585.1–585.974)
Compounds of the general formula I.1 where
$R^3$=methyl
$R^4$=$C_2H_5$
$R^5$=pyrimidin-2-yl
and the substituent $R^6$ for a compound corresponds to a line of Table A.

Table 586 (compounds 586.1–586.974)
Compounds of the general formula I.2 where
$R^3$=methyl
$R^4$=$C_2H_5$
$R^5$=pyrimidin-2-yl
and the substituent $R^6$ for a compound corresponds to a line of Table A.

Table 587 (compounds 587.1–587.974)
Compounds of the general formula I.3 where
$R^3$=methyl
$R^4$=$C_2H_5$
$R^5$=pyrimidin-2-yl
and the substituent $R^6$ for a compound corresponds to a line of Table A.

Table 588 (compounds 588.1–588.974)
Compounds of the general formula I.4 where
$R^3$=methyl
$R^4$=$C_2H_5$
$R^5$=pyrimidin-2-yl
and the substituent $R^6$ for a compound corresponds to a line of Table A.

Table 589 (compounds 589.1–589.974)
Compounds of the general formula I.1 where
$R^3$=methyl
$R^4$=$C_2H_5$
$R^5$=5-Cl-pyrimidin-2-yl
and the substituent $R^6$ for a compound corresponds to a line of Table A.

Table 590 (compounds 590.1–590.974)
Compounds of the general formula I.2 where
$R^3$=methyl
$R^4$=$C_2H_5$
$R^5$=5-Cl-pyrimidin-2-yl
and the substituent $R^6$ for a compound corresponds to a line of Table A.

Table 591 (compounds 591.1–591.974)
Compounds of the general formula I.3 where
$R^3$=methyl
$R^4$=$C_2H_5$
$R^5$=5-Cl-pyrimidin-2-yl
and the substituent $R^6$ for a compound corresponds to a line of Table A.

Table 592 (compounds 592.1–592.974)
Compounds of the general formula I.4 where
$R^3$=methyl
$R^4$=$C_2H_5$
$R^5$=5-Cl-pyrimidin-2-yl
and the substituent $R^6$ for a compound corresponds to a line of Table A.

Table 593 (compounds 593.1–583.974)
Compounds of the general formula I.1 where
$R^3$=methyl
$R^4$=$C_2H_5$
$R^5$=4-$CH_3$-pyrimidin-2-yl
and the substituent $R^6$ for a compound corresponds to a line of Table A.

Table 594 (compounds 594.1–594.974)
Compounds of the general formula I.2 where
$R^3$=methyl
$R^4$=$C_2H_5$
$R^5$=4-$CH_3$-pyrimidin-2-yl
and the substituent $R^6$ for a compound corresponds to a line of Table A.

Table 595 (compounds 595.1–59.974)
Compounds of the general formula I.3 where
$R^3$=methyl
$R^4$=$C_2H_5$
$R^5$=4-$CH_3$-pyrimidin-2-yl
and the substituent $R^6$ for a compound corresponds to a line of Table A.

Table 596 (compounds 596.1–596.974)
Compounds of the general formula I.4 where
$R^3$=methyl
$R^4$=$C_2H_5$
$R^5$=4-$CH_3$-pyrimidin-2-yl
and the substituent $R^6$ for a compound corresponds to a line of Table A.

Table 597 (compounds 597.1–597.974)
Compounds of the general formula I.1 where
$R^3$=methyl
$R^4$=$C_2H_5$
$R^5$=4-Cl-furan-2-yl
and the substituent $R^6$ for a compound corresponds to a line of Table A.

Table 598 (compounds 588.1–598.974)
Compounds of the general formula I.2 where
$R^3$=methyl
$R^4$=$C_2H_5$
$R^5$=4-Cl-furan-2-yl
and the substituent $R^6$ for a compound corresponds to a line of Table A.

Table 599 (compounds 599.1–599.974)
Compounds of the general formula I.3 where
$R^3$=methyl
$R^4$=$C_2H_5$
$R^5$=4-Cl-furan-2-yl
and the substituent $R^6$ for a compound corresponds to a line of Table A.

Table 600 (compounds 600.1–600.974)
Compounds of the general formula I.4 where
$R^3$=methyl
$R^4$=$C_2H_5$
$R^5$=4-Cl-furan-2-yl
and the substituent $R^6$ for a compound corresponds to a line of Table A.

Table 601 (compounds 601.1–601.974)
Compounds of the general formula I.1 where
$R^3$=methyl
$R^4$=$C_2H_5$
$R^5$=4-$CH_3$-furan-2-yl
and the substituent $R^6$ for a compound corresponds to a line of Table A.

Table 602 (compounds 602.1–602.974)
  Compounds of the general formula I.2 where
  $R^3$=methyl
  $R^4$=$C_2H_5$
  $R^5$=4-$CH_3$-furan-2-yl
  and the substituent $R^6$ for a compound corresponds to a line of Table A.
Table 603 (compounds 603.1–603.974)
  Compounds of the general formula I.3 where
  $R^3$=methyl
  $R^4$=$C_2H_5$
  $R^5$=4-$CH_3$-furan-2-yl
  and the substituent $R^6$ for a compound corresponds to a line of Table A.
Table 604 (compounds 604.1–604.974)
  Compounds of the general formula I.4 where
  $R^3$=methyl
  $R^4$=$C_2H_5$
  $R^5$=4-$CH_3$-furan-2-yl
  and the substituent $R^6$ for a compound corresponds to a line of Table A.
Table 605 (compounds 605.1–605.974)
  Compounds of the general formula I.1 where
  $R^3$=methyl
  $R^4$=$C_2H_5$
  $R^5$=thien-2-yl
  and the substituent $R^6$ for a compound corresponds to a line of Table A.
Table 606 (compounds 606.1–606.974)
  Compounds of the general formula I.2 where
  $R^3$=methyl
  $R^4$=$C_2H_5$
  $R^5$=thien-2-yl
  and the substituent $R^6$ for a compound corresponds to a line of Table A.
Table 607 (compounds 607.1–607.974)
  Compounds of the general formula I.3 where
  $R^3$=methyl
  $R^4$=$C_2H_5$
  $R^5$=thien-2-yl
  and the substituent $R^6$ for a compound corresponds to a line of Table A.
Table 608 (compounds 608.1–608.974)
  Compounds of the general formula I.4 where
  $R^3$=methyl
  $R^4$=$C_2H_5$
  $R^5$=thien-2-yl
  and the substituent $R^6$ for a compound corresponds to a line of Table A.
Table 609 (compounds 609.1–609.974)
  Compounds of the general formula I.1 where
  $R^3$=methyl
  $R^4$=$C_2H_5$
  $R^5$=thien-3-yl
  and the substituent $R^6$ for a compound corresponds to a line of Table A.
Table 610 (compounds 610.1–610.974)
  Compounds of the general formula I.2 where
  $R^3$=methyl
  $R^4$=$C_2H_5$
  $R^5$=thien-3-yl
  and the substituent $R^6$ for a compound corresponds to a line of Table A.
Table 611 (compounds 611.1–611.974)
  Compounds of the general formula I.3 where
  $R^3$=methyl
  $R^4$=$C_2H_5$
  $R^5$=thien-3-yl
  and the substituent $R^6$ for a compound corresponds to a line of Table A.
Table 612 (compounds 612.1–612.974)
  Compounds of the general formula I.4 where
  $R^3$=methyl
  $R^4$=$C_2H_5$
  $R^5$=thien-3-yl
  and the substituent $R^6$ for a compound corresponds to a line of Table A.
Table 613 (compounds 613.1–613.974)
  Compounds of the general formula I.1 where
  $R^3$=methyl
  $R^4$=$C_2H_5$
  $R^5$=oxazol-2-yl
  and the substituent $R^6$ for a compound corresponds to a line of Table A.
Table 614 (compounds 614.1–614.974)
  Compounds of the general formula I.2 where
  $R^3$=methyl
  $R^4$=$C_2H_5$
  $R^5$=oxazol-2-yl
  and the substituent $R^6$ for a compound corresponds to a line of Table A.
Table 615 (compounds 615.1–615.974)
  Compounds of the general formula I.3 where
  $R^3$=methyl
  $R^4$=$C_2H_5$
  $R^5$=oxazol-2-yl
  and the substituent $R^6$ for a compound corresponds to a line of Table A.
Table 616 (compounds 616.1–616.974)
  Compounds of the general formula I.4 where
  $R^3$=methyl
  $R^4$=$C_2H_5$
  $R^5$=oxazol-2-yl
  and the substituent $R^6$ for a compound corresponds to a line of Table A.
Table 617 (compounds 617.1–617.974)
  Compounds of the general formula I.1 where
  $R^3$=methyl
  $R^4$=$C_2H_5$
  $R^5$=isoxazol-3-yl
  and the substituent $R^6$ for a compound corresponds to a line of Table A.
Table 618 (compounds 618.1–618.974)
  Compounds of the general formula I.2 where
  $R^3$=methyl
  $R^4$=$C_2H_5$
  $R^5$=isoxazol-3-yl
  and the substituent $R^6$ for a compound corresponds to a line of Table A.
Table 619 (compounds 619.1–619.974)
  Compounds of the general formula I.3 where
  $R^3$=methyl
  $R^4$=$C_2H_5$
  $R^5$=isoxazol-3-yl
  and the substituent $R^6$ for a compound corresponds to a line of Table A.

Table 620 (compounds 620.1–620.974)
  Compounds of the general formula I.4 where
  $R^3$=methyl
  $R^4$=$C_2H_5$
  $R^5$=isoxazol-3-yl
  and the substituent $R^6$ for a compound corresponds to a line of Table A.

Table 621 (compounds 621.1–621.974)
  Compounds of the general formula I.1 where
  $R^3$=methyl
  $R^4$=$C_2H_5$
  $R^5$=isoxazol-4-yl
  and the substituent $R^6$ for a compound corresponds to a line of Table A.

Table 622 (compounds 622.1–622.974)
  Compounds of the general formula I.2 where
  $R^3$=methyl
  $R^4$=$C_2H_5$
  $R^5$=isoxazol-4-yl
  and the substituent $R^6$ for a compound corresponds to a line of Table A.

Table 623 (compounds 623.1–623.974)
  Compounds of the general formula I.3 where
  $R^3$=methyl
  $R^4$=$C_2H_5$
  $R^5$=isoxazol-4-yl
  and the substituent $R^6$ for a compound corresponds to a line of Table A.

Table 624 (compounds 624.1–624.974)
  Compounds of the general formula I.4 where
  $R^3$=methyl
  $R^4$=$C_2H_5$
  $R^5$=isoxazol-4-yl
  and the substituent $R^6$ for a compound corresponds to a line of Table A.

Table 625 (compounds 625.1–625.974)
  Compounds of the general formula I.1 where
  $R^3$=methyl
  $R^4$=$C_2H_5$
  $R^5$=pyrazol-3-yl
  and the substituent $R^6$ for a compound corresponds to a line of Table A.

Table 626 (compounds 626.1–626.974)
  Compounds of the general formula I.2 where
  $R^3$=methyl
  $R^4$=$C_2H_5$
  $R^5$=pyrazol-3-yl
  and the substituent $R^6$ for a compound corresponds to a line of Table A.

Table 627 (compounds 627.1–627.974)
  Compounds of the general formula I.3 where
  $R^3$=methyl
  $R^4$=$C_2H_5$
  $R^5$=pyrazol-3-yl
  and the substituent $R^6$ for a compound corresponds to a line of Table A.

Table 628 (compounds 628.1–628.974)
  Compounds of the general formula I.4 where
  $R^3$=methyl
  $R^4$=$C_2H_5$
  $R^5$=pyrazol-3-yl
  and the substituent $R^6$ for a compound corresponds to a line of Table A.

Table 629 (compounds 629.1–629.974)
  Compounds of the general formula I.1 where
  $R^3$=methyl
  $R^4$=$C_2H_5$
  $R^5$=1,3,4-oxadiazol-5-yl
  and the substituent $R^6$ for a compound corresponds to a line of Table A.

Table 630 (compounds 630.1–630.974)
  Compounds of the general formula I.2 where
  $R^3$=methyl
  $R^4$=$C_2H_5$
  $R^5$=1,3,4-oxadiazol-5-yl
  and the substituent $R^6$ for a compound corresponds to a line of Table A.

Table 631 (compounds 631.1–631.974)
  Compounds of the general formula I.3 where
  $R^3$=methyl
  $R^4$=$C_2H_5$
  $R^5$=1,3,4-oxadiazol-5-yl
  and the substituent $R^6$ for a compound corresponds to a line of Table A.

Table 632 (compounds 632.1–632.974)
  Compounds of the general formula I.4 where
  $R^3$=methyl
  $R^4$=$C_2H_5$
  $R^5$=1,3,4-oxadiazol-5-yl
  and the substituent $R^6$ for a compound corresponds to a line of Table A.

Table 633 (compounds 633.1–633.974)
  Compounds of the general formula I.1 where
  $R^3$=methyl
  $R^4$=$C_2H_5$
  $R^5$=1,2,4-triazol-3-yl
  and the substituent $R^6$ for a compound corresponds to a line of Table A.

Table 634 (compounds 634.1–634.974)
  Compounds of the general formula I.2 where
  $R^3$=methyl
  $R^4$=$C_2H_5$
  $R^5$=1,2,4-triazol-3-yl
  and the substituent $R^6$ for a compound corresponds to a line of Table A.

Table 635 (compounds 635.1–635.974)
  Compounds of the general formula I.3 where
  $R^3$=methyl
  $R^4$=$C_2H_5$
  $R^5$=1,2,4-triazol-3-yl
  and the substituent $R^6$ for a compound corresponds to a line of Table A.

Table 636 (compounds 636.1–636.974)
  Compounds of the general formula I.4 where
  $R^3$=methyl
  $R^4$=$C_2H_5$
  $R^5$=1,2,4-triazol-3-yl
  and the substituent $R^6$ for a compound corresponds to a line of Table A.

Table 637 (compounds 637.1–637.974)
  Compounds of the general formula I.1 where
  $R^3$=methyl
  $R^4$=$C_2H_5$
  $R^5$=pyrrol-2-yl
  and the substituent $R^6$ for a compound corresponds to a line of Table A.

Table 638 (compounds 638.1–638.974)
Compounds of the general formula I.2 where
$R^3$=methyl
$R^4$=$C_2H_5$
$R^5$=pyrrol-2-yl
and the substituent $R^6$ for a compound corresponds to a line of Table A.

Table 639 (compounds 639.1–639.974)
Compounds of the general formula I.3 where
$R^3$=methyl
$R^4$=$C_2H_5$
$R^5$=pyrrol-2-yl
and the substituent $R^6$ for a compound corresponds to a line of Table A.

Table 640 (compounds 640.1–640.974)
Compounds of the general formula I.4 where
$R^3$=methyl
$R^4$=$C_2H_5$
$R^5$=pyrrol-2-yl
and the substituent $R^6$ for a compound corresponds to a line of Table A.

Table 641 (compounds 641.1–641.974)
Compounds of the general formula I.1 where
$R^3$=methyl
$R^4$=$C_3H_3$
$R^5$=H
and the substituent $R^6$ for a compound corresponds to a line of Table A.

Table 642 (compounds 642.1–642.974)
Compounds of the general formula I.2 where
$R^3$=methyl
$R^4$=$C_3H_3$
$R^5$=H
and the substituent $R^6$ for a compound corresponds to a line of Table A.

Table 643 (compounds 643.1–643.974)
Compounds of the general formula I.3 where
$R^3$=methyl
$R^4$=$C_3H_3$
$R^5$=H
and the substituent $R^6$ for a compound corresponds to a line of Table A.

Table 644 (compounds 644.1–644.974)
Compounds of the general formula I.4 where
$R^3$=methyl
$R^4$=$C_3H_3$
$R^5$=H
and the substituent $R^6$ for a compound corresponds to a line of Table A.

Table 645 (compounds 645.1–645.974)
Compounds of the general formula I.1 where
$R^3$=methyl
$R^4$=$C_3H_3$
$R^5$=$CH_3$
and the substituent $R^6$ for a compound corresponds to a line of Table A.

Table 646 (compounds 646.1–646.974)
Compounds of the general formula I.2 where
$R^3$=methyl
$R^4$=$C_3H_3$
$R^5$=$CH_3$
and the substituent $R^6$ for a compound corresponds to a line of Table A.

Table 647 (compounds 647.1–647.974)
Compounds of the general formula I.3 where
$R^3$=methyl
$R^4$=$C_3H_3$
$R^5$=$CH_3$
and the substituent $R^6$ for a compound corresponds to a line of Table A.

Table 648 (compounds 648.1–648.974)
Compounds of the general formula I.4 where
$R^3$=methyl
$R^4$=$C_3H_3$
$R^5$=$CH_3$
and the substituent R for a compound corresponds to a line of Table A.

Table 649 (compounds 649.1–649.974)
Compounds of the general formula I.1 where
$R^3$=methyl
$R^4$=$C_3H_3$
$R^5$=$C_2H_5$
and the substituent $R^6$ for a compound corresponds to a line of Table A.

Table 650 (compounds 650.1–650.974)
Compounds of the general formula I.2 where
$R^3$=methyl
$R^4$=$C_3H_3$
$R^5$=$C_2H_5$
and the substituent $R^6$ for a compound corresponds to a line of Table A.

Table 651 (compounds 651.1–651.974)
Compounds of the general formula I.3 where
$R^3$=methyl
$R^4$=$C_3H_3$
$R^5$=$C_2H_5$
and the substituent $R^6$ for a compound corresponds to a line of Table A.

Table 652 (compounds 652.1–652.974)
Compounds of the general formula I.4 where
$R^3$=methyl
$R^4$=$C_3H_3$
$R^5$=$C_2H_5$
and the substituent $R^6$ for a compound corresponds to a line of Table A.

Table 653 (compounds 653.1–653.974)
Compounds of the general formula I.1 where
$R^3$=methyl
$R^4$=$C_3H_3$
$R^5$=n-$C_3H_7$
and the substituent $R^6$ for a compound corresponds to a line of Table A.

Table 654 (compounds 654.1–654.974)
Compounds of the general formula I.2 where
$R^3$=methyl
$R^4$=$C_3H_3$
$R^5$=n-$C_3H_7$
and the substituent $R^6$ for a compound corresponds to a line of Table A.

Table 655 (compounds 655.1–655.974)
Compounds of the general formula I.3 where
$R^3$=methyl
$R^4$=$C_3H_3$
$R^5$=n-$C_3H_7$
and the substituent $R^6$ for a compound corresponds to a line of Table A.

Table 656 (compounds 656.1–656.974)
  Compounds of the general formula I.4 where
  $R^3$=methyl
  $R^4$=$C_3H_3$
  $R^5$=n-$C_3H_7$
  and the substituent $R^6$ for a compound corresponds to a line of Table A.
Table 657 (compounds 657.1–657.974)
  Compounds of the general formula I.1 where
  $R^3$=methyl
  $R^4$=$C_3H_3$
  $R^5$=i-$C_3H_7$
  and the substituent $R^6$ for a compound corresponds to a line of Table A.
Table 658 (compounds 658.1–658.974)
  Compounds of the general formula I.2 where
  $R^3$=methyl
  $R^4$=$C_3H_3$
  $R^5$=i-$C_3H_7$
  and the substituent $R^6$ for a compound corresponds to a line of Table A.
Table 659 (compounds 659.1–659.974)
  Compounds of the general formula I.3 where
  $R^3$=methyl
  $R^4$=$C_3H_3$
  $R^5$=i-$C_3H_7$
  and the substituent $R^6$ for a compound corresponds to a line of Table A.
Table 660 (compounds 660.1–660.974)
  Compounds of the general formula I.4 where
  $R^3$=methyl
  $R^4$=$C_3H_3$
  $R^5$=i-$C_3H_7$
  and the substituent $R^6$ for a compound corresponds to a line of Table A.
Table 661 (compounds 661.1–661.974)
  Compounds of the general formula I.1 where
  $R^3$=methyl
  $R^4$=$C_3H_3$
  $R^5$=cyclopropyl
  and the substituent $R^6$ for a compound corresponds to a line of Table A.
Table 662 (compounds 662.1–662.974)
  Compounds of the general formula I.2 where
  $R^3$=methyl
  $R^4$=$C_3H_3$
  $R^5$=cyclopropyl
  and the substituent $R^6$ for a compound corresponds to a line of Table A.
Table 663 (compounds 663.1–663.974)
  Compounds of the general formula I.3 where
  $R^3$=methyl
  $R^4$=$C_3H_3$
  $R^5$=cyclopropyl
  and the substituent $R^6$ for a compound corresponds to a line of Table A.
Table 664 (compounds 664.1–664.974)
  Compounds of the general formula I.4 where
  $R^3$=methyl
  $R^4$=$C_3H_3$
  $R^5$=cyclopropyl
  and the substituent $R^6$ for a compound corresponds to a line of Table A.
Table 665 (compounds 665.1–665.974)
  Compounds of the general formula I.1 where
  $R^3$=methyl
  $R^4$=$C_3H_3$
  $R^5$=CN
  and the substituent $R^6$ for a compound corresponds to a line of Table A.
Table 666 (compounds 666.1–666.974)
  Compounds of the general formula I.2 where
  $R^3$=methyl
  $R^4$=$C_3H_3$
  $R^5$=CN
  and the substituent $R^6$ for a compound corresponds to a line of Table A.
Table 667 (compounds 667.1–667.974)
  Compounds of the general formula I.3 where
  $R^3$=methyl
  $R^4$=$C_3H_3$
  $R^5$=CN
  and the substituent $R^6$ for a compound corresponds to a line of Table A.
Table 668 (compounds 668.1–668.974)
  Compounds of the general formula I.4 where
  $R^3$=methyl
  $R^4$=$C_3H_3$
  $R^5$=CN
  and the substituent $R^6$ for a compound corresponds to a line of Table A.
Table 669 (compounds 669.1–669.974)
  Compounds of the general formula I.1 where
  $R^3$=methyl
  $R^4$=$C_3H_3$
  $R^5$=$C_6H_5$
  and the substituent $R^6$ for a compound corresponds to a line of Table A.
Table 670 (compounds 670.1–670.974)
  Compounds of the general formula I.2 where
  $R^3$=methyl
  $R^4$=$C_3H_3$
  $R^5$=$C_6H_5$
  and the substituent $R^6$ for a compound corresponds to a line of Table A.
Table 671 (compounds 671.1–671.974)
  Compounds of the general formula I.3 where
  $R^3$=methyl
  $R^4$=$C_3H_3$
  $R^5$=$C_6H_5$
  and the substituent $R^6$ for a compound corresponds to a line of Table A.
Table 672 (compounds 672.1–672.974)
  Compounds of the general formula I.4 where
  $R^3$=methyl
  $R^4$=$C_3H_3$
  $R^5$=$C_6H_5$
  and the substituent $R^6$ for a compound corresponds to a line of Table A.
Table 673 (compounds 673.1–673.974)
  Compounds of the general formula I.1 where
  $R^3$=methyl
  $R^4$=$C_3H_3$
  $R^5$=2-F—$C_6H_4$
  and the substituent $R^6$ for a compound corresponds to a line of Table A.

Table 674 (compounds 674.1–674.974)
Compounds of the general formula I.2 where
$R^3$=methyl
$R^4$=$C_3H_3$
$R^5$=2-F—$C_6H_4$
and the substituent $R^6$ for a compound corresponds to a line of Table A.

Table 675 (compounds 675.1–675.974)
Compounds of the general formula I.3 where
$R^3$=methyl
$R^4$=$C_3H_3$
$R^5$=2-F—$C_6H_4$
and the substituent $R^6$ for a compound corresponds to a line of Table A.

Table 676 (compounds 676.1–676.974)
Compounds of the general formula I.4 where
$R^3$=methyl
$R^4$=$C_3H_3$
$R^5$=2-F—$C_6H_4$
and the substituent $R^6$ for a compound corresponds to a line of Table A.

Table 677 (compounds 677.1–677.974)
Compounds of the general formula I.1 where
$R^3$=methyl
$R^4$=$C_3H_3$
$R^5$=3-F—$C_6H_4$
and the substituent $R^6$ for a compound corresponds to a line of Table A.

Table 678 (compounds 678.1–678.974)
Compounds of the general formula I.2 where
$R^3$=methyl
$R^4$=$C_3H_3$
$R^5$=3-F—$C_6H_4$
and the substituent $R^6$ for a compound corresponds to a line of Table A.

Table 679 (compounds 679.1–679.974)
Compounds of the general formula I.3 where
$R^3$=methyl
$R^4$=$C_3H_3$
$R^5$=3-F—$C_6H_4$
and the substituent $R^6$ for a compound corresponds to a line of Table A.

Table 680 (compounds 680.1–680.974)
Compounds of the general formula I.4 where
$R^3$=methyl
$R^4$=$C_3H_3$
$R^5$=3-F—$C_6H_4$
and the substituent $R^6$ for a compound corresponds to a line of Table A.

Table 681 (compounds 681.1–681.974)
Compounds of the general formula I.1 where
$R^3$=methyl
$R^4$=$C_3H_3$
$R^5$=4-F—$C_6H_4$
and the substituent $R^6$ for a compound corresponds to a line of Table A.

Table 682 (compounds 682.1–682.974)
Compounds of the general formula I.2 where
$R^3$=methyl
$R^4$=$C_3H_3$
$R^5$=4-F—$C_6H_4$
and the substituent $R^6$ for a compound corresponds to a line of Table A.

Table 683 (compounds 683.1–683.974)
Compounds of the general formula I.3 where
$R^3$=methyl
$R^4$=$C_3H_3$
$R^5$=4-F—$C_6H_4$
and the substituent $R^6$ for a compound corresponds to a line of Table A.

Table 684 (compounds 684.1–684.974)
Compounds of the general formula I.4 where
$R^3$=methyl
$R^4$=$C_3H_3$
$R^5$=4-F—$C_6H_4$
and the substituent $R^6$ for a compound corresponds to a line of Table A.

Table 685 (compounds 685.1–685.974)
Compounds of the general formula I.1 where
$R^3$=methyl
$R^4$=$C_3H_3$
$R^5$=2-Cl—$C_6H_4$
and the substituent $R^6$ for a compound corresponds to a line of Table A.

Table 686 (compounds 686.1–686.974)
Compounds of the general formula I.2 where
$R^3$=methyl
$R^4$=$C_3H_3$
$R^5$=2-Cl—$C_6H_4$
and the substituent $R^6$ for a compound corresponds to a line of Table A.

Table 687 (compounds 687.1–687.974)
Compounds of the general formula I.3 where
$R^3$=methyl
$R^4$=$C_3H_3$
$R^5$=2-Cl—$C_6H_4$
and the substituent $R^6$ for a compound corresponds to a line of Table A.

Table 688 (compounds 688.1–688.974)
Compounds of the general formula I.4 where
$R^3$=methyl
$R^4$=$C_3H_3$
$R^5$=2-Cl—$C_6H_4$
and the substituent $R^6$ for a compound corresponds to a line of Table A.

Table 689 (compounds 689.1–689.974)
Compounds of the general formula I.1 where
$R^3$=methyl
$R^4$=$C_3H_3$
$R^5$=3-Cl—$C_6H_4$
and the substituent $R^6$ for a compound corresponds to a line of Table A.

Table 690 (compounds 690.1–690.974)
Compounds of the general formula I.2 where
$R^3$=methyl
$R^4$=$C_3H_3$
$R^5$=3-Cl—$C_6H_4$
and the substituent $R^6$ for a compound corresponds to a line of Table A.

Table 691 (compounds 691.1–691.974)
Compounds of the general formula I.3 where
$R^3$=methyl
$R^4$=$C_3H_3$
$R^5$=3-Cl—$C_6H_4$
and the substituent $R^6$ for a compound corresponds to a line of Table A.

Table 692 (compounds 692.1–692.974)
Compounds of the general formula I.4 where
$R^3$=methyl
$R^4$=$C_3H_3$
$R^5$=3-Cl—$C_6H_4$
and the substituent $R^6$ for a compound corresponds to a line of Table A.

Table 693 (compounds 693.1–693.974)
Compounds of the general formula I.1 where
$R^3$=methyl
$R^4$=$C_3H_3$
$R^5$=4-Cl—$C_6H_4$
and the substituent $R^6$ for a compound corresponds to a line of Table A.

Table 694 (compounds 694.1–694.974)
Compounds of the general formula I.2 where
$R^3$=methyl
$R^4$=$C_3H_3$
$R^5$=4-Cl—$C_6H_4$
and the substituent $R^6$ for a compound corresponds to a line of Table A.

Table 695 (compounds 695.1–695.974)
Compounds of the general formula I.3 where
$R^3$=methyl
$R^4$=$C_3H_3$
$R^5$=4-Cl—$C_6H4$
and the substituent $R^6$ for a compound corresponds to a line of Table A.

Table 696 (compounds 696.1–696.974)
Compounds of the general formula I.4 where
$R^3$=methyl
$R^4$=$C_3H_3$
$R^5$=4-Cl—$C_6H_4$
and the substituent $R^6$ for a compound corresponds to a line of Table A.

Table 697 (compounds 697.1–697.974)
Compounds of the general formula I.1 where
$R^3$=methyl
$R^4$=$C_3H_3$
$R^5$=2-Br—$C_6H_4$
and the substituent $R^6$ for a compound corresponds to a line of Table A.

Table 698 (compounds 698.1–698.974)
Compounds of the general formula I.2 where
$R^3$=methyl
$R^4$=$C_3H_3$
$R^5$=2-Br—$C_6H_4$
and the substituent $R^6$ for a compound corresponds to a line of Table A.

Table 699 (compounds 699.1–699.974)
Compounds of the general formula I.3 where
$R^3$=methyl
$R^4$=$C_3H_3$
$R^5$=2-Br—$C_6H_4$
and the substituent $R^6$ for a compound corresponds to a line of Table A.

Table 700 (compounds 700.1–700.974)
Compounds of the general formula I.4 where
$R^3$=methyl
$R^4$=$C_3H_3$
$R^5$=2-Br—$C_6H_4$
and the substituent $R^6$ for a compound corresponds to a line of Table A.

Table 701 (compounds 701.1–701.974)
Compounds of the general formula I.1 where
$R^3$=methyl
$R^4$=$C_3H_3$
$R^5$=3-Br—$C_6H_4$
and the substituent $R^6$ for a compound corresponds to a line of Table A.

Table 702 (compounds 702.1–702.974)
Compounds of the general formula I.2 where
$R^3$=methyl
$R^4$=$C_3H_3$
$R^5$=3-Br—$C_6H_4$
and the substituent $R^6$ for a compound corresponds to a line of Table A.

Table 703 (compounds 708.1 [sic]-703.974)
Compounds of the general formula I.3 where
$R^3$=methyl
$R^4$=$C_3H_3$
$R^5$=3-Br—$C_6H_4$
and the substituent $R^6$ for a compound corresponds to a line of Table A.

Table 704 (compounds 704.1–704.974)
Compounds of the general formula I.4 where
$R^3$=methyl
$R^4$=$C_3H_3$
$R^5$=3-Br—$C_6H_4$
and the substituent $R^6$ for a compound corresponds to a line of Table A.

Table 705 (compounds 705.1–705.974)
Compounds of the general formula I.1 where
$R^3$=methyl
$R^4$=$C_3H_3$
$R^5$=4-Br—$C_6H_4$
and the substituent $R^6$ for a compound corresponds to a line of Table A.

Table 706 (compounds 706.1–706.974)
Compounds of the general formula I.2 where
$R^3$=methyl
$R^4$=$C_3H_3$
$R^5$=4-Br—$C_6H_4$
and the substituent $R^6$ for a compound corresponds to a line of Table A.

Table 707 (compounds 707.1–707.974)
Compounds of the general formula I.3 where
$R^3$=methyl
$R^4$=$C_3H_3$
$R^5$=4-Br—$C_6H_4$
and the substituent $R^6$ for a compound corresponds to a line of Table A.

Table 708 (compounds 708.1–708.974)
Compounds of the general formula I.4 where
$R^3$=methyl
$R^4$=$C_3H_3$
$R^5$=4-Br—$C_6H_4$
and the substituent $R^6$ for a compound corresponds to a line of Table A.

Table 709 (compounds 709.1–709.974)
Compounds of the general formula I.1 where
$R^3$=methyl
$R^4$=$C_3H_3$
$R^5$=2,3-$F_2$—$C_6H_3$
and the substituent $R^6$ for a compound corresponds to a line of Table A.

Table 710 (compounds 710.1–710.974)
Compounds of the general formula I.2 where
$R^3$=methyl
$R^4$=$C_3H_3$
$R^5$=2,3-$F_2$—$C_6H_3$
and the substituent $R^6$ for a compound corresponds to a line of Table A.

Table 711 (compounds 711.1–711.974)
Compounds of the general formula I.3 where
$R^3$=methyl
$R^4$=$C_3H_3$
$R^5$=2,3-$F_2$—$C_6H_3$
and the substituent $R^6$ for a compound corresponds to a line of Table A.

Table 712 (compounds 712.1–712.974)
Compounds of the general formula I.4 where
$R^3$=methyl
$R^4$=$C_3H_3$
$R^5$=2,3-$F_2$—$C_6H_3$
and the substituent $R^6$ for a compound corresponds to a line of Table A.

Table 713 (compounds 713.1–713.974)
Compounds of the general formula I.1 where
$R^3$=methyl
$R^4$=$C_3H_3$
$R^5$=2,4-$F_2$—$C_6H_3$
and the substituent $R^6$ for a compound corresponds to a line of Table A.

Table 714 (compounds 714.1–714.974)
Compounds of the general formula I.2 where
$R^3$=methyl
$R^4$=$C_3H_3$
$R^5$=2,4-$F_2$—$C_6H_3$
and the substituent $R^6$ for a compound corresponds to a line of Table A.

Table 715 (compounds 715.1–755.974 [sic])
Compounds of the general formula I.3 where
$R^3$=methyl
$R^4$=$C_3H_3$
$R^5$=2,4-$F_2$—$C_6H_3$
and the substituent $R^6$ for a compound corresponds to a line of Table A.

Table 716 (compounds 716.1–716.974)
Compounds of the general formula I.4 where
$R^3$=methyl
$R^4$=$C_3H_3$
$R^5$=2,4-$F_2$—$C_6H_3$
and the substituent $R^6$ for a compound corresponds to a line of Table A.

Table 717 (compounds 717.1–717.974)
Compounds of the general formula I.1 where
$R^3$=methyl
$R^4$=$C_3H_3$
$R^5$=2,5-$F_2$—$C_6H_3$
and the substituent $R^6$ for a compound corresponds to a line of Table A.

Table 718 (compounds 718.1–718.974)
Compounds of the general formula I.2 where
$R^3$=methyl
$R^4$=$C_3H_3$
$R^5$=2,5-$F_2$—$C_6H_3$
and the substituent $R^6$ for a compound corresponds to a line of Table A.

Table 719 (compounds 719.1–719.974)
Compounds of the general formula I.3 where
$R^3$=methyl
$R^4$=$C_3H_3$
$R^5$=2,5-$F_2$—$C_6H_3$
and the substituent $R^6$ for a compound corresponds to a line of Table A.

Table 720 (compounds 720.1–720.974)
Compounds of the general formula I.4 where
$R^3$=methyl
$R^4$=$C_3H_3$
$R^5$=2,5-$F_2$—$C_6H_3$
and the substituent $R^6$ for a compound corresponds to a line of Table A.

Table 721 (compounds 721.1–721.974)
Compounds of the general formula I.1 where
$R^3$=methyl
$R^4$=$C_3H_3$
$R^5$=3,4-$F_2$—$C_6H_3$
and the substituent $R^6$ for a compound corresponds to a line of Table A.

Table 722 (compounds 722.1–722.974)
Compounds of the general formula I.2 where
$R^3$=methyl
$R^4$=$C_3H_3$
$R^5$=3,4-$F_2$—$C_6H_3$
and the substituent $R^6$ for a compound corresponds to a line of Table A.

Table 723 (compounds 723.1–723.974)
Compounds of the general formula I.3 where
$R^3$=methyl
$R^4$=$C_3H_3$
$R^5$=3,4-$F_2$—$C_6H_3$
and the substituent $R^6$ for a compound corresponds to a line of Table A.

Table 724 (compounds 724.1–724.974)
Compounds of the general formula I.4 where
$R^3$=methyl
$R^4$=$C_3H_3$
$R^5$=3,4-$F_2$—$C_6H_3$
and the substituent $R^6$ for a compound corresponds to a line of Table A.

Table 725 (compounds 725.1–725.974)
Compounds of the general formula I.1 where
$R^3$=methyl
$R^4$=$C_3H_3$
$R^5$=3,5-$F_2$—$C_6H_3$
and the substituent $R^6$ for a compound corresponds to a line of Table A.

Table 726 (compounds 726.1–726.974)
Compounds of the general formula I.2 where
$R^3$=methyl
$R^4$=$C_3H_3$
$R^5$=3,5-$F_2$—$C_6H_3$
and the substituent $R^6$ for a compound corresponds to a line of Table A.

Table 727 (compounds 727.1–727.974)
Compounds of the general formula I.3 where
$R^3$=methyl
$R^4$=$C_3H_3$
$R^5$=3,5-$F_2$—$C_6H_3$
and the substituent $R^6$ for a compound corresponds to a line of Table A.

Table 728 (compounds 728.1–728.974)
Compounds of the general formula I.4 where
$R^3$=methyl
$R^4$=$C_3H_3$
$R^5$=3,5-$F_2$—$C_6H_3$
and the substituent $R^6$ for a compound corresponds to a line of Table A.

Table 729 (compounds 729.1–729.974)
Compounds of the general formula I.1 where
$R^3$=methyl
$R^4$=$C_3H_3$
$R^5$=2,3-$Cl_2$—$C_6H_3$
and the substituent $R^6$ for a compound corresponds to a line of Table A.

Table 730 (compounds 730.1–730.974)
Compounds of the general formula I.2 where
$R^3$=methyl
$R^4$=$C_3H_3$
$R^5$=2,3-$Cl_2$—$C_6H_3$
and the substituent $R^6$ for a compound corresponds to a line of Table A.

Table 731 (compounds 731.1–731.974)
Compounds of the general formula I.3 where
$R^3$=methyl
$R^4$=$C_3H_3$
$R^5$=2,3-$Cl_2$—$C_6H_3$
and the substituent $R^6$ for a compound corresponds to a line of Table A.

Table 732 (compounds 732.1–732.974)
Compounds of the general formula I.4 where
$R^3$=methyl
$R^4$=$C_3H_3$
$R^5$=2,3-$Cl_2$—$C_6H_3$
and the substituent $R^6$ for a compound corresponds to a line of Table A.

Table 733 (compounds 733.1–733.974)
Compounds of the general formula I.1 where
$R^3$=methyl
$R^4$=$C_3H_3$
$R^5$=2,4-$Cl_2$—$C_6H_3$
and the substituent $R^6$ for a compound corresponds to a line of Table A.

Table 734 (compounds 734.1–734.974)
Compounds of the general formula I.2 where
$R^3$=methyl
$R^4$=$C_3H_3$
$R^5$=2,4-$Cl_2$—$C_6H_3$
and the substituent $R^6$ for a compound corresponds to a line of Table A.

Table 735 (compounds 735.1–735.974)
Compounds of the general formula I.3 where
$R^3$=methyl
$R^4$=$C_3H_3$
$R^5$=2,4-$Cl_2$—$C_6H_3$
and the substituent $R^6$ for a compound corresponds to a line of Table A.

Table 736 (compounds 736.1–736.974)
Compounds of the general formula I.4 where
$R^3$=methyl
$R^4$=$C_3H_3$
$R^5$=2,4-$Cl_2$—$C_6H_3$
and the substituent $R^6$ for a compound corresponds to a line of Table A.

Table 737 (compounds 737.1–737.974)
Compounds of the general formula I.1 where
$R^3$=methyl
$R^4$=$C_3H_3$
$R^5$=2,5-$Cl_2$—$C_6H_3$
and the substituent $R^6$ for a compound corresponds to a line of Table A.

Table 738 (compounds 738.1–738.974)
Compounds of the general formula I.2 where
$R^3$=methyl
$R^4$=$C_3H_3$
$R^5$=2,5-$Cl_2$—$C_6H_3$
and the substituent $R^6$ for a compound corresponds to a line of Table A.

Table 739 (compounds 739.1–739.974)
Compounds of the general formula I.3 where
$R^3$=methyl
$R^4$=$C_3H_3$
$R^5$=2,5-$Cl_2$—$C_6H_3$
and the substituent $R^6$ for a compound corresponds to a line of Table A.

Table 740 (compounds 740.1–740.974)
Compounds of the general formula I.4 where
$R^3$=methyl
$R^4$=$C_3H_3$
$R^5$=2,5-$Cl_2$—$C_6H_3$
and the substituent $R^6$ for a compound corresponds to a line of Table A.

Table 741 (compounds 741.1–741.974)
Compounds of the general formula I.1 where
$R^3$=methyl
$R^4$=$C_3H_3$
$R^5$=3,4-$Cl_2$—$C_6H_3$
and the substituent $R^6$ for a compound corresponds to a line of Table A.

Table 742 (compounds 742.1–742.974)
Compounds of the general formula I.2 where
$R^3$=methyl
$R^4$=$C_3H_3$
$R^5$=3,4-$Cl_2$—$C_6H_3$
and the substituent $R^6$ for a compound corresponds to a line of Table A.

Table 743 (compounds 743.1–743.974)
Compounds of the general formula I.3 where
$R^3$=methyl
$R^4$=$C_3H_3$
$R^5$=3,4-$Cl_2$—$C_6H_3$
and the substituent $R^6$ for a compound corresponds to a line of Table A.

Table 744 (compounds 744.1–744.974)
Compounds of the general formula I.4 where
$R^3$=methyl
$R^4$=$C_3H_3$
$R^5$=3,4-$Cl_2$—$C_6H_3$
and the substituent $R^6$ for a compound corresponds to a line of Table A.

Table 745 (compounds 745.1–745.974)
Compounds of the general formula I.1 where
$R^3$=methyl
$R^4$=$C_3H_3$
$R^5$=3,5-$Cl_2$—$C_6H_3$
and the substituent $R^6$ for a compound corresponds to a line of Table A.

Table 746 (compounds 746.1–746.974)
Compounds of the general formula I.2 where
$R^3$=methyl
$R^4=C_3H_3$
$R^5$=3,5-$Cl_2$—$C_6H_3$
and the substituent $R^6$ for a compound corresponds to a line of Table A.

Table 747 (compounds 747.1–747.974)
Compounds of the general formula I.3 where
$R^3$=methyl
$R^4=C_3H_3$
$R^5$=3,5-$Cl_2$—$C_6H_3$
and the substituent $R^6$ for a compound corresponds to a line of Table A.

Table 748 (compounds 748.1–748.974)
Compounds of the general formula I.4 where
$R^3$=methyl
$R^4=C_3H_3$
$R^5$=3,5-$Cl_2$—$C_6H_3$
and the substituent $R^6$ for a compound corresponds to a line of Table A.

Table 749 (compounds 749.1–749.974)
Compounds of the general formula I.1 where
$R^3$=methyl
$R^4=C_3H_3$
$R^5$=2-F; 3-Cl—$C_6H_3$
and the substituent $R^6$ for a compound corresponds to a line of Table A.

Table 750 (compounds 750.1–750.974)
Compounds of the general formula I.2 where
$R^3$=methyl
$R^4=C_3H_3$
$R^5$=2-F; 3-Cl—$C_6H_3$
and the substituent $R^6$ for a compound corresponds to a line of Table A.

Table 751 (compounds 751.1–751.974)
Compounds of the general formula I.3 where
$R^3$=methyl
$R^4=C_3H_3$
$R^5$=2-F; 3-Cl—$C_6H_3$
and the substituent $R^6$ for a compound corresponds to a line of Table A.

Table 752 (compounds 752.1–752.974)
Compounds of the general formula I.4 where
$R^3$=methyl
$R^4=C_3H_3$
$R^5$=2-F; 3-Cl—$C_6H_3$
and the substituent $R^6$ for a compound corresponds to a line of Table A.

Table 753 (compounds 753.1–753.974)
Compounds of the general formula I.1 where
$R^3$=methyl
$R^4=C_3H_3$
$R^5$=2-F; 4-Cl—$C_6H_3$
and the substituent $R^6$ for a compound corresponds to a line of Table A.

Table 754 (compounds 754.1–754.974)
Compounds of the general formula I.2 where
$R^3$=methyl
$R^4=C_3H_3$
$R^5$=2-F; 4-Cl—$C_6H_3$
and the substituent $R^6$ for a compound corresponds to a line of Table A.

Table 755 (compounds 755.1–755.974)
Compounds of the general formula I.3 where
$R^3$=methyl
$R^4=C_3H_3$
$R^5$=2-F; 4-Cl—$C_6H_3$
and the substituent $R^6$ for a compound corresponds to a line of Table A.

Table 756 (compounds 756.1–756.974)
Compounds of the general formula I.4 where
$R^3$=methyl
$R^4=C_3H_3$
$R^5$=2-F; 4-Cl—$C_6H_3$
and the substituent $R^6$ for a compound corresponds to a line of Table A.

Table 757 (compounds 757.1–757.974)
Compounds of the general formula I.1 where
$R^3$=methyl
$R^4=C_3H_3$
$R^5$=3-F; 4-Cl—$C_6H_3$
and the substituent $R^6$ for a compound corresponds to a line of Table A.

Table 758 (compounds 758.1–758.974)
Compounds of the general formula I.2 where
$R^3$=methyl
$R^4=C_3H_3$
$R^5$=3-F; 4-Cl—$C_6H_3$
and the substituent $R^6$ for a compound corresponds to a line of Table A.

Table 759 (compounds 759.1–759.974)
Compounds of the general formula I.3 where
$R^3$=methyl
$R^4=C_3H_3$
$R^5$=3-F; 4-Cl—$C_6H_3$
and the substituent $R^6$ for a compound corresponds to a line of Table A.

Table 760 (compounds 760.1–760.974)
Compounds of the general formula I.4 where
$R^3$=methyl
$R^4=C_3H_3$
$R^5$=3-F; 4-Cl—$C_6H_3$
and the substituent $R^6$ for a compound corresponds to a line of Table A.

Table 761 (compounds 761.1–761.974)
Compounds of the general formula I.1 where
$R^3$=methyl
$R^4=C_3H_3$
$R^5$=4-F; 3,5-$Cl_2$—$C_6H_2$
and the substituent $R^6$ for a compound corresponds to a line of Table A.

Table 762 (compounds 762.1–762.974)
Compounds of the general formula I.2 where
$R^3$=methyl
$R^4=C_3H_3$
$R^5$=4-F; 3,5-$Cl_2$—$C_6H_2$
and the substituent $R^6$ for a compound corresponds to a line of Table A.

Table 763 (compounds 763.1–763.974)
Compounds of the general formula I.3 where
$R^3$=methyl
$R^4=C_3H_3$
$R^5$=4-F; 3,5-$Cl_2$—$C_6H_2$
and the substituent $R^6$ for a compound corresponds to a line of Table A.

Table 764 (compounds 764.1–764.974)
Compounds of the general formula I.4 where
$R^3$=methyl
$R^4$=$C_3H_3$
$R^5$=4-F; 3,5-$Cl_2$—$C_6H_2$
and the substituent $R^6$ for a compound corresponds to a line of Table A.

Table 765 (compounds 765.1–765.974)
Compounds of the general formula I.1 where
$R^3$=methyl
$R^4$=$C_3H_3$
$R^5$=2,3,4-$Cl_3$—$C_6H_2$
and the substituent $R^6$ for a compound corresponds to a line of Table A.

Table 766 (compounds 766.1–766.974)
Compounds of the general formula I.2 where
$R^3$=methyl
$R^4$=$C_3H_3$
$R^5$=2,3,4-$Cl_3$—$C_6H_2$
and the substituent $R^6$ for a compound corresponds to a line of Table A.

Table 767 (compounds 767.1–767.974)
Compounds of the general formula I.3 where
$R^3$=methyl
$R^4$=$C_3H_3$
$R^5$=2,3,4-$Cl_3$—$C_6H_2$
and the substituent $R^6$ for a compound corresponds to a line of Table A.

Table 768 (compounds 768.1–768.974)
Compounds of the general formula I.4 where
$R^3$=methyl
$R^4$=$C_3H_3$
$R^5$=2,3,4-$Cl_3$—$C_6H_2$
and the substituent $R^6$ for a compound corresponds to a line of Table A.

Table 769 (compounds 769.1–769.974)
Compounds of the general formula I.1 where
$R^3$=methyl
$R^4$=$C_3H_3$
$R^5$=2,3,5-$Cl_3$—$C_6H_2$
and the substituent $R^6$ for a compound corresponds to a line of Table A.

Table 770 (compounds 770.1–770.974)
Compounds of the general formula I.2 where
$R^3$=methyl
$R^4$=$C_3H_3$
$R^5$=2,3,5-$Cl_3$—$C_6H_2$
and the substituent $R^6$ for a compound corresponds to a line of Table A.

Table 771 (compounds 771.1–771.974)
Compounds of the general formula I.3 where
$R^3$=methyl
$R^4$=$C_3H_3$
$R^5$=2,3,5-$Cl_3$—$C_6H_2$
and the substituent $R^6$ for a compound corresponds to a line of Table A.

Table 772 (compounds 772.1–772.974)
Compounds of the general formula I.4 where
$R^3$=methyl
$R^4$=$C_3H_3$
$R^5$=2,3,5-$Cl_3$—$C_6H_2$
and the substituent $R^6$ for a compound corresponds to a line of Table A.

Table 773 (compounds 773.1–773.974)
Compounds of the general formula I.1 where
$R^3$=methyl
$R^4$=$C_3H_3$
$R^5$=2,4,5-$Cl_3$—$C_6H_2$
and the substituent $R^6$ for a compound corresponds to a line of Table A.

Table 774 (compounds 774.1–774.974)
Compounds of the general formula I.2 where
$R^3$=methyl
$R^4$=$C_3H_3$
$R^5$=2,4,5-$Cl_3$—$C_6H_2$
and the substituent $R^6$ for a compound corresponds to a line of Table A.

Table 775 (compounds 775.1–775.974)
Compounds of the general formula I.3 where
$R^3$=methyl
$R^4$=$C_3H_3$
$R^5$=2,4,5-$Cl_3$—$C_6H_2$
and the substituent $R^6$ for a compound corresponds to a line of Table A.

Table 776 (compounds 776.1–776.974)
Compounds of the general formula I.4 where
$R^3$=methyl
$R^4$=$C_3H_3$
$R^5$=2,4,5-$Cl_3$—$C_6H_2$
and the substituent $R^6$ for a compound corresponds to a line of Table A.

Table 777 (compounds 777.1–777.974)
Compounds of the general formula I.1 where
$R^3$=methyl
$R^4$=$C_3H_3$
$R^5$=2-CN—$C_6H_4$
and the substituent $R^6$ for a compound corresponds to a line of Table A.

Table 778 (compounds 778.1–778.974)
Compounds of the general formula I.2 where
$R^3$=methyl
$R^4$=$C_3H_3$
$R^5$=2-CN—$C_6H_4$
and the substituent $R^6$ for a compound corresponds to a line of Table A.

Table 779 (compounds 779.1–779.974)
Compounds of the general formula I.3 where
$R^3$=methyl
$R^4$=$C_3H_3$
$R^5$=2-CN—$C_6H_4$
and the substituent $R^6$ for a compound corresponds to a line of Table A.

Table 780 (compounds 780.1–780.974)
Compounds of the general formula I.4 where
$R^3$=methyl
$R^4$=$C_3H_3$
$R^5$=2-CN—$C_6H_4$
and the substituent $R^6$ for a compound corresponds to a line of Table A.

Table 781 (compounds 781.1–781.974)
Compounds of the general formula I.1 where
$R^3$=methyl
$R^4$=$C_3H_3$
$R^5$=3-CN—$C_6H_4$
and the substituent $R^6$ for a compound corresponds to a line of Table A.

Table 782 (compounds 782.1–782.974)
Compounds of the general formula I.2 where
$R^3$=methyl
$R^4$=$C_3H_3$
$R^5$=3-CN—$C_6H_4$
and the substituent $R^6$ for a compound corresponds to a line of Table A.

Table 783 (compounds 783.1–783.974)
Compounds of the general formula I.3 where
$R^3$=methyl
$R^4$=$C_3H_3$
$R^5$=3-CN—$C_6H_4$
and the substituent $R^6$ for a compound corresponds to a line of Table A.

Table 784 (compounds 784.1–784.974)
Compounds of the general formula I.4 where
$R^3$=methyl
$R^4$=$C_3H_3$
$R^5$=3-CN—$C_6H_4$
and the substituent $R^6$ for a compound corresponds to a line of Table A.

Table 785 (compounds 785.1–785.974)
Compounds of the general formula I.1 where
$R^3$=methyl
$R^4$=$C_3H_3$
$R^5$=4-CN—$C_6H_4$
and the substituent $R^6$ for a compound corresponds to a line of Table A.

Table 786 (compounds 786.1–786.974)
Compounds of the general formula I.2 where
$R^3$=methyl
$R^4$=$C_3H_3$
$R^5$=4-CN—$C_6H_4$
and the substituent $R^6$ for a compound corresponds to a line of Table A.

Table 787 (compounds 7867.1 [sic]-787.974)
Compounds of the general formula I.3 where
$R^3$=methyl
$R^4$=$C_3H_3$
$R^5$=4-CN—$C_6H_4$
and the substituent $R^6$ for a compound corresponds to a line of Table A.

Table 788 (compounds 788.1–788.974)
Compounds of the general formula I.4 where
$R^3$=methyl
$R^4$=$C_3H_3$
$R^5$=4-CN—$C_6H_4$
and the substituent $R^6$ for a compound corresponds to a line of Table A.

Table 789 (compounds 789.1–789.974)
Compounds of the general formula I.1 where
$R^3$=methyl
$R^4$=$C_3H_3$
$R^5$=2-$NO_2$—$C_6H_4$
and the substituent $R^6$ for a compound corresponds to a line of Table A.

Table 790 (compounds 790.1–790.974)
Compounds of the general formula I.2 where
$R^3$=methyl
$R^4$=$C_3H_3$
$R^5$=2-$NO_2$—$C_6H_4$
and the substituent $R^6$ for a compound corresponds to a line of Table A.

Table 791 (compounds 791.1–791.974)
Compounds of the general formula I.3 where
$R^3$=methyl
$R^4$=$C_3H_3$
$R^5$=2-$NO_2$—$C_6H_4$
and the substituent $R^6$ for a compound corresponds to a line of Table A.

Table 792 (compounds 792.1–792.974)
Compounds of the general formula I.4 where
$R^3$=methyl
$R^4$=$C_3H_3$
$R^5$=2-$NO_2$—$C_6H_4$
and the substituent $R^6$ for a compound corresponds to a line of Table A.

Table 793 (compounds 793.1–793.974)
Compounds of the general formula I.1 where
$R^3$=methyl
$R^4$=$C_3H_3$
$R^5$=3-$NO_2$—$C_6H_4$
and the substituent $R^6$ for a compound corresponds to a line of Table A.

Table 794 (compounds 794.1–794.974)
Compounds of the general formula I.2 where
$R^3$=methyl
$R^4$=$C_3H_3$
$R^5$=3-$NO_2$—$C_6H_4$
and the substituent $R^6$ for a compound corresponds to a line of Table A.

Table 795 (compounds 795.1–795.974)
Compounds of the general formula I.3 where
$R^3$=methyl
$R^4$=$C_3H_3$
$R^5$=3-$NO_2$—$C_6H_4$
and the substituent $R^6$ for a compound corresponds to a line of Table A.

Table 796 (compounds 796.1–796.974)
Compounds of the general formula I.4 where
$R^3$=methyl
$R^4$=$C_3H_3$
$R^5$=3-$NO_2$—$C_6H_4$
and the substituent $R^6$ for a compound corresponds to a line of Table A.

Table 797 (compounds 797.1–797.974)
Compounds of the general formula I.1 where
$R^3$=methyl
$R^4$=$C_3H_3$
$R^5$=4-$NO_2$—$C_6H_4$
and the substituent $R^6$ for a compound corresponds to a line of Table A.

Table 798 (compounds 798.1–798.974)
Compounds of the general formula I.2 where
$R^3$=methyl
$R^4$=$C_3H_3$
$R^5$=4-$NO_2$—$C_6H_4$
and the substituent $R^6$ for a compound corresponds to a line of Table A.

Table 799 (compounds 799.1–799.974)
Compounds of the general formula I.3 where
$R^3$=methyl
$R^4$=$C_3H_3$
$R^5$=4-$NO_2$—$C_6H_4$
and the substituent $R^6$ for a compound corresponds to a line of Table A.

Table 800 (compounds 800.1–800.974)
Compounds of the general formula I.4 where
$R^3$=methyl
$R^4$=$C_3H_3$
$R^5$=4-$NO_2$—$C_6H_4$
and the substituent $R^6$ for a compound corresponds to a line of Table A.

Table 801 (compounds 801.1–801.974)
Compounds of the general formula I.1 where
$R^3$=methyl
$R^4$=$C_3H_3$
$R^5$=2-$CH_3$—$C_6H_4$
and the substituent $R^6$ for a compound corresponds to a line of Table A.

Table 802 (compounds 802.1–802.974)
Compounds of the general formula I.2 where
$R^3$=methyl
$R^4$=$C_3H_3$
$R^5$=2-$CH_3$—$C_6H_4$
and the substituent $R^6$ for a compound corresponds to a line of Table A.

Table 803 (compounds 803.1–803.974)
Compounds of the general formula I.3 where
$R^3$=methyl
$R^4$=$C_3H_3$
$R^5$=2-$CH_3$—$C_6H_4$
and the substituent $R^6$ for a compound corresponds to a line of Table A.

Table 804 (compounds 804.1–804.974)
Compounds of the general formula I.4 where
$R^3$=methyl
$R^4$=$C_3H_3$
$R^5$=2-$CH_3$—$C_6H_4$
and the substituent $R^6$ for a compound corresponds to a line of Table A.

Table 805 (compounds 805.1–805.974)
Compounds of the general formula I.1 where
$R^3$=methyl
$R^4$=$C_3H_3$
$R^5$=3-$CH_3$—$C_6H_4$
and the substituent $R^6$ for a compound corresponds to a line of Table A.

Table 806 (compounds 806.1–806.974)
Compounds of the general formula I.2 where
$R^3$=methyl
$R^4$=$C_3H_3$
$R^5$=3-$CH_3$—$C_6H_4$
and the substituent $R^6$ for a compound corresponds to a line of Table A.

Table 807 (compounds 807.1–807.974)
Compounds of the general formula I.3 where
$R^3$=methyl
$R^4$=$C_3H_3$
$R^5$=3-$CH_3$—$C_6H_4$
and the substituent $R^6$ for a compound corresponds to a line of Table A.

Table 808 (compounds 808.1–808.974)
Compounds of the general formula I.4 where
$R^3$=methyl
$R^4$=$C_3H_3$
$R^5$=3-$CH_3$—$C_6H_4$
and the substituent $R^6$ for a compound corresponds to a line of Table A.

Table 809 (compounds 809.1–809.974)
Compounds of the general formula I.1 where
$R^3$=methyl
$R^4$=$C_3H_3$
$R^5$=4-$CH_3$—$C_6H_4$
and the substituent $R^6$ for a compound corresponds to a line of Table A.

Table 810 (compounds 810.1–810.974)
Compounds of the general formula I.2 where
$R^3$=methyl
$R^4$=$C_3H_3$
$R^5$=4-$CH_3$—$C_6H_4$
and the substituent $R^6$ for a compound corresponds to a line of Table A.

Table 811 (compounds 811.1–811.974)
Compounds of the general formula I.3 where
$R^3$=methyl
$R^4$=$C_3H_3$
$R^5$=4-$CH_3$—$C_6H_4$
and the substituent $R^6$ for a compound corresponds to a line of Table A.

Table 812 (compounds 812.1–812.974)
Compounds of the general formula I.4 where
$R^3$=methyl
$R^4$=$C_3H_3$
$R^5$=4-$CH_3$—$C_6H_4$
and the substituent $R^6$ for a compound corresponds to a line of Table A.

Table 813 (compounds 813.1–813.974)
Compounds of the general formula I.1 where
$R^3$=methyl
$R^4$=$C_3H_3$
$R^5$=2,4-$(CH_3)_2$—$C_6H_3$
and the substituent $R^6$ for a compound corresponds to a line of Table A.

Table 814 (compounds 814.1–814.974)
Compounds of the general formula I.2 where
$R^3$=methyl
$R^4$=$C_3H_3$
$R^5$=2,4-$(CH_3)_2$—$C_6H_3$
and the substituent $R^6$ for a compound corresponds to a line of Table A.

Table 815 (compounds 815.1–815.974)
Compounds of the general formula I.3 where
$R^3$=methyl
$R^4$=$C_3H_3$
$R^5$=2,4-$(CH_3)_2$—$C_6H_3$
and the substituent $R^6$ for a compound corresponds to a line of Table A.

Table 816 (compounds 816.1 816.974)
Compounds of the general formula I.4 where
$R^3$=methyl
$R^4$=$C_3H_3$
$R^5$=2,4-$(CH_3)_2$—$C_6H_3$
and the substituent $R^6$ for a compound corresponds to a line of Table A.

Table 817 (compounds 817.1–817.974)
Compounds of the general formula I.1 where
$R^3$=methyl
$R^4$=$C_3H_3$
$R^5$=2,5-$(CH_3)_2$—$C_6H_3$
and the substituent $R^6$ for a compound corresponds to a line of Table A.

Table 818 (compounds 818.1–818.974)
Compounds of the general formula I.2 where
$R^3$=methyl
$R^4$=$C_3H_3$
$R^5$=2,5-$(CH_3)_2$—$C_6H_3$
and the substituent $R^6$ for a compound corresponds to a line of Table A.

Table 819 (compounds 819.1–819.974)
Compounds of the general formula I.3 where
$R^3$=methyl
$R^4$=$C_3H_3$
$R^5$=2,5-$(CH_3)_2$—$C_6H_3$
and the substituent $R^6$ for a compound corresponds to a line of Table A.

Table 820 (compounds 820.1–820.974)
Compounds of the general formula I.4 where
$R^3$=methyl
$R^4$=$C_3H_3$
$R^5$=2,5-$(CH_3)_2$—$C_6H_3$
and the substituent $R^6$ for a compound corresponds to a line of Table A.

Table 821 (compounds 821.1–821.974)
Compounds of the general formula I.1 where
$R^3$=methyl
$R^4$=$C_3H_3$
$R^5$=3,4-$(CH_3)_2$—$C_6H_3$
and the substituent $R^6$ for a compound corresponds to a line of Table A.

Table 822 (compounds 822.1–822.974)
Compounds of the general formula I.2 where
$R^3$=methyl
$R^4$=$C_3H_3$
$R^5$=3,4-$(CH_3)_2$—$C_6H_3$
and the substituent $R^6$ for a compound corresponds to a line of Table A.

Table 823 (compounds 823.1–823.974)
Compounds of the general formula I.3 where
$R^3$=methyl
$R^4$=$C_3H_3$
$R^5$=3,4-$(CH_3)_2$—$C_6H_3$
and the substituent $R^6$ for a compound corresponds to a line of Table A.

Table 824 (compounds 824.1–824.974)
Compounds of the general formula I.4 where
$R^3$=methyl
$R^4$=$C_3H_3$
$R^5$=3,4-$(CH_3)_2$—$C_6H_3$
and the substituent $R^6$ for a compound corresponds to a line of Table A.

Table 825 (compounds 825.1–825.974)
Compounds of the general formula I.1 where
$R^3$=methyl
$R^4$=$C_3H_3$
$R^5$=3,5-$(CH_3)_2$—$C_6H_3$
and the substituent $R^6$ for a compound corresponds to a line of Table A.

Table 826 (compounds 826.1–826.974)
Compounds of the general formula I.2 where
$R^3$=methyl
$R^4$=$C_3H_3$
$R^5$=3,5-$(CH_3)_2$—$C_6H_3$
and the substituent $R^6$ for a compound corresponds to a line of Table A.

Table 827 (compounds 827.1–827.974)
Compounds of the general formula I.3 where
$R^3$=methyl
$R^4$=$C_3H_3$
$R^5$=3,5-$(CH_3)_2$—$C_6H_3$
and the substituent $R^6$ for a compound corresponds to a line of Table A.

Table 828 (compounds 828.1–828.974)
Compounds of the general formula I.4 where
$R^3$=methyl
$R^4$=$C_3H_3$
$R^5$=3,5-$(CH_3)_2$—$C_6H_3$
and the substituent $R^6$ for a compound corresponds to a line of Table A.

Table 829 (compounds 829.1–829.974)
Compounds of the general formula I.1 where
$R^3$=methyl
$R^4$=$C_3H_3$
$R^5$=3,4,5-$(CH_3)_3$—$C_6H_2$
and the substituent $R^6$ for a compound corresponds to a line of Table A.

Table 830 (compounds 830.1–830.974)
Compounds of the general formula I.2 where
$R^3$=methyl
$R^4$=$C_3H_3$
$R^5$=3,4,5-$(CH_3)_3$—$C_6H_2$
and the substituent $R^6$ for a compound corresponds to a line of Table A.

Table 831 (compounds 831.1–831.974)
Compounds of the general formula I.3 where
$R^3$=methyl
$R^4$=$C_3H_3$
$R^5$=3,4,5-$(CH_3)_3$—$C_6H_2$
and the substituent $R^6$ for a compound corresponds to a line of Table A.

Table 832 (compounds 832.1–832.974)
Compounds of the general formula I.4 where
$R^3$=methyl
$R^4$=$C_3H_3$
$R^5$=3,4,5-$(CH_3)_3$—$C_6H_2$
and the substituent $R^6$ for a compound corresponds to a line of Table A.

Table 833 (compounds 833.1–833.974)
Compounds of the general formula I.1 where
$R^3$=methyl
$R^4$=$C_3H_3$
$R^5$=4-$C_6H_5$—$C_6H_4$
and the substituent $R^6$ for a compound corresponds to a line of Table A.

Table 834 (compounds 834.1–834.974)
Compounds of the general formula I.2 where
$R^3$=methyl
$R^4$=$C_3H_3$
$R^5$=4-$C_6H_5$—$C_6H_4$
and the substituent $R^6$ for a compound corresponds to a line of Table A.

Table 835 (compounds 835.1–835.974)
Compounds of the general formula I.3 where
$R^3$=methyl
$R^4$=$C_3H_3$
$R^5$=4-$C_6H_5$—$C_6H_4$
and the substituent $R^6$ for a compound corresponds to a line of Table A.

Table 836 (compounds 836.1–836.974)
  Compounds of the general formula I.4 where
  $R^3$=methyl
  $R^4$=$C_3H_3$
  $R^5$=4-$C_6H_5$—$C_6H_4$
  and the substituent $R^6$ for a compound corresponds to a line of Table A.
Table 837 (compounds 837.1–837.974)
  Compounds of the general formula I.1 where
  $R^3$=methyl
  $R^4$=$C_3H_3$
  $R^5$=3-Cl-4-$CH_3$—$C_6H_3$
  and the substituent $R^6$ for a compound corresponds to a line of Table A.
Table 838 (compounds 838.1–838.974)
  Compounds of the general formula I.2 where
  $R^3$=methyl
  $R^4$=$C_3H_3$
  $R^5$=3-Cl-4-$CH_3$—$C_6H_3$
  and the substituent $R^6$ for a compound corresponds to a line of Table A.
Table 839 (compounds 839.1–839.974)
  Compounds of the general formula I.3 where
  $R^3$=methyl
  $R^4$=$C_3H_3$
  $R^5$=3-Cl-4-$CH_3$—$C_6H_3$
  and the substituent $R^6$ for a compound corresponds to a line of Table A.
Table 840 (compounds 840.1–840.974)
  Compounds of the general formula I.4 where
  $R^3$=methyl
  $R^4$=$C_3H_3$
  $R^5$=3-Cl-4-$CH_3$—$C_6H_3$
  and the substituent $R^6$ for a compound corresponds to a line of Table A.
Table 841 (compounds 841.1–841.974)
  Compounds of the general formula I.1 where
  $R^3$=methyl
  $R^4$=$C_3H_3$
  $R^5$=2-$OCH_3$—$C_6H_4$
  and the substituent $R^6$ for a compound corresponds to a line of Table A.
Table 842 (compounds 842.1–842.974)
  Compounds of the general formula I.2 where
  $R^3$=methyl
  $R^4$=$C_3H_3$
  $R^5$=2-$OCH_3$—$C_6H_4$
  and the substituent $R^6$ for a compound corresponds to a line of Table A.
Table 843 (compounds 843.1–843.974)
  Compounds of the general formula I.3 where
  $R^3$=methyl
  $R^4$=$C_3H_3$
  $R^5$=2-$OCH_3$—$C_6H_4$
  and the substituent $R^6$ for a compound corresponds to a line of Table A.
Table 844 (compounds 844.1–844.974)
  Compounds of the general formula I.4 where
  $R^3$=methyl
  $R^4$=$C_3H_3$
  $R^5$=2-$OCH_3$—$C_6H_4$
  and the substituent $R^6$ for a compound corresponds to a line of Table A.
Table 845 (compounds 845.1–845.974)
  Compounds of the general formula I.1 where
  $R^3$=methyl
  $R^4$=$C_3H_3$
  $R^5$=3-$OCH_3$—$C_6H_4$
  and the substituent $R^6$ for a compound corresponds to a line of Table A.
Table 846 (compounds 846.1–846.974)
  Compounds of the general formula I.2 where
  $R^3$=methyl
  $R^4$=$C_3H_3$
  $R^5$=2-$OCH_3$—$C_6H_4$
  and the substituent $R^6$ for a compound corresponds to a line of Table A.
Table 847 (compounds 847.1–847.974)
  Compounds of the general formula I.3 where
  $R^3$=methyl
  $R^4$=$C_3H_3$
  $R^5$=3-$OCH_3$—$C_6H_4$
  and the substituent $R^6$ for a compound corresponds to a line of Table A.
Table 848 (compounds 848.1–848.974)
  Compounds of the general formula 528 [sic] I.4 where
  $R^3$=methyl
  $R^4$=$C_3H_3$
  $R^5$=3-$OCH_3$—$C_6H_4$
  and the substituent $R^6$ for a compound corresponds to a line of Table A.
Table 849 (compounds 849.1–849.974)
  Compounds of the general formula I.1 where
  $R^3$=methyl
  $R^4$=$C_3H_3$
  $R^5$=4-$OCH_3$—$C_6H_4$
  and the substituent $R^6$ for a compound corresponds to a line of Table A.
Table 850 (compounds 850.1–850.974)
  Compounds of the general formula I.2 where
  $R^3$=methyl
  $R^4$=$C_3H_3$
  $R^5$=4-$OCH_3$—$C_6H_4$
  and the substituent $R^6$ for a compound corresponds to a line of Table A.
Table 851 (compounds 851.1–851.974)
  Compounds of the general formula I.3 where
  $R^3$=methyl
  $R^4$=$C_3H_3$
  $R^5$=4-$OCH_3$—$C_6H_4$
  and the substituent $R^6$ for a compound corresponds to a line of Table A.
Table 852 (compounds 852.1–852.974)
  Compounds of the general formula I.4 where
  $R^3$=methyl
  $R^4$=$C_3H_3$
  $R^5$=4-$OCH_3$—$C_6H_4$
  and the substituent $R^6$ for a compound corresponds to a line of Table A.
Table 853 (compounds 853.1–853.974)
  Compounds of the general formula I.1 where
  $R^3$=methyl
  $R^4$=$C_3H_3$
  $R^5$=2-$OCF_3$—$C_6H_4$
  and the substituent $R^6$ for a compound corresponds to a line of Table A.

Table 854 (compounds 854.1–854.974)
Compounds of the general formula I.2 where
$R^3$=methyl
$R^4$=$C_3H_3$
$R^5$=2-$OCF_3$—$C_6H_4$
and the substituent $R^6$ for a compound corresponds to a line of Table A.

Table 855 (compounds 855.1–855.974)
Compounds of the general formula I.3 where
$R^3$=methyl
$R^4$=$C_3H_3$
$R^5$=2-$OCF_3$—$C_6H_4$
and the substituent $R^6$ for a compound corresponds to a line of Table A.

Table 856 (compounds 856.1–856.974)
Compounds of the general formula I.4 where
$R^3$=methyl
$R^4$=$C_3H_3$
$R^5$=2-$OCF_3$—$C_6H_4$
and the substituent $R^6$ for a compound corresponds to a line of Table A.

Table 857 (compounds 857.1–857.974)
Compounds of the general formula I.1 where
$R^3$=methyl
$R^4$=$C_3H_3$
$R^5$=3-$OCF_3$—$C_6H_4$
and the substituent $R^6$ for a compound corresponds to a line of Table A.

Table 858 (compounds 858.1–858.974)
Compounds of the general formula I.2 where
$R^3$=methyl
$R^4$=$C_3H_3$
$R^5$=3-$OCF_3$—$C_6H_4$
and the substituent $R^6$ for a compound corresponds to a line of Table A.

Table 859 (compounds 859.1–859.974)
Compounds of the general formula I.3 where
$R^3$=methyl
$R^4$=$C_3H_3$
$R^5$=3-$OCF_3$—$C_6H_4$
and the substituent $R^6$ for a compound corresponds to a line of Table A.

Table 860 (compounds 860.1–860.974)
Compounds of the general formula I.4 where
$R^3$=methyl
$R^4$=$C_3H_3$
$R^5$=3-$OCF_3$—$C_6H_4$
and the substituent $R^6$ for a compound corresponds to a line of Table A.

Table 861 (compounds 861.1–861.974)
Compounds of the general formula I.1 where
$R^3$=methyl
$R^4$=$C_3H_3$
$R^5$=4-$OCF_3$—$C_6H_4$
and the substituent $R^6$ for a compound corresponds to a line of Table A.

Table 862 (compounds 862.1–862.974)
Compounds of the general formula I.2 where
$R^3$=methyl
$R^4$=$C_3H_3$
$R^5$=4-$OCF_3$—$C_6H_4$
and the substituent $R^6$ for a compound corresponds to a line of Table A.

Table 863 (compounds 863.1–863.974)
Compounds of the general formula I.3 where
$R^3$=methyl
$R^4$=$C_3H_3$
$R^5$=4-$OCF_3$—$C_6H_4$
and the substituent $R^6$ for a compound corresponds to a line of Table A.

Table 864 (compounds 864.1–864.974)
Compounds of the general formula I.4 where
$R^3$=methyl
$R^4$=$C_3H_3$
$R^5$=4-$OCF_3$—$C_6H_4$
and the substituent $R^6$ for a compound corresponds to a line of Table A.

Table 865 (compounds 865.1–865.974)
Compounds of the general formula I.1 where
$R^3$=methyl
$R^4$=$C_3H_3$
$R^5$=3-Cl; 4-$OCH_3$—$C_6H_3$
and the substituent $R^6$ for a compound corresponds to a line of Table A.

Table 866 (compounds 866.1–866.974)
Compounds of the general formula I.2 where
$R^3$=methyl
$R^4$=$C_3H_3$
$R^5$=3-Cl; 4-$OCH_3$—$C_6H_3$
and the substituent $R^6$ for a compound corresponds to a line of Table A.

Table 867 (compounds 867.1–867.974)
Compounds of the general formula I.3 where
$R^3$=methyl
$R^4$=$C_3H_3$
$R^5$=3-Cl; 4-$OCH_3$—$C_6H_3$
and the substituent $R^6$ for a compound corresponds to a line of Table A.

Table 868 (compounds 868.1–868.974)
Compounds of the general formula I.4 where
$R^3$=methyl
$R^4$=$C_3H_3$
$R^5$=3-Cl; 4-$OCH_3$—$C_6H_3$
and the substituent $R^6$ for a compound corresponds to a line of Table A.

Table 869 (compounds 869.1–869.974)
Compounds of the general formula I.1 where
$R^3$=methyl
$R^4$=$C_3H_3$ $R^5$ = 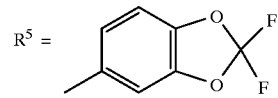

and the substituent $R^6$ for a compound corresponds to a line of Table A.

Table 870 (compounds 870.1–870.974)
  Compounds of the general formula I.2 where
  $R^3$=methyl
  $R^4$=$C_3H_3$

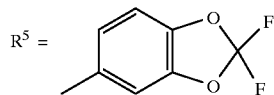

and the substituent $R^6$ for a compound corresponds to a line of Table A.
Table 871 (compounds 871.1–871.974)
  Compounds of the general formula I.3 where
  $R^3$=methyl
  $R^4$=$C_3H_3$

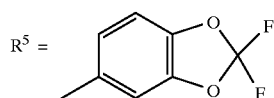

and the substituent $R^6$ for a compound corresponds to a line of Table A.
Table 872 (compounds 872.1–872.974)
  Compounds of the general formula I.4 where
  $R^3$=methyl
  $R^4$=$C_3H_3$

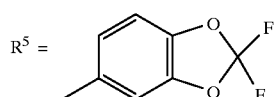

and the substituent $R^6$ for a compound corresponds to a line of Table A.
Table 873 (compounds 873.1–873.974)
  Compounds of the general formula I.1 where
  $R^3$=methyl
  $R^4$=$C_3H_3$
  $R^5$=pyridin-2-yl
and the substituent $R^6$ for a compound corresponds to a line of Table A.
Table 874 (compounds 874.1–874.974)
  Compounds of the general formula I.2 where
  $R^3$=methyl
  $R^4$=$C_3H_3$
  $R^5$=pyridin-2-yl
and the substituent $R^6$ for a compound corresponds to a line of Table A.
Table 875 (compounds 875.1–875.974)
  Compounds of the general formula I.3 where
  $R^3$=methyl
  $R^4$=$C_3H_3$
  $R^5$=pyridin-2-yl
and the substituent $R^6$ for a compound corresponds to a line of Table A.
Table 876 (compounds 876.1–876.974)
  Compounds of the general formula I.4 where
  $R^3$=methyl
  $R^4$=$C_3H_3$
  $R^5$=pyridin-2-yl
and the substituent $R^6$ for a compound corresponds to a line of Table A.
Table 877 (compounds 877.1–877.974)
  Compounds of the general formula I.1 where
  $R^3$=methyl
  $R^4$=$C_3H_3$
  $R^5$=pyridin-3-yl
and the substituent $R^6$ for a compound corresponds to a line of Table A.
Table 878 (compounds 878.1–878.974)
  Compounds of the general formula I.2 where
  $R^3$=methyl
  $R^4$=$C_3H_3$
  $R^5$=pyridin-3-yl
and the substituent $R^6$ for a compound corresponds to a line of Table A.
Table 879 (compounds 879.1–879.974)
  Compounds of the general formula I.3 where
  $R^3$=methyl
  $R^4$=$C_3H_3$
  $R^5$=pyridin-3-yl
and the substituent $R^6$ for a compound corresponds to a line of Table A.
Table 880 (compounds 880.1–880.974)
  Compounds of the general formula I.4 where
  $R^3$=methyl
  $R^4$=$C_3H_3$
  $R^5$=pyridin-3-yl
and the substituent $R^6$ for a compound corresponds to a line of Table A.
Table 881 (compounds 881.1–881.974)
  Compounds of the general formula I.1 where
  $R^3$=methyl
  $R^4$=$C_3H_3$
  $R^5$=pyridin-4-yl
and the substituent $R^6$ for a compound corresponds to a line of Table A.
Table 882 (compounds 882.1–882.974)
  Compounds of the general formula I.2 where
  $R^3$=methyl
  $R^4$=$C_3H_3$
  $R^5$=pyridin-4-yl
and the substituent $R^6$ for a compound corresponds to a line of Table A.
Table 883 (compounds 883.1–883.974)
  Compounds of the general formula I.3 where
  $R^3$=methyl
  $R^4$=$C_3H_3$
  $R^5$=pyridin-4-yl
and the substituent $R^6$ for a compound corresponds to a line of Table A.
Table 884 (compounds 884.1–884.974)
  Compounds of the general formula I.4 where
  $R^3$=methyl
  $R^4$=$C_3H_3$
  $R^5$=pyridin-4-yl
and the substituent $R^6$ for a compound corresponds to a line of Table A.
Table 885 (compounds 885.1–885.974)
  Compounds of the general formula I.1 where
  $R^3$=methyl
  $R^4$=$C_3H_3$
  $R^5$=3-$CH_3$-pyridin-2-yl
and the substituent $R^6$ for a compound corresponds to a line of Table A.

Table 886 (compounds 886.1–886.974)
Compounds of the general formula I.2 where
$R^3$=methyl
$R^4=C_3H_3$
$R^5$=3-$CH_3$-pyridin-2-yl
and the substituent $R^6$ for a compound corresponds to a line of Table A.

Table 887 (compounds 887.1–887.974)
Compounds of the general formula I.3 where
$R^3$=methyl
$R^4=C_3H_3$
$R^5$=3-$CH_3$-pyridin-2-yl
and the substituent $R^6$ for a compound corresponds to a line of Table A.

Table 888 (compounds 888.1–888.974)
Compounds of the general formula I.4 where
$R^3$=methyl
$R^4=C_3H_3$
$R^5$=3-$CH_3$-pyridin-2-yl
and the substituent $R^6$ for a compound corresponds to a line of Table A.

Table 889 (compounds 889.1–889.974)
Compounds of the general formula I.1 where
$R^3$=methyl
$R^4=C_3H_3$
$R^5$ 4-$CH_3$-pyridin-2-yl
and the substituent $R^6$ for a compound corresponds to a line of Table A.

Table 890 (compounds 890.1–890.974)
Compounds of the general formula I.2 where
$R^3$=methyl
$R^4=C_3H_3$
$R^5$=4-$CH_3$-pyridin-2-yl
and the substituent $R^6$ for a compound corresponds to a line of Table A.

Table 891 (compounds 891.1–891.974)
Compounds of the general formula I.3 where
$R^3$=methyl
$R^4=C_3H_3$
$R^5$=4-$CH_3$-pyridin-2-yl
and the substituent $R^6$ for a compound corresponds to a line of Table A.

Table 892 (compounds 892.1–892.974)
Compounds of the general formula I.4 where
$R^3$=methyl
$R^4=C_3H_3$
$R^5$=4-$CH_3$-pyridin-2-yl
and the substituent $R^6$ for a compound corresponds to a line of Table A.

Table 893 (compounds 893.1–893.974)
Compounds of the general formula I.1 where
$R^3$=methyl
$R^4=C_3H_3$
$R^5$=3-$OCH_3$-pyridin-2-yl
and the substituent $R^6$ for a compound corresponds to a line of Table A.

Table 894 (compounds 894.1–894.974)
Compounds of the general formula I.2 where
$R^3$=methyl
$R^4=C_3H_3$
$R^5$=3-$OCH_3$-pyridin-2-yl
and the substituent $R^6$ for a compound corresponds to a line of Table A.

Table 895 (compounds 895.1–895.974)
Compounds of the general formula I.3 where
$R^3$=methyl
$R^4=C_3H_3$
$R^5$=3-$OCH_3$-pyridin-2-yl
and the substituent $R^6$ for a compound corresponds to a line of Table A.

Table 896 (compounds 896.1–896.974)
Compounds of the general formula I.4 where
$R^3$=methyl
$R^4=C_3H_3$
$R^5$=3-$OCH_3$-pyridin-2-yl
and the substituent $R^6$ for a compound corresponds to a line of Table A.

Table 897 (compounds 897.1–897.974)
Compounds of the general formula I.1 where
$R^3$=methyl
$R^4=C_3H_3$
$R^5$=4-Cl-pyridin-2-yl
and the substituent $R^6$ for a compound corresponds to a line of Table A.

Table 898 (compounds 898.1–898.974)
Compounds of the general formula I.2 where
$R^3$=methyl
$R^4=C_3H_3$
$R^5$=4-Cl-pyridin-2-yl
and the substituent $R^6$ for a compound corresponds to a line of Table A.

Table 899 (compounds 899.1–899.974)
Compounds of the general formula I.3 where
$R^3$=methyl
$R^4=C_3H_3$
$R^5$=4-Cl-pyridin-2-yl
and the substituent $R^6$ for a compound corresponds to a line of Table A.

Table 900 (compounds 900.1–900.974)
Compounds of the general formula I.4 where
$R^3$=methyl
$R^4=C_3H_3$
$R^5$=4-Cl-pyridin-2-yl
and the substituent $R^6$ for a compound corresponds to a line of Table A.

Table 901 (compounds 901.1–901.974)
Compounds of the general formula I.1 where
$R^3$=methyl
$R^4=C_3H_3$
$R^5$=5-Cl-pyridin-2-yl
and the substituent $R^6$ for a compound corresponds to a line of Table A.

Table 902 (compounds 902.1–902.974)
Compounds of the general formula I.2 where
$R^3$=methyl
$R^4=C_3H_3$
$R^5$=5-Cl-pyridin-2-yl
and the substituent $R^6$ for a compound corresponds to a line of Table A.

Table 903 (compounds 903.1–903.974)
Compounds of the general formula I.3 where
$R^3$=methyl
$R^4=C_3H_3$
$R^5$=5-Cl-pyridin-2-yl
and the substituent $R^6$ for a compound corresponds to a line of Table A.

Table 904 (compounds 904.1–904.974)
Compounds of the general formula I.4 where
$R^3$=methyl
$R^4$=$C_3H_3$
$R^5$=5-Cl-pyridin-2-yl
and the substituent $R^6$ for a compound corresponds to a line of Table A.

Table 905 (compounds 905.1–905.974)
Compounds of the general formula I.1 where
$R^3$=methyl
$R^4$=$C_3H_3$
$R^5$=pyrimidin-2-yl
and the substituent $R^6$ for a compound corresponds to a line of Table A.

Table 906 (compounds 906.1–906.974)
Compounds of the general formula I.2 where
$R^3$=methyl
$R^4$=$C_3H_3$
$R^5$=pyrimidin-2-yl
and the substituent $R^6$ for a compound corresponds to a line of Table A.

Table 907 (compounds 907.1–907.974)
Compounds of the general formula I.3 where
$R^3$=methyl
$R^4$=$C_3H_3$
$R^5$=pyrimidin-2-yl
and the substituent $R^6$ for a compound corresponds to a line of Table A.

Table 908 (compounds 908.1–908.974)
Compounds of the general formula I.4 where
$R^3$=methyl
$R^4$=$C_3H_3$
$R^5$=pyrimidin-2-yl
and the substituent $R^6$ for a compound corresponds to a line of Table A.

Table 909 (compounds 909.1–909.974)
Compounds of the general formula I.1 where
$R^3$=methyl
$R^4$=$C_3H_3$
$R^5$=5-Cl-pyrimidin-2-yl
and the substituent $R^6$ for a compound corresponds to a line of Table A.

Table 910 (compounds 910.1–910.974)
Compounds of the general formula I.2 where
$R^3$=methyl
$R^4$=$C_3H_3$
$R^5$=5-Cl-pyrimidin-2-yl
and the substituent $R^6$ for a compound corresponds to a line of Table A.

Table 911 (compounds 911.1–911.974)
Compounds of the general formula I.3 where
$R^3$=methyl
$R^4$=$C_3H_3$
$R^5$=5-Cl-pyrimidin-2-yl
and the substituent $R^6$ for a compound corresponds to a line of Table A.

Table 912 (compounds 912.1–912.974)
Compounds of the general formula I.4 where
$R^3$=methyl
$R^4$=$C_3H_3$
$R^5$=5-Cl-pyrimidin-2-yl
and the substituent $R^6$ for a compound corresponds to a line of Table A.

Table 913 (compounds 913.1–913.974)
Compounds of the general formula I.1 where
$R^3$=methyl
$R^4$=$C_3H_3$
$R^5$=4-$CH_3$-pyrimidin-2-yl
and the substituent $R^6$ for a compound corresponds to a line of Table A.

Table 914 (compounds 914.1–914.974)
Compounds of the general formula I.2 where
$R^3$=methyl
$R^4$=$C_3H_3$
$R^5$=4-$CH_3$-pyrimidin-2-yl
and the substituent $R^6$ for a compound corresponds to a line of Table A.

Table 915 (compounds 915.1–915.974)
Compounds of the general formula I.3 where
$R^3$=methyl
$R^4$=$C_3H_3$
$R^5$=4-$CH_3$-pyrimidin-2-yl
and the substituent $R^6$ for a compound corresponds to a line of Table A.

Table 916 (compounds 916.1–916.974)
Compounds of the general formula I.4 where
$R^3$=methyl
$R^4$=$C_3H_3$
$R^5$=4-$CH_3$-pyrimidin-2-yl
and the substituent $R^6$ for a compound corresponds to a line of Table A.

Table 917 (compounds 917.1–917.974)
Compounds of the general formula I.1 where
$R^3$=methyl
$R^4$=$C_3H_3$
$R^5$=4-Cl-furan-2-yl
and the substituent $R^6$ for a compound corresponds to a line of Table A.

Table 918 (compounds 918.1–918.974)
Compounds of the general formula I.2 where
$R^3$=methyl
$R^4$=$C_3H_3$
$R^5$=4-Cl-furan-2-yl
and the substituent $R^6$ for a compound corresponds to a line of Table A.

Table 919 (compounds 919.1–919.974)
Compounds of the general formula I.3 where
$R^3$=methyl
$R^4$=$C_3H_3$
$R^5$=4-Cl-furan-2-yl
and the substituent $R^6$ for a compound corresponds to a line of Table A.

Table 920 (compounds 920.1–920.974)
Compounds of the general formula I.4 where
$R^3$=methyl
$R^4$=$C_3H_3$
$R^5$=4-Cl-furan-2-yl
and the substituent $R^6$ for a compound corresponds to a line of Table A.

Table 921 (compounds 921.1–921.974)
Compounds of the general formula I.1 where
$R^3$=methyl
$R^4$=$C_3H_3$
$R^5$=4-$CH_3$-furan-2-yl
and the substituent $R^6$ for a compound corresponds to a line of Table A.

Table 922 (compounds 922.1–922.974)
Compounds of the general formula I.2 where
$R^3$=methyl
$R^4$=$C_3H_3$
$R^5$=4-$CH_3$-furan-2-yl
and the substituent $R^6$ for a compound corresponds to a line of Table A.

Table 923 (compounds 923.1–923.974)
Compounds of the general formula I.3 where
$R^3$=methyl
$R^4$=$C_3H_3$
$R^5$=4-$CH_3$-furan-2-yl
and the substituent $R^6$ for a compound corresponds to a line of Table A.

Table 924 (compounds 924.1–924.974)
Compounds of the general formula I.4 where
$R^3$=methyl
$R^4$=$C_3H_3$
$R^5$=4-$CH_3$-furan-2-yl
and the substituent $R^6$ for a compound corresponds to a line of Table A.

Table 925 (compounds 925.1–925.974)
Compounds of the general formula I.1 where
$R^3$=methyl
$R^4$=$C_3H_3$
$R^5$=thien-2-yl
and the substituent $R^6$ for a compound corresponds to a line of Table A.

Table 926 (compounds 926.1–926.974)
Compounds of the general formula I.2 where
$R^3$=methyl
$R^4$=$C_3H_3$
$R^5$=thien-2-yl
and the substituent $R^6$ for a compound corresponds to a line of Table A.

Table 927 (compounds 927.1–927.974)
Compounds of the general formula I.3 where
$R^3$=methyl
$R^4$=$C_3H_3$
$R^5$=thien-2-yl
and the substituent $R^6$ for a compound corresponds to a line of Table A.

Table 928 (compounds 928.1–928.974)
Compounds of the general formula I.4 where
$R^3$=methyl
$R^4$=$C_3H_3$
$R^5$=thien-2-yl
and the substituent $R^6$ for a compound corresponds to a line of Table A.

Table 929 (compounds 929.1–929.974)
Compounds of the general formula I.1 where
$R^3$=methyl
$R^4$=$C_3H_3$
$R^5$=thien-3-yl
and the substituent $R^6$ for a compound corresponds to a line of Table A.

Table 930 (compounds 930.1–930.974)
Compounds of the general formula I.2 where
$R^3$=methyl
$R^4$=$C_3H_3$
$R^5$=thien-3-yl
and the substituent $R^6$ for a compound corresponds to a line of Table A.

Table 931 (compounds 931.1–931.974)
Compounds of the general formula I.3 where
$R^3$=methyl
$R^4$=$C_3H_3$
$R^5$=thien-3-yl
and the substituent $R^6$ for a compound corresponds to a line of Table A.

Table 932 (compounds 932.1–932.974)
Compounds of the general formula I.4 where
$R^3$=methyl
$R^4$=$C_3H_3$
$R^5$=thien-3-yl
and the substituent $R^6$ for a compound corresponds to a line of Table A.

Table 933 (compounds 933.1–933.974)
Compounds of the general formula I.1 where
$R^3$=methyl
$R^4$=$C_3H_3$
$R^5$=oxazol-2-yl
and the substituent $R^6$ for a compound corresponds to a line of Table A.

Table 934 (compounds 934.1–934.974)
Compounds of the general formula I.2 where
$R^3$=methyl
$R^4$=$C_3H_3$
$R^5$=oxazol-2-yl
and the substituent $R^6$ for a compound corresponds to a line of Table A.

Table 935 (compounds 935.1–935.974)
Compounds of the general formula I.3 where
$R^3$=methyl
$R^4$=$C_3H_3$
$R^5$=oxazol-2-yl
and the substituent $R^6$ for a compound corresponds to a line of Table A.

Table 936 (compounds 936.1–936.974)
Compounds of the general formula I.4 where
$R^3$=methyl
$R^4$=$C_3H_3$
$R^5$=oxazol-2-yl
and the substituent $R^6$ for a compound corresponds to a line of Table A.

Table 937 (compounds 937.1–937.974)
Compounds of the general formula I.1 where
$R^3$=methyl
$R^4$=$C_3H_3$
$R^5$=isoxazol-3-yl
and the substituent $R^6$ for a compound corresponds to a line of Table A.

Table 938 (compounds 938.1–938.974)
Compounds of the general formula I.2 where
$R^3$=methyl
$R^4$=$C_3H_3$
$R^5$=isoxazol-3-yl
and the substituent $R^6$ for a compound corresponds to a line of Table A.

Table 939 (compounds 939.1–939.974)
Compounds of the general formula I.3 where
$R^3$=methyl
$R^4$=$C_3H_3$
$R^5$=isoxazol-3-yl
and the substituent $R^6$ for a compound corresponds to a line of Table A.

Table 940 (compounds 940.1–940.974)
  Compounds of the general formula I.4 where
    $R^3$=methyl
    $R^4$=$C_3H_3$
    $R^5$=isoxazol-3-yl
  and the substituent $R^6$ for a compound corresponds to a line of Table A.

Table 941 (compounds 941.1–941.974)
  Compounds of the general formula I.1 where
    $R^3$=methyl
    $R^4$=$C_3H_3$
    $R^5$=isoxazol-4-yl
  and the substituent $R^6$ for a compound corresponds to a line of Table A.

Table 942 (compounds 942.1–942.974)
  Compounds of the general formula I.2 where
    $R^3$=methyl
    $R^4$=$C_3H_3$
    $R^5$=isoxazol-4-yl
  and the substituent $R^6$ for a compound corresponds to a line of Table A.

Table 943 (compounds 943.1–943.974)
  Compounds of the general formula I.3 where
    $R^3$=methyl
    $R^4$=$C_3H_3$
    $R^5$=isoxazol-4-yl
  and the substituent $R^6$ for a compound corresponds to a line of Table A.

Table 944 (compounds 944.1–944.974)
  Compounds of the general formula I.4 where
    $R^3$=methyl
    $R^4$=$C_3H_3$
    $R^5$=isoxazol-4-yl
  and the substituent $R^6$ for a compound corresponds to a line of Table A.

Table 945 (compounds 945.1–945.974)
  Compounds of the general formula I.1 where
    $R^3$=methyl
    $R^4$=$C_3H_3$
    $R^5$=pyrazol-3-yl
  and the substituent $R^6$ for a compound corresponds to a line of Table A.

Table 946 (compounds 946.1–946.974)
  Compounds of the general formula I.2 where
    $R^3$=methyl
    $R^4$=$C_3H_3$
    $R^5$=pyrazol-3-yl
  and the substituent $R^6$ for a compound corresponds to a line of Table A.

Table 947 (compounds 947.1–947.974)
  Compounds of the general formula I.3 where
    $R^3$=methyl
    $R^4$=$C_3H_3$
    $R^5$=pyrazol-3-yl
  and the substituent $R^6$ for a compound corresponds to a line of Table A.

Table 948 (compounds 948.1–948.974)
  Compounds of the general formula I.4 where
    $R^3$=methyl
    $R^4$=$C_3H_3$
    $R^5$=pyrazol-3-yl
  and the substituent $R^6$ for a compound corresponds to a line of Table A.

Table 949 (compounds 949.1–949.974)
  Compounds of the general formula I.1 where
    $R^3$=methyl
    $R^4$=$C_3H_3$
    $R^5$=1,3,4-oxadiazol-5-yl
  and the substituent $R^6$ for a compound corresponds to a line of Table A.

Table 950 (compounds 950.1–950.974)
  Compounds of the general formula I.2 where
    $R^3$=methyl
    $R^4$=$C_3H_3$
    $R^5$=1,3,4-oxadiazol-5-yl
  and the substituent $R^6$ for a compound corresponds to a line of Table A.

Table 951 (compounds 951.1–951.974)
  Compounds of the general formula I.3 where
    $R^3$=methyl
    $R^4$=$C_3H_3$
    $R^5$=1,3,4-oxadiazol-5-yl
  and the substituent $R^6$ for a compound corresponds to a line of Table A.

Table 952 (compounds 952.1–952.974)
  Compounds of the general formula I.4 where
    $R^3$=methyl
    $R^4$=$C_3H_3$
    $R^5$=1,3,4-oxadiazol-5-yl
  and the substituent $R^6$ for a compound corresponds to a line of Table A.

Table 953 (compounds 953.1–953.974)
  Compounds of the general formula I.1 where
    $R^3$=methyl
    $R^4$=$C_3H_3$
    $R^5$=1,2,4-triazol-3-yl
  and the substituent $R^6$ for a compound corresponds to a line of Table A.

Table 954 (compounds 954.1–954.974)
  Compounds of the general formula I.2 where
    $R^3$=methyl
    $R^4$=$C_3H_3$
    $R^5$=1,2,4-triazol-3-yl
  and the substituent $R^6$ for a compound corresponds to a line of Table A.

Table 955 (compounds 955.1–955.974)
  Compounds of the general formula I.3 where
    $R^3$=methyl
    $R^4$=$C_3H_3$
    $R^5$=1,2,4-triazol-3-yl
  and the substituent $R^6$ for a compound corresponds to a line of Table A.

Table 956 (compounds 956.1–956.974)
  Compounds of the general formula I.4 where
    $R^3$=methyl
    $R^4$=$C_3H_3$
    $R^5$=1,2,4-triazol-3-yl
  and the substituent $R^6$ for a compound corresponds to a line of Table A.

Table 957 (compounds 957.1–957.974)
  Compounds of the general formula I.1 where
    $R^3$=methyl
    $R^4$=$C_3H_3$
    $R^5$=pyrrol-2-yl
  and the substituent $R^6$ for a compound corresponds to a line of Table A.

Table 958 (compounds 558.1 [sic] 658.974 [sic])
  Compounds of the general formula I.2 where
    $R^3$=methyl
    $R^4$=$C_3H_3$
    $R^5$=pyrrol-2-yl
  and the substituent $R^6$ for a compound corresponds to a line of Table A.
Table 959 (compounds 959.1–959.974)
  Compounds of the general formula I.3 where
    $R^3$=methyl
    $R^4$=$C_3H_3$
    $R^5$=pyrrol-2-yl
  and the substituent $R^6$ for a compound corresponds to a line of Table A.
Table 960 (compounds 960.1–960.974)
  Compounds of the general formula I.4 where
    $R^3$=methyl
    $R^4$=$C_3H_3$
    $R^5$=pyrrol-2-yl
  and the substituent $R^6$ for a compound corresponds to a line of Table A.
Table 961 (compounds 961.1–961.974)
  Compounds of the general formula I.1 where
    $R^3$=trifluoromethyl
    $R^4$=$CH_3$
    $R^5$=$CH_3$
  and the substituent $R^6$ for a compound corresponds to a line of Table A.
Table 962 (compounds 962.1–962.974)
  Compounds of the general formula I.2 where
    $R^3$=trifluoromethyl
    $R^4$=$CH_3$
    $R^5$=$CH_3$
  and the substituent $R^6$ for a compound corresponds to a line of Table A.
Table 963 (compounds 963.1–963.974)
  Compounds of the general formula I.3 where
    $R^3$=trifluoromethyl
    $R^4$=$CH_3$
    $R^5$=$CH_3$
  and the substituent $R^6$ for a compound corresponds to a line of Table A.
Table 964 (compounds 964.1–964.974)
  Compounds of the general formula I.4 where
    $R^3$=trifluoromethyl
    $R^4$=$CH_3$
    $R^5$=$CH_3$
  and the substituent $R^6$ for a compound corresponds to a line of Table A.
Table 965 (compounds 965.1–965.974)
  Compounds of the general formula I.1 where
    $R^3$=trifluoromethyl
    $R^4$=$C_2H_5$
    $R^5$=$CH_3$
  and the substituent $R^6$ for a compound corresponds to a line of Table A.
Table 966 (compounds 966.1–966.974)
  Compounds of the general formula I.2 where
    $R^3$=trifluoromethyl
    $R^4$=$C_2H_5$
    $R^5$=$CH_3$
  and the substituent $R^6$ for a compound corresponds to a line of Table A.
Table 967 (compounds 967.1–967.974)
  Compounds of the general formula I.3 where
    $R^3$=trifluoromethyl
    $R^4$=$C_2H_5$
    $R^5$=$CH_3$
  and the substituent $R^6$ for a compound corresponds to a line of Table A.
Table 968 (compounds 968.1–968.974)
  Compounds of the general formula I.4 where
    $R^3$=trifluoromethyl
    $R^4$=$C_2H_5$
    $R^5$=$CH_3$
  and the substituent $R^6$ for a compound corresponds to a line of Table A.
Table 969 (compounds 969.1–969.974)
  Compounds of the general formula I.1 where
    $R^3$=trifluoromethyl
    $R^4$=$C_3H_3$
    $R^5$=$CH_3$
  and the substituent $R^6$ for a compound corresponds to a line of Table A.
Table 970 (compounds 970.1–970.974)
  Compounds of the general formula I.2 where
    $R^3$=trifluoromethyl
    $R^4$=$C_3H_3$
    $R^5$=$CH_3$
  and the substituent $R^6$ for a compound corresponds to a line of Table A.
Table 971 (compounds 971.1–971.974)
  Compounds of the general formula I.3 where
    $R^3$=trifluoromethyl
    $R^4$=$C_3H_3$
    $R^5$=$C_3H_5$
  and the substituent $R^6$ for a compound corresponds to a line of Table A.
Table 972 (compounds 972.1–972.974)
  Compounds of the general formula I.4 where
    $R^3$=trifluoromethyl
    $R^4$=$C_3H_3$
    $R^5$=$CH_3$
  and the substituent $R^6$ for a compound corresponds to a line of Table A.
Table 973 (compounds 973.1–731.974 [sic])
  Compounds of the general formula I.1 where
    $R^3$=cyclopropyl
    $R^4$=$CH_3$
    $R^5$=$CH_3$
  and the substituent $R^6$ for a compound corresponds to a line of Table A.
Table 974 (compounds 974.1–974.974)
  Compounds of the general formula I.2 where
    $R^3$=cyclopropyl
    $R^4$=$CH_3$
    $R^5$=$CH_3$
  and the substituent $R^6$ for a compound corresponds to a line of Table A.
Table 975 (compounds 975.1–975.974)
  Compounds of the general formula I.3 where
    $R^3$=cyclopropyl
    $R^4$=$CH_3$
    $R^5$=$CH_3$
  and the substituent $R^6$ for a compound corresponds to a line of Table A.

Table 976 (compounds 976.1–976.974)
  Compounds of the general formula I.4 where
  $R^3$=cyclopropyl
  $R^4$=$CH_3$
  $R^5$=$CH_3$
  and the substituent $R^6$ for a compound corresponds to a line of Table A.
Table 977 (compounds 977.1–977.974)
  Compounds of the general formula I.1 where
  $R^3$=cyclopropyl
  $R^4$=$C_2H_5$
  $R^5$=$CH_3$
  and the substituent $R^6$ for a compound corresponds to a line of Table A.
Table 978 (compounds 978.1–978.974)
  Compounds of the general formula I.2 where
  $R^3$=cyclopropyl
  $R^4$=$C_2H_5$
  $R^5$=$CH_3$
  and the substituent $R^6$ for a compound corresponds to a line of Table A.
Table 979 (compounds 979.1–979.974)
  Compounds of the general formula I.3 where
  $R^3$=cyclopropyl
  $R^4$=$C_2H_5$
  $R^5$=$CH_3$
  and the substituent $R^6$ for a compound corresponds to a line of Table A.
Table 980 (compounds 980.1–980.974)
  Compounds of the general formula I.4 where
  $R^3$=cyclopropyl
  $R^4$=$C_2H_5$
  $R^5$=$CH_3$
  and the substituent $R^6$ for a compound corresponds to a line of Table A.
Table 981 (compounds 981.1–981.974)
  Compounds of the general formula I.1 where
  $R^3$=cyclopropyl
  $R^4$=$C_3H_3$
  $R^5$=$CH_3$
  and the substituent $R^6$ for a compound corresponds to a line of Table A.
Table 982 (compounds 982.1–982.974)
  Compounds of the general formula I.2 where
  $R^3$=cyclopropyl
  $R^4$=$C_3H_3$
  $R^5$=$CH_3$
  and the substituent $R^6$ for a compound corresponds to a line of Table A.
Table 983 (compounds 983.1–983.974)
  Compounds of the general formula I.3 where
  $R^3$=cyclopropyl
  $R^4$=$C_3H_3$
  $R^5$=$CH_3$
  and the substituent $R^6$ for a compound corresponds to a line of Table A.
Table 984 (compounds 984.1–984.974)
  Compounds of the general formula I.4 where
  $R^3$=cyclopropyl
  $R^4$=$C_3H_3$
  $R^5$=$CH_3$
  and the substituent $R^6$ for a compound corresponds to a line of Table A.
Table 985 (compounds 985.1–985.974)
  Compounds of the general formula I.1 where
  $R^3$=cyano
  $R^4$=$CH_3$
  $R^5$=$CH_3$
  and the substituent $R^6$ for a compound corresponds to a line of Table A.
Table 986 (compounds 986.1–986.974)
  Compounds of the general formula I.2 where
  $R^3$=cyano
  $R^4$=$CH_3$
  $R^5$=$CH_3$
  and the substituent $R^6$ for a compound corresponds to a line of Table A.
Table 987 (compounds 987.1–987.974)
  Compounds of the general formula I.3 where
  $R^3$=cyano
  $R^4$=$CH_3$
  $R^5$=$CH_3$
  and the substituent $R^6$ for a compound corresponds to a line of Table A.
Table 988 (compounds 988.1–988.974)
  Compounds of the general formula I.4 where
  $R^3$=cyano
  $R^4$=$CH_3$
  $R^5$=$CH_3$
  and the substituent $R^6$ for a compound corresponds to a line of Table A.
Table 989 (compounds 989.1–989.974)
  Compounds of the general formula I.1 where
  $R^3$=cyano
  $R^4$=$C_2H_5$
  $R^5$=$C_2H_5$
  and the substituent $R^6$ for a compound corresponds to a line of Table A.
Table 990 (compounds 990.1–990.974)
  Compounds of the general formula I.2 where
  $R^3$=cyano
  $R^4$=$C_2H_5$
  $R^5$=$CH_3$
  and the substituent $R^6$ for a compound corresponds to a line of Table A.
Table 991 (compounds 991.1–991.974)
  Compounds of the general formula I.3 where
  $R^3$=cyano
  $R^4$=$C_2H_5$
  $R^5$=$CH_3$
  and the substituent $R^6$ for a compound corresponds to a line of Table A.
Table 992 (compounds 992.1–992.974)
  Compounds of the general formula I.4 where
  $R^3$=cyano
  $R^4$=$C_2H_5$
  $R^5$=$CH_3$
  and the substituent $R^6$ for a compound corresponds to a line of Table A.
Table 993 (compounds 993.1–993.974)
  Compounds of the general formula I.1 where
  $R^3$=cyano
  $R^4$=$C_3H_3$
  $R^5$=$CH_3$
  and the substituent $R^6$ for a compound corresponds to a line of Table A.

Table 994 (compounds 994.1–994.974)
  Compounds of the general formula I.2 where
  $R^3$=cyano
  $R^4=C_3H_3$
  $R^5=CH_3$
  and the substituent $R^6$ for a compound corresponds to a line of Table A.
Table 995 (compounds 995.1–995.974)
  Compounds of the general formula I.3 where
  $R^3$=cyano
  $R^4=C_3H_3$
  $R^5=CH_3$
  and the substituent $R^6$ for a compound corresponds to a line of Table A.
Table 996 (compounds 996.1–996.974)
  Compounds of the general formula I.4 where
  $R^3$=cyano
  $R^4=C_3H_3$
  $R^5=CH_3$
  and the substituent $R^6$ for a compound corresponds to a line of Table A.

The compounds I are suitable for use as fungicides.

The compounds I are distinguished by an outstanding activity against a wide spectrum of phytopathogenic fungi, in particular from the classes of the Ascomycetes, Phycomycetes and Basidiomycetes. Some of them act systemically and can therefore be employed in crop protection as foliar- and soil-acting fungicides.

They are especially important for controlling a large number of fungi in a variety of crop plants such as wheat, rye, barley, oats, rice, maize, grass, cotton, soybeans, coffee, sugar cane, grapevine, fruit species, ornamentals and vegetable species such as cucumbers, beans and cucurbits, and in the seeds of these plants.

They are particularly suitable for controlling the following plant diseases: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, *Septoria nodorum* in wheat, *Botrytis cinerea* (gray mold) in strawberries, vegetable species, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, Fusarium and Verticillium species in a variety of plants, *Plasmopara viticola* in grapevines, Alternaria species in vegetables and fruit.

The compounds I are moreover suitable for controlling harmful fungi in the protection of materials (eg. wood, paper, fibers or fabrics) and in the protection of stored products.

The compounds I are used by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the intended purpose; in any case, it should ensure fine and uniform distribution of the compound according to the invention. The formulations are prepared in a manner known per se, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly-disperse silica, silicates); emulsifiers, such as non-ionic and anionic emulsifiers (eg. polyoxyethylene fatty alcohol ethers, alkylsulfonates and arylsulfonates) and dispersants such as lignosulfite waste liquors and methylcellulose.

The fungicidal compositions generally comprise from 0.1 to 95, preferably from 0.5 to 90%, by weight of active ingredient.

The rates of application for use in crop protection are from 0.01 to 2.0 kg of active ingredient per ha, depending on the nature of the desired effect.

In the treatment of seeds, amounts of 0.001 to 0.1 g, preferably 0.01 to 0.05 g, of active ingredient are generally required per kilogram of seed.

When used in the protection of materials or stored products, the rate of application of active ingredient depends on the nature of the intended use and the desired effect. Usual rates of application for the protection of materials are, for example, 0.001 g to 2 kg, preferably 0.005 g to 1 kg, of active ingredient per cubic meter of material treated.

When using the agents according to the invention as fungicides, they can be present, in the use form, together with other active ingredients, the [sic] eg. with herbicides, insecticides, growth regulators, fungicides or else with fertilizers.

In many cases, a mixture with fungicides results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediamine-bis-dithiocarbamate, tetramethylthiuram disulfides [sic], ammonia complex of zinc (N,N-ethylenebisdithiocarbamate), ammonia complex of zink (N,N'-propylenebisdithiocarbamate), zinc (N,N'-propylenebisdithiocarbamate), N,N'-polypropylenebis(thiocarbamoyl) disulfide;

nitro derivatives, such as dinitro(1-methylheptyl)phenyl crotonate, 2-sec-butyl-4,6-dinitrophenyl-3,3-dimethyl acrylate, 2-sec-butyl-4,6-dinitrophenyl isopropylcarbonate, di-isopropyl 5-nitroisophthalate;

heterocyclic substances, such as 2-heptadecyl-2-imidazoline acetate, 2,4-dichlor-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichlor-2,5-dimethoxybenzene, 4-(2-chlorophenylhydrazono)-3-methyl-5-isoxazolone, pyridin 2-thio-1-oxide, 8-hydroxyquinoline and its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-Cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(l-(2,2,2-trichloroethyl)formamide [sic], 1-(3,4-dichloranilino)-1-formylamino-2,2,2-trichloroethane, 2,6-dimethyl-N-tridecylmorpholine and its salts, 2,6-dimethyl-N-cyclododecylmorpholine and its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, methyl N-(2,6-dimethylphenyl)-N-(2'-methoxyacetyl)-DL-alaninate, N-(2,6-dimethylphenyl)-N-chloroacetyl-D,L-2-aminobutyrolactone, methyl N-(2,6-dimethylphenyl)-N-(phenylacetyl)-DL-alaninate, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorphenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethyl-phenyl)-5-trifluormethyl-3-chloro-2-aminopyridine, 1-((bis(4-fluorophenyl)methylsilyl)methyl)-1H-1,2,4-triazole.

The compounds of the formula I are furthermore suitable for efficiently controlling pests from the classes of the insects, arachnids and nematodes. They can be employed as pesticides in crop protection and in the hygiene, stored-product and veterinary sectors.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera) for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina), such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot eelworms, eg. *Meloidogyne hapla, Meloidogyne incognita, Meloidogyne javanica,* cyst nematodes, eg. *Globodera rostochiensis, Heterodera avenae, Heterodera glycines, Heterodera schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be applied as such, in the form of their formulations or the use forms prepared therefrom, eg. in the form of ready-to-spray solutions, powders, suspensions or dispersions, emulsions, oil dispersions, pastes, dusts, materials for spreading, or granules, by means of spraying, atomizing, dusting, spreading or pouring. The use forms depend entirely on the intended purposes; in any case, they should ensure the finest possible distribution of the active ingredients according to the invention.

The concentrations of active ingredient in the ready-to-use preparations can be varied within substantial ranges.

They are generally from 0.0001 to 10%, preferably from 0.01 to 1%.

The active ingredients can also be used successfully in the ultra-low-volume method (ULV), it being possible to apply formulations comprising more than 95% by weight of active ingredient, or even the active ingredient without additives.

For controlling pests, the rate of application of active ingredient is 0.1 to 2.0, preferably 0.2 to 1.0, kg/ha under field conditions.

Substances which are suitable for the preparation of ready-to-spray solutions, emulsions, pastes or oil dispersions are mineral oil fractions of medium to high boiling point, such as kerosene or diesel oil, furthermore coaltar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone, water.

Aqueous use forms can be prepared from emulsion concentrates, pastes or wettable powders (spraying powders, oil dispersions) by adding water. To prepare emulsions, pastes or oil dispersions, the substances, as such or dissolved in an oil or solvent, can be homogenized in water by means of wetting agent, adhesive, dispersant or emulsifier. Alternatively, it is possible to prepare concentrates composed of active ingredient, wetting agent, adhesive, dispersant or emulsifier and, if desired, solvent or oil, which are suitable for dilution with water.

Suitable surfactants are alkali metal salts, alkaline earth metal salts and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal salts and alkaline earth metal salts, salts of sulfated fatty alcohol glycol ether, condensates of sulfonated naphthalene and naphthalene derivatives with formaldehyde, condensate of naphthalene or of the naphthalenesulfonic acid with phenol and formaldehyde, polyoxyethylene octylphenol ether, ethoxylated isooctylphenol, octylphenol, nonylphenol, alkylphenol [sic] polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Powders, materials for spreading and dusts can be prepared by mixing or grinding the active ingredients together with a solid carrier.

In general the formulations comprise from 0.01 to 95% by weight, preferably from 0.1 to 90% by weight, of the active ingredient. The active ingredients are employed in a purity of from 90% to 100%, preferably 95% to 100% (according to NMR spectrum). Examples of formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 80 parts by weight of paraffin oil which had been sprayed onto the surface of this silica gel. This gives a preparation of the active ingredient with good adherence (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, and this gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of a pulverulent silica gel and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients to solid carriers. Examples of solid carriers are mineral earths, such as silica gel, silicas, silica gels [sic], silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

Various types of oils, or herbicides, fungicides, other pesticides and bactericides can also be added to the active ingredients, if desired only just prior to use (tank mix). These products can be admixed with the products according to the invention in a weight ratio of 1:10 to 10:1.

SYNTHESIS EXAMPLES

The protocols given in the synthesis examples which follow were used for obtaining other compounds I by choosing suitable different starting materials. The resulting compounds are listed in the tables which follow together with physical data.

Example 1

Synthesis of pentane-2,3-dione 2-oxime 250 ml of hydrogen-chloride-saturated diethyl ether are added dropwise at −20° C. to 66.2 g (0.77 mol) of 3-pentanone in 300 ml of toluene.

A solution of 88 g (0.85 mol) of n-butyl nitrite in 250 ml of diethyl ether is carefully added dropwise at −20° C. to this mixture, and stirring of the entire reaction mixture is continued for two hours at 0° C. and a further 12 hours at room temperature. After 250 ml of water has been added, the organic phase is separated and extracted three times using in each case 200 ml of 1N sodium hydroxide solution. This aqueous phase is brought to a pH of 4 by adding 1N hydrochloric acid and extracted three times using in each case 200 ml of dichloromethane. After the organic phase has been dried over sodium sulfate, it is evaporated in vacuo. This gives 56 g of an oil (63%), which crystallizes rapidly.

Melting point: 58–60° C. $^1$H NMR (CDCl$_3$): δ=1.16 (+, 3H); 2.02 (s, 3H); 2.84 (q, 2H); 9.64 (s, 1H).

Example 2

Synthesis of pentane-2,3-dione 2-(O-methyloxime)

49.7 g (0.35 mol) of methyl iodide are added dropwise at room temperature to a solution of 40.2 g (0.55 mol) of pentane-2,3-dione 2-oxime and 52.0 g (0.38 mol) of potassium carbonate in 400 ml of acetone, and stirring is continued for 12 hours at this temperature.

After the inorganic salts have been removed by filtration, the acetone solution is evaporated in vacuo, the residue is partitioned between methyl tert-butyl ether and water, and the organic phase is washed with water, dried over sodium sulfate and concentrated. This gives 37.7 g (83%) of an oil.

$^1$H NMR (CDCl$_3$): δ=1.09 (t, 3H); 1.91 (s, 3H); 2,81 (q, 2H); 4.04 (s, 3H).

Example 3

Synthesis of pentane-2,3,4-trione 4-(O-methyl oxime)-2-oxime 10.3 g (0.1 mol) of n-butyl nitrite and then 54 g of a 30% strength solution of sodium methylate in methanol are carefully added dropwise at 10° C. to a solution of 12.9 g (0.1 mol) of pentane-2,3-dione 2-(O-methyl oxime) in 120 ml of methanol. The mixture is allowed to come to room temperature and is stirred for 12 hours at this temperature. The mixture is worked up by adding dilute hydrochloric acid to a pH of 7 and subsequent evaporation in vacuo. The residue is taken up in 100 ml of water and extracted twice using in each case 100 ml of diethyl ether. The organic phase is dried over sodium sulfate and evaporated in vacuo. This gives 7.7 g (49%) of an oil.

$^1$H NMR (CDCl$_3$): δ=1.99, 2.11 (2s, 6H); 4.05 (s, 3H); 10,40 (s, 1H).

Example 4

Synthesis of pentane-2,3,4-trione 3,4-bis-(O-methyl oxime)-2-oxime 4.7 ml (0.06 mol) of pyridine and 1.7 g (0.02 mol) of O-methylhydroxylamine hydrochloride are added at room temperature to a solution of 3.2 g (0.02 mol) of pentane-2, 3,4-trione 4-(O-methyl oxime)-2-oxime in 60 ml of methanol. After the mixture has been stirred for two hours at room temperature, it is concentrated in vacuo, the product is taken up in 50 ml of diethyl ether, and the mixture is washed twice using in each case 20 ml of dilute hydrochloric acid and twice using in each case 20 ml of water, dried over $Na_2SO_4$ and evaporated in vacuo. Column chromatography on silica gel (cyclohexane/ethyl acetate: 99:1→95:5) gives two diastereomers as oils.

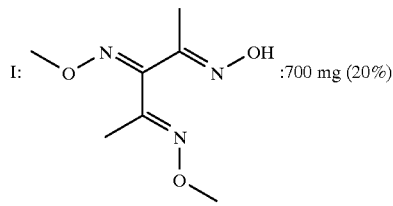

I: :700 mg (20%)

$^1$H NMR (CDCl$_3$): δ=1.92, 2.12 (2s, 6H); 3.92, 3.99 (2s, 6H); 9.92 (s, 1H).

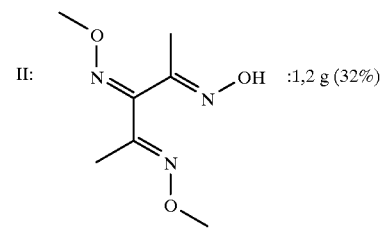

II: :1,2 g (32%)

$^1$H NMR (CDCl$_3$): δ=2.02, 2.11 (2s, 6H); 3.84, 4.07 (2s, 6H); 9.23 (s, 1H).

Example 5
Synthesis of Methyl [2-(2,3-bismethoxyimino-1-methylbutylideneaminooxymethyl)phenyl]methoxyiminoacetate 1.4 g (4.8 mmol) of methyl 2-methoxyimino-2-(2)-bromomethyl)phenylacetate [sic] are added to a solution of 0.9 g (4.8 mmol) of pentane-2,3,4-trione 3,4-bis(O-methyl oxime)-2-oxime and 0.4 g of potassium hydroxide in 20 ml of dry dimethylformamide and the mixture is stirred for 30 minutes at room temperature. The mixture is worked up by adding 50 ml of ice-water and then by three extractions using in each case 20 ml of diethyl ether. The combined organic phases are dried over sodium sulfate and evaporated in vacuo. The residue is recrystallized from diisopropyl ether. This gives 0.6 g (32%) of white crystals with a melting point of 105° C.

$^1$H NMR (CDCl$_3$): δ=1.88, 2.02 (2s, 6H); 3.83, 3.91, 3.93, 4.02 (4s, 12H); 5.05 (s, 2H); 7.15 (m, 1H); 7.39 (m, 3H).

Example 6
Synthesis of N-methyl-[2-(2,3-bismethoxyimino-1-methylbutylideneaminooxymethyl)phenyl]methoxyiminoacetamide 2 ml of 40% strength aqueous methylamine solution are added to a solution of 0.6 g (1.5 mmol) of methyl [2-(2,3-bismethoxyimino-1-methylbutylideneaminooxymethyl)phenyl]methoxyiminoacetate in 10 ml of tetrahydrofuran, and the mixture is stirred for 12 hours at room temperature. For working up, the reaction mixture is evaporated in vacuo, taken up in 20 ml of diethyl ether, washed using 20 ml of water, dried over sodium sulfate and evaporated in vacuo. This gives 0.6 g (98%) of an oil.

$^1$H NMR (CDCl$_3$): δ=1.90, 1.98 (2s, 6H); 2.88 (d, 3H); 3.93, 3.94 (3s, 9H); 5.05 (s, 2H); 6.72 (m, 1H); 7.20 (m, 1H); 7.38 (m, 3H).

TABLE B

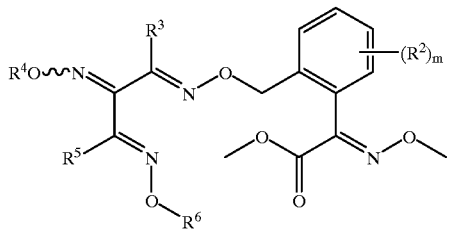

| No. | $R^2$ | $R^3$ | $R^4$ | $R^5$ | $R^6$ | Data - M.p. °C., $^1$H NMR |
|---|---|---|---|---|---|---|
| B1 Isomer I | H | CH$_3$ | CH$_3$ | CH$_3$ | CH$_3$ | 73–74 |
| B1 Isomer II | H | CH$_3$ | CH$_3$ | CH$_3$ | CH$_3$ | 79–80 |
| B2 Isomer I | H | CH$_3$ | C$_2$H$_5$ | CH$_3$ | CH$_3$ | 87–88 |
| B2 Isomer II | H | CH$_3$ | C$_2$H$_5$ | CH$_3$ | CH$_3$ | |
| B3 Isomer I | H | CH$_3$ | C$_3$H$_3$ | CH$_3$ | CH$_3$ | $^1$H: 1.88, 2.05 (2s, 6H), 2.48 (t, 1H), 3.85, 3.92, 4.05 (3s, 9H), 4.72 (d, 2H), 5.05 (s, 2H), 7.11–7.44 (m, 4H) |
| B3 Isomer II | H | CH$_3$ | C$_3$H$_3$ | CH$_3$ | CH$_3$ | $^1$H: 1.98, 2.04 (2s, 6H), 2.47 (t, 1H), 3.82, 3.95, 4.05 (3s, 9H), 4.74 (d 2H), 5.09 (s, 2H), 7.10–7.54 (m, 4H) |
| B4 Isomer I | H | CH$_3$ | CH$_3$ | CH$_3$ | C$_2$H$_5$ | 89–91 |
| B4 Isomer II | H | CH$_3$ | CH$_3$ | CH$_3$ | C$_2$H$_5$ | 64–65 |
| B5 Isomer I | H | CH$_3$ | C$_2$H$_5$ | CH$_3$ | C$_2$H$_5$ | 83–85 |

TABLE B-continued

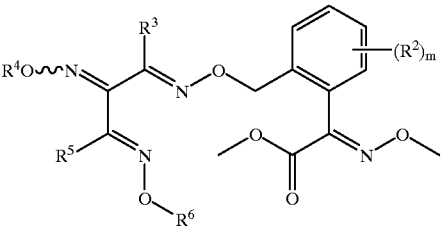

| No. | R² | R³ | R⁴ | R⁵ | R⁶ | Data - M.p. °C., ¹H NMR |
|---|---|---|---|---|---|---|
| B5 Isomer II | H | $CH_3$ | $C_2H_5$ | $CH_3$ | $C_2H_5$ | ¹H: 1.21, 1.22 (2t, 6H), 1.99, 2.02 (2s, 6H), 3.81, 4.02 (2s, 6H), 4.19 (m, 4H), 5.09 (s, 2H), 7.11–7.53 (m, 4H) |
| B6 Isomer I | H | $CH_3$ | $CH_3$ | $CH_3$ | $CH(CH_3)_2$ | 75–76 |
| B6 Isomer II | H | $CH_3$ | $CH_3$ | $CH_3$ | $CH(CH_3)_2$ | ¹H: 1.18 (t, 3H), 1.98, 2.04 (2s, 6H), 3.82, 3.95, 4.08 (3s, 9H), 4.36 (q, 2H), 5.06 (s, 2H), 7.19–7.54 (m, 4H) |
| B7 Isomer I | H | $CH_3$ | $C_2H_5$ | $CH_3$ | $CH(CH_3)_2$ | 98–101 |
| B8 Isomer I | H | $CH_3$ | $C_3H_3$ | $CH_3$ | $C_2H_5$ | 75–78 |
| B8 Isomer II | H | $CH_3$ | $C_3H_3$ | $CH_3$ | $C_2H_5$ | ¹H: 1.25 (t, 3H), 1.62 (d, 3H), 1.88, 2.02 (2s, 6H), 3.70, 3.80 (2s, 6H), 4.18 (q, 2H), 4.78 (8d, 2H), 5.10 (s, 2H), 7.10–7.38 (m, 4H), 7.58 (s, 1H). |
| B9 Isomer I | H | $CH_3$ | $C_3H_3$ | $CH_3$ | $CH(CH_3)_2$ | ¹H: 1.21 (d, 3H), 1.90, 2.03 (2s, 6H), 2.43 (t, 1H), 3.85, 4.02 (2s, 6H), 4.38 (s, 1H), 4.71 (d, 2H), 5.08 (s, 2H), 7.11–7.41 (m, 4H) |
| B10 Isomer I | H | $CH_3$ | $CH_3$ | $CH_3$ | $C_3H_3$ | 71–73 |

TABLE C

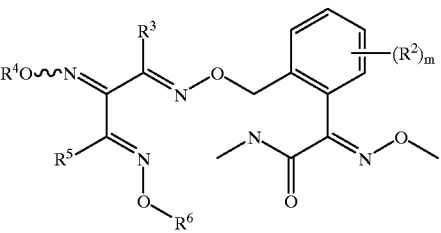

| No. | R² | R³ | R⁴ | R⁵ | R⁶ | Data - M.p. °C., ¹H NMR |
|---|---|---|---|---|---|---|
| C1 Isomer I | H | $CH_3$ | $CH_3$ | $CH_3$ | $CH_3$ | 84–85 |
| C1 Isomer II | H | $CH_3$ | $CH_3$ | $CH_3$ | $CH_3$ | 84–85 |
| C2 Isomer I | H | $CH_3$ | $C_2H_5$ | $CH_3$ | $CH_3$ | ¹H: 1.30 (t, 3H), 1.91, 1.99 (2s, 6H), 2.85 (d, 2H), 3.94 (2s, 6H), 4.09 (q, 2H), 5.05 (s, 2H), 6.82 (d, 1H), 7.13–7.42 (m, 4H) |
| C2 Isomer II | H | $CH_3$ | $C_2H_5$ | $CH_3$ | $CH_3$ | |
| C3 Isomer I | H | $CH_3$ | $C_3H_3$ | $CH_3$ | $CH_3$ | ¹H: 1.92, 2.03 (2s, 6H), 2.46 (t, 1H), 3.68, 3.79, 3.91 (3s, 9H), 4.72 (d, 2H), 5.09 (s, 2H), 7.11–7.44 (m, 4H), 7.55 (s 1H) |
| C3 Isomer II | H | $CH_3$ | $C_3H_3$ | $CH_3$ | $CH_3$ | ¹H: 1.98, 2.05 (2s, 6H), 2.50 (t, 1H), 2.88 (d, 3H), 3.95 (1s, 6H), 4.73 (d, 2H), 5.09 (s, 2H), 6.80 (d, 1H), 7.10–7.54 (m, 4H) |
| C4 Isomer I | H | $CH_3$ | $CH_3$ | $CH_3$ | $C_2H_5$ | ¹H: 1.30 (t, 3H), 1.95, 1.99 (2s, 6H), 2.88 (d, 3H), 3.92 (s, 6H), 4.14 (q, 2H), 5.04 (s, 2H), 6.78 (d, 1H), 7.15–7.34 (m, 4H) |
| C4 Isomer II | H | $CH_3$ | $CH_3$ | $CH_3$ | $C_2H_5$ | ¹H: 1.23 (t, 3H), 1.89, 2.03 (2s, 6H), 2.82 (d, 3H), 3.93, 3.95 (2s, 6H), 4.15 (q, 2H), |

TABLE C-continued

| No. | R² | R³ | R⁴ | R⁵ | R⁶ | Data - M.p. °C., ¹H NMR |
|---|---|---|---|---|---|---|
| | | | | | | 5.08 (s, 2H), 6.83 (d, 1H), 7.21–7.48 (m, 4H) |
| C5 Isomer I | H | CH₃ | C₂H₅ | CH₃ | C₂H₅ | ¹H: 1.28 (t, 6H), 1.92, 197 (2s, 6H), 2.86 (d, 3H), 3.95 (s, 3H), 4.14 (q, 4H), 5.08 (s, 2H), 6.85 (d, 1H), 7.19–7.42 (m, 4H) |
| C5 Isomer II | H | CH₃ | C₂H₅ | CH₃ | C₂H₅ | 82–86 |
| C6 Isomer I | H | CH₃ | CH₃ | CH₃ | CH(CH₃)₂ | ¹H: 1.19 (d, 6H), 1.92, 1.99 (2s, 6H), 2.92 (d, 3H), 3.98 (s, 6H), 4.35 (sept, 1H), 5.03 (s, 2H), 6.82 (d, 1H), 7.13–7.41 (m, 4H) |
| C6 Isomer II | H | CH₃ | CH₃ | CH₃ | CH(CH₃)₂ | ¹H: 1.19 (d, 6H), 1.93, 2.04 (2s, 6H), 2.84 (d, 3H), 3.94 (s, 6H), 4.16 (q, 2H), 5.04 (s, 2H), 6.72 (q, 1H), 7.20–7.43 (m, 4H) |
| C7 Isomer I | H | CH₃ | C₂H₅ | CH₃ | CH(CH₃)₂ | ¹H: 1.26 (m, 9H), 1.93, 2.05 (2s, 6H), 2.89 (d, 3H), 3.95 (s, 6H), 4.22 (q, 2H), 4.39 (sept, 1H), 5.06 (s, 2H), 6.86 (d, 1H), 7.18–7.43 (m, 4H) |
| C8 Isomer I | H | CH₃ | C₃H₃ | CH₃ | C₂H₅ | 124–127 |
| C9 Isomer I | H | CH₃ | C₃H₃ | CH₃ | CH(CH₃)₂ | ¹H: 1.22 (2d, 6H), 1.90, 1.98 (2s, 6H), 2.42 (t, 1H), 2.90 (d, 3H), 3.94 (s, 3H), 4.28 (s, 1H), 4.78 (d, 2H), 5.04 (s, 2H), 6.80 (d, 1H), 7.20–7.41 (m, 4H) |
| C10 Isomer I | H | CH₃ | CH₃ | CH₃ | C₃H₃ | ¹H: 1.94, 2.00 (2s, 6H), 2.48 (t, 1H), 2.90 (d, 3H), 3.95 (s, 6H), 4.80 (d, 2H), 5.01 (s, 2H), 6.83 (d, 1H), 7.18–7.43 (m, 4H) |

TABLE D

| No. | R² | R³ | R⁴ | R⁵ | R⁶ | Data - M.p. °C., ¹H NMR |
|---|---|---|---|---|---|---|
| D1 Isomer I | H | CH₃ | CH₃ | CH₃ | CH₃ | 113 |
| D1 Isomer II | H | CH₃ | CH₃ | CH₃ | CH₃ | ¹H: 1.99, 2.02 (2s, 6H), 3.73 (s, 3H), 3.83, 3.93, 3.95 (3s, 9H), 5.08 (s, 2H), 7.04–7.36 (m, 4H), 7.61 (s, 1H) |
| D2 Isomer I | H | CH₃ | C₂H₅ | CH₃ | CH₃ | ¹H: 1.33 (t, 3H), 1.95, 2.04 (2s, 6H), 3.72 (s, 3H), 3.82, 3.93 (2s, 6H), 4.11 (q, 2H), 5.05 (s, 2H), 7.03–7.33 (m, 4H), 7.60 (s, 1H) |
| D2 Isomer II | H | CH₃ | C₂H₅ | CH₃ | CH₃ | |
| D3 Isomer I | H | CH₃ | C₃H₃ | CH₃ | CH₃ | ¹H: 1.91, 2.01 (2s, 6H), 2.46 (t, 1H), 2.88 (d, 3H), 3.95 (s, 6H), 4.74 (d, 2H), 5.09 (s, 2H), 6.85 (d, 1H), 7.11–7.44 (m, 4H) |
| D3 Isomer II | H | CH₃ | C₃H₃ | CH₃ | CH₃ | ¹H: 2.02, 2.04 (2s, 6H), 2.48 (t, 1H), 3.69, 3.82, 3.98 (3s, 9H), 4.76 (d, 2H), 5.10 |

TABLE D-continued

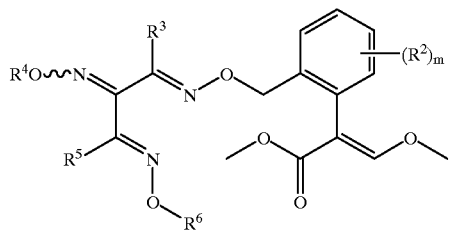

| No. | $R^2$ | $R^3$ | $R^4$ | $R^5$ | $R^6$ | Data - M.p. °C., $^1$H NMR |
|---|---|---|---|---|---|---|
| D4 Isomer I | H | $CH_3$ | $CH_3$ | $CH_3$ | $C_2H_5$ | (s, 2H), 7.10–7.49 (m, 4H), 7.52 (s, 1H) 114–116 |
| D4 Isomer II | H | $CH_3$ | $CH_3$ | $CH_3$ | $C_2H_5$ | $^1$H: 1.26 (t, 3H), 1.98, 2.03 (2s, 6H), 3.69, 3.79, 3.98 (3s, 6H), 4.19 (q, 2H), 5.12 (s, 2H), 7.11–7.53 (m, 5H) |
| D5 Isomer I | H | $CH_3$ | $C_2H_5$ | $CH_3$ | $C_2H_5$ | 84–86 |
| D6 Isomer I | H | $CH_3$ | $CH_3$ | $CH_3$ | $CH(CH_3)_2$ | 108–110 |
| D7 Isomer I | H | $CH_3$ | $C_2H_5$ | $CH_3$ | $CH(CH_3)_2$ | 101–105 |
| D8 Isomer I | H | $CH_3$ | $C_3H_3$ | $CH_3$ | $CH(CH_3)_2$ | 84–86 |
| D9 Isomer I | H | $CH_3$ | $CH_3$ | $CH_3$ | $C_3H_3$ | $^1$H: 1.95, 2.01 (2s, 6H), 2.46 (t, 1H), 3.68, 3.80, 3.95 (3s, 9H), 4.72 (d, 2H), 5.10 (s, 2H), 7.11–7.45 (m, 4H), 7.58 (s, 1H) |

TABLE E

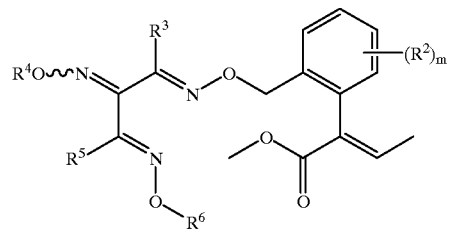

| No. | $R^2$ | $R^3$ | $R^4$ | $R^5$ | $R^6$ | Data - M.p. °C., $^1$H NMR |
|---|---|---|---|---|---|---|
| E1 Isomer I | H | $CH_3$ | $CH_3$ | $CH_3$ | $CH_3$ | |
| E2 Isomer I | H | $CH_3$ | $CH_3$ | $CH_3$ | $C_2H_5$ | 57–62 |
| E3 Isomer I | H | $CH_3$ | $C_2H_5$ | $CH_3$ | $C_2H_5$ | $^1$H: 1.28 (t, 6H), 1.58 (d, 3H), 1.91, 2.01 (2s, 6H), 3.72 (s, 3H), 4.18 (q, 4H), 5.02 (s, 2H), 7.05–7.42 (m, 5H) |
| E3 Isomer II | H | $CH_3$ | $CH_3$ | $CH_3$ | $C_2H_5$ | $^1$H: 1.25 (t, 3H), 1.59 (d, 3H), 1.95, 2.01 (2s, 6H), 3.69, 3.98 (2s, 6H), 4.12 (q, 2H), 5.01 (s, 2H), 7.02–7.56 (m, 5H) |
| E4 Isomer I | H | $CH_3$ | $CH_3$ | $CH_3$ | $CH(CH_3)_2$ | $^1$H: 1.19 (d, 6H), 1.92, 1.99 (2s, 6H), 2.92 (d, 3H), 3.98 (s, 6H), 4.35 (sept. 1H), 5.03 (s, 2H), 6.82 (d, 1H), 7.13–7.41 (m, 4H) |
| E5 Isomer I | H | $CH_3$ | $C_2H_5$ | $CH_3$ | $CH_3$ | $^1$H: 1.25 (t, 3H), 1.62 (d, 3H), 1.88, 2.02 (2s, 6H), 3.70, 3.90 (2s, 6H), 4.18 (q, 2H), 4.99 (s, 2H), 7.03 (q, 1H), 7.21–7.44 (m, 4H) |
| E6 Isomer I | H | $CH_3$ | $C_3H_3$ | $CH_3$ | $CH_3$ | $^1$H: 1.63 (d, 3H), 1.89, 2.04 (2s, 6H), 2.42 (t, 1H), 3.71, 3.90 (2s, 6H), 4.72 (d, 2H), 5.01 (s, 2H), 7.05 (q, 1H), 7.22–7.42 (m, 4H) |
| E7 Isomer I | H | $CH_3$ | $C_3H_3$ | $CH_3$ | $C_2H_5$ | 68–70 |
| E8 Isomer I | H | $CH_3$ | $C_3H_3$ | $CH_3$ | $CH(CH_3)_2$ | $^1$H: 1.19 (d, 6H), 1.62 (d, 3H), 1.89, 2.06 (2s, 6H), 2.44 (t, 1H), 3.70 (s, 3H), |

TABLE E-continued

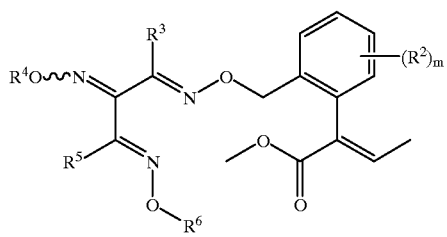

| No. | R² | R³ | R⁴ | R⁵ | R⁶ | Data - M.p. °C., ¹H NMR |
|---|---|---|---|---|---|---|
| | | | | | | 4.38 (s, 1H), 4.72 (d, 2H), 4.99 (s, 2H), 7.02 (q, 1H), 7.18–7.44 (m, 4H) |

Use Example 1
Activity Against Powdery Mildew of Wheat

Leaves of wheat seedlings cv. "Frühgold" grown in pots were sprayed with an aqueous spray mixture comprising 80% of active ingredient and 20% of emulsifier in the dry matter and, 24 hours after the spray coating had dried on, dusted with oidia (spores) of powdery mildew of wheat (*Erysiphe graminis* var. *tritici*). The test plants were subsequently placed in the greenhouse at from 20 to 22° C. and a relative atmospheric humidity of 75 to 80%. After 7 days, the extent of mildew development was determined in % diseased leaf area.

| Active Ingredient No. | Diseased leaf area in % after application of aqueous preparation comprising 4 ppm of active ingredient |
|---|---|
| B1, isomer I | 0 |
| B2, isomer I | 15 |
| B4, isomer I | 0 |
| B5, isomer I | 15 |
| B6, isomer I | 0 |
| B7, isomer I | 15 |
| B8, isomer I | 5 |
| B8, isomer II | 15 |
| B9, isomer I | 15 |
| C1, isomer I | 5 |
| C2, isomer I | 15 |
| C4, isomer I | 5 |
| C5, isomer I | 5 |
| C6, isomer I | 15 |
| C7, isomer I | 15 |
| D1, isomer I | 15 |
| D2, isomer I | 5 |
| D4, isomer I | 15 |
| D5, isomer I | 5 |
| D6, isomer I | 15 |
| D8, isomer I | 15 |
| E2, isomer I | 0 |
| E3, isomer I | 0 |
| E4, isomer I | 5 |
| E5, isomer I | 5 |
| E6, isomer I | 15 |
| E7, isomer I | 15 |
| E8, isomer I | 5 |
| Untreated | 75 |

Use Example 2
Activity Against *Plasmopara viticola*

Leaves of grapevines cv. "Müller-Thurgau" in pots were sprayed with an aqueous spray mixture comprising 80% of active ingredient and 20% of emulsifier in the dry matter. To be able to assess the duration of action of the active ingredients, the plants were placed in the greenhouse for 8 days after the spray coating had dried on. Only then were the leaves infected with a zoospore suspension of Plasmopara viticola (downy mildew of grapevines). Then, the grapevines were first placed in a water-vapor-saturated chamber at 24° C. for 48 hours and subsequently in a greenhouse at from 20 to 30° C. for 5 days. After this period, the plants were returned to the humid chamber for 16 hours to accelerate the eruption of sporangiophores. The extent of the fungal eruption was then assessed in % diseased area on the undersides of the leaves.

| Active Ingredient No. | Diseased leaf area in % after application of aqueous preparation comprising 16 ppm of active ingredient |
|---|---|
| B1, isomer I | 5 |
| B2, isomer I | 5 |
| B3, isomer I | 0 |
| B4, isomer I | 15 |
| B6, isomer I | 10 |
| B7, isomer I | 15 |
| B8, isomer II | 5 |
| C1, isomer I | 3 |
| C2, isomer I | 10 |
| C3, isomer I | 3 |
| C3, isomer II | 10 |
| C4, isomer I | 0 |
| C4, isomer II | 15 |
| C5, isomer I | 3 |
| C6, isomer I | 3 |
| C6, isomer II | 10 |
| C7, isomer I | 3 |
| C9, isomer I | 15 |
| C10, isomer I | 0 |
| D1, isomer I | 3 |
| D1, isomer II | 3 |
| D2, isomer I | 0 |
| D3, isomer I | 0 |
| D4, isomer I | 0 |
| D4, isomer II | 5 |
| D5, isomer I | 10 |
| D6, isomer I | 0 |
| D7, isomer I | 10 |
| D8, isomer I | 15 |
| D9, isomer I | 0 |
| Untreated | 80 |

Use Example 3
Activity Against *Pyricularia oryzae* (protective)

Leaves of rice seedlings cv. "Tai-Nong 67" grown in pots were sprayed to drip point with aqueous emulsions comprising 80% of active ingredient and 20% of emulsifier in the dry matter and, 24 hours later, inoculated with an aqueous spore suspension of *Pyricularia oryzae*. The test plants were subsequently placed in controlled-environment cabinets at 22 to 24° C. and a relative atmospheric humidity of 95 to 99%. After 6 days, the extent of the disease level was determined.

| Active ingredient No. | Diseased leaf area in % after application of aqueous preparation comprising 4 ppm of active ingredient |
|---|---|
| B1, isomer I | 15 |
| B2, isomer I | 15 |
| B3, isomer I | 5 |
| C1, isomer I | 0 |
| C2, isomer I | 15 |
| C3, isomer I | 0 |
| C5, isomer I | 15 |
| C6, isomer I | 15 |
| C7, isomer I | 15 |
| C10, isomer I | 15 |
| D1, isomer I | 0 |
| D1, isomer II | 15 |
| D2, isomer I | 0 |
| D3, isomer I | 0 |
| D4, isomer I | 15 |
| D6, isomer I | 15 |
| D7, isomer I | 15 |
| D9, isomer I | 15 |
| E5, isomer I | 15 |
| Untreated | 85 |

We claim:

1. A phenylacetic acid derivative of the formula I

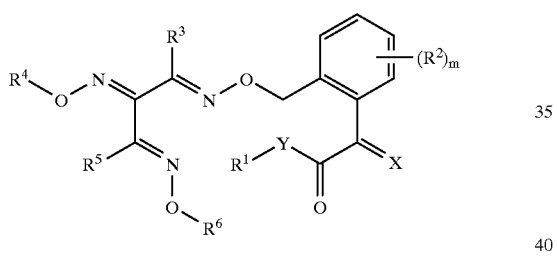

where the substituents and the index have the following meanings:

X is $NOCH_3$, $CHOCH_3$, $CHCH_3$;

Y is O, NR $R^1$, R independently of one another are hydrogen and $C_1-C_4$-alkyl;

$R^2$ is cyano, nitro, trifluoromethyl, halogen, $C_1-C_4$-alkyl and $C_1-C_4$-alkoxy;

m is 0, 1 or 2, it being possible for the radicals $R^2$ to be different when m is 2;

$R^3$ is hydrogen, cyano, $C_1-C_4$-alkyl, $C_1-C_4$-haloalkyl, $C_3-C_6$-cycloalkyl;

$R^4, R^6$ independently of one another are hydrogen, $C_1-C_{10}$-alkyl, $C_3-C_6$-cycloalkyl, $C_2-C_{10}$-alkenyl, $C_2-C_{10}$-alkynyl, $C_1-C_{10}$-alkylcarbonyl, $C_2-C_{10}$-alkenylcarbonyl, $C_3-C_{10}$-alkynylcarbonyl or $C_1-C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1-C_6$-alkyl, $C_1-C_6$-haloalkyl, $C_1-C_6$-alkylsulfonyl, $C_1-C_6$-alkylsulfoxyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, $C_3-C_6$-cycloalkyl, $C_3-C_6$-cycloalkyloxy, heterocyclyl, heterocyclyloxy, benzyl, benzyloxy, aryl, aryloxy, arylthio, hetaryl, hetaryloxy and hetarylthio, it being possible for the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1-C_6$-alkyl, $C_1-C_6$-haloalkyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkyloxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, benzyl, benzyloxy, aryl, aryloxy, arylthio, hetaryl, hetaryloxy, hetarylthio or $C(=NOR^7)-A_n-R^8$;

aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1-C_6$-alkyl, $C_1-C_6$-haloalkyl, $C_1-C_6$-alkylcarbonyl, $C_1-C_6$-alkylsulfonyl, $C_1-C_6$-alkylsulfoxyl, $C_3-C_6$-cycloalkyl, $C_1-C_6$-alkoxy, $C_1-C_6$-haloalkoxy, $C_1-C_6$-alkyloxycarbonyl, $C_1-C_6$-alkylthio, $C_1-C_6$-alkylamino, di-$C_1-C_6$-alkylamino, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_2-C_6$-alkenyl, $C_2-C_6$-alkenyloxy, benzyl, benzyloxy, aryl, aryloxy, hetaryl, hetaryloxy or $C(=NOR^7)-A_n-R^8$;

$R^5$ is hydrogen, $C_1-C_6$-alkyl, $C_2-C_6$-alkenyl, $C_2-C_6$-alkynyl, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, $C_1-C_6$-alkylaminocarbonyl, di-$C_1-C_6$-alkylaminocarbonyl, $C_1-C_6$-alkylaminothiocarbonyl, di-$C_1-C_6$-alkylaminothiocarbonyl, $C_1-C_6$-alkylsulfonyl, $C_1-C_6$-alkylsulfoxyl, $C_1-C_6$-alkoxy, $C_1-C_6$-haloalkoxy, $C_1-C_6$-alkoxycarbonyl, $C_1-C_6$-alkylthio, $C_1-C_6$-alkylamino, di-$C_1-C_6$-alkylamino, $C_2-C_6$-alkenyloxy, $C_3-C_6$-cycloalkyl, $C_3-C_6$-cycloalkyloxy, heterocyclyl, heterocyclyloxy, aryl, aryloxy, aryl-$C_1-C_4$-alkoxy, arylthio, aryl-$C_1-C_4$-alkylthio, hetaryl, hetaryloxy, hetaryl-$C_1-C_4$-alkoxy, hetarylthio, hetaryl-$C_1-C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1-C_6$-alkyl, $C_1-C_6$-haloalkyl, $C_1-C_6$-alkylsulfonyl, $C_1-C_6$-alkylsulfoxyl, $C_3-C_6$-cycloalkyl, $C_1-C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and C(=NOR$^7$)—A$_n$—R$^8$;

$C_3$–$C_6$-cycloalkyl, $C_3$–$C_6$-cycloalkenyl, heterocyclyl, aryl, hetaryl, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy;

where

A is oxygen, sulfur or nitrogen and where the nitrogen has attached to it hydrogen or $C_1$–$C_6$-alkyl;

n is 0 or 1;

$R^7$ is hydrogen or $C_1$–$C_6$-alkyl and $R^8$ is hydrogen or $C_1$–$C_6$-alkyl, or a salt thereof.

2. A compound of the formula I as claimed in claim 1, where X is NOCH$_3$.

3. A compound of the formula I as claimed in claim 1 or 2, where X is CHOCH$_3$.

4. A compound of the formula I as claimed in any of claims 1 to 3 where X is CHCH$_3$.

5. A compound of the formula I as claimed in any of claims 1 to 4 where m is 0.

6. A compound of the formula I as claimed in any of claims 1 to 5 where $R^1$ is methyl.

7. A compound of the formula I as claimed in any of claims 1 to 6 where $R^3$ is hydrogen, cyano, cyclopropyl, methyl, ethyl or 1-methylethyl.

8. A compound of the formula I as claimed in any of claims 1 to 7 where $R^4$ is hydrogen, $C_1$–$C_6$-alkyl, $C_2$–$C_6$-alkenyl, $C_2$–$C_6$-alkynyl, allyl, arylalkyl, hetarylalkyl, aryloxyalkyl, hetaryloxyalkyl, aryl or hetaryl.

9. A compound of the formula I as claimed in any of claims 1 to 8 where $R^5$ is hydrogen, cyclopropyl, methyl, ethyl, iso-propyl, unsubstituted or substituted aryl or hetaryl.

10. A compound of the formula I as claimed in any of claims 1 to 9 where $R^6$ is $C_1$–$C_6$-alkyl, $C_2$–$C_6$-alkenyl, $C_2$–$C_6$-alkynyl, arylalkyl, hetarylalkyl, aryloxyalkyl or hetaryloxyalkyl.

11. A process for the preparation of the compounds of the formula I which comprises reacting a benzyl derivative of the formula II with a hydroxyimine of the formula III

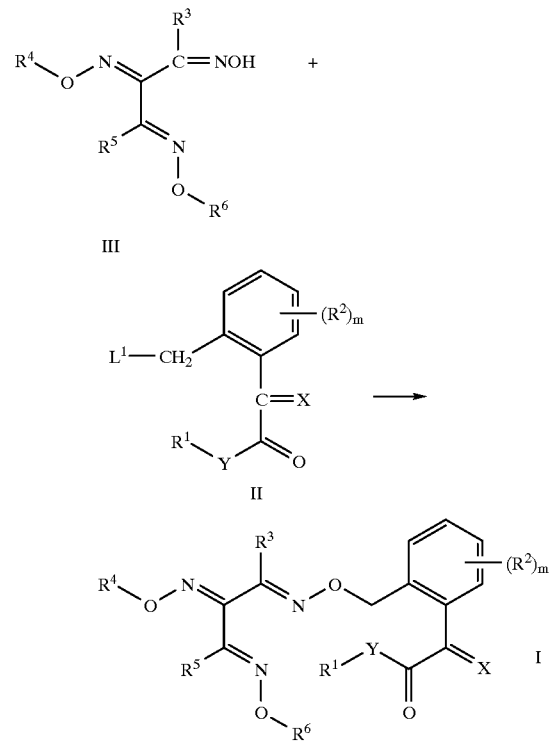

where $L^1$ is a nucleophilically exchangeable leaving group.

12. A composition against animal pests or harmful fungi comprising customary additives and an effective amount of a compound of the formula I as claimed in claim 1.

13. A composition as claimed in claim 12 for controlling animal pests from the classes of the insects, arachnids or nematodes.

14. A method of controlling animal pests or harmful fungi which comprises treating the pests or harmful fungi, their environment, or the plants, areas, materials or spaces to be kept free from them with an effective amount of at least one compound of the formula I as claimed in claim 1.

* * * * *